United States Patent
Danishefsky et al.

(10) Patent No.: US 7,115,651 B2
(45) Date of Patent: Oct. 3, 2006

(54) MACROCYCLES AND USES THEREOF

(75) Inventors: Samuel J. Danishefsky, Englewood, NJ (US); Robert M. Garbaccio, Lansdale, PA (US); Daniel K. Baeschlin, Arlesheim (CH); Shawn J. Stachel, Perkasie, PA (US); David Solit, New York, NY (US); Neal Rosen, Englewood, NJ (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 676 days.

(21) Appl. No.: 09/938,754

(22) Filed: Aug. 24, 2001

(65) Prior Publication Data

US 2002/0091151 A1 Jul. 11, 2002

Related U.S. Application Data

(60) Provisional application No. 60/304,553, filed on Jul. 11, 2001, provisional application No. 60/228,277, filed on Aug. 25, 2000.

(51) Int. Cl.
*A61P 7/00* (2006.01)
*A61K 31/385* (2006.01)
*A61K 31/335* (2006.01)
*C07D 339/00* (2006.01)
*C07D 313/00* (2006.01)

(52) U.S. Cl. .................. 514/434; 514/63; 514/436; 514/450; 549/4; 549/22; 549/214; 549/215; 549/268; 549/269; 549/270

(58) Field of Classification Search ............. 514/63, 514/434, 436, 450; 549/4, 22, 214, 215, 549/268, 269, 270
See application file for complete search history.

(56) References Cited

U.S. PATENT DOCUMENTS

| | | | |
|---|---|---|---|
| 3,373,038 A | | 3/1968 | Hodge et al. |
| 3,373,039 A | * | 3/1968 | Wehrmeister et al. ...... 514/450 |
| 3,621,036 A | * | 11/1971 | Jensen et al. ............... 549/269 |
| 3,751,431 A | * | 8/1973 | Wehrmeister et al. ...... 549/269 |
| 3,764,614 A | * | 10/1973 | Wehrmeister et al. ...... 549/269 |
| 3,901,921 A | * | 8/1975 | Urry et al. .................. 549/269 |
| 4,035,504 A | * | 7/1977 | Hidy et al. .................. 514/450 |
| 4,088,658 A | * | 5/1978 | Robertson ................... 549/270 |
| 4,228,079 A | | 10/1980 | Calton .................... 260/343.41 |
| 5,597,846 A | | 1/1997 | Sugimura et al. ........... 514/450 |
| 5,650,430 A | | 7/1997 | Sugimura et al. ........... 514/450 |
| 5,731,343 A | | 3/1998 | Feng et al. ................. 514/450 |
| 5,977,165 A | * | 11/1999 | Agatsuma et al. .......... 514/450 |
| 6,239,168 B1 | | 5/2001 | Ino et al. .................... 514/450 |

FOREIGN PATENT DOCUMENTS

| EP | 0 606 044 | | 7/1994 |
|---|---|---|---|
| JP | 09-202781 | * | 8/1997 |
| WO | WO 98/18780 | | 5/1998 |
| WO | WO 99/55689 | | 11/1999 |
| WO | WO 00/61578 | | 10/2000 |
| WO | WO 01/45751 | | 6/2001 |

OTHER PUBLICATIONS

Ayer et al., Minor Metabolites of Monocillium Nordinii, Phytochemistry, vol. 26, No. 5, pp. 1353-1355, 1987.*

Ayer et al., The Isolation, Identification, and Bioassay of the Antifungal Metabolites Produced by Monocillium Nordinii, Canadian Journal of Microbiology, vol. 26, No. 7, pp. 766-773, 1980.*

CAPLUS printout of Brooks et al., Uterotrophic and Antiimplantation Activities of Certain Resorcylic Acid Lactone Derivatives, Proceedings of the Society for Experimental Biology and Medicine, vol. 137, No. 1, pp. 101-104, 1971.*

Wehrmeister et al., Total Synthesis of the Macrocyclic Lactone, Dideoxyzearalane, The Journal of Organic Chemistry, vol. 33, No. 11, pp. 4173-4176, Nov. 1968.*

Armstrong, et al., "Synthesis of Sulphur-Containing Heterocycles by Ring Closing Diene Metathesis", *Tetrahedron Letters*, 37(52): 9373-9376, 1996.

Blanchette, et al., "Horner-Wadsworth-Emmons Reactions: Use of Lithium Chloride and an Amine for Base-Sensitive Compounds", *Tetrahedron Letters*, 25(21): 2183-2186, 1984.

Buchner, J., "Hsp90& Co.—A Holding for Folding", *TIBS*, 136-141, Apr. 1999.

Chatterjee, et al., "Synthesis of Functionalized Olefins by Cross and Ring-Closing Metatheses", *J. Am. Chem. Soc.* 122: 3783-3784, 2000.

(Continued)

Primary Examiner—Brenda Coleman
(74) Attorney, Agent, or Firm—Choate, Hall & Stewart, LLP; Brenda H. Jarrell; C. Hunter Baker

(57) ABSTRACT

The present invention relates to compounds having the structure (and pharmaceutically acceptable derivatives thereof)

(I)

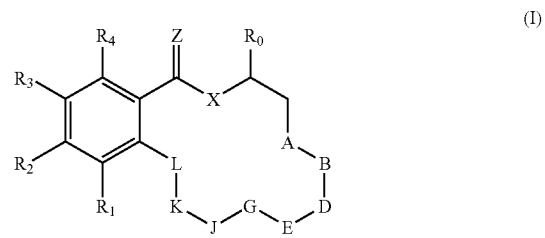

wherein $R_0$–$R_4$, Z, X, A—B, D—E, G—J, and K—L are as defined herein, the synthesis thereof and the use of these compounds as therapeutic agents.

42 Claims, 34 Drawing Sheets

OTHER PUBLICATIONS

Chiosis, et al., "A Small Molecule Designed to Bind to the Adenine Nucleotide Pocket of Hsp90 Causes Her2 Degradation and the Growth Arrest and Differentiation of Breast Cancer Cells", *Chemistry & Biology*, 8: 289-299, 2001.

Delmotte, et al., "A New Antifungal Substance of Fungal Origin", *Nature*, 17: 344, 1953.

Fang, et al., "Regio-Diastereoselective Reactions of Dithio-Substituted Crotyllithium and Aldehydes", *J. Org. Chem.* 51: 2828-2829, 1986.

Fukuyama, et al., "Total Synthesis of Gliotoxin, Dehydrogliotoxin and Hyalodendrin", *Tetrahedron*, 37: 2045-2078, 1981.

Fürstner, et al., "Macrocycles by Ring-Closing-Metathesis, XI[1]: Syntheses of (R)-(+)-Lasiodiplodin, Zeranol and Truncated Salicylihalamides", *Tetrahedron*, 55: 8215-8230, 1999.

Garbaccio, et al., "Efficient Asymmetric Synthesis of Radicicol Dimethyl Ether: A Novel Application of Ring-Forming Olefin Metathesis", *Org. Lett.* 2(20): 3127-3129, 2000.

Kishi, et al., "A New Method for the Synthesis of Epidithiodiketopiperazines", Journal of the American Chemical Society, *J. Am. Chem. Soc.*, 95(19): 6490-6492, 1973.

Kuduk, et al., "Synthesis and Evaluation of Geldanamycin-Estradiol Hybrids", *Bioorganic & Medicinal Chemistry Letters*, 9: 1233-1238, 1999.

Kuduk, et al., "Synthesis and Evaluation of Geldanamycin-Testosterone Hybrids", *Bioorganic & Medicinal Chemistry Letters*, 10: 1303-1306, 2000.

Makara, et al., "An Improved Synthesis of 5,7-Dimethoxy-4-Methy-Phthalide, A Key Intermediate in the Synthesis of Mycophenolic Acid", *Synthetic Communications*, 26(10): 1935-1942, 1996.

Kwon, et al., "Radicicol, An Agent Inducing the Reversal of Transformed Phenotypes of src-Transformed Fibroblasts", *Biosci. Biotech. Biochem.* 56(3): 538-539, 1992.

Lampilas, et al., Convergent Stereospecific Total Synthesis of Monocillin I and Monorden (or Radicicol), *Tetrahedron Letters*, 33(6): 777-780, 1992.

Lampilas, et al., "Convergent Stereospecific Total Synthesis of Monochiral Monocillin I Related Macrolides", *Tetrahedron Letters*, 33(6): 773-776, 1992.

Makara, et al., "An Improved Synthesis of 5,7-Dimethoxy-4-Methy-Phthalide, A Key Intermediate in the Synthesis of Mycophenolic Acid", *Synthetic Communications*, 26(10): 1935-1942, 1996.

McCapra, et al., "The Constitution of Monorden, An Antibiotic with Tranquilising Action", *Tetrahedron Letters*, 15: 869-875, 1964.

Mirrington, et al., "The Constitution of Radicicol", *Tetrahedron Letters*, 7: 365-370, 1964.

Münster, et al., "Inhibition of Heat Shock Protein 90 Function by Ansamycins Causes the Morphological and Functional Differentiation of Breast Cancer Cells" *Cancer Research*, 61: 2945-2952, 2001.

Münster, et al., "Modulation of Hsp90 Function by Ansamycins Sensitizes Breast Cancer Cells to Chemotherapy-Induced Apoptosis in an RB-and Schedule-Dependent Manner", *Clinical Cancer Research*, 7: 2228-2236, 2001.*

Murphy, et al., "Lithium Keten Thioacetalides. Factors Influencing α—Versus γ-Alkyl-ation", *J. Chem. Soc. Perkin I*, 2678-2682, 1980.*

Roe, et al., "Structural Basis for Inhibition of the Hsp90 Molecular Chaperone by the Antitumor Antibiotics Radicicol and Geldanamycin", *J. Med. Chem.* 42: 260-266, 1999.*

Sausville, Edward., "Combining Cytotoxics and 17-Allylamino, 17-Demethoxygeldanamycin: Sequence and Tumor Biology Matters" *Clinical Cancer Research*, 7: 2155-2158, 2001.*

Schlede, et al., "Efficient Enantioselective Synthesis of a β-Hydroxyepoxide Building Block for the Construction of Macrocyclic Natural Products", *Tetrahedron Letters*, 39: 1143-1144, 1998.*

Scholl, et al., "Synthesis and Activity of a New Generation of Ruthenium-Based Olefin Metathesis Catalysts Coordinated with 1,3-Dimesityl-4,5-Dihydroimidazol-2-Ylidene Ligands", *Organic Letters*, 1(6): 953-956, 1999.*

Smith, et al., "Synthesis of (−)—Bertyadionol", *J. Am Chem. Soc.* 108: 3110-3112, 1986.*

Solit, "394 17-(Allylamino)-17-Demethoxygeldanamycin (17-AAG) Inhibits Intra-Cellular Akt Kinase Activity in HER2 Overexpressing Breast Cancer Cell Lines and Enhances the Apoptosis Induced by Cytotoxic Agents", http://www.aacr.org/newdrugs00/394.html, 2000.*

Uemura, et al., "Chlorination and Chloroiodination of Acetylenes with Copper(II) Chloride", *J. Chem. Soc. Perkin I*, 676-680, 1977.*

Zhao, et al., "Suppression of RAS and MOS Transformation by Radicicol", *Oncogene*, 11: 161-173, 1995.*

Zheng, et al., "Identification of a Geldanamycin Dimer that Induces the Selective Degradation of HER-Family Tyrosine Kinases", *Cancer Research*, 60: 2090-2094, 2000.*

* cited by examiner (a) TBDPSCl, imid.,>95%; (b) DIBAL-H,−78 °C, 92%;
(c) LiCl, DIPEA (EtO)$_2$P(O)CH$_2$CO$_2$Et, 95%;
(d) DIBAL-H, −20 °C, 96%; (e) (+)-DET, Ti(OiPr$_4$), TBHP,90%,>95%ee; (f) SO$_3$*pyridine, Et$_3$N, DMSO, 90%;
(g) PH$_3$PCH$_3$Br, NaHMDS, 0 °C, 82%; (h) TBAF, 89%.

(a) DEAD, PPh₃, 70%; (b.) iPr₂NEt, 70%; (c.) 50% (4:1)

a. n-BuLi, −78 °C, 50% (6:1); b. TBSCl, 83%; c. 42 C, 70%; d. (i) mCPBA, (ii) Ac₂O, Et₃N, H₂O, 60 °C, (iii) NaHCO₃, MeOH, 60%; e. SO₂Cl₂, 50% a. TBSCl, pyridine; b. NIS or NBS, TsOH; c. Pd(PPh$_3$)$_3$, RSnBu$_3$, d. nBu$_4$NF

TO FIG. 11-2

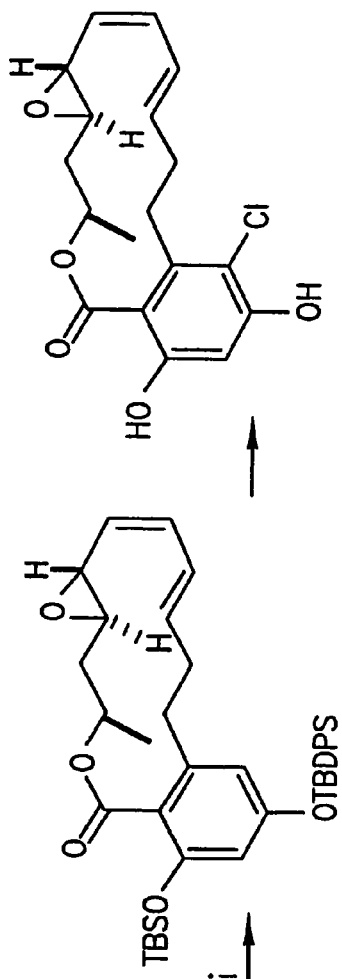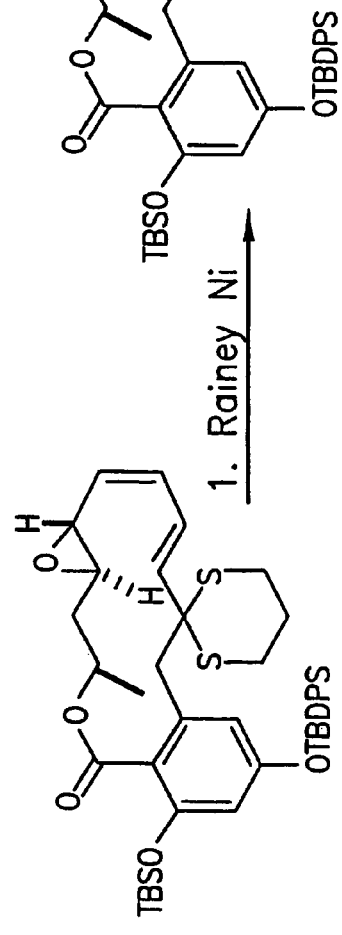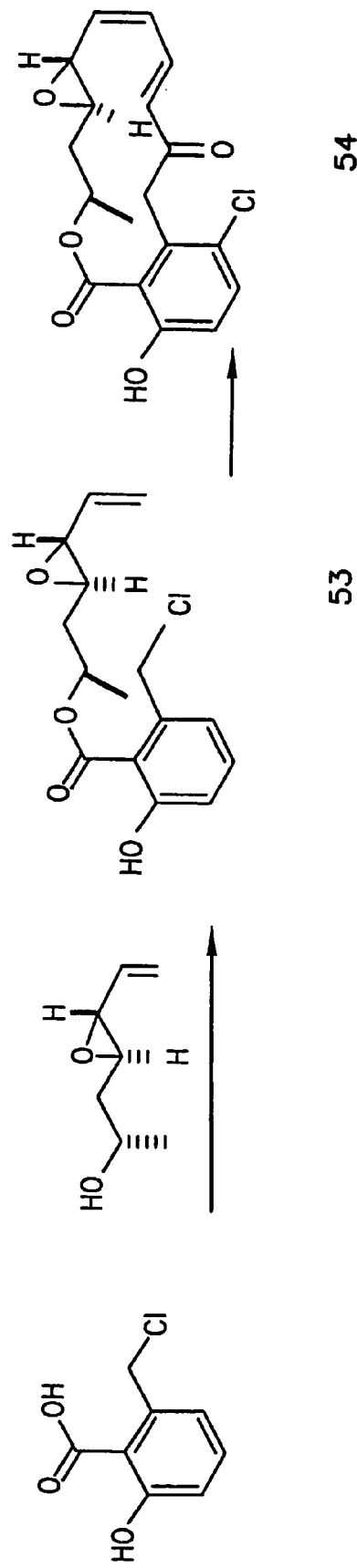
FIG. 12-2 a(a) TBDPSCl, imid.,>95%; (b) DIBAL-H,−78 °C, 92%;
(c) LiCl, DIPEA (EtO)$_2$P(O)CH$_2$CO$_2$Et, 95%; (d) DIBAL-H
−20 °C, 96%; (e) (+)-tetramethyltartaricacid diamide-BBu,
Et$_2$Zn, CH$_2$I$_2$, 9 >95% ee; (f) SO$_3$*pyridine, Et$_3$N,
DMSO, 90%; (g) Ph$_3$PCH NaHMDS,
0 °C, 82%; (h) TBAF, 89%;
(i) 7, P(furyl)$_3$, DIA benzene, 60% a. n-BuLi, −78 °C, 75% (3:1); b. TBSCl, 83%; c. 42 °C, 20%; d. (i) mCPBA, (ii) Ac₂O, Et₃N, H₂O, 60 °C, (iii) NaHCO₃, MeOH, 60%; e. SO₂Cl₂, 80%

TO FIG. 15-2

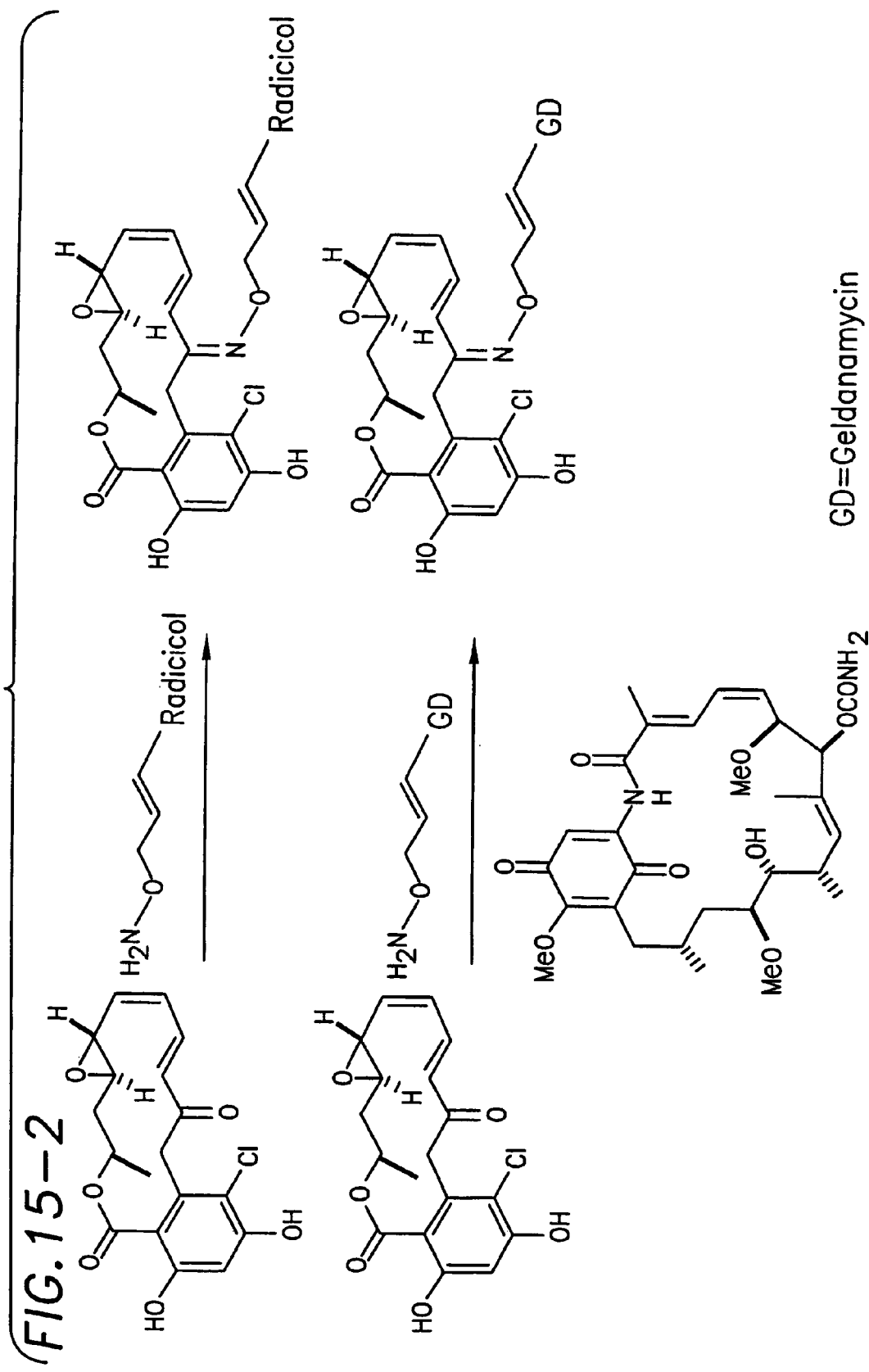

TO FIG. 16-2

FIG. 17-1
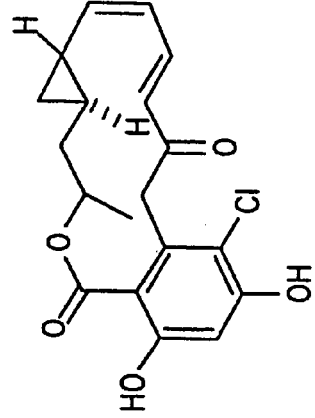
III. Cyclopropyl radicicol
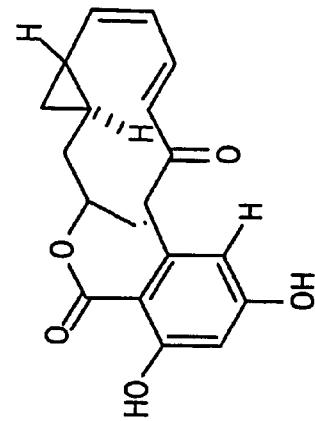
IV. Cyclopropyl monocillin
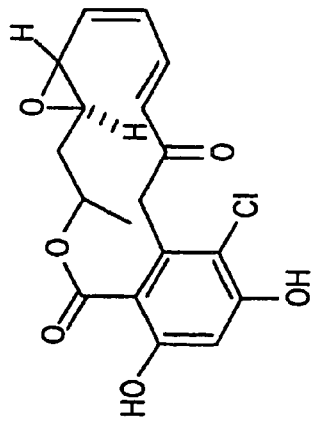
I. Radicicol
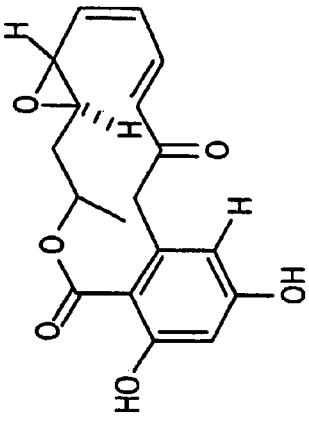
II. Monocillin I
TO FIG. 17-2

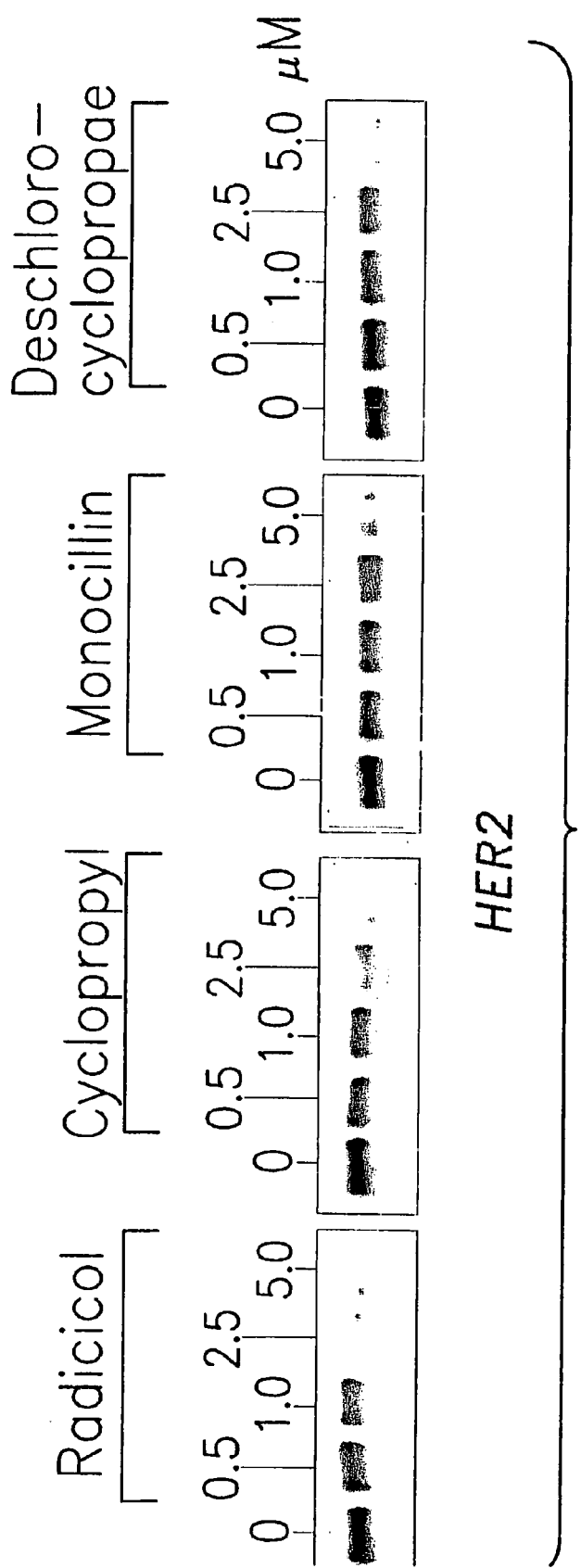
FIG. 17-2  MCF7 Cells Treated with Radiciciol and Analogues

FIG. 17-3
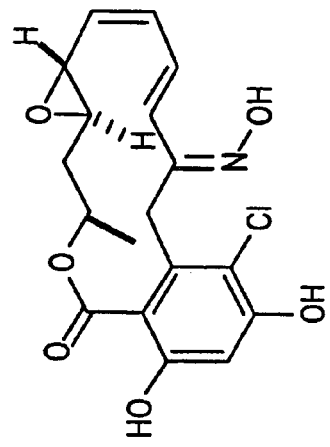
VII. Radicicol Oxime
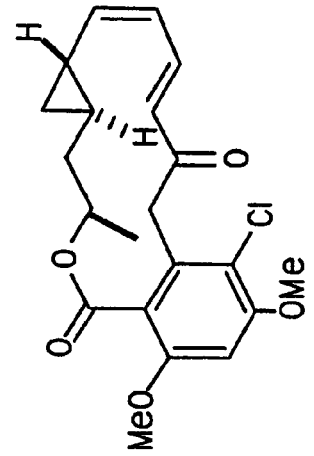
VI. Dimethyl Radicicol
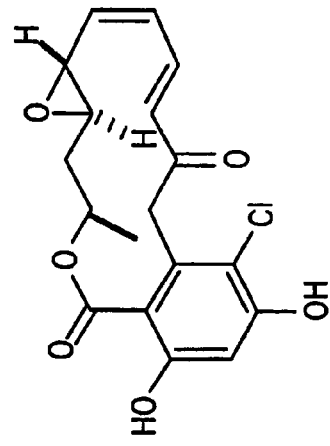
I. Radicicol
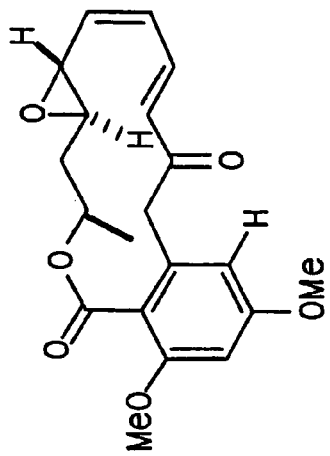
V. Dimethyl Monocillin I FIG. 18-1
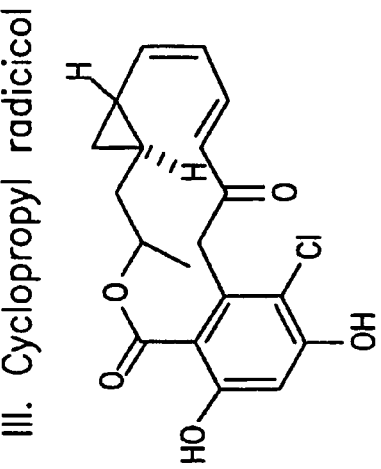
I. Radicicol
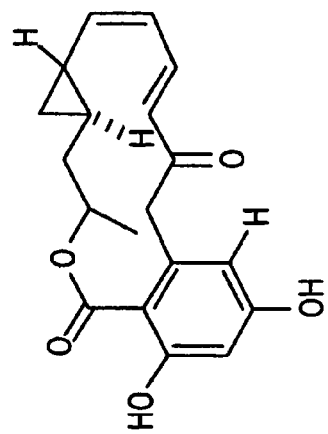
II. Monocillin I
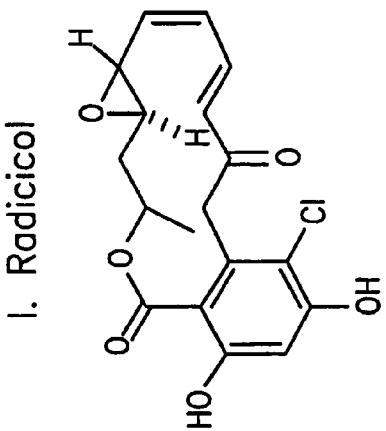
III. Cyclopropyl radicicol
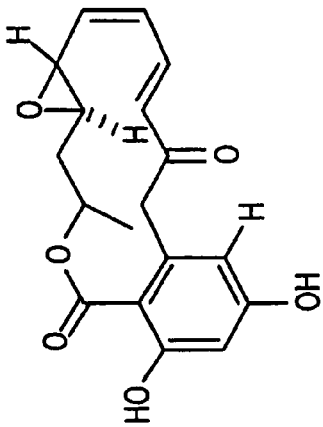
IV. Cyclopropyl monocillin
TO FIG. 18-2

BT474 Cells Treated with Novel Radiciols (24hrs.)

MACROCYCLES AND USES THEREOF

PRIORITY INFORMATION

This application claims priority under 35 U.S.C. § 119(e) to U.S. Provisional Patent Application No. 60/228,277, filed Aug. 25, 2000, entitled "Concise Asymmetric Synthetic Method for Generation of Radicicol Analogs and Radicicol Conjugates", and U.S. Provisional Patent Application No. 60/304,553, filed Jul. 11, 2001, entitled "Concise Asymmetric Synthetic Methods for Generation of Monocillin, Radicicol and Their Analogs and Conjugates, and the entire contents of each of these applications are hereby incorporated by reference in their entirety.

GOVERNMENT SUPPORT

The present invention was made with support from a grant from the National Institutes of Health (Number CA-28824; Samuel J. Danishefsky). Additionally, the present invention was made with support from a grant from the United States Army Breast Cancer Research Program (Xudong Geng). Therefore, the government may have certain rights in the invention.

BACKGROUND OF THE INVENTION

Many natural products, usually bacterial metabolites, feature a macrolide fused to a monocyclic benzenoid matrix, bearing a resorcinol-like substitution pattern. Not infrequently, the resorcinol moiety carries additional functionality, resulting in higher levels of oxidation. Natural products in this family (cf. inter alia radicicol (Delmotte, P.; Delmotte-Plaquee, J. *Nature* 1953, 171, 344; incorporated herein by reference), LL-Z-1640s (McGahren, W. J. J. Org. Chem. 1978, 43, 2339–2343; which is incorporated herein by reference), monocillins (Ayer, W. A.; Lee, S. P.; Tsuneda, A.; Hiratsuka, Y. *Can. J. Microb.* 1980, 26, 766–773; incorporated herein by reference), nordinone (Ayer, W. A.; Pena-Rodriguez, L. *Phytochemistry* 1987, 26, 1353–1355; incorporated herein by reference) and zearelenone (Sugawara, F.; Kim, K. W.; Kobayashi, K.; Uzawa, J.; Yoshida, S.; Murofushi, N.; Takahashi, N.; Strobel, G. A. *Phytochemistry* 1992, 31, 1987–1990; incorporated herein by reference) possess potentially exploitable patterns of antitumor, antibiotic, and antimalarial activity.

Radicicol (Delmotte et al. *Nature* 1953, 171, 344; Ayer et al. *Canad. J. Microbiol.* 1980, 26, 766) (1) and monocillin I (Ayer et al. *Canad. J. Microbiol.* 1980, 26, 766) (2) are resorcylic macrolides which can both be isolated from Monocillium nordinii (Ayer et al. *Canad. J. Microbiol.* 1980, 26, 766) (FIG. 1). While the skeletal structure of radicicol was determined in 1964, (McCapra et al. *Tetrahedron Lett.* 1964, 869; Mirrington et al. *Tetrahedron Lett.* 1964, 365) its relative and absolute stereochemical configuration was not unambiguously established until 1987 (Cutler et al. *Agric. Biol. Chem.* 1987, 51, 3331). The structure of monocillin I was confirmed by its direct conversion into radicicol. Affirmation of these structures was achieved by their only total synthesis through the efforts of Lett and Lampilas (Lampilas et al. *Tetrahedron Lett.* 1992, 33, 773 and 777).

Both radicicol (1) and monocillin I (2) (see FIG. 1) exhibit a variety of antifungal and antibiotic properties not shared by other members of this class of natural products. Recently, the antitumor properties of radicicol have come into focus as its ability to suppress the transformed phenotype caused by various oncogenes such as src, ras, and raf has been linked to its tight binding (20 nM) and inhibition of the Hsp90 molecular chaperone (Roe et al. *J. Med. Chem.* 1999, 42, 260–266). This 'anti-chaperone' activity may stimulate depletion of oncogenic proteins, and could therefore be of clinical interest. Specifically, occupancy of the ATP binding pocket of Hsp90 is believed to lead to the degradation in the proteasome of a subset of proteins involved in signal transduction that require Hsp90 for conformational maturation (see, Schneider et al. *Proc. Natl. Acad. Sci. USA* 93: 14536–14541, 1996; Mimnaugh et al. *J. Biol. Chem.* 271: 22796–22801, 1996; Whitesell et al. *Mol. Endocrinol.* 10: 705–712, 1996). These proteins include the HER and insulin receptor families of tyrosine kinases, Raf-1 serine kinase and steroid receptors to name a few. Downregulation of any of these would be expected to have positive antiproliferative effects, so that Hsp90 is an attractive target for the development of antitumor drugs.

More recently, five new 14-membered resorcyclic macrolides, termed aigailomycins A–E, were isolated from the marine mangrove fungus *Aigialus parvus* BCC5311 (Isaka, M.; Suyarnsestakorn, C.; Tanticharoen, M.; Kongsaeree, P.; Thebtaranonth, Y. *J. Org. Chem.* 2002, 67, 1561–1566; incorporated herein by reference). Among the aigailomycins, aigailomycin D exhibits potent antimalarial activity ($IC_{50}$: 6.6 μg/mL against *P. falciparum*) and antitumor activity ($IC_{50}$: 3.0 μg/mL against KB cells) (Isaka, M.; Suyarnsestakorn, C.; Tanticharoen, M.; Kongsaeree, P.; Thebtaranonth, Y. *J. Org. Chem.* 2002, 67, 1561–1566; incorporated herein by reference).

The demonstrated ability of radicicol to bind to and inhibit the activity of Hsp90 has generated an interest in further exploring the biological and pharmacological activity of radicicol and analogues thereof. Significantly, to date, only one synthesis of radicicol itself has been recorded (Lampilas et al. *Tetrahedron Lett.* 1992, 33, 773 and 777). Other groups have accessed a variety of analogues from the natural product itself (see, U.S. Pat. No. 5,650,430; U.S. Pat. No. 5,731,343; U.S. Pat. No. 6,239,168; U.S. Pat. No. 5,977,165; and U.S. Pat. No. 5,597,846; each of which is incorporated herein by reference), but have been limited in the range of analogues that can be generated. Thus, there remains a need to develop a practical synthesis of radicicol and other resorcyclic macrolides to generate novel analogs and conjugates to explore novel biological and pharmacological activities, and to improve the stability and therapeutic efficacy of radicicol, monocillin, and aigialomycins in the treatment of cancer.

DESCRIPTION OF THE DRAWING

FIG. 17 depicts the results of MCF7 cells (HER2 over-expressed, Rb positive) treated with radicicol and analogues.

DESCRIPTION OF THE INVENTION

Figure 1:
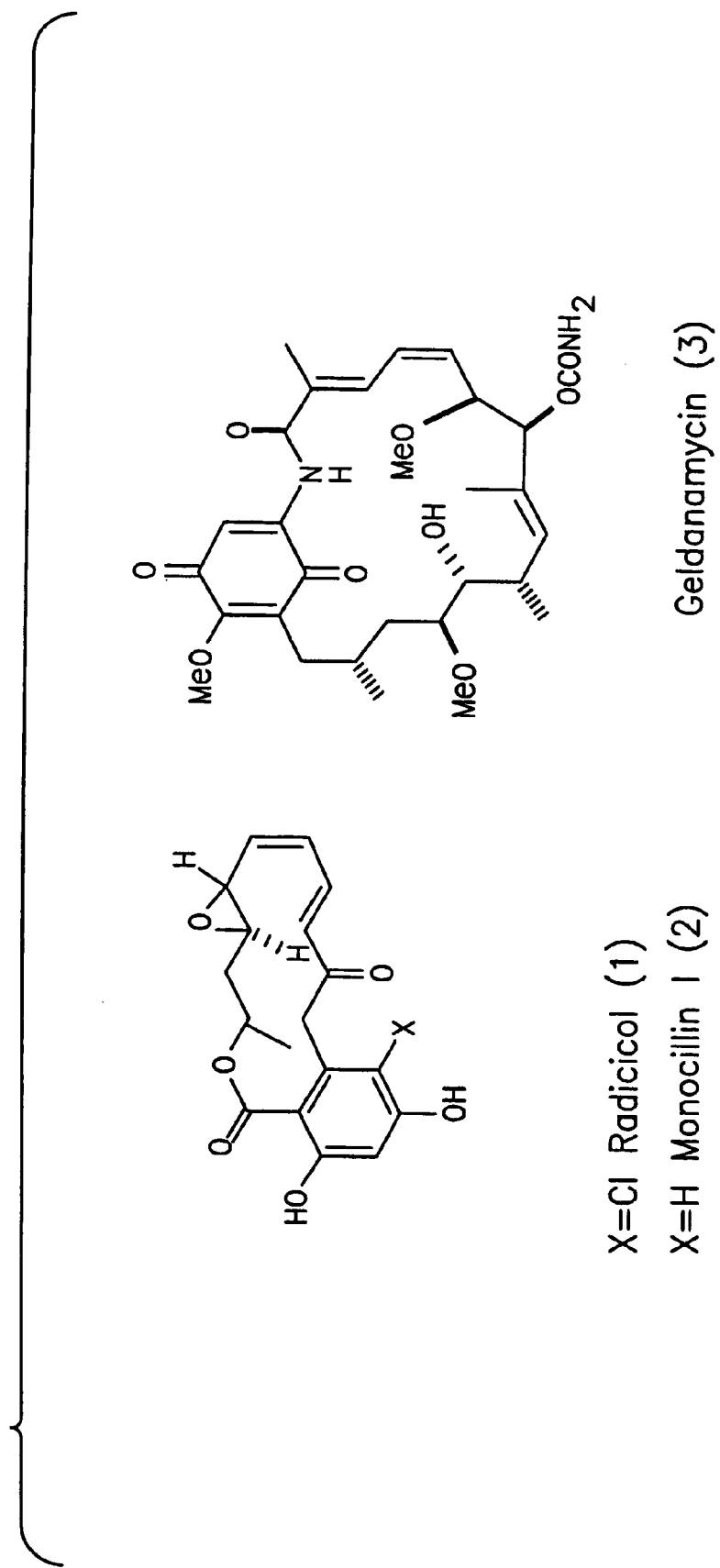
FIG. 1 depicts structures of Monocillin I (2), Radicicol (1) and Geldanamycin (3).
Figure 2:
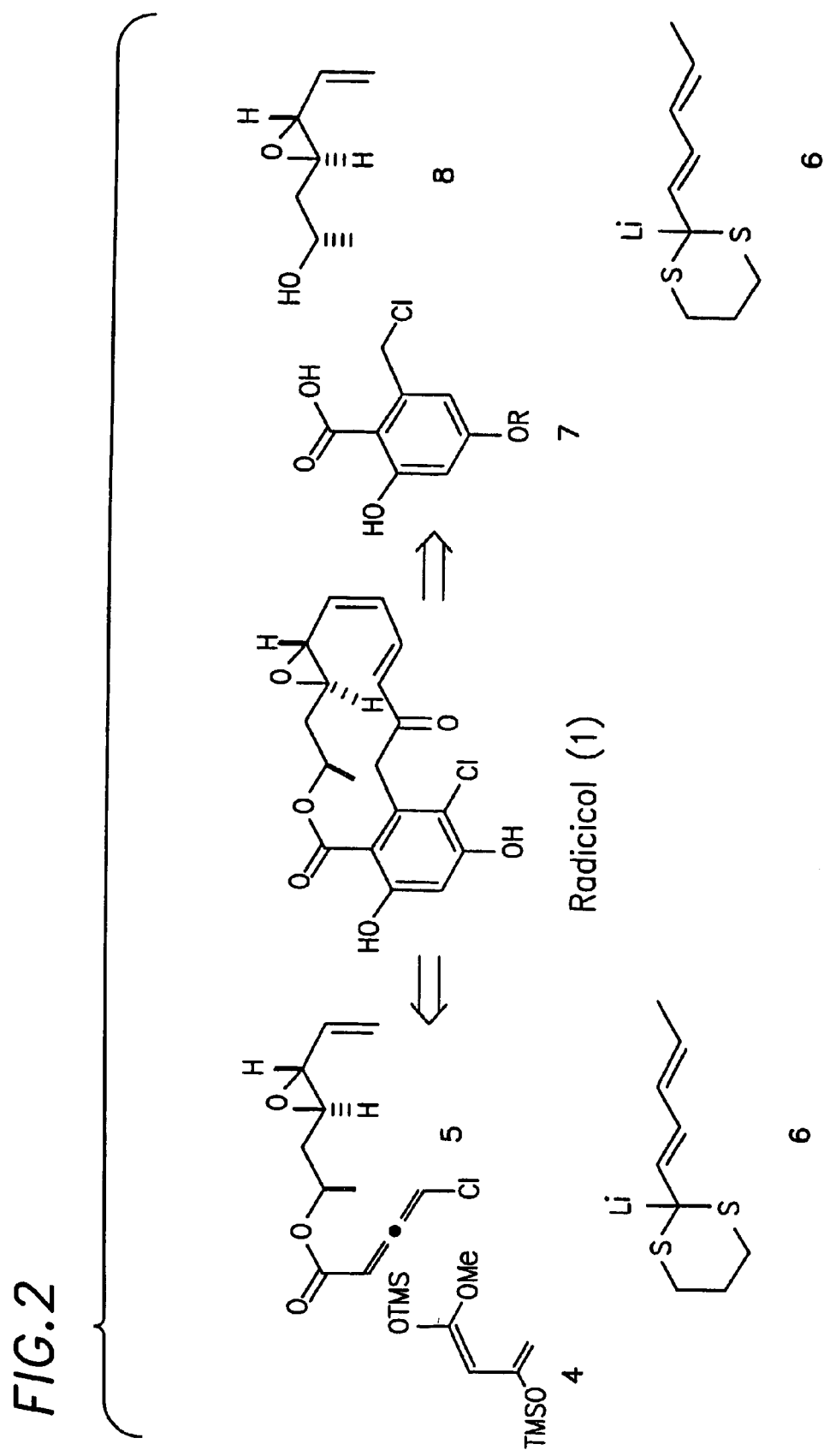
FIG. 2 depicts two strategies for the synthesis of radicicol (1) and monocillin (2).
Figure 3:
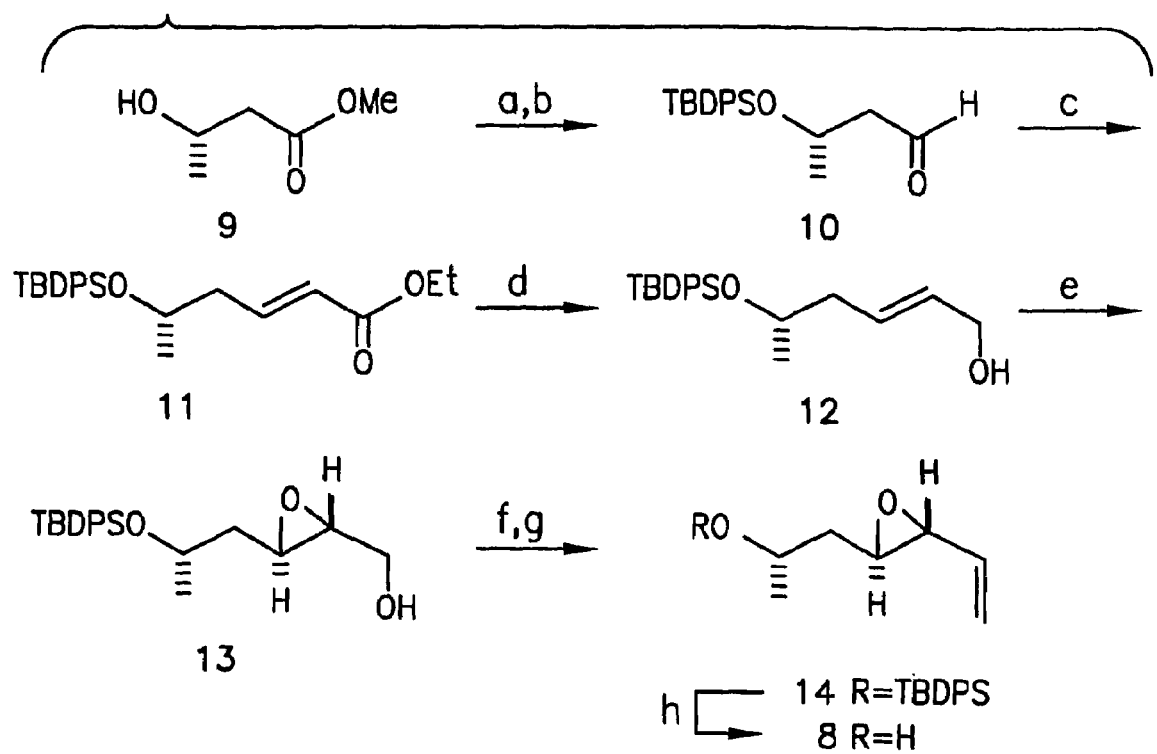
FIG. 3 depicts the synthetic strategy for the construction of the chiral allylic alcohol.
Figure 3:
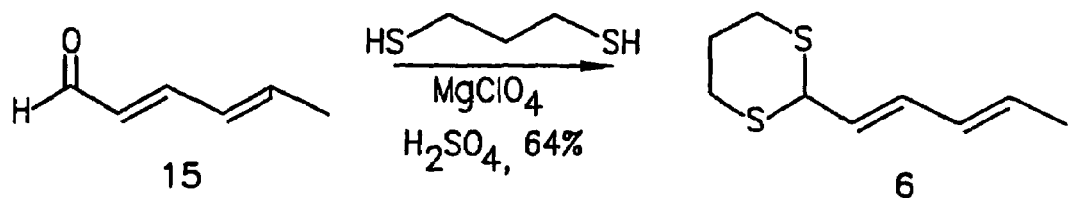
Figure 4:
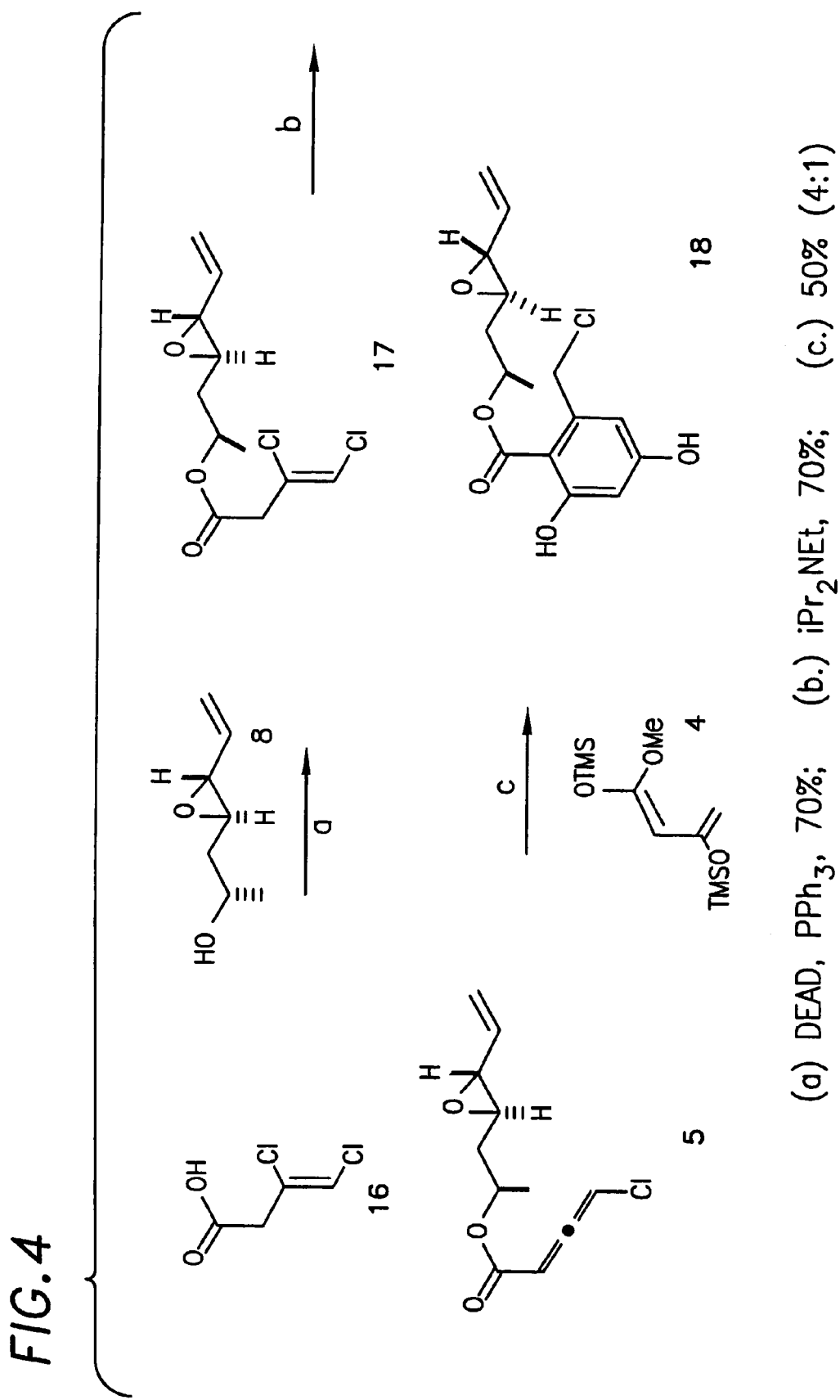
FIG. 4 depicts the synthetic strategy for the construction of intermediate (18).
Figure 5:
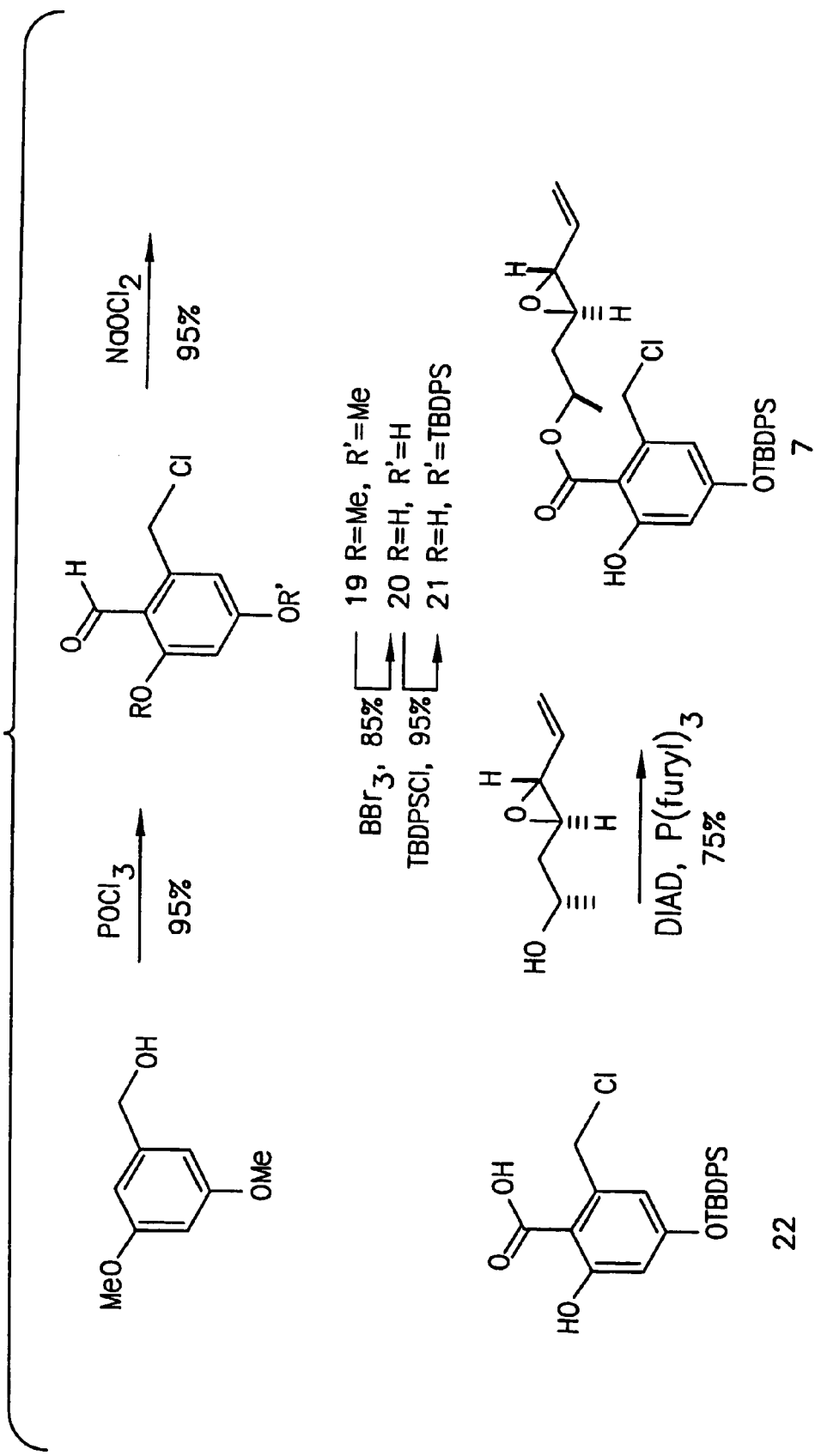
FIG. 5 depicts the synthetic strategy for the construction of intermediate (7) via a Mitsunobou esterification.
Figure 6:
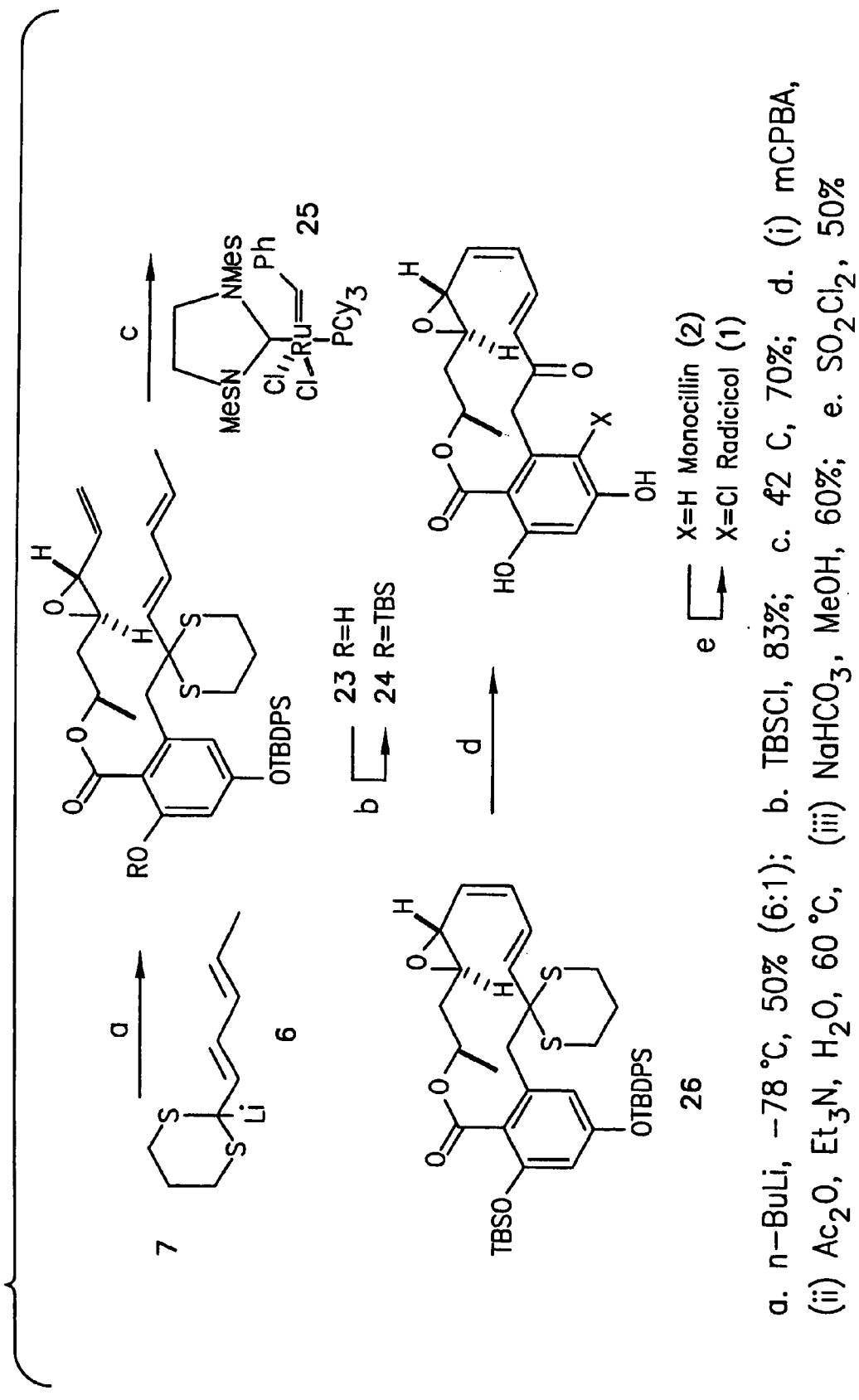
FIG. 6 depicts a synthetic strategy for the synthesis of radicicol (1) and monocillin (2).
Figure 7:
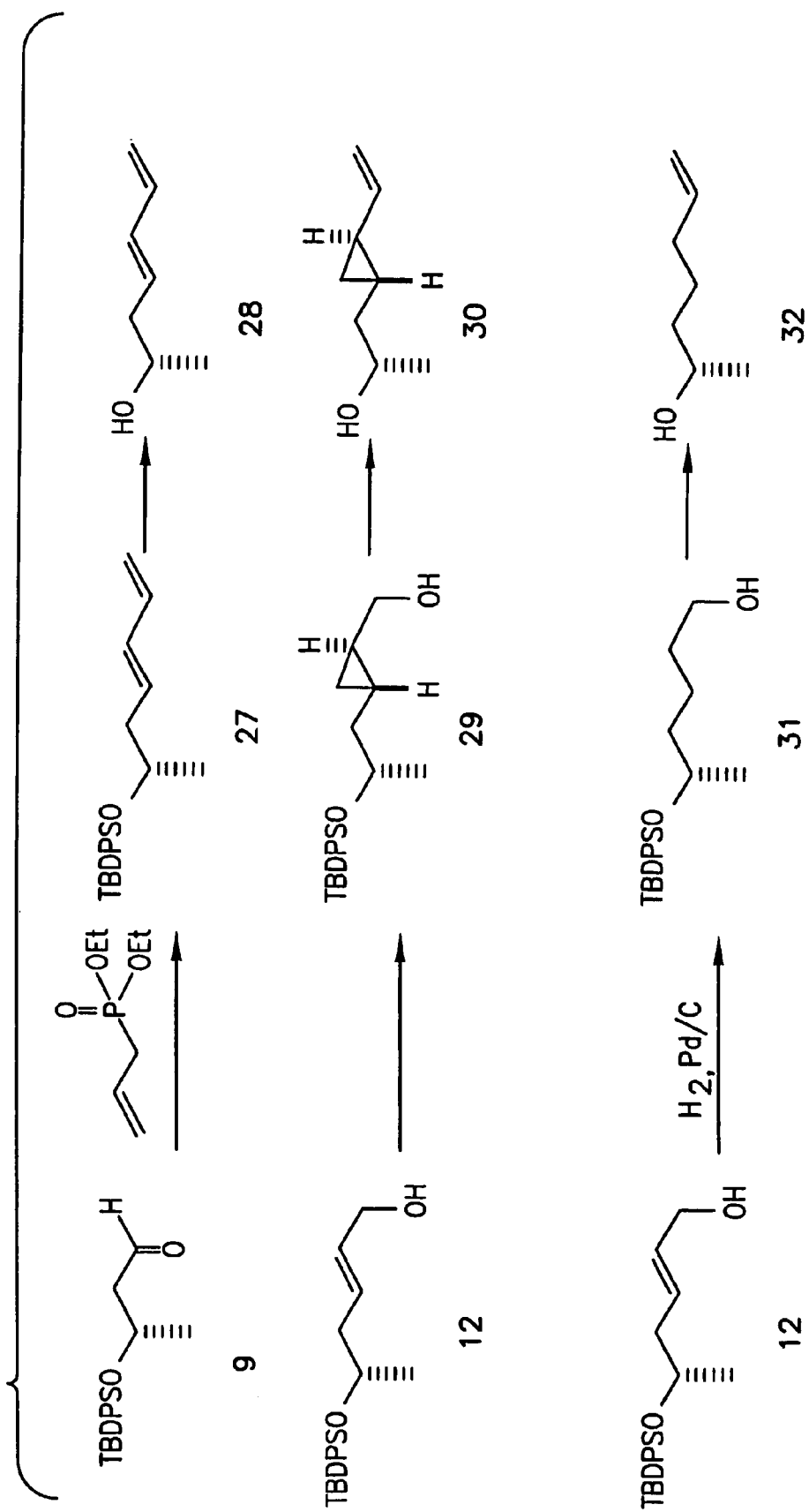
FIG. 7 depicts the synthesis of a variety of chiral components (28), (30) and (32).
Figure 8:
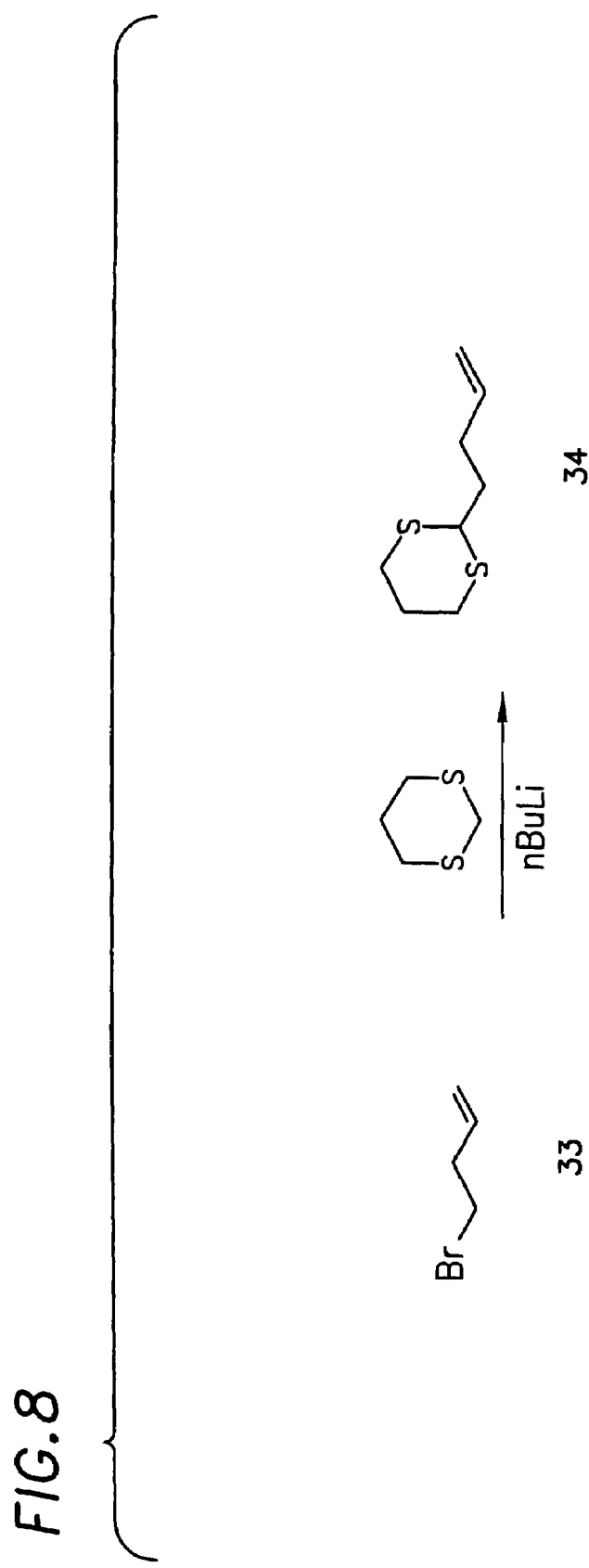
FIG. 8 depicts the synthesis of dithiane fragment (34).
Figure 9:
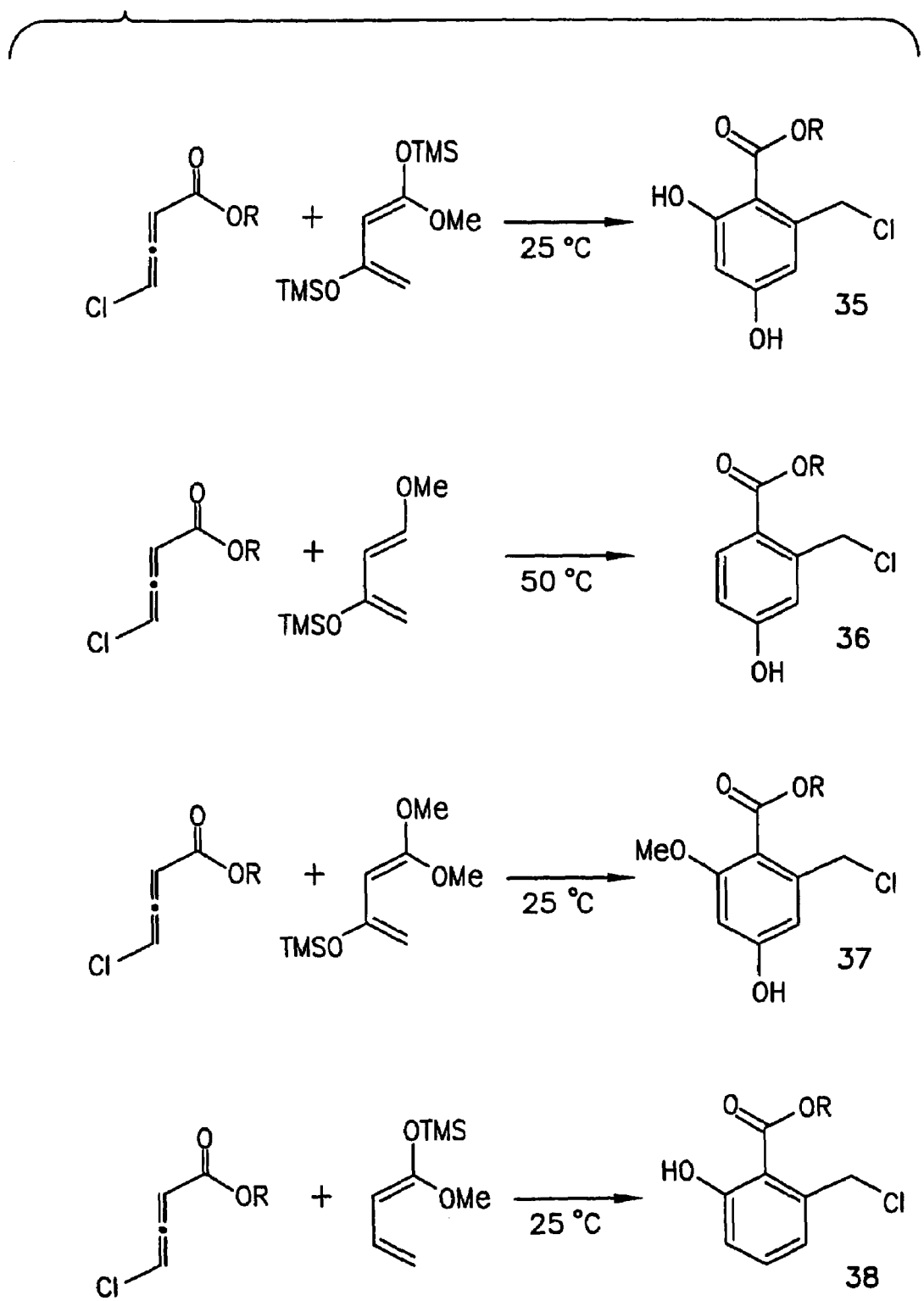
FIG. 9 depicts the synthesis of a variety of benzoic acid components (35), (36), (37) and (38).

In recognition of the need to develop novel and effective cancer therapies, the present invention provides novel synthetic methodologies enabling access to macrocycles having a broad range of biological and pharmacological activity. In certain embodiments, the inventive compounds are useful in the treatment of cancer. In certain other embodiments of special interest, the compounds are useful for the treatment of cancers comprising Rb negative cancer cells.

1) General Description of Compounds of the Invention

The compounds of the invention include compounds of the general formula (II) as further defined below:

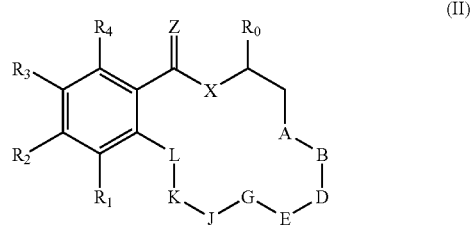

(II)

wherein $R_0$ is hydrogen, halogen, cyano, —$OR_Z$, —$N(R_Z)_2$, —$SR_Z$, —$O(C=O)R_Z$, —$N(R_Z)(C=O)(R_Z)$, —$C(O)R_Z$, —$C(O)OR_Z$, —$CON(R_Z)_2$, —$OCO_2R_Z$, or an aliphatic, heteroaliphatic, aryl, heteroaryl, alkylaryl, or alkylheteroaryl moiety, wherein each occurrence of $R_Z$ is independently hydrogen, a protecting group, or an aliphatic, heteroaliphatic, aryl, heteroaryl, alkylaryl, or alkylheteroaryl moiety $R_1$ is hydrogen, halogen, cyano, —$OR_A$, —$N(R_A)_2$, —$SR_A$, —$O(C=O)R_A$, —$N(R_A)(C=O)(R_A)$, —$C(O)R_A$, —$C(O)OR_A$, —$CON(R_A)_2$, —$OCO_2R_A$, or an aliphatic, heteroaliphatic, aryl, heteroaryl, alkylaryl, or alkylheteroaryl moiety, wherein each occurrence of $R_A$ is independently hydrogen, a protecting group, or an aliphatic, heteroaliphatic, aryl, heteroaryl, alkylaryl, or alkylheteroaryl moiety;

$R_2$ is hydrogen, halogen, cyano, —$OR_B$, —$N(R_B)_2$, —$SR_B$, —$O(C=O)R_B$, —$N(R_B)(C=O)(R_B)$, —$C(O)R_B$, —$C(O)OR_B$, —$CON(R_B)_2$, —$OCO_2R_B$, or an aliphatic, heteroaliphatic, aryl, heteroaryl, alkylaryl, or alkylheteroaryl moiety, wherein each occurrence of $R_B$ is independently hydrogen, a protecting group or an aliphatic, heteroaliphatic, aryl, heteroaryl, alkylaryl, or alkylheteroaryl moiety;

$R_3$ is hydrogen, halogen, cyano, —$OR_C$, —$N(R_C)_2$, —$SR_C$, —$O(C=O)R_C$, —$N(R_C)(C=O)(R_C)$, —$C(O)R_C$, —$C(O)OR_C$, —$CON(R_C)_2$, —$OCO_2R_C$, or an aliphatic, heteroaliphatic, aryl, heteroaryl, alkylaryl, or alkylheteroaryl moiety, wherein each occurrence of $R_C$ is independently hydrogen, a protecting group, or an aliphatic, heteroaliphatic, aryl, heteroaryl, alkylaryl, or alkylheteroaryl moiety;

$R_4$ is hydrogen, halogen, cyano, —$OR_D$, —$N(R_D)_2$, —$SR_D$, —$O(C=O)R_D$, —$N(R_D)(C=O)(R_D)$, —$C(O)R_D$, —$C(O)OR_D$, —$CON(R_D)_2$, —$OCO_2R_D$, or an aliphatic, heteroaliphatic, aryl, heteroaryl, alkylaryl, or alkylheteroaryl moiety, wherein each occurrence of $R_D$ is independently hydrogen, a protecting group or an aliphatic, heteroaliphatic, aryl, heteroaryl, alkylaryl, or alkylheteroaryl moiety;

Z is O, S, or $NR_E$, wherein $R_E$ is hydrogen, a protecting group, an aliphatic, heteroaliphatic, aryl, heteroaryl, alkylaryl, or alkylheteroaryl moiety, or $OR_F$, wherein $R_F$ is hydrogen, a protecting group, an aliphatic, heteroaliphatic, aryl, heteroaryl, alkylaryl, or alkylheteroaryl moiety;

X is O, S or $NR_G$, wherein $R_G$ is hydrogen or lower alkyl;

A and B together represent

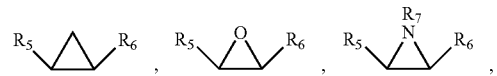

—$CHR_5$—$CHR_6$—, —$CR_5$=$CR_6$—, wherein $R_5$ and $R_6$ are each independently hydrogen, halogen, cyano, —$OR_J$, —$N(R_J)_2$, —$SR_J$, —$O(C=O)R_J$, —$O(S=O)R_J$, —$N(R_J)(C=O)(R_J)$, —$C(=O)R_J$, —$C(=O)OR_J$, —$CON(R_J)_2$, —$OCO_2R_J$, —$OS(=O)OR_J$ or an aliphatic, heteroaliphatic, aryl, heteroaryl, alkylaryl, or alkylheteroaryl moiety, wherein each occurrence of $R_J$ is independently hydrogen, a protecting group, or an aliphatic, heteroaliphatic, aryl, heteroaryl, alkylaryl, or alkylheteroaryl moiety, and wherein $R_7$ is hydrogen, a protecting group, —$OR_K$, —$SR_K$, —$C(O)OR_K$, —$C(O)NR_K$, —$S(O)_2R_K$, —$O(C=O)R_K$, —$N(R_K)(C=O)(R_K)$, —$C(O)R_K$, —$C(O)OR_K$, —$CON(R_K)_2$, —$OCO_2R_K$, or an aliphatic, heteroaliphatic, aryl, heteroaryl, alkylaryl, or alkylheteroaryl moiety, wherein each occurrence of $R_K$ is independently hydrogen, a protecting group or an aliphatic, heteroaliphatic, aryl, heteroaryl, alkylaryl, or alkylheteroaryl moiety, or when A and B together represent —CHR$_5$—CHR$_6$—, R$_5$ and R$_6$ taken together represent a substituted or unsubstituted 3–7 membered aliphatic, heteroaliphatic, aryl or heteroaryl ring;

D and E together represent

—CHR$_8$—CHR$_9$—, —CR$_8$=CR$_9$—, wherein R$_8$ and R$_9$ are each independently hydrogen, halogen, cyano, —OR$_J$, —N(R$_J$)$_2$, —SR$_J$, —O(C=O)R$_J$, —O(S=O)R$_J$, —N(R$_J$)(C=O)(R$_J$), —C(=O)R$_J$, —C(=O)OR$_J$, —CON(R$_J$)$_2$, —OCO$_2$R$_J$, —OS(=O)OR$_J$ or an aliphatic, heteroaliphatic, aryl, heteroaryl, alkylaryl, or alkylheteroaryl moiety, wherein each occurrence of R$_J$ is independently hydrogen, a protecting group, or an aliphatic, heteroaliphatic, aryl, heteroaryl, alkylaryl, or alkylheteroaryl moiety, and wherein R$_{10}$ is hydrogen, a protecting group, —OR$_K$, —SR$_K$, —C(O)OR$_K$, —C(O)NR$_K$, —S(O)$_2$R$_K$, —O(C=O)R$_K$, —N(R$_K$)(C=O)(R$_K$), —C(O)R$_K$, —C(O)OR$_K$, —CON(R$_K$)$_2$, —OCO$_2$R$_K$, or an aliphatic, heteroaliphatic, aryl, heteroaryl, alkylaryl, or alkylheteroaryl moiety, wherein each occurrence of R$_K$ is independently hydrogen, a protecting group or an aliphatic, heteroaliphatic, aryl, heteroaryl, alkylaryl, or alkylheteroaryl moiety, or when A and B together represent —CHR$_8$—CHR$_9$—, R$_8$ and R$_9$ taken together represent a substituted or unsubstituted 3–7 membered aliphatic, heteroaliphatic, aryl or heteroaryl ring;

G and J together represent

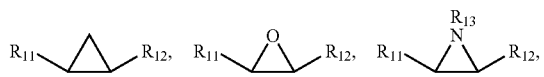

—CHR$_{11}$—CHR$_{12}$—, —CR$_{11}$=CR$_{12}$—, wherein R$_{11}$ and R$_{12}$ are each independently hydrogen, halogen, cyano, —OR$_J$, —N(R$_J$)$_2$, —SR$_J$, —O(C=O)R$_J$, —O(S=O)R$_J$, —N(R$_J$)(C=O)(R$_J$), —C(=O)R$_J$, —C(=O)OR$_J$, —CON(R$_J$)$_2$, —OCO$_2$R$_J$, —OS(=O)OR$_J$ or an aliphatic, heteroaliphatic, aryl, heteroaryl, alkylaryl, or alkylheteroaryl moiety, wherein each occurrence of R$_J$ is independently hydrogen, a protecting group, or an aliphatic, heteroaliphatic, aryl, heteroaryl, alkylaryl, or alkylheteroaryl moiety, and wherein R$_{13}$ is hydrogen, a protecting group, —OR$_K$, —SR$_K$, —C(O)OR$_K$, —C(O)NR$_K$, —S(O)$_2$R$_K$, —O(C=O)R$_K$, —N(R$_K$)(C=O)(R$_K$), —C(O)R$_K$, —C(O)OR$_K$, —CON(R$_K$)$_2$, —OCO$_2$R$_K$, or an aliphatic, heteroaliphatic, aryl, heteroaryl, alkylaryl, or alkylheteroaryl moiety, wherein each occurrence of R$_K$ is independently hydrogen, a protecting group or an aliphatic, heteroaliphatic, aryl, heteroaryl, alkylaryl, or alkylheteroaryl moiety, or when A and B together represent —CHR$_{11}$—CHR$_{12}$—, R$_{11}$ and R$_{12}$ taken together represent a substituted or unsubstituted 3–7 membered aliphatic, heteroaliphatic, aryl or heteroaryl ring;

K and L together represent

—CHR$_{14}$—CHR$_{15}$—, —CR$_{14}$=CR$_{15}$—, wherein R$_{14}$ and R$_{15}$ are each independently hydrogen, halogen, cyano, —OR$_J$, —N(R$_J$)$_2$, —SR$_J$, —O(C=O)R$_J$, —O(S=O)R$_J$, —N(R$_J$)(C=O)(R$_J$), —C(=O)R$_J$, —C(=O)OR$_J$, —CON(R$_J$)$_2$, —OCO$_2$R$_J$, —OS(=O)OR$_J$ or an aliphatic, heteroaliphatic, aryl, heteroaryl, alkylaryl, or alkylheteroaryl moiety, wherein each occurrence of R$_J$ is independently hydrogen, a protecting group, or an aliphatic, heteroaliphatic, aryl, heteroaryl, alkylaryl, or alkylheteroaryl moiety, and wherein R$_{16}$ is hydrogen, a protecting group, —OR$_K$, —SR$_K$, —C(O)OR$_K$, —C(O)NR$_K$, —S(O)$_2$R$_K$, —O(C=O)R$_K$, —N(R$_K$)(C=O)(R$_K$), —C(O)R$_K$, —C(O)OR$_K$, —CON(R$_K$)$_2$, —OCO$_2$R$_K$, or an aliphatic, heteroaliphatic, aryl, heteroaryl, alkylaryl, or alkylheteroaryl moiety, wherein each occurrence of R$_K$ is independently hydrogen, a protecting group or an aliphatic, heteroaliphatic, aryl, heteroaryl, alkylaryl, or alkylheteroaryl moiety, or when A and B together represent —CHR$_{14}$——CHR$_{15}$—, R$_{14}$ and R$_{15}$ taken together represent a substituted or unsubstituted 3–7 membered aliphatic, heteroaliphatic, aryl or heteroaryl ring;

whereby each of the foregoing aliphatic and heteroaliphatic moieties may independently be substituted or unsubstituted, cyclic or acyclic, or branched or unbranched, and each aryl, heteroaryl, alkylaryl, and alkylheteroaryl moiety may be substituted or unsubstituted; and pharmaceutically acceptable derivatives thereof.

In certain other embodiments of the invention the compounds are subject to one or more, or all of the following limitations:

if Z is O; if X is O; if R$_0$ is methyl; if A and B together are —CR$_4$=CR$_5$— and R$_5$ and R$_6$ are each hydrogen; if D and E together are —COH=COH—; if G and J together are —CH$_2$—CH$_2$—; if K and L together are —CH=CH—; if R$_1$ is hydrogen; and if R$_3$ is hydrogen;

then R$_2$ and R$_4$ are each not —OR$_B$, wherein R$_B$ is hydrogen or an alkyl, alkoxy, alkenyl, alkenyloxy, alkynyl, aryl, aryloxy, heterocycle, cycloalkyl, cycloalkenyl, or cycloalkenyl fused to an aryl group.

In certain embodiments of the invention, the genuses or subclasses of compounds of the invention exclude aigailomycins A–E.

2) Featured Classes of Compounds

It will be appreciated that for compounds as generally described above, certain classes of compounds are of special interest. For example, one class of compounds of special interest includes those compounds having the structure of formula (II) in which Z and X are each O, and the compound has the structure:

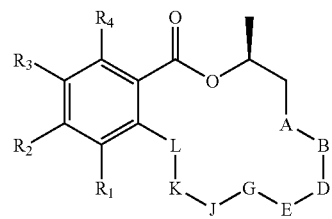

and R$_1$, R$_2$, R$_3$, R$_4$, A—B, D—E, G—J, and K—L are as defined above and in subclasses herein.

Another class of compounds of special interest consists of compounds having the structure of formula (I) in which Z is O and X is NR$_G$, and the compound has the structure:

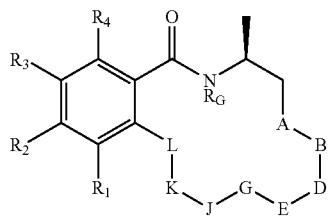

and $R_1$, $R_2$, $R_3$, $R_4$, $R_G$, A—B, D—E, G—J, and K—L are as defined above and in subclasses herein.

Another class of compounds of special interest consists of compounds having the structure of formula (I) in which G and J together represent —CH$_2$—CH$_2$— and the compound has the structure:

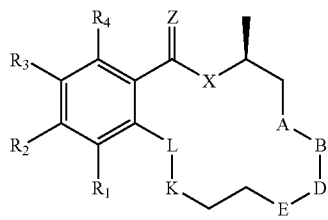

and $R_1$, $R_2$, $R_3$, $R_4$, Z, X, A—B, D—E, and K—L are as defined above and in subclasses herein.

Another class of compounds of special interest consists of compounds having the structure of formula (I) in which A and B together represent —CH=CH— and the compound has the structure:

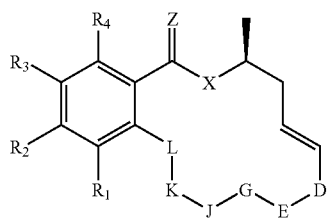

and $R_1$, $R_2$, $R_3$, $R_4$, $R_5$, $R_6$, Z, X, D—E, G—J, and K—L are as defined above and in subclasses herein.

Another class of compounds of special interest consists of compounds having the structure of formula (I) in which K and L together represent —CH=CH— and the compound has the structure:

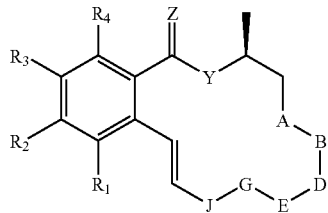

and $R_1$, $R_2$, $R_3$, $R_4$, Z, X, A—B, D—E, and G—J are as defined above and in subclasses herein.

Another class of compounds of special interest consists of compounds having the structure of formula (I) in which D and E together represent —CHOH=CHOH— and the compound has the structure:

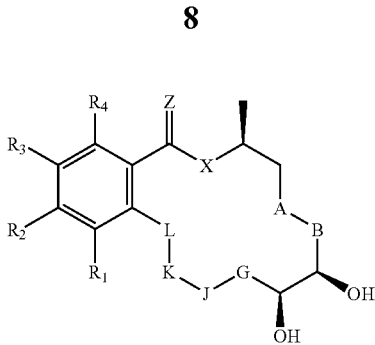

and $R_1$, $R_2$, $R_3$, $R_4$, $R_7$, Z, X, A—B, G—J, and K—L are as defined above and in subclasses herein.

Another class of compounds of special interest consists of compounds having the structure of formula (I) in which the compound has the structure:

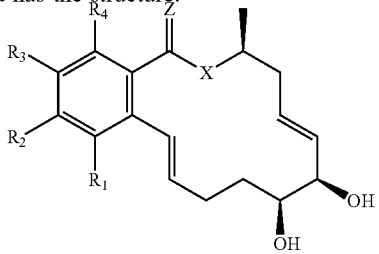

and $R_1$, $R_2$, $R_3$, $R_4$, Z, and X are as defined above and in subclasses herein. In certain embodiments, Z is oxygen and X is NR$_G$, wherein R$_G$ is defined above. In other embodiments, Z is oxygen an X is NH.

Another class of compounds of special interest consists of compounds having the structure of formula (I) in which the compound has the structure:

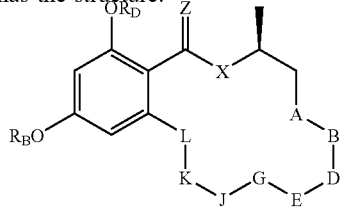

and Z, X, A—B, D—E, G—J, and K—L are as defined above and in subclasses herein. In certain embodiments, R$_D$ and R$_B$ are each hydrogen.

Another class of compounds of special interest consists of compounds having the structure of formula (I) in which the compound has the structure:

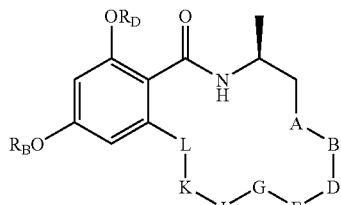

and R$_D$, R$_B$, A—B, D—E, G—J, and K—L are as defined above and in subclasses herein.

Another class of compounds of special interests consists of compounds having the structure of formula (I) in which the compound has the structure:

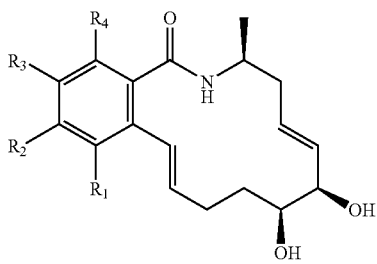

and $R_1$, $R_2$, $R_3$, and $R_4$ are as defined above and in subclasses herein.

Another class of compounds of special interest consists of compounds having the structure of formula (I) in which the compound has the structure:

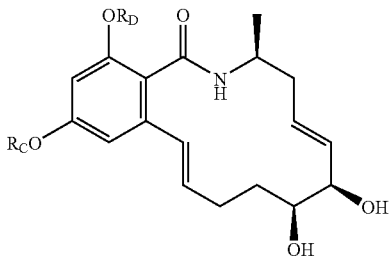

and $R_C$ and $R_D$ are as defined above and in subclasses herein. In certain embodiments, $R_D$ and $R_C$ are each hydrogen.

Another class of compounds of special interest consists of compounds having the structure of formula (I) in which the compound has the structure:

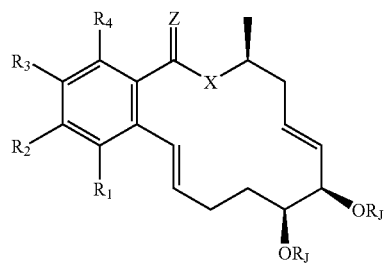

and $R_1$, $R_2$, $R_3$, $R_4$, $R_J$, Z, and X are as defined above and in subclasses herein. In certain embodiments, Z is oxygen and X is oxygen. In other embodiments, Z is oxygen and X is NH.

The following structures illustrate several exemplary types of compounds of these classes. Others will be readily apparent to the reader.

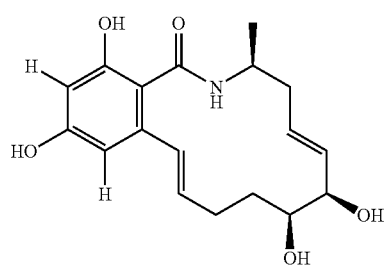

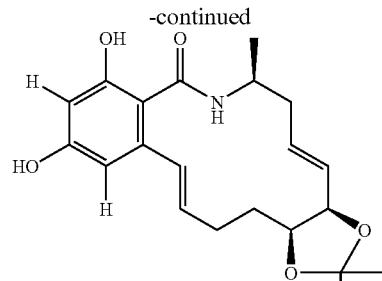

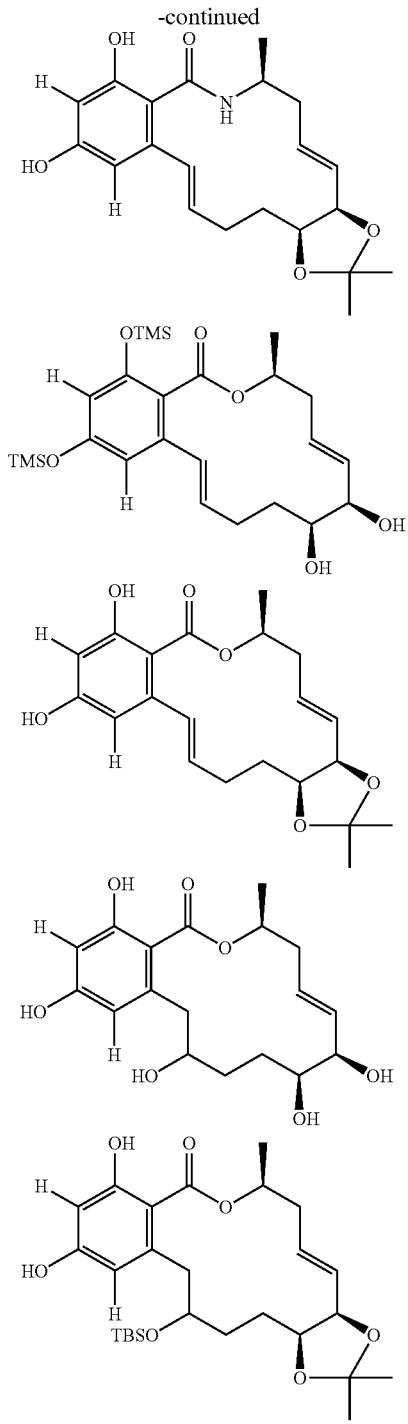

A number of important subclasses of each of the foregoing classes deserve separate mention; these subclasses include subclasses of the foregoing classes in which:

i) Z and X are each O;
ii) Z is O and X is NH;
iii) A and B together are a trans carbon—carbon double bond;
iv) A and B together are a carbon—carbon single bond;
v) D and E together are —CHOH—CHOH—;
vi) J and G together are a carbon—carbon single bond;

vii) K and L together are a trans carbon—carbon double bond;

viii) $R_2$ and $R_4$ are each independently hydrogen, halogen, cyano, —$OR_J$, —$N(RJ)_2$, —$SR_J$, —$O(C=O)R_J$, —$O(S=O)R_J$, —$N(R_J)(C=O)(R_J)$, or —$OCO_2R_J$, —$OSO_2R_J$, and each occurrence of $R_J$ is independently hydrogen, a protecting group or an aliphatic, heteroaliphatic, aryl, heteroaryl, alkylaryl, or alkylheteroaryl moiety;

ix) $R_2$ and $R_4$ are each independently hydroxy;

x) D and E together are —$CHR_8$—$CHR_9$—;

xi) D and E together are —$CR_8=CR_9$—;

xii) $R_1$ and $R_3$ are each hydrogen;

xiii) G and J together are —$CHR_{10}$—$CHR_{11}$—;

xiv) G and J together are —$CR_{10}=CR_{11}$—;

xv) $R_{10}$ and $R_{11}$ are each hydrogen;

xvi) Z is O;

xvii) Z is S;

xviii) X is S;

xix) X is $NR_G$;

xx) X is O;

xxi) $R_1$ is hydrogen, halogen, lower alkyl, lower heteroalkyl, lower alkylaryl, lower alkylheteroaryl, or $N(R_A)_2$, wherein each occurrence of $R_A$ is independently hydrogen, a protecting group, or an aliphatic, heteroaliphatic, aryl, heteroaryl, alkylaryl, or alkylheteroaryl moiety and $R_3$ is hydrogen, halogen, lower alkyl, lower heteroalkyl, lower alkylaryl, lower alkylheteroaryl, or —$N(R_C)_2$, wherein each occurrence of $R_C$ is independently hydrogen, a protecting group, or an aliphatic, heteroaliphatic, aryl, heteroaryl, alkylaryl, or alkylheteroaryl moiety;

xxii) $R_1$ and $R_3$ are each independently halogen, hydrogen, or lower alkyl;

xxiii) $R_2$ is hydrogen, halogen, —$OR_B$, —$N(R_B)_2$, —$SR_B$, —$O(C=O)R_B$, —$N(R_B)(C=O)(R_B)$, —$C(O)R_B$, —$C(O)OR_B$, —$CON(R_B)_2$, —$OCO_2R_B$, or lower alkyl, lower heteroalkyl, lower alkylaryl, lower alkylheteroaryl, wherein each occurrence of $R_B$ is independently hydrogen, a protecting group or an aliphatic, heteroaliphatic, aryl, heteroaryl, alkylaryl, or alkylheteroaryl moiety, and $R_4$ is hydrogen, halogen, —$OR_D$, —$N(R_D)_2$, —$SR_D$, —$O(C=O)R_D$, —$N(R_D)(C=O)(R_D)$, —$C(O)R_D$, —$C(O)OR_D$, —$CON(R_D)_2$, —$OCO_2R_D$, or lower alkyl, lower heteroalkyl, lower alkylaryl, lower alkylheteroaryl, wherein each occurrence of $R_D$ is independently hydrogen, a protecting group or an aliphatic, heteroaliphatic, aryl, heteroaryl, alkylaryl, or alkylheteroaryl moiety;

xxiv) $R_2$ is hydrogen or —$OR_B$, wherein each occurrence of $R_B$ is independently hydrogen, a protecting group or an aliphatic, heteroaliphatic, aryl, heteroaryl, alkylaryl, or alkylheteroaryl moiety, and $R_4$ is hydrogen or —$OR_D$, wherein each occurrence of $R_D$ is independently hydrogen, a protecting group or an aliphatic, heteroaliphatic, aryl, heteroaryl, alkylaryl, or alkylheteroaryl moiety;

xxv) $R_0$ is hydrogen or aliphatic;

xxvi) $R_0$ is methyl;

xxvii) K and L together are a cis carbon—carbon double bond.

In certain embodiments of the compounds described above, $R_1$ and $R_3$ are each independently halogen, hydrogen, or lower alkyl; $R_2$ is hydrogen or —$OR_B$, wherein each occurrence of $R_B$ is independently hydrogen, a protecting group or an aliphatic, heteroaliphatic, aryl, heteroaryl, alkylaryl, or alkylheteroaryl moiety, and $R_4$ is hydrogen or —$OR_D$, wherein each occurrence of $R_D$ is independently hydrogen, a protecting group or an aliphatic, heteroaliphatic, aryl, heteroaryl, alkylaryl, or alkylheteroaryl moiety.

Some of the foregoing compounds can exist in various isomeric forms. The invention encompasses the compounds as individual isomers substantially free of other isomers and alternatively, as mixtures of various isomers, e.g., racemic mixtures of stereoisomers, cis and trans isomers. The invention also encompasses tautomers of specific compounds as described above. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of this invention which are of particular interest include those which:

exhibit cytotoxic or growth inhibitory effect on cancer cell lines maintained in vitro or in animal studies using a scientifically acceptable cancer cell xenograft model;

exhibit cytotoxic or growth inhibitory effect on cancer cell lines comprising Rb negative cells;

exhibit antimalarial activity;

exhibit antibacterial activity;

bind to and/or inhibit the Hsp90 family of chaperones;

exhibit cytotoxic or growth inhibitory effect on cancer cell lines comprising Rb positive cells.

This invention also provides a pharmaceutical preparation comprising at least one of the compounds as described above and herein, or a pharmaceutically acceptable derivative thereof, which compounds are capable of inhibiting the growth of or killing cancer cells, and, in certain embodiments of special interest are capable of inhibiting the growth of or killing cancer cells.

The invention further provides a method for inhibiting tumor growth and/or tumor metastasis. The method involves the administration of a therapeutically effective amount of the compound or a pharmaceutically acceptable derivative thereof to a subject (including, but not limited to a human or animal) in need of it. In certain embodiments, the inventive compounds are useful for the treatment of solid tumors. In still other embodiments of interest, the inventive compounds are useful for the treatment of glioblastoma, retinoblastoma or small cell lung cancer.

3) Compounds and Definitions

As discussed above, this invention provides novel compounds with a range of biological properties. Compounds of this invention have biological activities relevant for the treatment of diseases or other disorders such as proliferative diseases, including, but not limited to cancer. More generally, the compounds are useful in the regulation of the cell cycle pathway.

Compounds of this invention include those specifically set forth above and described herein, and are illustrated in part by the various classes, subgenera and species disclosed elsewhere herein.

It will be appreciated by one of ordinary skill in the art that asymmetric centers may exist in the compounds of the present invention. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, a mixtures of stereoisomers or diastereomers are provided.

Additionally, the present invention provides pharmaceutically acceptable derivatives of the inventive compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other funcational groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative disorders, including, but not limited to cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1–6 carbon atoms.

In certain embodiments, the alkyl, alkenyl and alkynyl groups employed in the invention contain 1–20 aliphatic carbon atoms. In certain other embodiments, the alkyl, alkenyl, and alkynyl groups employed in the invention contain 1–10 aliphatic carbon atoms. In yet other embodiments, the alkyl, alkenyl, and alkynyl groups employed in the invention contain 1–8 aliphatic carbon atoms. In still other embodiments, the alkyl, alkenyl, and alkynyl groups employed in the invention contain 1–6 aliphatic carbon atoms. In yet other embodiments, the alkyl, alkenyl, and alkynyl groups employed in the invention contain 1–4 carbon atoms. Illustrative aliphatic groups thus include, but are not limited to, for example, methyl, ethyl, n-propyl, isopropyl, cyclopropyl, —CH$_2$-cyclopropyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alkoxy", or "thioalkyl" as used herein refers to an alkyl group, as previously defined, attached to the parent molecular moiety through an oxygen atom or through a sulfur atom. In certain embodiments, the alkyl group contains 1–20 alipahtic carbon atoms. In certain other embodiments, the alkyl group contains 1–10 aliphatic carbon atoms. In yet other embodiments, the alkyl, alkenyl, and alkynyl groups employed in the invention contain 1–8 aliphatic carbon atoms. In still other embodiments, the alkyl group contains 1–6 aliphatic carbon atoms. In yet other embodiments, the alkyl group contains 1–4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. In certain embodiments, the alkyl group contains 1–20 aliphatic carbon atoms. In certain other embodiments, the alkyl group contains 1–10 aliphatic carbon atoms. In yet other embodiments, the alkyl, alkenyl, and alkynyl groups employed in the invention contain 1–8 aliphatic carbon atoms. In still other embodiments, the alkyl group contains 1–6 aliphatic carbon atoms. In yet other embodiments, the alkyl group contains 1–4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3–14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or hetercyclic moieties, may optionally be substituted with substituents including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic", as used herein, refers to aliphatic moieties which contain one or more oxygen, sulfur, nitrogen, phosphorus or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH;

—CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

4) Synthetic Methodology

Access to resorcyclic macrolides such as radicicol and monocillin was previously limited to compounds accessed via the natural products (see, for example, U.S. Pat. No. 5,650,430; U.S. Pat. No. 5,731,343; U.S. Pat. No. 6,239,168; U.S. Pat. No. 5,977,165; and U.S. Pat. No. 5,597,846; each of which is incorporated herein by reference). An efficient and practical synthesis of radicicol and monocillin was previously described in U.S. Ser. No. 09/938,754, filed Aug. 25, 2001, which is incorporated herein by reference. In recognition of the need for a more efficient and practical route to this class of therapeutic agents, the present invention also provides novel synthetic methodologies for the synthesis of radicicol, monocillin, and analogues thereof as well as aigialomycins and analogues thereof. Although the synthesis of radicicol and aigialomycin D is described specifically herein directly below (and in the Examples), it will be appreciated that this methodology is generally applicable to the generation of analogues and conjugates as discussed in more detail after the discussion of the synthesis of radicicol and aigialomycin D.

a) Synthesis of Radicicol and Monocillin:

As described in more detail below, a novel synthetic route to radicicol and monocillin has been developed, which methodology allows for the efficient generation of a variety of analogues of radicicol, monocillin, homodimers, heterodimers, and conjugates thereof.

The underlying general scheme for this new synthesis of radicicol is shows in the scheme below, which is directed to the synthesis of cycloproparadicicol. The central element of the synthesis is the production of an "ynolide" intermediate, which is prepared by olefin metathesis, and its reaction with a diene via a Diel-Alder cycloaddition to form the benzo-fused macrolide.

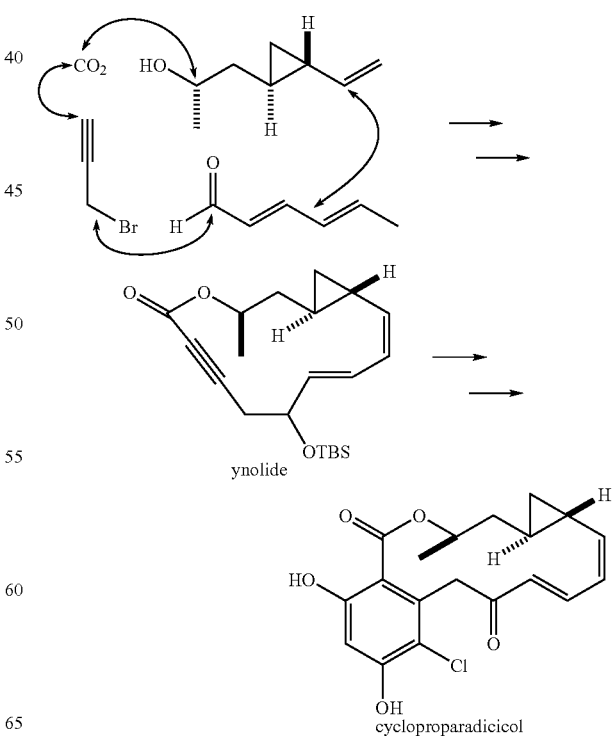

The same general approach has also been used to synthesize compounds of the invention including aigialomycin D as shown below.

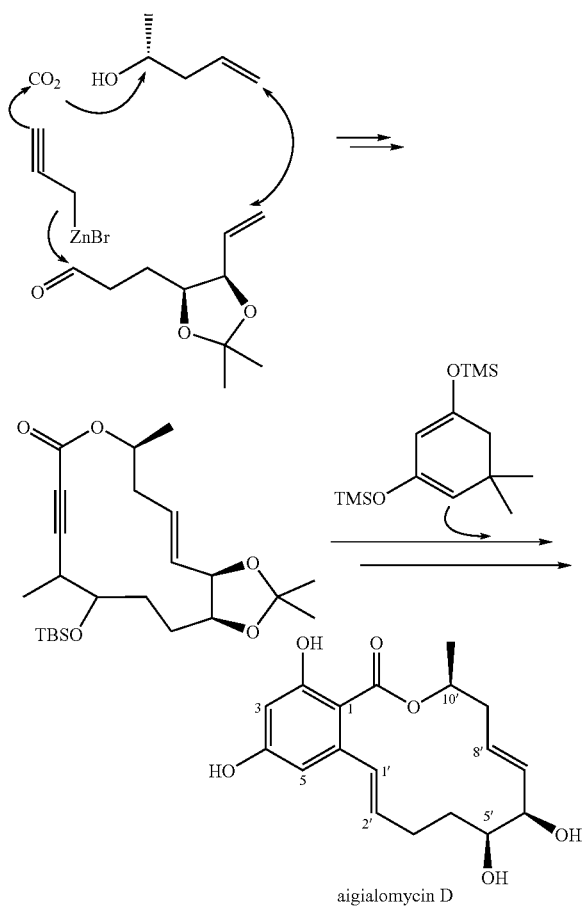

aigialomycin D b) General Synthetic Methodology:

This new synthetic methodology provides for the rapid synthesis of a variety of analogues of radicicol, monocillin, dimers, and conjugates thereof. It will be appreciated that the ability to rapidly generate a range of analogues is important because it is believed that in vivo activity is lost due to certain structural characteristics of radicicol and monocillin. For example, it is postulated that in vivo activity is lost due to the nucleophilic action of cellular thiols (i.e. glutathione) on either the epoxide or the α,β unsaturated ketone of radicicol. This nucleophilic addition changes the overall conformation of radicicol, and results in an inability to bind to Hsp90. A second likely pathway of deactivation involves the conjugation of the aromatic ring, or perhaps cytochrome P-450 oxidation.

Without wishing to be bound by any particular theory, one strategy to restore in vivo activity would be to reduce the affinity of radicicol to nucleophiles such as thiols, specifically to deactivate electrophilic sites in radicicol. Here care must be taken not to dramatically change the overall conformation of the natural product. Thus these analogues have been designed to attenuate electrophilicity with simple alterations to the structure that should not affect the overall conformation. It should be emphasized that the analogues as described using the methodology herein cannot be made from the natural product. The three component nature of the synthetic process described above and described more generally below emphasizes the ability to generate numerous analogues by the modification of one component and its incorporation into a short and efficient process.

In general, the method involves the synthesis of analogues from four easily obtainable and diversifiable components. Depicted below is a general retrosynthetic strategy for the synthesis of analogues:

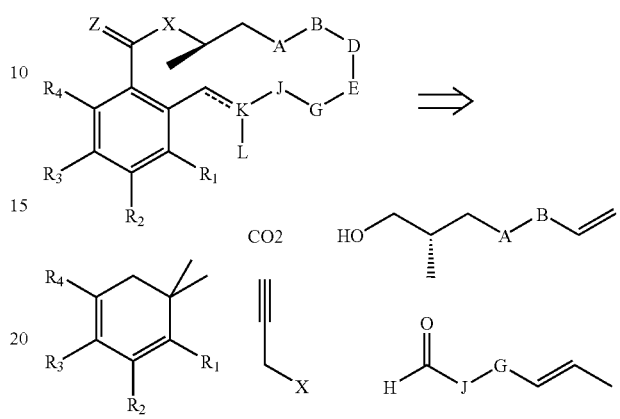

It should be noted that these analogs can be generated either with a single modification, or they may be combined in a single entity to maximize their benefit if they are found to be synergistic. It will also be appreciated, as described in more detail herein, that each of the components can be diversified prior to formation of the macrocycle, or alternatively or additionally, can be diversified after formation of the macrocycle.

As depicted generally below, the synthesis of analogues can be carried out in a similar fashion to the synthesis of radicicol and monocillin as described above. The synthesis of the acyclic alkynoic ester is shown below:

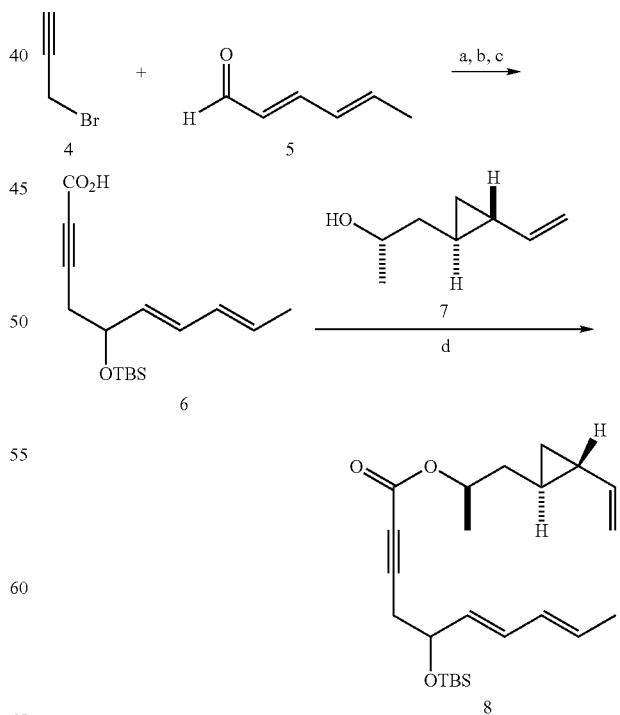

Reagents and conditions: (a) (i) Zn, THF, 66%; (b) TBSCl, imidazole, DMAP, CH₂Cl₂, 100%; (c) BuLi, −78° C.; then CO₂; (d) DIAD, Ph₃P, THF, −20° C., 47% (two steps).

The resulting triene 8 is then treated with dicobalt carbonyl to complex with the acetylene. The combalt complex 14 is then cyclized under ring closing metathesis conditions to form 15. The cobalt is then removed to give 16.

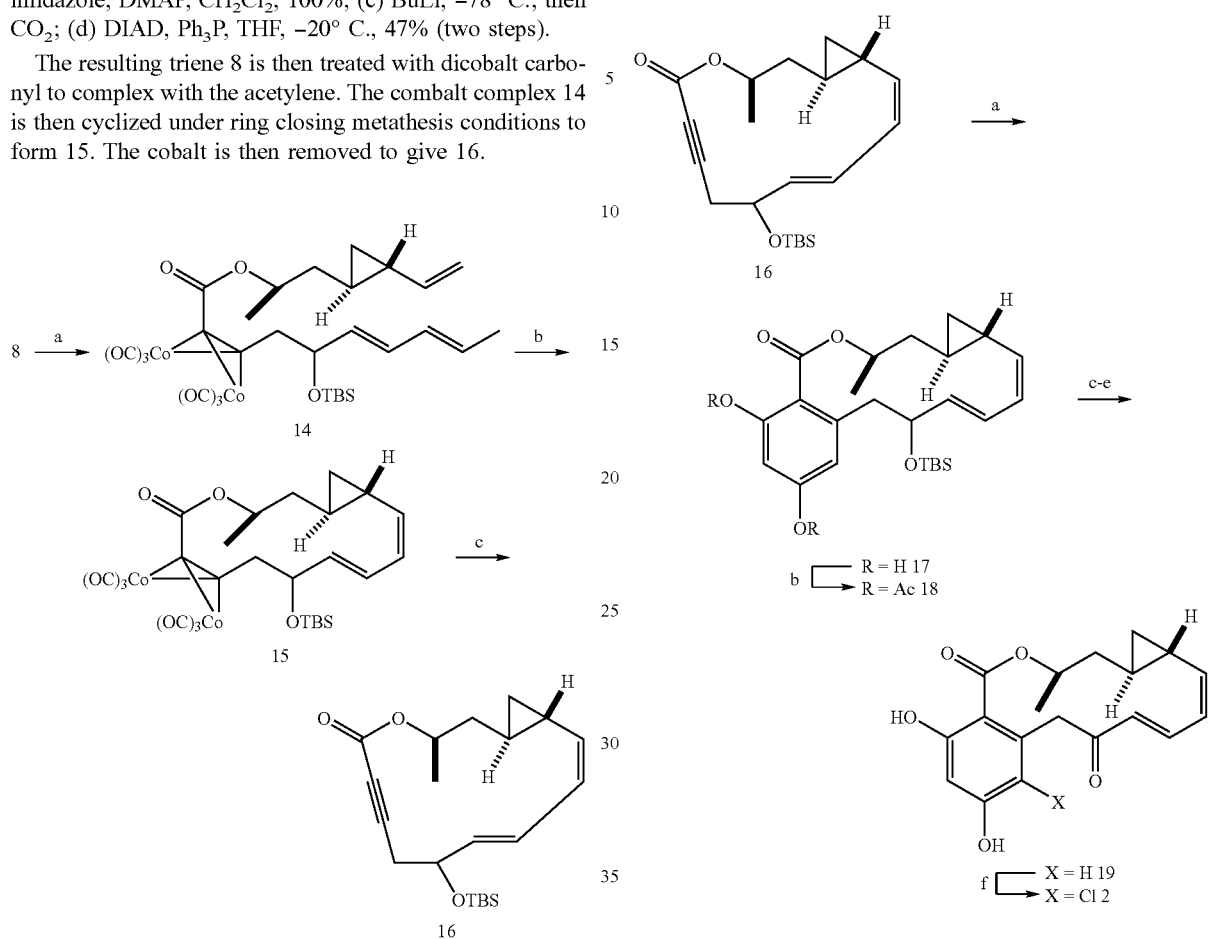

Reagents and conditions: (a) Co₂(CO)₈, PhMe, 100%; (b) 2$^{nd}$ genera-tion Grubbs catalyst (25 mol %), CH₂Cl₂ (0.2 mM), 45° C., 57%; (c) I₂, THF, 0° C., 69%.

The resulting ynolide 16 is then reacted with a diene using a Diels-Alder cycloaddition to yield 17, which is then oxidized and chlorinated to give the desired product, cyclo-proparadicicol (2).

Reagents and conditions: (a) 12, 140° C., neat, 75%; (b) Ac₂O, DMAP, DMF, 87%; (c) HF/Pyr. THF; (d) Dess-Martin periodinane, CH₂Cl₂, 68% (two steps); (e) 5% NaHCO₃/MeOH, 92%; (f) SO₂Cl₂, CH₂Cl₂, 0° C., 61%.

This basic approach can be used to prepare a variety of benofused macrolactones, including aigialomycin D. First the ring closing metathesis precurusor is made starting from D-2-deoxyribose.

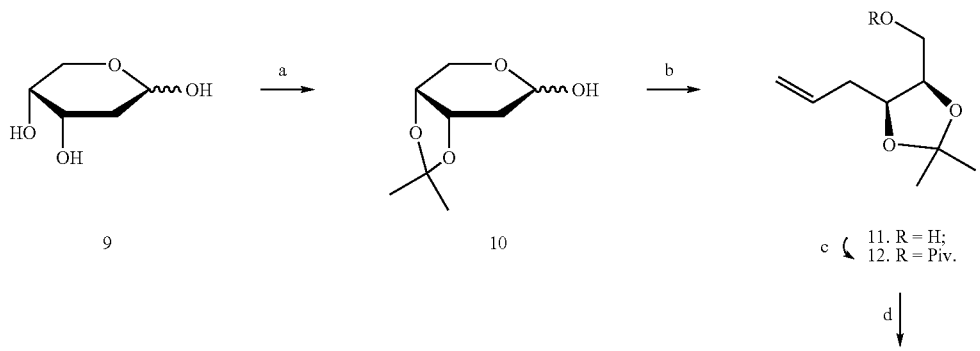

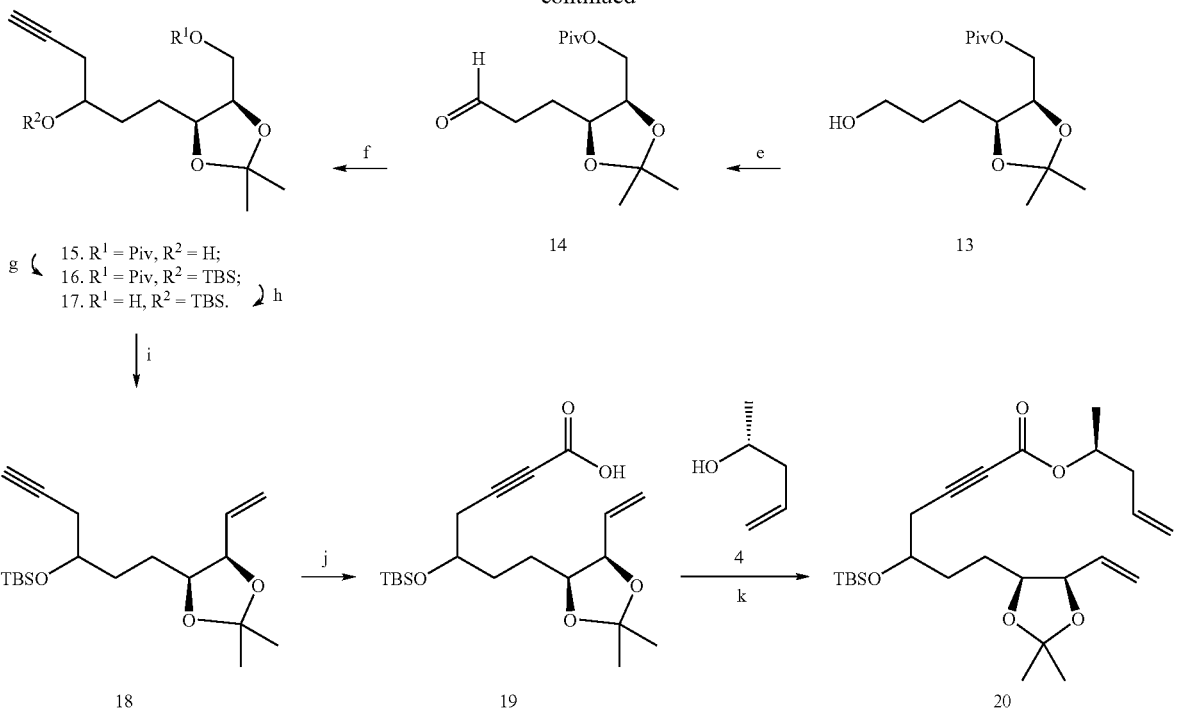

a) 2-methoxypropene, p-TSA, DMF, 3 h, 62%; b) KHMDS, Ph$_3$P$^+$CH$_3$I$^{-1}$, THF, −78° C. to r.t., 10 h, 68%; c) PivCl, Et$_3$N, DMAP, CH$_2$Cl$_2$, 10 h, 90%; d) 9-BBN, THF, 0° C. to r.t., 4 h, then NaOH, H$_2$O$_2$, H$_2$O, 2.5 h, 88%; e) SO$_3$-Pyr., DMSO, CH$_2$Cl$_2$, Et$_3$N, 0° C., 1 h; f) propargyl bromide, zinc, THF, 0° C., 2 h; g) TBSOTf, 2,6-lutidine, CH$_2$Cl$_2$, 10 h, 89% from 13; h) NaOMe/MeOH, 10 h, 88%; i) SO$_3$-Pyr., DMSO, CH$_2$Cl$_2$, Et$_3$N, 0° C., 2 h, then KHMDS, Ph$_3$P$^+$CH$_3$I$^−$, THF, −78° C. to r.t., 10 h, 86% for two steps; j) BuLi, dry ice, −78° C. to r.t., 2 h; k) 4, DIAD, PPh$_3$, tol., 10 h, 85% for two steps.

The precursor is treated with dicobalt hexacarbonyl, and the resulting cobalt-complex is cyclized using a ring closing metathesis reaction.

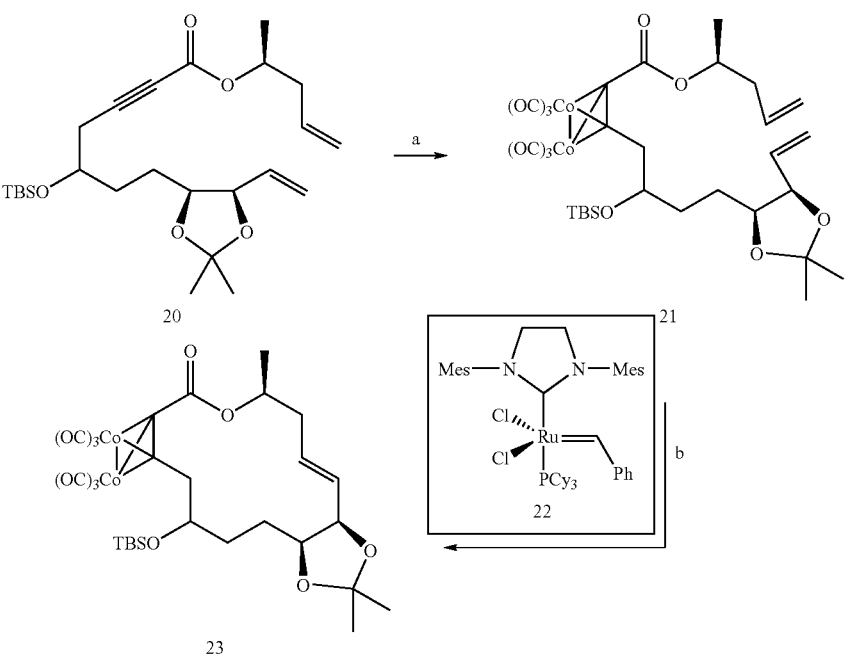

a) Co$_2$(CO)$_8$, tol., 30 min, 94%; b) 2$^{nd}$ generation Grubbs catalyst (25 mol %), CH$_2$Cl$_2$, 10 h, 23A, 38%; 23B, 42%.

The marocycle was then decomplexed and reacted with disiloxydiene to yield a benzo-fused macrocycle. The styrene double bond was installed, and the protecting groups were removed to yield aigialomycin D.

a). CAN, acetone, −10° C., 15 min, 7A, 94%; 7B 95%; b). 8 neat, 140° C., 36 h, 24A, 74%; 24B, 84%; c) MOMCl, DIPEA, CH$_2$Cl$_2$, 10 h, 25A, 78%; 25B, 83%; d) HF-pyr., pyr., THF, 10 h, 26A, 78%; 26B, 87%; e) [PhC(CF$_3$)$_2$O]$_2$SPh$_2$, CH$_2$Cl$_2$, 0° C. to r.t., 2 h, from 26A to 27, 90%; from 26B to 27, 84%; f) 0.5 N HCl, H$_2$O/MeOH, 2 d, 69%.

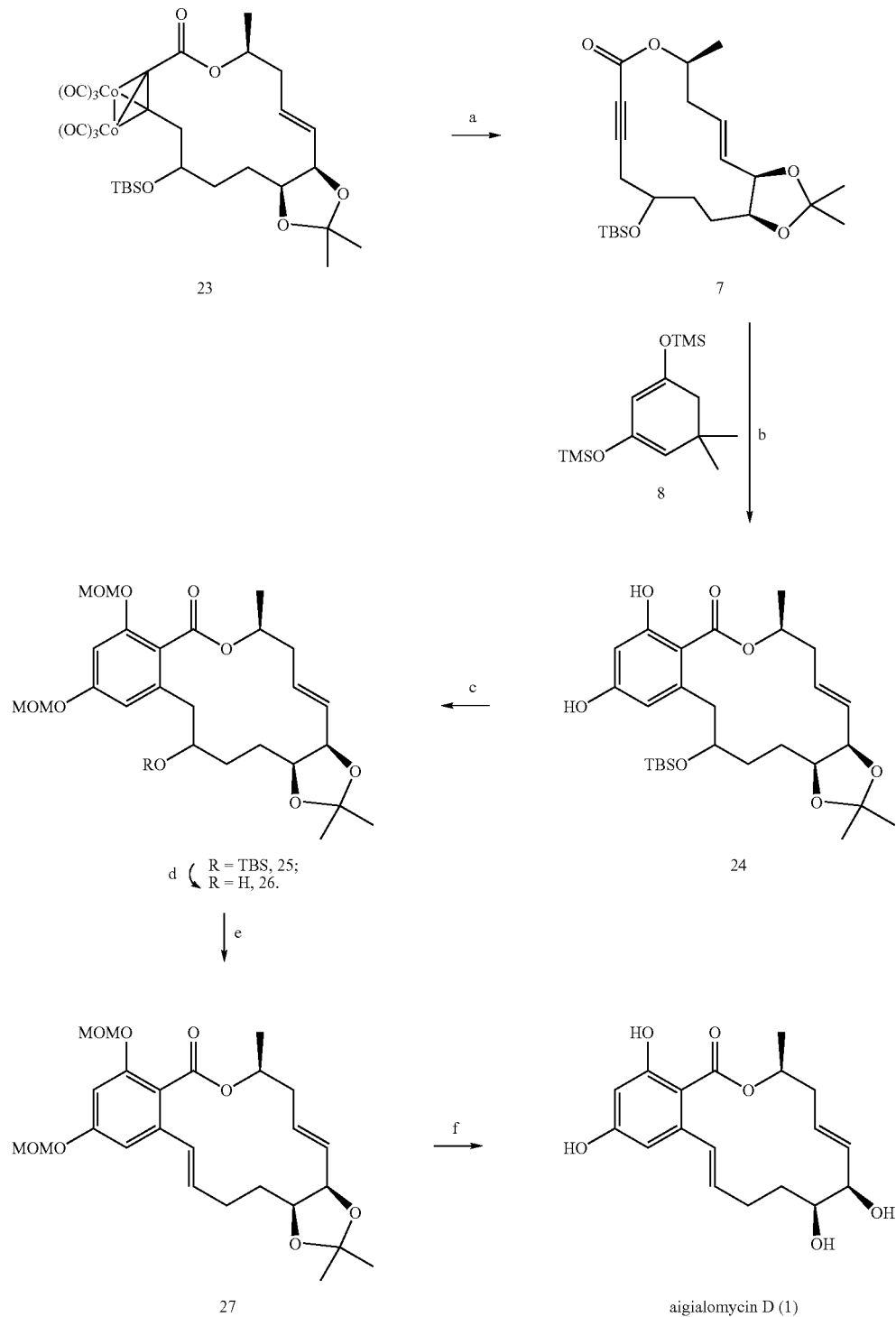

Thus, in addition to providing cycloproparadicicol as described above and herein, the present invention additionally provides a method for the synthesis of compounds having the general structure (I):

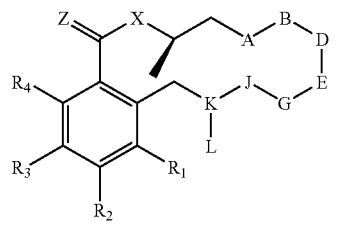

wherein $R_1$ is hydrogen, halogen, an aliphatic, heteroaliphatic, aryl, heteroaryl, alkylaryl, or alkylheteroaryl moiety, or $N(R_A)_2$, wherein each occurrence of $R_A$ is independently hydrogen, a protecting group, or an aliphatic, heteroaliphatic, aryl, heteroaryl, alkylaryl, or alkylheteroaryl moiety;

$R_2$ is hydrogen, halogen, cyano, —$OR_B$, —$N(R_B)_2$, —$SR_B$, —$O(C=O)R_B$, —$N(R_B)(C=O)(R_B)$, —$C(O)R_B$, —$C(O)OR_B$, —$CON(R_B)_2$, —$OCO_2R_B$, or an aliphatic, heteroaliphatic, aryl, heteroaryl, alkylaryl, or alkylheteroaryl moiety, wherein each occurrence of $R_B$ is independently hydrogen, a protecting group or an aliphatic, heteroaliphatic, aryl, heteroaryl, alkylaryl, or alkylheteroaryl moiety;

$R_3$ is hydrogen, halogen, an aliphatic, heteroaliphatic, aryl, heteroaryl, alkylaryl, or alkylheteroaryl moiety, or —$N(R_C)_2$, wherein each occurrence of $R_C$ is independently hydrogen, a protecting group, or an aliphatic, heteroaliphatic, aryl, heteroaryl, alkylaryl, or alkylheteroaryl moiety;

$R_4$ is hydrogen, halogen, cyano, —$OR_D$, —$N(R_D)_2$, —$SR_D$, —$O(C=O)R_D$, —$N(R_D)(C=O)(R_D)$, —$C(O)R_D$, —$C(O)OR_D$, —$CON(R_D)_2$, —$OCO_2R_D$, or an aliphatic, heteroaliphatic, aryl, heteroaryl, alkylaryl, or alkylheteroaryl moiety, wherein each occurrence of $R_D$ is independently hydrogen, a protecting group or an aliphatic, heteroaliphatic, aryl, heteroaryl, alkylaryl, or alkylheteroaryl moiety;

Z is O, S or $NR_E$, wherein $R_E$ is hydrogen, a protecting group, an aliphatic, heteroaliphatic, aryl, heteroaryl, alkylaryl, or alkylheteroaryl moiety, or $OR_F$, wherein $R_F$ is hydrogen, a protecting group, an aliphatic, heteroaliphatic, aryl, heteroaryl, alkylaryl, or alkylheteroaryl moiety;

X is O, S or $NR_G$, wherein $R_G$ is hydrogen or lower alkyl;

A and B together represent

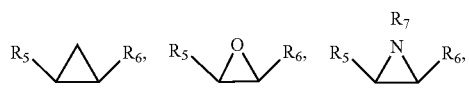

—$CHR_5$—$CHR_6$—, —$CR_5$=$CR_6$—, wherein $R_5$ and $R_6$ are each independently hydrogen, halogen, cyano, —$OR_J$, —$N(R_J)_2$, —$SR_J$, —$O(C=O)R_J$, —$O(S=O)R_J$, —$N(R_J)(C=O)(R_J)$, —$C(=O)R_J$, —$C(=O)OR_J$, —$CON(R_J)_2$, —$OCO_2R_J$, —$OS(=O)OR_J$ or an aliphatic, heteroaliphatic, aryl, heteroaryl, alkylaryl, or alkylheteroaryl moiety, wherein each occurrence of $R_J$ is independently hydrogen, a protecting group, or an aliphatic, heteroaliphatic, aryl, heteroaryl, alkylaryl, or alkylheteroaryl moiety, and wherein $R_7$ is hydrogen, a protecting group, —$OR_K$, —$SR_K$, —$C(O)OR_K$, —$C(O)NR_K$, —$S(O)_2R_K$, —$O(C=O)R_K$, —$N(R_K)(C=O)(R_K)$, —$C(O)R_K$, —$C(O)OR_K$, —$CON(R_K)_2$, —$OCO_2R_K$, or an aliphatic, heteroaliphatic, aryl, heteroaryl, alkylaryl, or alkylheteroaryl moiety, wherein each occurrence of $R_K$ is independently hydrogen, a protecting group or an aliphatic, heteroaliphatic, aryl, heteroaryl, alkylaryl, or alkylheteroaryl moiety, or when A and B together represent —$CHR_5$—$CHR_6$—, $R_5$ and $R_6$ taken together represent a substituted or unsubstituted 3–7 membered aliphatic, heteroaliphatic, aryl or heteroaryl ring, D and E together represent —$CHR_8$—$CHR_9$—, —$CR_8$=$CR_9$—, wherein $R_8$ and $R_9$ are each independently hydrogen or lower alkyl;

G and J together represent —$CHR_{10}$—$CHR_{11}$—, —$CR_{10}$=$CR_{11}$—, wherein $R_{10}$ and $R_{11}$ are each independently hydrogen or lower alkyl;

K and L together represent C=O, C=S, CH—$CH_3$, CH—$CH(R_L)_2$, C=$C(R_L)_2$, —$CH_2$—, —$C(—S(CH_2)_3S—)$—, CH—$OR_L$, CH—$SR_L$, CH—$N(R_L)_2$, CH—$N(R_L)(C=O)(R_L)$, C=N—O—$R_L$, CH—N=O, C=$C(R_L)$—$N(R_L)_2$, C=N—$R_L$, C=N—$N(R_L)_2$, or, if the dotted line - - - represents a bond, whereby a double bond is present, then K and L together represent C—$N(R_L)_2$, wherein each occurrence of $R_L$ is independently hydrogen, a protecting group, an aliphatic, heteroaliphatic, aryl, heteroaryl, alkylaryl, or alkylheteroaryl moiety, or two occurrences of $R_L$ taken together represent a 3 to 7-membered cyclic aliphatic, heteroaliphatic, aromatic or heteroaromatic moiety;

whereby each of the foregoing aliphatic and heteroaliphatic moieties may independently be substituted or unsubstituted, cyclic or acyclic, or branched or unbranched, and each aryl, heteroaryl, alkylaryl, and alkylheteroaryl moiety may be substituted or unsubstituted; wherein one or any two of $R_1$, $R_A$, $R_2$, $R_B$, $R_3$, $R_C$, $R_4$, $R_D$, $R_5$, $R_6$, $R_J$, or $R_L$ are optionally a linker covalently bonded to a compound selected from the group consisting of radicicol, monocillin, analogues of radicicol and monocillin, geldanamycin, analogues of geldanamycin, and steroids, said method comprising:

(1) reacting an acidic component having the structure:

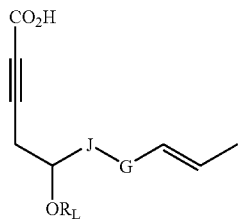

wherein $R_L$, J, and G are as defined above, with a chiral component having the structure:

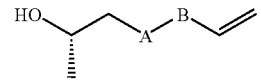

wherein A and B are as defined above, in the presence of an esterification reagent to generate an intermediate having the structure:

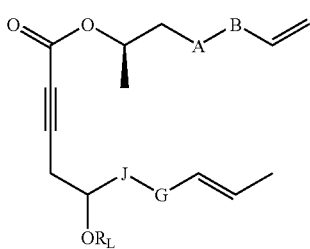

(2) complexing the intermediate with a cobalt, such as dicobalt hexcarbonyl, to yield a structure:

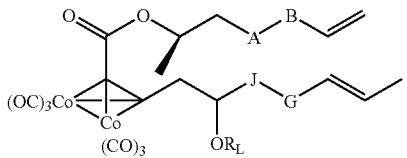

(3) cyclizing the combalt complex in the presence of an olefin metathesis catalyst to generate the compound:

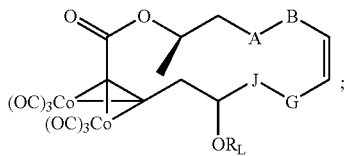

(4) removing the cobalt to form a ynolide;
(5) reacting the alkyne moiety of the ynolide with a diene under cyclcoaddition conditions to generate the compound:

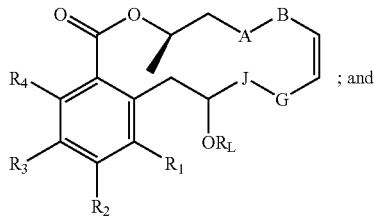

(6) optionally further reacting the macrocycle with one or more reagents to diversify and optionally deprotecting the macrocycle to generate a compound having the formula (I).

Thus, in addition to providing aigialomycin D as described above and herein, the present invention additionally provides a method for the synthesis of compounds having the general structure (IIa):

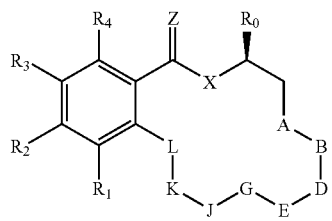

(IIa)

wherein $R_0$ is hydrogen, halogen, cyano, $-OR_Z$, $-N(R_Z)_2$, $-SR_Z$, $-O(C=O)R_Z$, $-N(R_Z)(C=O)(R_Z)$, $-C(O)R_Z$, $-C(O)OR_Z$, $-CON(R_Z)_2$, $-OCO_2R_Z$, or an aliphatic, heteroaliphatic, aryl, heteroaryl, alkylaryl, or alkylheteroaryl moiety, wherein each occurrence of $R_Z$ is independently hydrogen, a protecting group, or an aliphatic, heteroaliphatic, aryl, heteroaryl, alkylaryl, or alkylheteroaryl moiety $R_1$ is hydrogen, halogen, cyano, $-OR_A$, $-N(R_A)_2$, $-SR_A$, $-O(C=O)R_A$, $-N(R_A)(C=O)(R_A)$, $-C(O)R_A$, $-C(O)OR_A$, $-CON(R_A)_2$, $-OCO_2R_A$, or an aliphatic, heteroaliphatic, aryl, heteroaryl, alkylaryl, or alkylheteroaryl moiety, wherein each occurrence of $R_A$ is independently hydrogen, a protecting group, or an aliphatic, heteroaliphatic, aryl, heteroaryl, alkylaryl, or alkylheteroaryl moiety;

$R_2$ is hydrogen, halogen, cyano, $-OR_B$, $-N(R_B)_2$, $-SR_B$, $-O(C=O)R_B$, $-N(R_B)(C=O)(R_B)$, $-C(O)R_B$, $-C(O)OR_B$, $-CON(R_B)_2$, $-OCO_2R_B$, or an aliphatic, heteroaliphatic, aryl, heteroaryl, alkylaryl, or alkylheteroaryl moiety, wherein each occurrence of $R_B$ is independently hydrogen, a protecting group or an aliphatic, heteroaliphatic, aryl, heteroaryl, alkylaryl, or alkylheteroaryl moiety;

$R_3$ is hydrogen, halogen, cyano, $-OR_C$, $-N(R_C)_2$, $-SR_C$, $-O(C=O)R_C$, $-N(R_C)(C=O)(R_C)$, $-C(O)R_C$, $-C(O)OR_C$, $-CON(R_C)_2$, $-OCO_2R_C$, or an aliphatic, heteroaliphatic, aryl, heteroaryl, alkylaryl, or alkylheteroaryl moiety, wherein each occurrence of $R_C$ is independently hydrogen, a protecting group, or an aliphatic, heteroaliphatic, aryl, heteroaryl, alkylaryl, or alkylheteroaryl moiety;

$R_4$ is hydrogen, halogen, cyano, $-OR_D$, $-N(R_D)_2$, $-SR_D$, $-O(C=O)R_D$, $-N(R_D)(C=O)(R_D)$, $-C(O)R_D$, $-C(O)OR_D$, $-CON(R_D)_2$, $-OCO_2R_D$, or an aliphatic, heteroaliphatic, aryl, heteroaryl, alkylaryl, or alkylheteroaryl moiety, wherein each occurrence of $R_D$ is independently hydrogen, a protecting group or an aliphatic, heteroaliphatic, aryl, heteroaryl, alkylaryl, or alkylheteroaryl moiety;

Z is O, S, or $NR_E$, wherein $R_E$ is hydrogen, a protecting group, an aliphatic, heteroaliphatic, aryl, heteroaryl, alkylaryl, or alkylheteroaryl moiety, or $OR_F$, wherein $R_F$ is hydrogen, a protecting group, an aliphatic, heteroaliphatic, aryl, heteroaryl, alkylaryl, or alkylheteroaryl moiety;

X is O, S or $NR_G$, wherein $R_G$ is hydrogen or lower alkyl;

A and B together represent

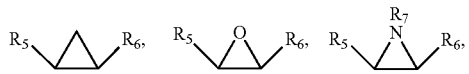

$-CHR_5-CHR_6-$, $-CR_5=CR_6-$, wherein $R_5$ and $R_6$ are each independently hydrogen, halogen, cyano, $-OR_J$, $-N(R_J)_2$, $-SR_J$, $-O(C=O)R_J$, $-O(S=O)R_J$, $-N(R_J)(C=O)(R_J)$, $-C(=O)R_J$, $-C(=O)OR_J$, $-CON(R_J)_2$, $-OCO_2R_J$, $-OS(=O)OR_J$ or an aliphatic, heteroaliphatic, aryl, heteroaryl, alkylaryl, or alkylheteroaryl moiety, wherein each occurrence of $R_J$ is independently hydrogen, a protecting group, or an aliphatic, heteroaliphatic, aryl, heteroaryl, alkylaryl, or alkylheteroaryl moiety, and wherein $R_7$ is hydrogen, a protecting group, $-OR_K$, $-SR_K$, $-C(O)OR_K$, $-C(O)NR_K$, $-S(O)_2R_K$, $-O(C=O)R_K$, $-N(R_K)(C=O)(R_K)$, $-C(O)R_K$, $-C(O)OR_K$, $-CON(R_K)_2$, $-OCO_2R_K$, or an aliphatic, heteroaliphatic, aryl, heteroaryl, alkylaryl, or alkylheteroaryl moiety, wherein each occurrence of $R_K$ is independently hydrogen, a protecting group or an aliphatic, heteroaliphatic, aryl, heteroaryl, alkylaryl, or alkylheteroaryl moiety, or when A and B together represent $-CHR_5-CHR_6-$, $R_5$ and $R_6$ taken together represent a substituted or unsubstituted 3–7 membered aliphatic, heteroaliphatic, aryl or heteroaryl ring, D and E together represent

—CHR$_8$—CHR$_9$—, —CR$_8$=CR$_9$—, wherein R$_8$ and R$_9$ are each independently hydrogen, halogen, cyano, —OR$_J$, —N(R$_J$)$_2$, —SR$_J$, —O(C=O)R$_J$, —O(S=O)R$_J$, —N(R$_J$)(C=O)(R$_J$), —C(=O)R$_J$, —C(=O)OR$_J$, —CON(R$_J$)$_2$, —OCO$_2$R$_J$, —OS(=O)OR$_J$ or an aliphatic, heteroaliphatic, aryl, heteroaryl, alkylaryl, or alkylheteroaryl moiety, wherein each occurrence of R$_J$ is independently hydrogen, a protecting group, or an aliphatic, heteroaliphatic, aryl, heteroaryl, alkylaryl, or alkylheteroaryl moiety, and wherein R$_{10}$ is hydrogen, a protecting group, —OR$_K$, —SR$_K$, —C(O)OR$_K$, —C(O)NR$_K$, —S(O)$_2$R$_K$, —O(C=O)R$_K$, —N(R$_K$)(C=O)(R$_K$), —C(O)R$_K$, —C(O)OR$_K$, —CON(R$_K$)$_2$, —OCO$_2$R$_K$, or an aliphatic, heteroaliphatic, aryl, heteroaryl, alkylaryl, or alkylheteroaryl moiety, wherein each occurrence of R$_K$ is independently hydrogen, a protecting group or an aliphatic, heteroaliphatic, aryl, heteroaryl, alkylaryl, or alkylheteroaryl moiety, or when A and B together represent —CHR$_8$—CHR$_9$—, R$_9$ and R$_9$ taken together represent a substituted or unsubstituted 3–7 membered aliphatic, heteroaliphatic, aryl or heteroaryl ring;

G and J together represent

—CHR$_{11}$—CHR$_{12}$—, —CR$_{11}$=CR$_{12}$—, wherein R$_{11}$ and R$_{12}$ are each independently hydrogen, halogen, cyano, —OR$_J$, —N(R$_J$)$_2$, —SR$_J$, —O(C=O)R$_J$, —O(S=O)R$_J$, —N(R$_J$)(C—O)(R$_J$), —C(=O)R$_J$, —C(=O)OR$_J$, —CON(R$_J$)$_2$, —OCO$_2$R$_J$, —OS(=O)OR$_J$ or an aliphatic, heteroaliphatic, aryl, heteroaryl, alkylaryl, or alkylheteroaryl moiety, wherein each occurrence of R$_J$ is independently hydrogen, a protecting group, or an aliphatic, heteroaliphatic, aryl, heteroaryl, alkylaryl, or alkylheteroaryl moiety, and wherein R$_{13}$ is hydrogen, a protecting group, —OR$_K$, —SR$_K$, —C(O)OR$_K$, —C(O)NR$_K$, —S(O)$_2$R$_K$, —O(C=O)R$_K$, —N(R$_K$)(C=O)(R$_K$), —C(O)R$_K$, —C(O)OR$_K$, —CON(R$_K$)$_2$, —OCO$_2$R$_K$, or an aliphatic, heteroaliphatic, aryl, heteroaryl, alkylaryl, or alkylheteroaryl moiety, wherein each occurrence of R$_K$ is independently hydrogen, a protecting group or an aliphatic, heteroaliphatic, aryl, heteroaryl, alkylaryl, or alkylheteroaryl moiety, or when A and B together represent —CHR$_{11}$—CHR$_{12}$—, R$_{11}$ and R$_{12}$ taken together represent a substituted or unsubstituted 3–7 membered aliphatic, heteroaliphatic, aryl or heteroaryl ring;

K and L together represent

—CHR$_{14}$—CHR$_{15}$—, —CR$_{14}$=CR$_{15}$—, wherein R$_{14}$ and R$_{15}$ are each independently hydrogen, halogen, cyano, —OR$_J$, —N(R$_J$)$_2$, —SR$_J$, —O(C=O)R$_J$, —O(S=O)R$_J$, —N(R$_J$)(C=O)(R$_J$), —C(=O)R$_J$, —C(=O)OR$_J$, —CON(R$_J$)$_2$, —OCO$_2$R$_J$, —OS(=O)OR$_J$ or an aliphatic, heteroaliphatic, aryl, heteroaryl, alkylaryl, or alkylheteroaryl moiety, wherein each occurrence of R$_J$ is independently hydrogen, a protecting group, or an aliphatic, heteroaliphatic, aryl, heteroaryl, alkylaryl, or alkylheteroaryl moiety, and wherein R$_{16}$ is hydrogen, a protecting group, —OR$_K$, —SR$_K$, —C(O)OR$_K$, —C(O)NR$_K$, —S(O)$_2$R$_K$, —O(C=O)R$_K$, —N(R$_K$)(C=O)(R$_K$), —C(O)R$_K$, —C(O)OR$_K$, —CON(R$_K$)$_2$, —OCO$_2$R$_K$, or an aliphatic, heteroaliphatic, aryl, heteroaryl, alkylaryl, or alkylheteroaryl moiety, wherein each occurrence of R$_K$ is independently hydrogen, a protecting group or an aliphatic, heteroaliphatic, aryl, heteroaryl, alkylaryl, or alkylheteroaryl moiety, or when A and B together represent —CHR$_{14}$—CHR$_{15}$—, R$_{14}$ and R$_{15}$ taken together represent a substituted or unsubstituted 3–7 membered aliphatic, heteroaliphatic, aryl or heteroaryl ring;

whereby each of the foregoing aliphatic and heteroaliphatic moieties may independently be substituted or unsubstituted, cyclic or acyclic, or branched or unbranched, and each aryl, heteroaryl, alkylaryl, and alkylheteroaryl moiety may be substituted or unsubstituted, said method comprising:

(1) reacting a component having the structure:

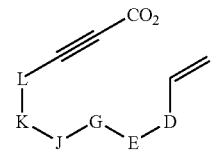

wherein R$_L$, J, and G are as defined above, with a chiral component having the structure:

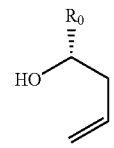

wherein A, B, D, E, G, J, K, and L are as defined above, in the presence of an esterification reagent to generate an intermediate having the structure:

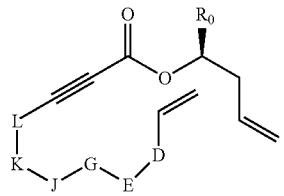

(2) complexing the intermediate with a cobalt, such as dicobalt hexcarbonyl, to yield a structure:

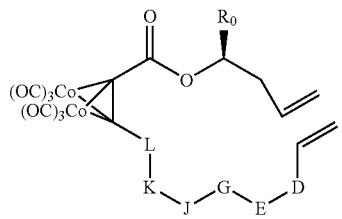

(3) cyclizing the combalt complex in the presence of an olefin metathesis catalyst to generate the compound:

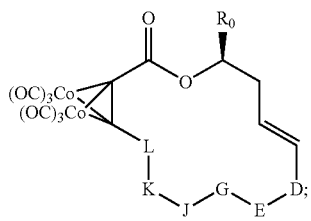

(4) removing the cobalt to form a ynolide;

(5) reacting the alkyne moiety of the ynolide with a diene under cyclcoaddition conditions to generate the compound:

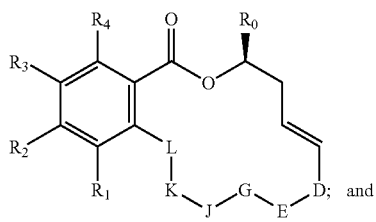

(6) optionally further reacting the macrocycle with one or more reagents to diversify and optionally deprotecting the macrocycle to generate a compound having the formula (IIa).

In addition to the general method described and depicted above, the present invention provides additional synthetic methods, and compounds, as described herein, in which each of the intermediate steps and intermediate compounds are provided, as described below and generically herein. It will be appreciated that the classes, and subclasses, as described above for the inventive compounds are also intended to encompass the inventive methods and intermediate compounds as described above and herein. Thus, certain classes and subclasses of interest in which the moieties $R_0$–$R_4$, Z, X, A—B, D—E, G—J and K—L are specifically defined (and moieties defined within those definitions) also apply to the inventive methods and intermediate compounds. It will be appreciated that certain exemplary species of the compounds of formula (I) and (IIa) and intermediates thereto are described herein, but are not limited to those species.

In certain embodiments, if any one or more of $R_0$–$R_4$ is a protected thio, amino or hydroxyl group, the method further comprises optionally deprotecting said unprotected group.

In still other embodiments, the method optionally further comprises reacting the intermediates with one or more reagents to diversify the macrocycle and generate a compound having the structure (I) or (IIa). In one embodiment, the one or more positions on the benzene ring are halogenated (e.g., chlorinated). In yet other embodiments, the method further comprises optionally deprotecting the compound having the structure (I) or (IIa), to generate a deprotected compound having the structure (I) or (IIa).

It will also be appreciated that each of the steps as described above can be carried out using reagents and conditions as described for the synthesis of radicicol or aigialomycins (as described below in the Examples), or they may be modified using other available reagents. For example, a variety of esterification conditions and olefin metathesis conditions are well-known in the art and can be utilized in the method of the invention. See generally, March, *Advanced Organic Chemistry*, John Wiley & Sons, 1992.

As mentioned above, it will also be appreciated that each of the components used in the synthesis of analogues can be diversified either before synthesis or alternatively after the construction of the macrocycle. As used herein, the term "diversifying" or "diversify" means reacting an inventive compound or intermediate, as defined herein, at one or more reactive sites to modify a functional moiety or to add a functional moiety. For example, the aromatic ring can be diversified to either add functionality (e.g., where hydrogen is present, a halogen, e.g., Cl, can be added) or to modify functionality (e.g., where a hydroxyl group is present on the aromatic ring, the aromatic ring can be diversified by reacting with a reagent to protect the hydroxyl group, or in another example, by reacting with a reagent to add a linker moiety that has a conjugate (e.g., geldanamycin, etc.) attached thereto). Described generally below are a variety of schemes to assist the reader in the synthesis of a variety of analogues, either by diversification of the intermediate components or by diversification of the macrocyclic structures.

Figure 10:
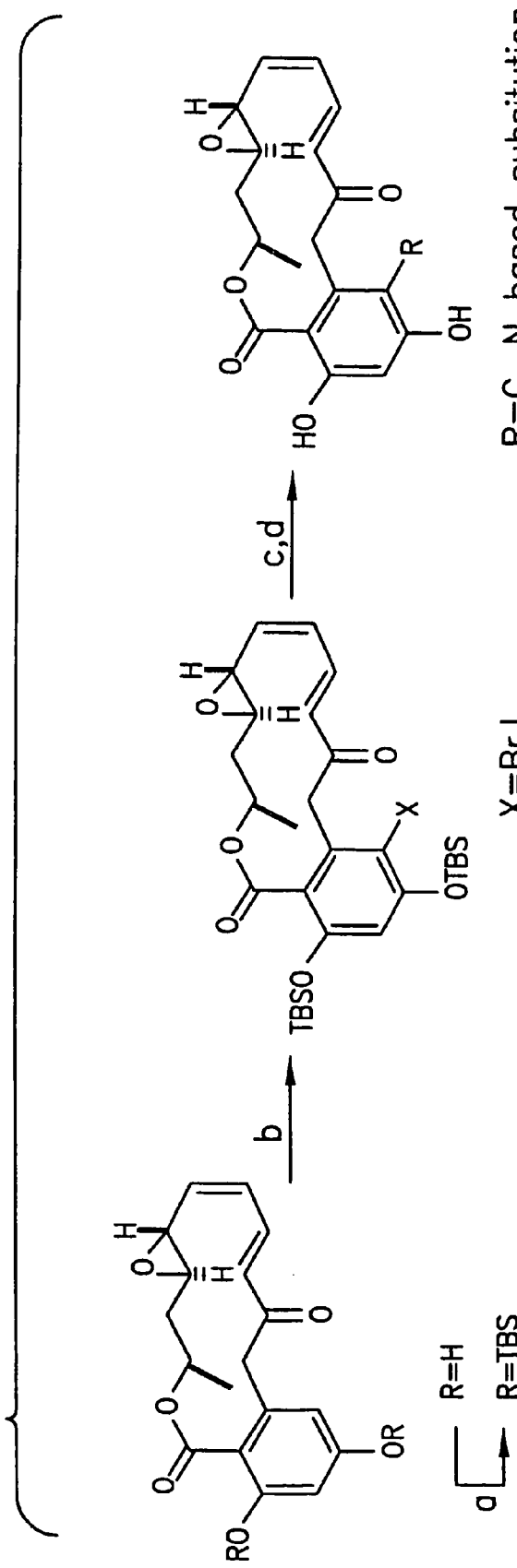
FIG. 10 depicts the generation of diversity at aromatic positions in the macrocycle.
Figures 1, 11:
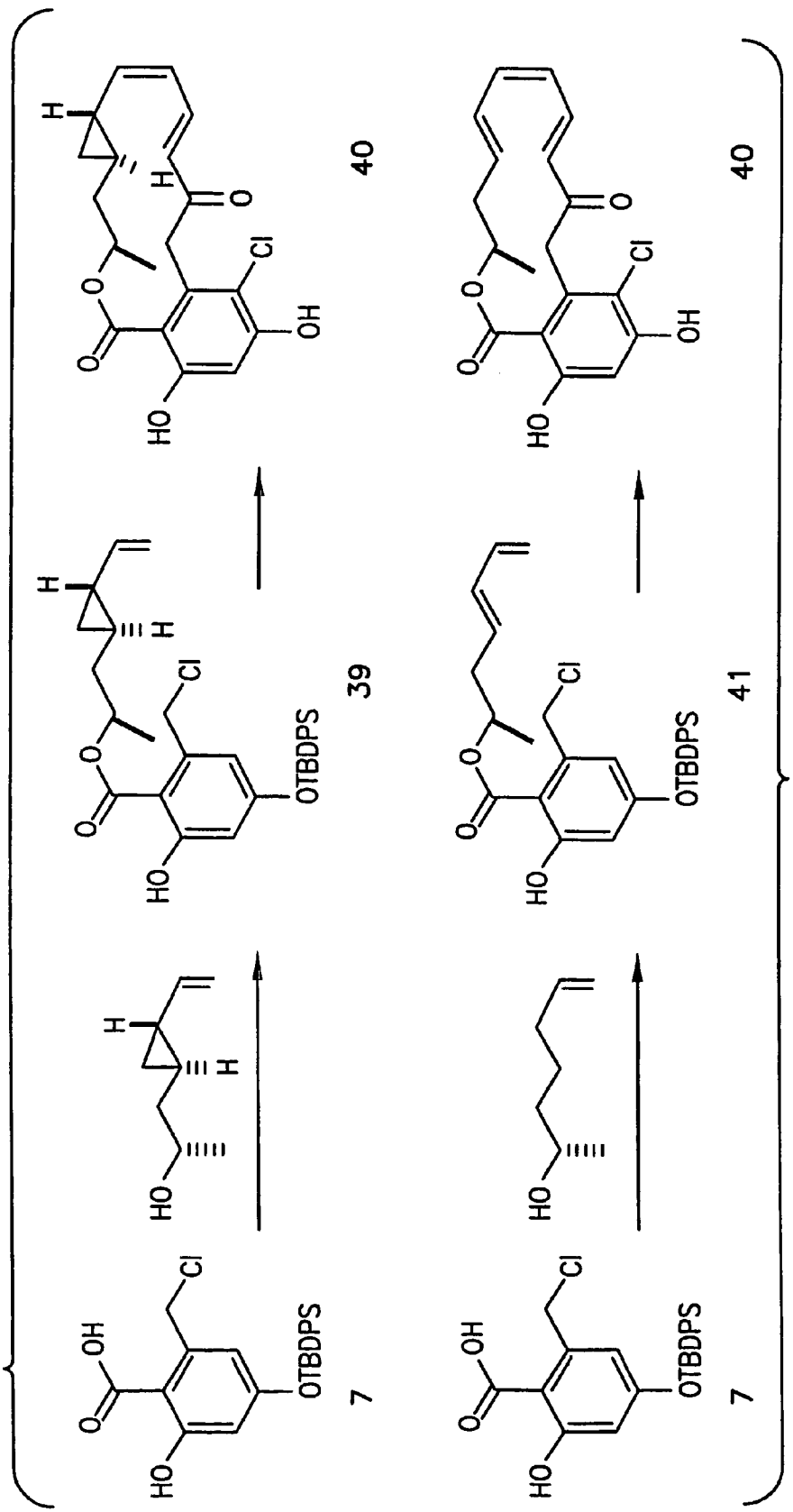
FIG. 11 depicts the synthesis of a variety of analogues (40), (42), (44) and (46).
Figure 11:
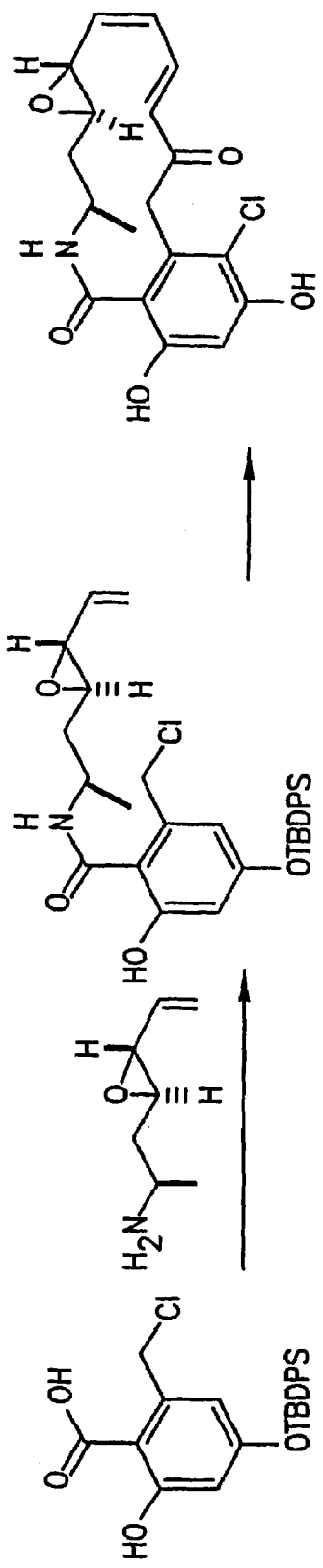
Figure 2:
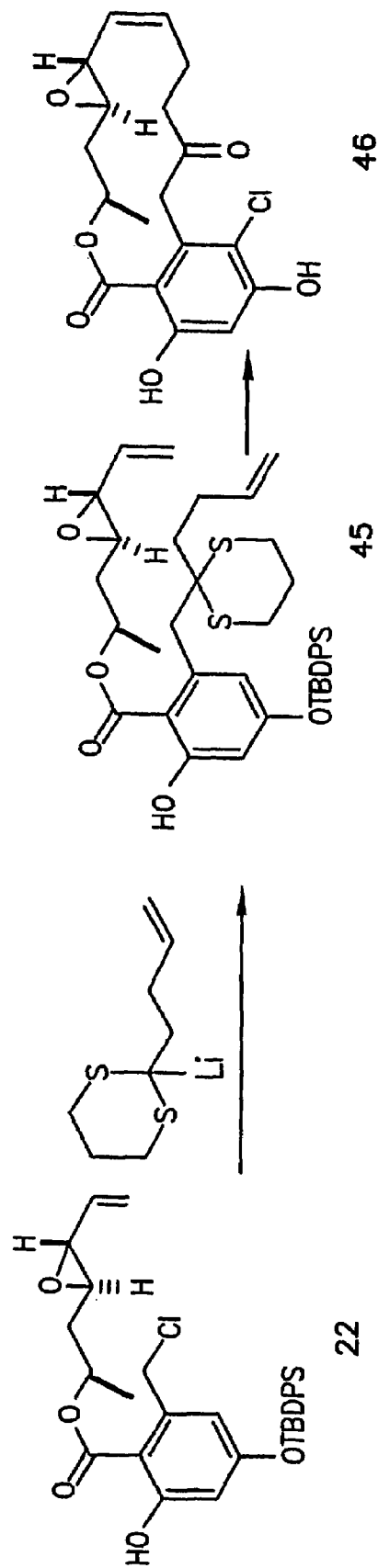
Figures 1, 12:
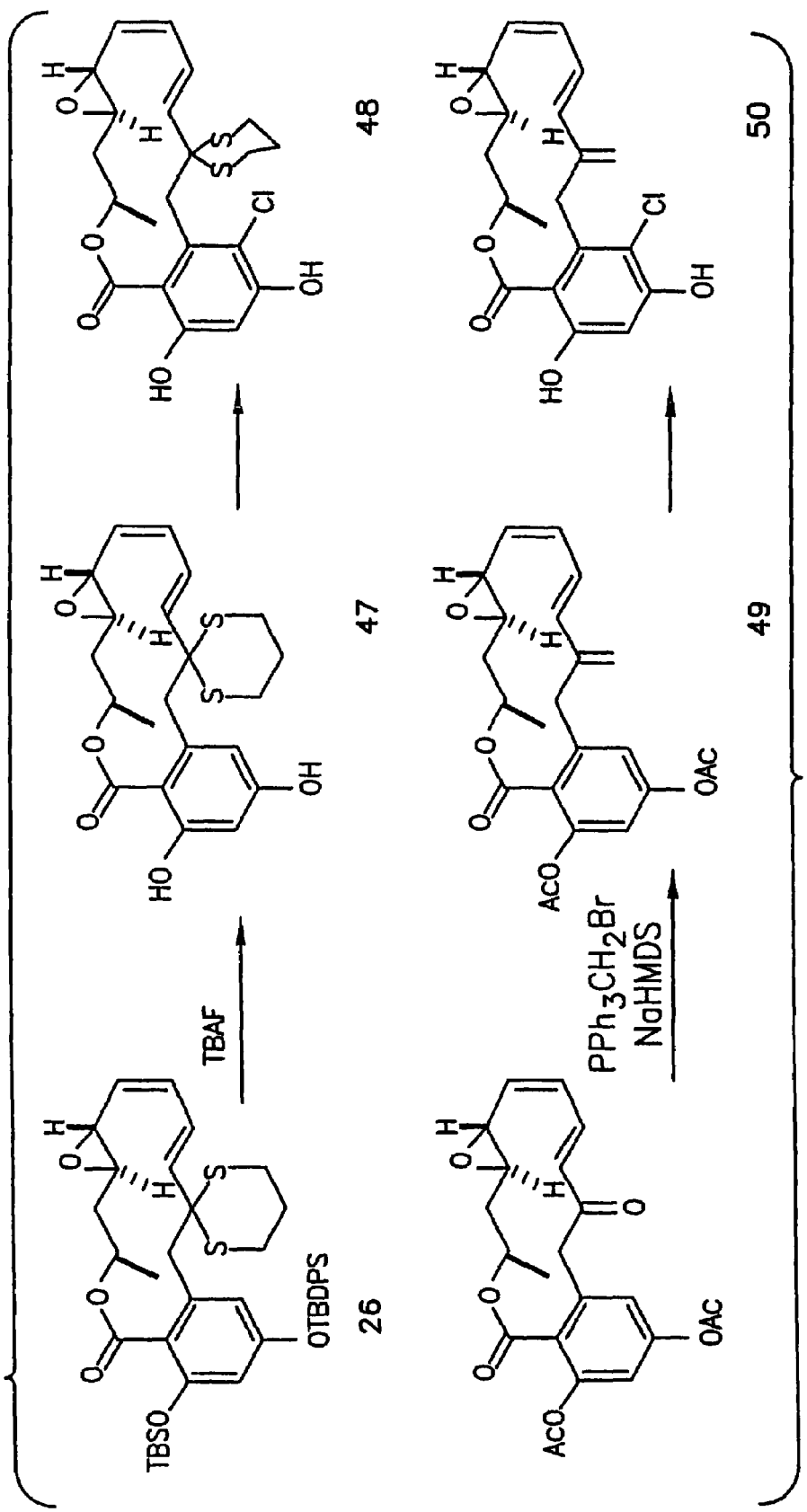
FIG. 12 depicts the synthesis of a variety of analogues (48), (50), (52) and (54).
Figure 13:
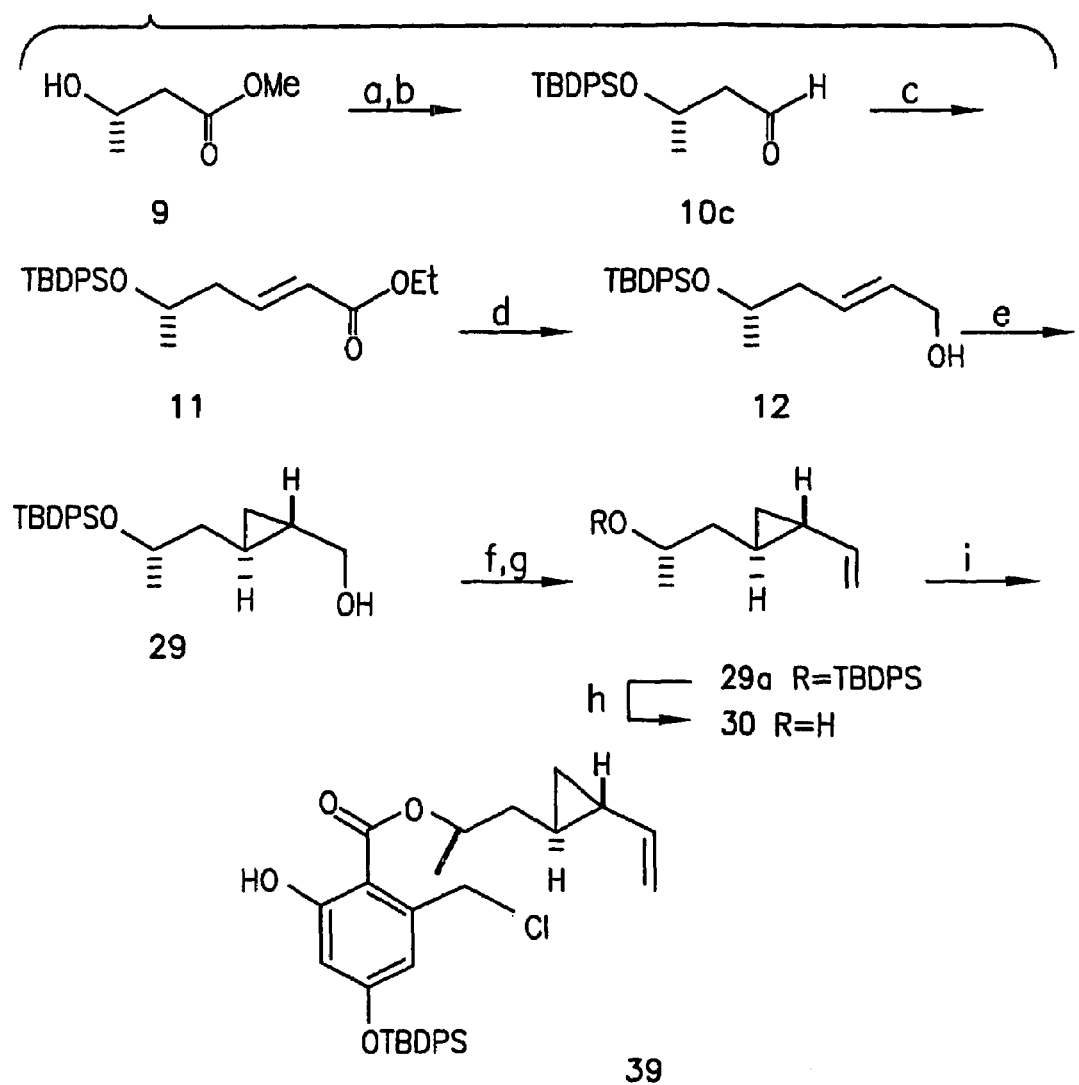
FIG. 13 depicts the synthesis of the chiral cyclopropyl moiety (30) and generation of intermediate (39).
Figure 14:
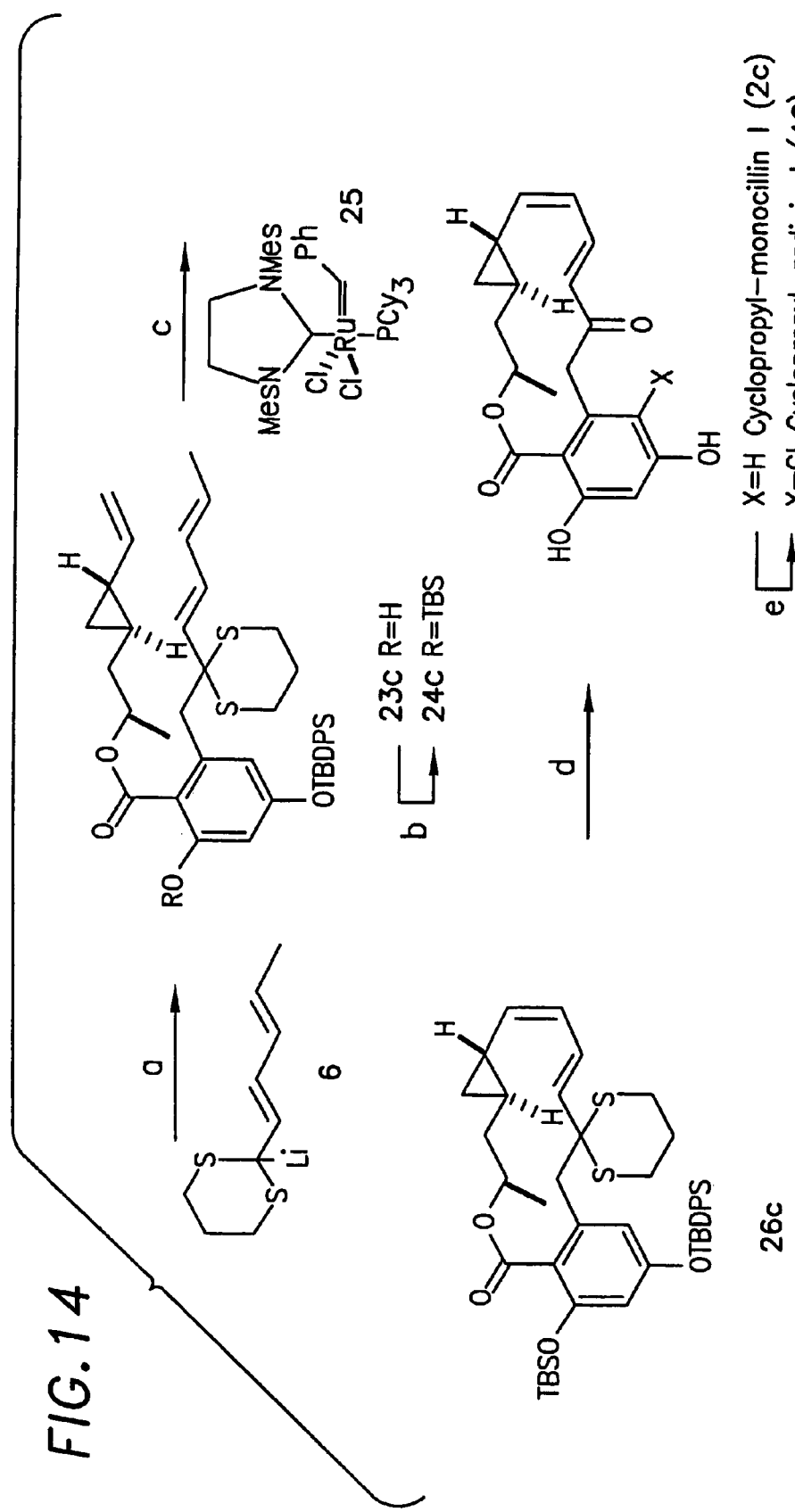
FIG. 14 depicts the synthetic scheme for cyclopropyl-monocillin I (2c) and cyclopropyl-radicicol (40).

The aromatic ring can incorporate numerous changes. Novel Diels Alder methodolgy can be utilized to present different substitution patterns around the benzene ring. It will be appreciated that traditional aromatic synthesis can also be utilized to access permutations on the aromatic core. For example, as shown in FIG. 10, diversity can be generated at aromatic positions, in one embodiment, after generation of the core structure. Specifically, $R_1$ and $R_3$ include substitution patterns arising from a cross-coupling strategy as depicted to enable introduction of amino, aliphatic, heteroaliphatic, aryl, heteroaryl, and alkylheteroaryl moieties.

Another analog serves to replace the labile ester functionality with a stronger amide component. Esterase activity is responsible for the premature metabolism of many potential therapeutic agents, and therefore this analogs aims to prevent this activity. Simple modification of the chiral component and incorporation into this process provides a facile route to an amide analog.

Figures 1, 15:
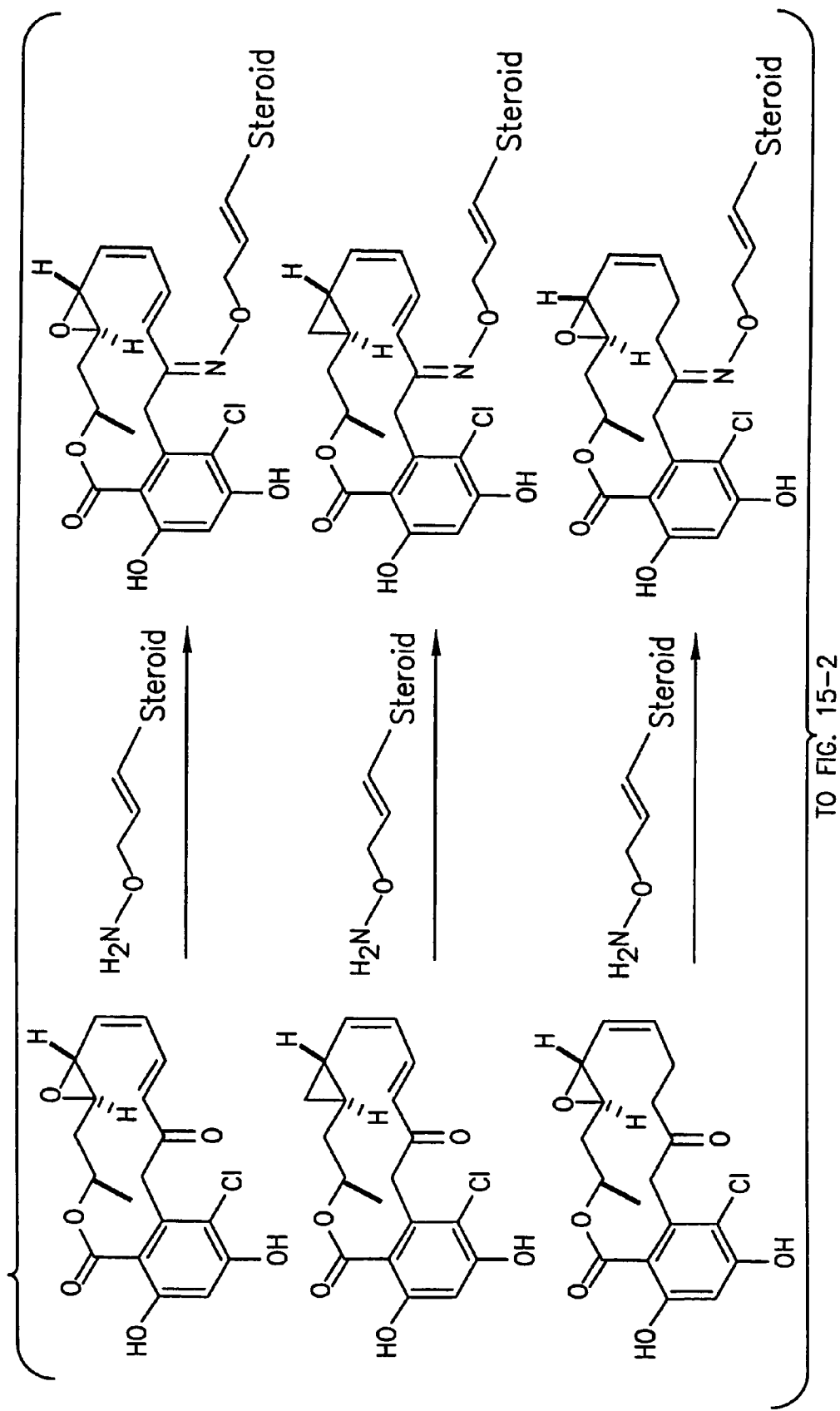
FIG. 15 depicts the synthesis of a variety of inventive conjugates.

As detailed above, a variety of reactions can be utilized to diversify the radicicol and/or monocillin and aigialomycin core structures either during assembly or after assembly of the macrocycle. An alternative strategy endeavours not only to restore in vivo activity and achieve diversity, but also to enhance it. In a fashion similar to that produced with geldanamycin, a number of known steroid hormones can be linked to radicicol and analogs via an oxime technology that has already been shown to restore in vivo activity (see U.S. Pat. No. 6,239,168; U.S. Pat. No. 5,977,165; Soga et al. *Cancer Res.* 1999, 59, 2931–2938; each of which is incorporated herein by reference). The steroid hormones bind specifically to receptors found in important Hsp90 complexes. In addition, dimers of radicicol or heterodimers of radicicol and geldanamycin will be used to probe the activity of bifunctional binding agents on Hsp90 activity (see FIG. 15).

Figures 1, 16:
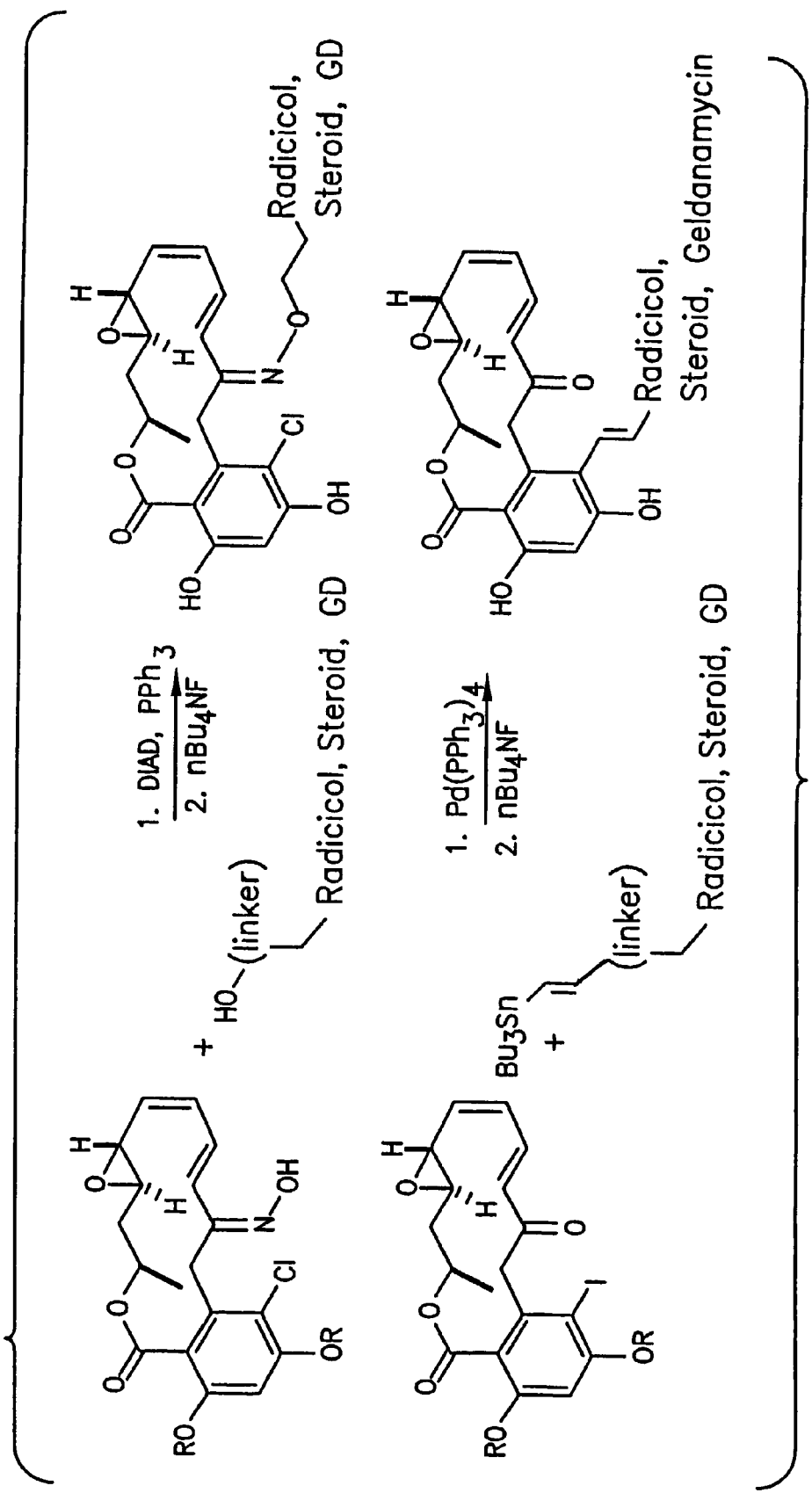
FIG. 16 depicts the synthesis of a variety of inventive conjugates.
Figures 2, 16:
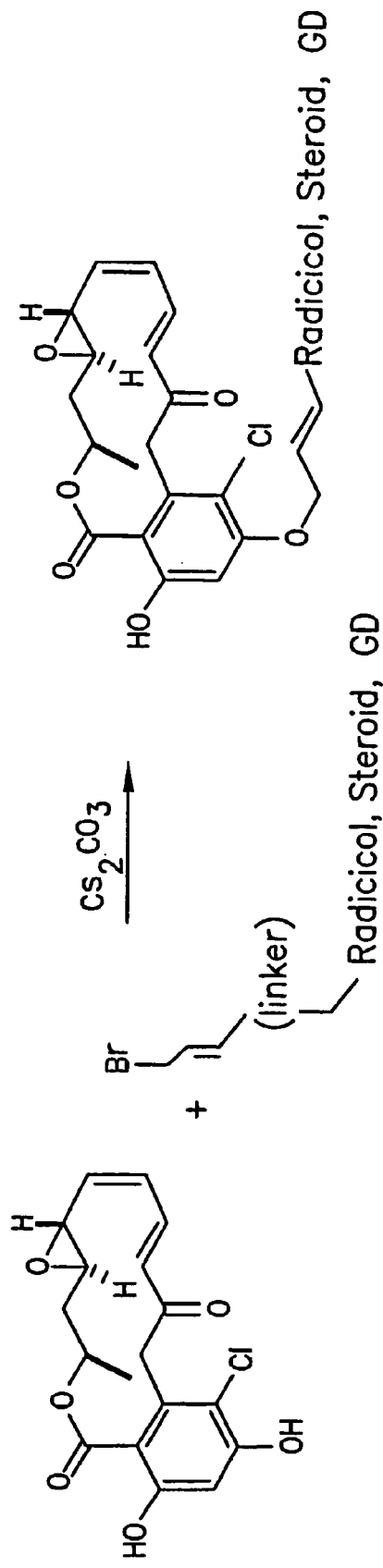

In addition to conjugation via oxime technology as described above and depicted in FIG. 15, it will be appreciated that conjugation can be effected through available functionality on the aromatic ring or through the A—B moiety, as described generally herein. FIG. 16 depicts a variety of methods that can be utilized to effect conjugation.

It will be appreciated that a variety of linkers can be utilized to effect conjugation of geldanamycin, radicicol, monocillin and analogues thereof and steroids to the inventive compounds. As described above, any one or any two of $R_1$, $R_A$, $R_2$, $R_B$, $R_3$, $R_C$, $R_4$, $R_D$, $R_5$, $R_6$, $R_J$, or $R_L$ may potentially be a site for conjugation and conjugation can be effected through a linker covalently bonded to a compound to be conjugated. The term "linker" as used herein, is intended to encompass a chemical moiety that is capable of effecting a stable (e.g., sufficiently unhindered that the conjugation can be performed) covalent linkage between an inventive compound as described herein, and another conjugate (geldanamycin, radicicol, monocillin, analogues thereof as described herein and elsewhere) and steroids. It will be appreciated that a variety of linkers can be utilized, including, but not limited to heteroatom linkages (e.g., O—S(=O)O, —O—(C=O)—O—, heteroalkyl, etc.), and aliphatic or heteroaliphatic linkages, in which the aliphatic and heteroaliphatic linkages may be substituted or unsubstituted, branched or unbranched, or cyclic or acyclic. In certain embodiments for the compounds as described above, the linker is an aliphatic or heteroaliphatic moiety, whereby said aliphatic or heteroaliphatic moiety is substituted or unsubstituted, branched or unbranched, or cyclic or acyclic. For example, it will be appreciated that this linker may be of varying length, and that altering the length of the linker may, in certain circumstances, confer a therapeutic benefit. In general, the linker may be 1–12 carbon atoms in length, and may also be 1–10, 1–6, or 1–4 carbon atoms in length, in other embodiments of special interest. As described above, the linker may be a linear chain or a substituted chain, for example incorporating double or triple bonds, an aryl group or a secondary or tertiary amine. In certain other embodiments for the compounds as described above, the linker is a moiety having one of the structures —$(CH_2)_n$—CH=CH—$(CH_2)_m$, —$(CH_2)_p$—C≡C—$(CH_2)_q$—, or —$CH_2(CH_2)_s$ $CH_2$—, wherein each occurrence of n, m, p, q and s is independently an integer from 0–10. As described generally above, it will be appreciated that one or more of the hydrogen atoms may be replaced with a substituent including, but not limited to alkyl, heteroalkyl, secondary or tertiary amine, hydroxyl, thiol, aryl, heteroaryl, alkylaryl, or alkylheteroaryl. Similar dimers, trimers, and conjugates and linkers used for the conjugation thereof are described in more detail in Kuduk et al., *Bioorg. Med. Chem. Lett.* 2000, 10, 1303–1306; Kuduk et al. *Bioorg. Med. Chem. Lett.,* 1999, 9, 1233–1238; Zheng et al. *Cancer Res.* 2000, 60, 2090–2094; and WO00/61578; each of which is incorporated herein by reference). Additional guidance for the preparation of conjugates can be found in U.S. Pat. No. 5,977,165 (which is incorporated herein by reference) (in which, for example, two radiciciol derivatives are linked via —O—S(=O)—O—).

In certain embodiments, the compound to be conjugated is selected from the group consisting of radicicol, monocillin, analogues of radicicol and monocillin, geldanamycin, analogues of geldanamycin, and steroids. In particular, any of the compounds of the present invention may be conjugated with one or two compounds of the same structure or with one or two compounds of different structures, such as geldanamycin, analogues thereof and steroids. The term "analogues", as used herein, is intended to encompass radiciciol analogues as described herein and elsewhere (see, e.g., U.S. Pat. Nos. 5,977,165, 5,731,343, and 5,597,846; each of which is incorporated herein by reference) and geldanamycin analogues generally described in the art (see, e.g., WO00/61578; incorporated herein by reference). It will be appreciated that a variety of steroids can be utilized in the method of the present invention. In certain embodiments, steroids are utilized to develop selective cytotoxic agents directed towards cancer cells that express steroid receptors (e.g., estrogen receptor). Suitable steroids for use in the present invention include, but are not limited to, estradiol, estradiol valerate, estradiol cypionate, ethinyl estradiol, mestranol, quinestrol, estrone, estrone sulfate, equilin, testosterone, androstenedione, dehydroepiandrosterone, estriol 16α-hydroxydehydro-epiandrosterone, and 16α-hydroxyandrostenedione, to name a few.

5) Uses, Formulation and Administration

Pharmaceutical Compositions

As discussed above this invention provides novel compounds which have biological properties which make them of interest for the treatment of cancer, in particular those cancers characterized in that they comprise Rb negative cancer cells. Accordingly, in another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be a cytotoxic agent or anticancer agent approved for the treatment of cancer, as discussed in more detail herein, or it may be any one of a number of agents undergoing approval in the Food and Drug Administration that ultimately obtain approval for the treatment of cancer (e.g., epothilones, geldanamycin, to name a few). It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-viral compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds of the Invention

As described in more detail herein, in general, the present invention provides compounds useful for their ability to inhibit the growth of or kill cancer cells and thus are useful in the treatment of cancer. The compounds of the invention are also useful as inhibitors of Hsp90 and thus are useful, more generally as inhibitors of proteins such as transmembrane receptors (e.g., HER2, androgen receptor, erbB, EGFR, etc.), tyrosine kinases, serine and/or threonine kinases, transcriptional regulators, or of proteins that regulate them. In certain embodiments, the inventive compounds are also useful for the inhibition of the growth of or for the killing of Rb negative cancer cells and thus are useful in the treatment of cancers comprising Rb negative cancer cells. In certain other embodiments, the inventive compounds are also useful for the destruction of cells expressing a HER-family tyrosine kinase. In still other embodiments, the inventive compounds are useful as inhibitors of the androgen receptor.

In general, the unregulated growth characteristic of cancer cells typically results from disruption of a mitogenic signal transduction pathway. Such pathways can be disrupted at any of a number of points, through activation or inhibition of proteins such as transmembrane receptors (e.g., HER2, which is often overexpressed in breast cancers; steroid receptors such as the androgen receptor, which is often overexpressed in prostate cancers; erbB; EGFR; etc.), tyrosine kinases (including those that are domains of transmembrane receptors), serine and/or threonine kinases (e.g., Akt; Raf; Src; etc.), transcriptional regulators (e.g., Rb; STATs; etc.), or of proteins that regulate them. For instance, the molecular chaperone Hsp90 is required for proper folding of a variety of signal transduction proteins, including, for example, steroid receptors, HER2, met, Akt, Raf, etc. When Hsp90 activity is blocked, these proteins are degraded, and mitogenic signal transduction is attenuated.

It has been previously demonstrated that geldanamycin acts as an Hsp90 inhibitor; administration of this compound to tumor cells results in degradation of Hsp90-regulated proteins and arrest in the G1 phase of the cell cycle. Tumors that express high levels of HER2 are particularly sensitive to such agents. For example, treatment of tumors with geldamycin leads to a dose dependent reduction in HER2 levels as well as visible cellular differentiation. Unfortunately, the cell cycle arrest observed after treatment with these compounds is dependent upon the retinoblastoma (Rb) protein. Geldanamycin is currently in Phase II clinical trials, however, geldanamycin has been shown to be ineffective for the treatment of tumor cells with defective Rb function.

Unexpectedly, the present invention demonstrates that radicicol and radicicol analogs function as Hsp90 inhibitors independent of Rb function. Tumor cells treated with these compounds arrest in G1 in the presence of Rb, and arrest in the prometaphase stage of mitosis in the absence of Rb. Unlike geldanamycin, such compounds are therefore useful for the treatment of Rb-positive and Rb-negative cancers. Importantly, there are cancers which currently lack sufficient treatment, and are comprised of Rb negative cells. These include, but are not limited to, small-cell lung carcinoma, glioblastoma (brain) and retinoblastoma (eye). Small-cell lung carcinoma does not have an effective treatment, results in a high mortality rate, and represents 25% of lung cancers. In some embodiments, it may be desirable to combine administration of the inventive compounds described herein with proapoptotic chemotherapeutic agents and/or with radiation therapy in order to encourage arrested cells to enter apoptosis.

Figures 2, 18:
FIG. 18 depicts the results of BT474 cells (HER2 over-expressed, Rb positive) treated with radicicol and analogues. The gels demonstrate reduction of HER2 levels over a range of concentrations.

As demonstrated herein (see FIGS. 17–21), radicicol and certain of its analogues have been tested for their cytotoxicity in a panel of cancer cell lines, and importantly, for their ability to lead to the reduction of HER2. As depicted in FIGS. 17 and 18, four analogues have been tested for their ability to reduce HER2 in MCF7 and BT474 cells. Radicicol (I), monocillin I (II), cyclopropyl radicicol (III) and cyclopropyl monocillin I (IV) were each tested at similar concentrations (0.5 µM through 5 µM). These results demonstrate two previously unknown properties with respect to structure-activity relationships: the aromatic chloride contributes to efficacy, and the oxygen of the epoxide does not, despite its binding implication in the known crystal structure. Radicicol is approximately 10× superior in effecting destruction of Her-2 than monocillin I, which only lacks the aromatic chloride. In addition, the cyclopropane analog (III) is at least as effective, if not better than radicicol merely by replacing the oxygen of the epoxide with a $CH_2$ group. Significantly, currently, the cyclopropane analog can only be made by the route as detailed herein. Furthermore, while the vinyl epoxide, a reactive moiety, may be responsible for undesired cytotoxicity, the cyclopropane is far more stabile to non-productive cellular nucleophiles.

Figure 19:
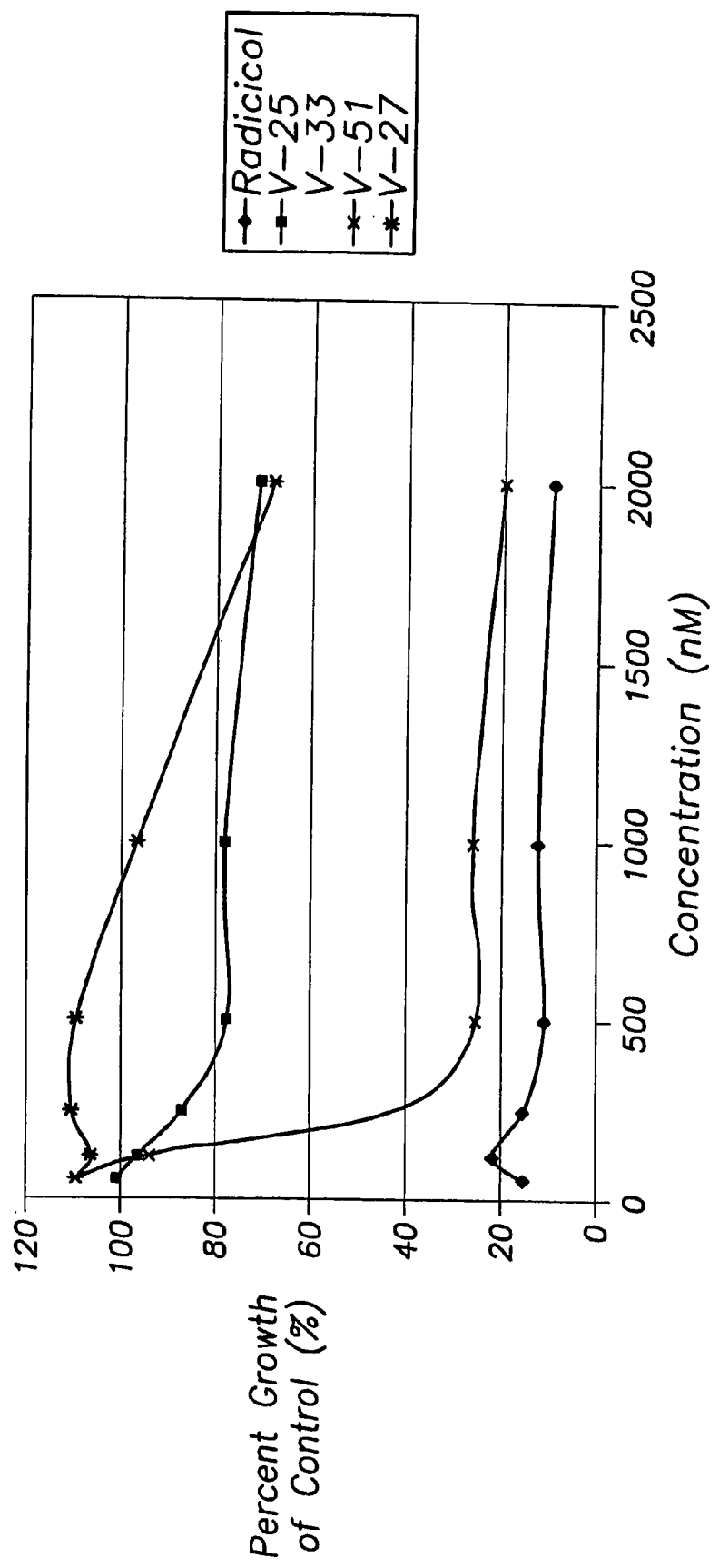
FIG. 19 depicts the growth of MCF7 cells (HER2 over-expressed, Rb positive) treated with radicicol and analogues.

Additionally, the dimethyl ethers of both radicicol and monocillin (V and VI respectively) have been tested, as well as the oxime disclosed by Kyowa Hakko (VII) in a side by side experiment with radicicol. Radicicol again demonstrated efficacy, as did the oxime analog VII which has been reported to also be active in vivo. As shown in FIG. 19, MCF7 cells (HER2 overexpressed, Rb positive) were treated with radicicol (V-27), radicicol oxime (VI-51), dimethyl monocillin (V-25) and dimethyl radicicol (V-33) and the growth of the MCF7 cells was monitored.

As discussed above, the action of geldanamycin and radicicol on Hsp90 in Rb (retinoblastoma) positive cells results in a clear $G_1$ (growth) phase block of the cell cycle, degradation of HER2, and eventual reversion, apoptosis or necrosis. Interestingly, and without a clear explanation, when radicicol is applied to Rb negative cells, the cells are blocked in the M (mitosis) phase. While geldanamycin and its derivatives are demonstrating success in Rb positive cell lines, they are much less effective in their ability to halt growth in the corresponding Rb negative cells. Radicicol and derivatives appear to have an advantage in these Rb negative cell lines as they demonstrate superior efficacy blocking these cells in mitosis.

In addition, it has also been shown that 17-allylaminogeldanamycin (17-AGG), an ansamycin derivative, is much more potent against cells with wild type Rb than in cells with defective Rb function. It has also been shown that radicicol and cyclopropyl radicicol are potent inhibitors of both a breast cancer cell with wild type Rb and a small cell lung cancer cell line with defective Rb function (See FIG. 20). Significantly, they have been found to be much more potent than 17-AGG in the latter cell type. These data suggest that radicicol derivatives are useful in the treatment of the 15–20% of human tumors with mutated Rb gene and especially in small lung cell cancer, in which the gene is almost always mutated.

Figure 20:
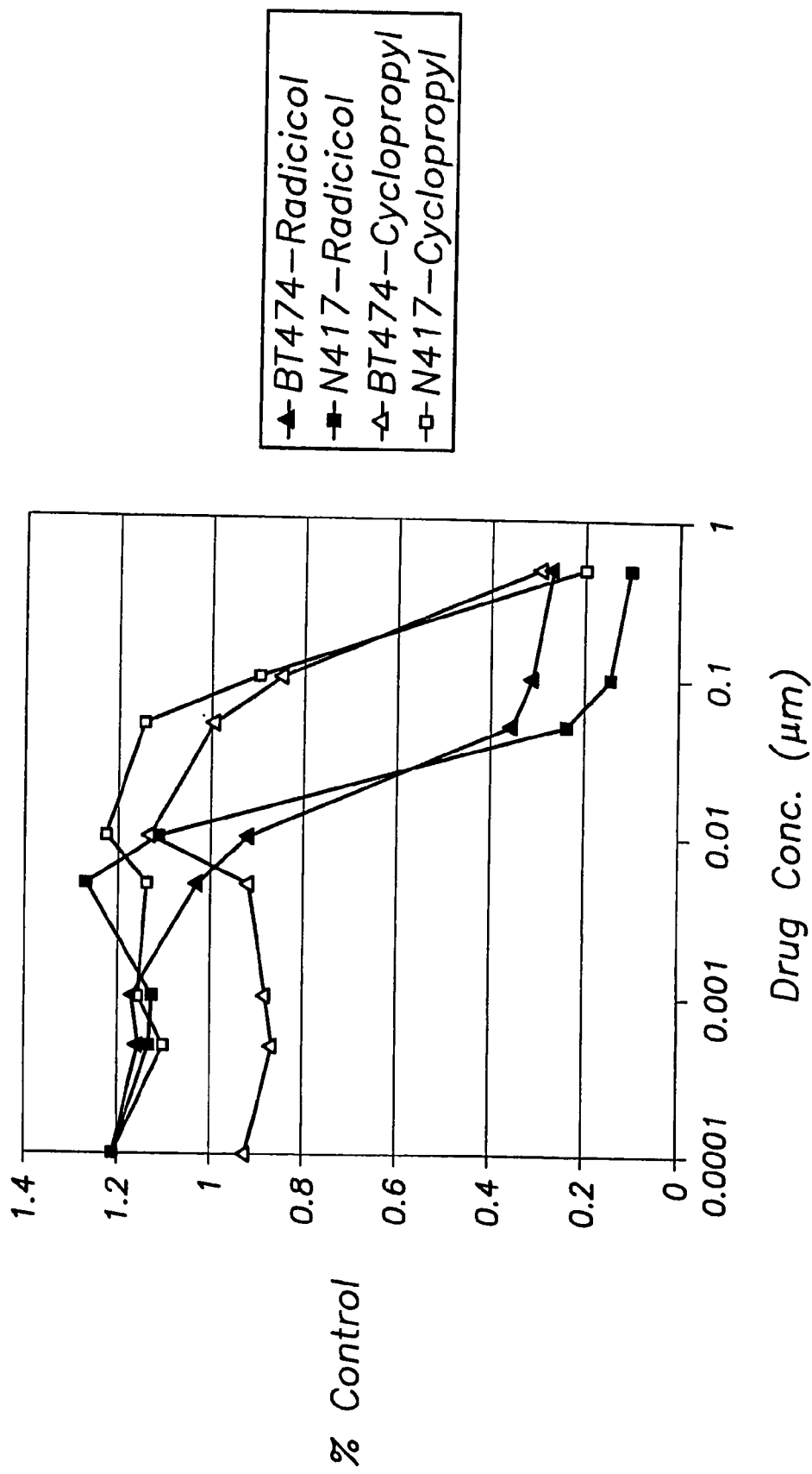
FIG. 20 depicts the ability of radicicol and cyclopropyl radicicol to inhibit breast cancer cells with wild type Rb and small cell lung cancer cells with defective Rb function.
Figure 21:
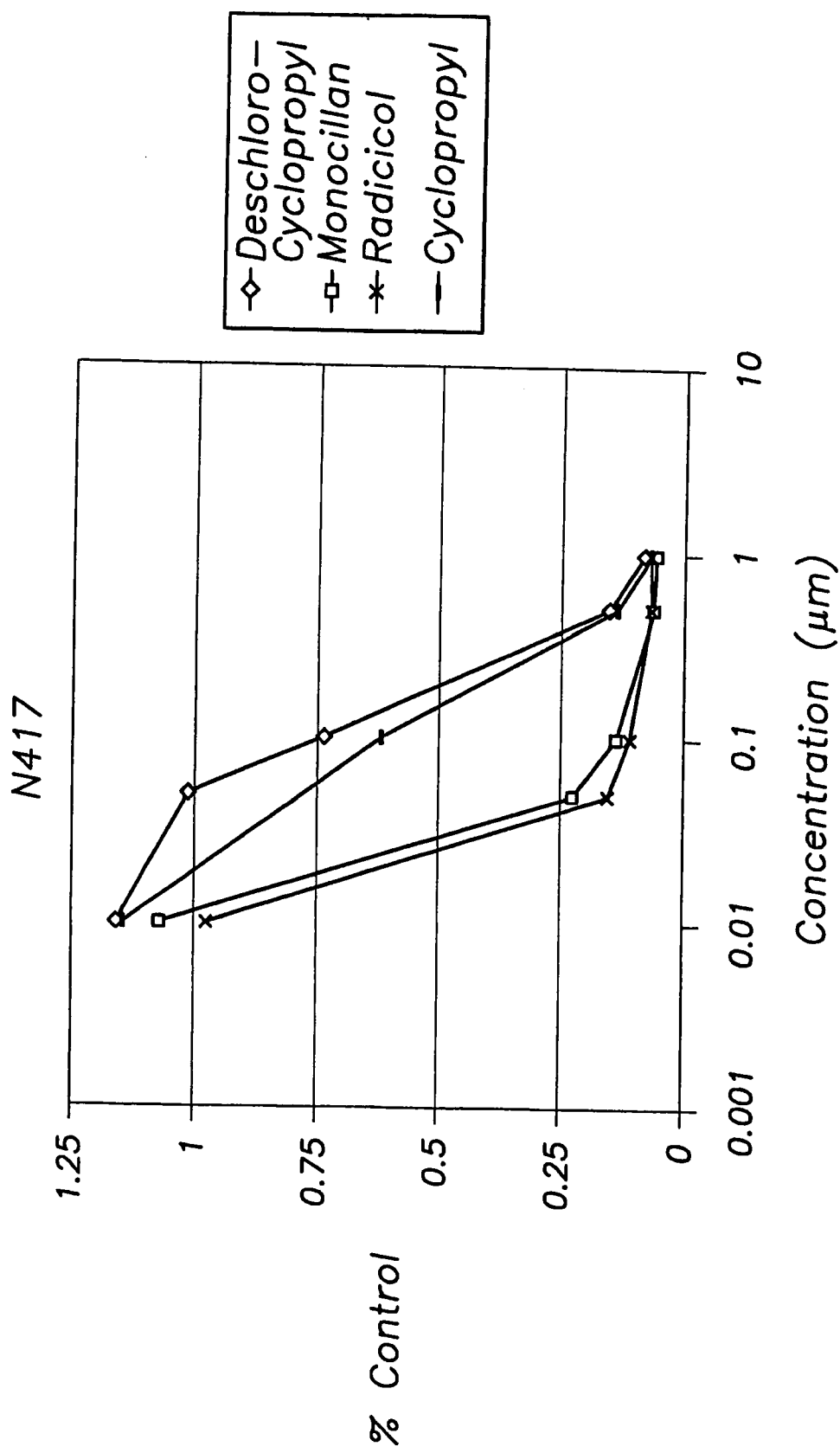
FIG. 21 depicts the growth curve for N417 cells (Rb negative cell line) for radicicol and analogues thereof.
Figure 22:
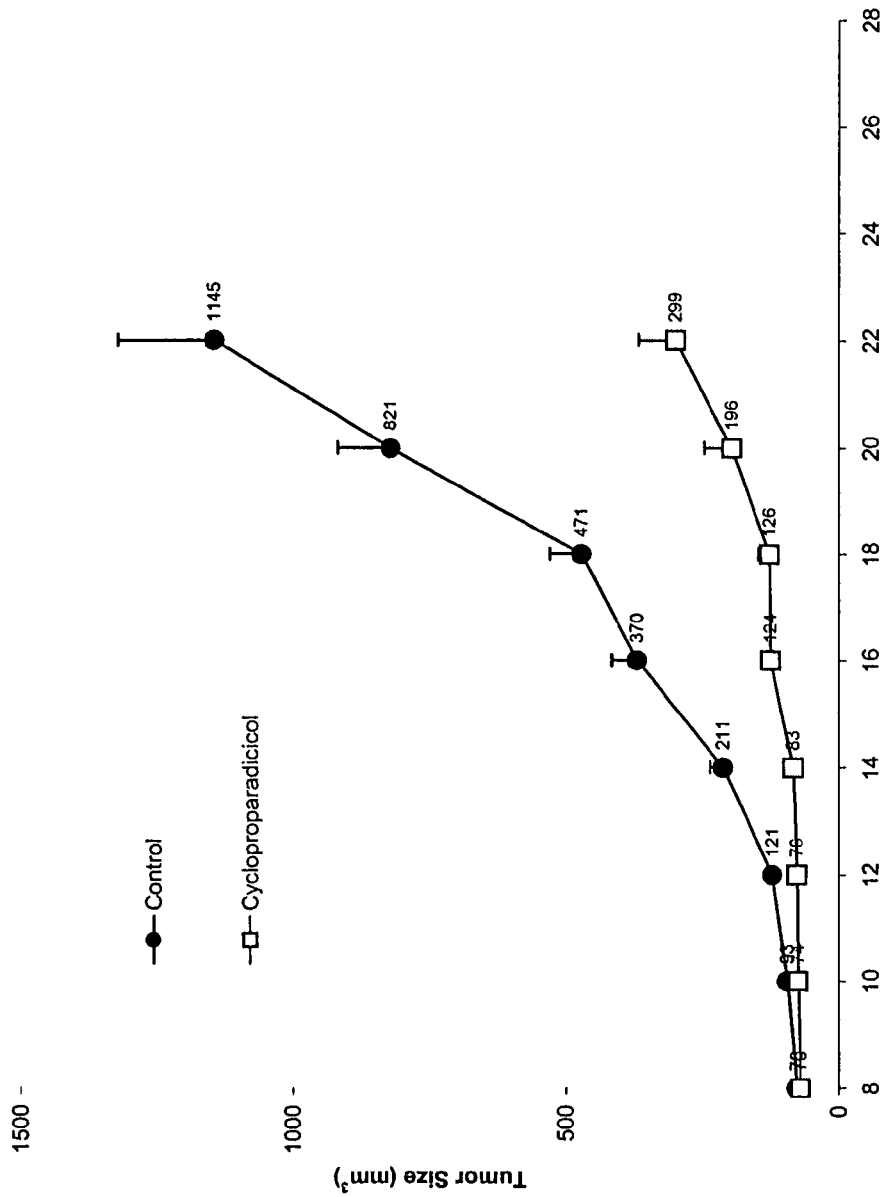
FIG. 22 shows the effect of cycloparadicicol in nude mice bearing human mammary carcinoma MX-1 xenograft (Q2Dx7, iv injection).
Figure 23:
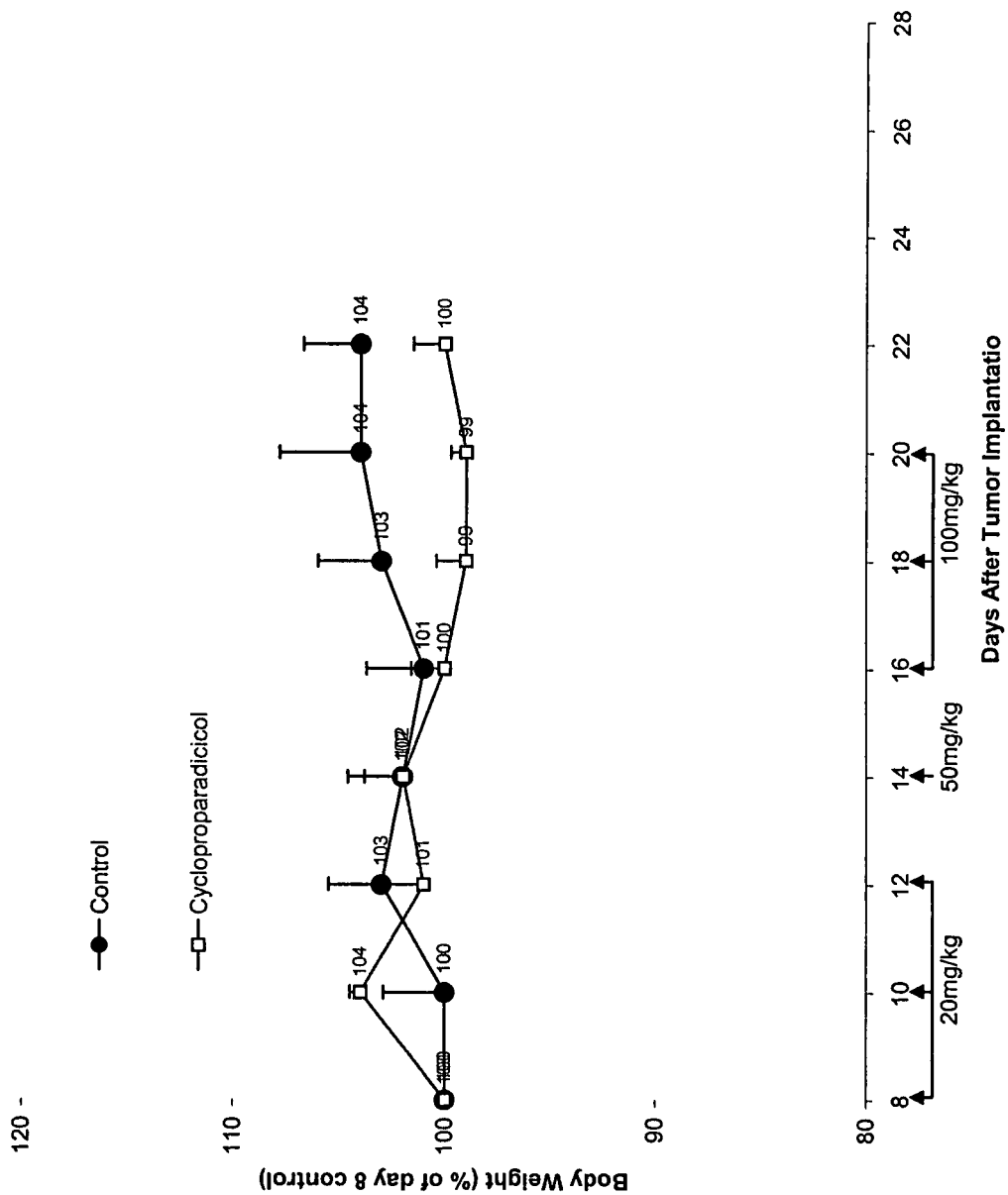
FIG. 23 shows the effect of cycloproparadicicol on body weight.
Figure 24:
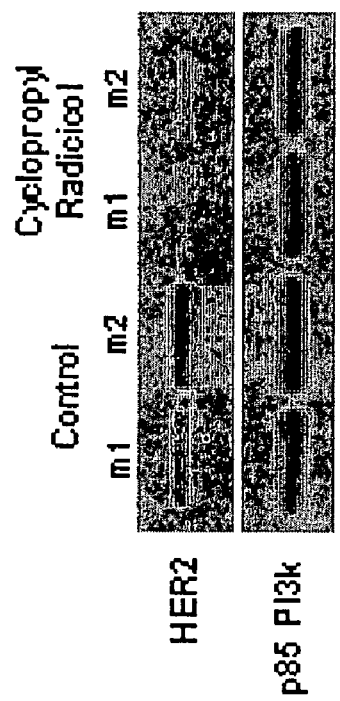
FIG. 24 shows the effect of cycloproparadicicol on HER2 degradation.
Figure 25:
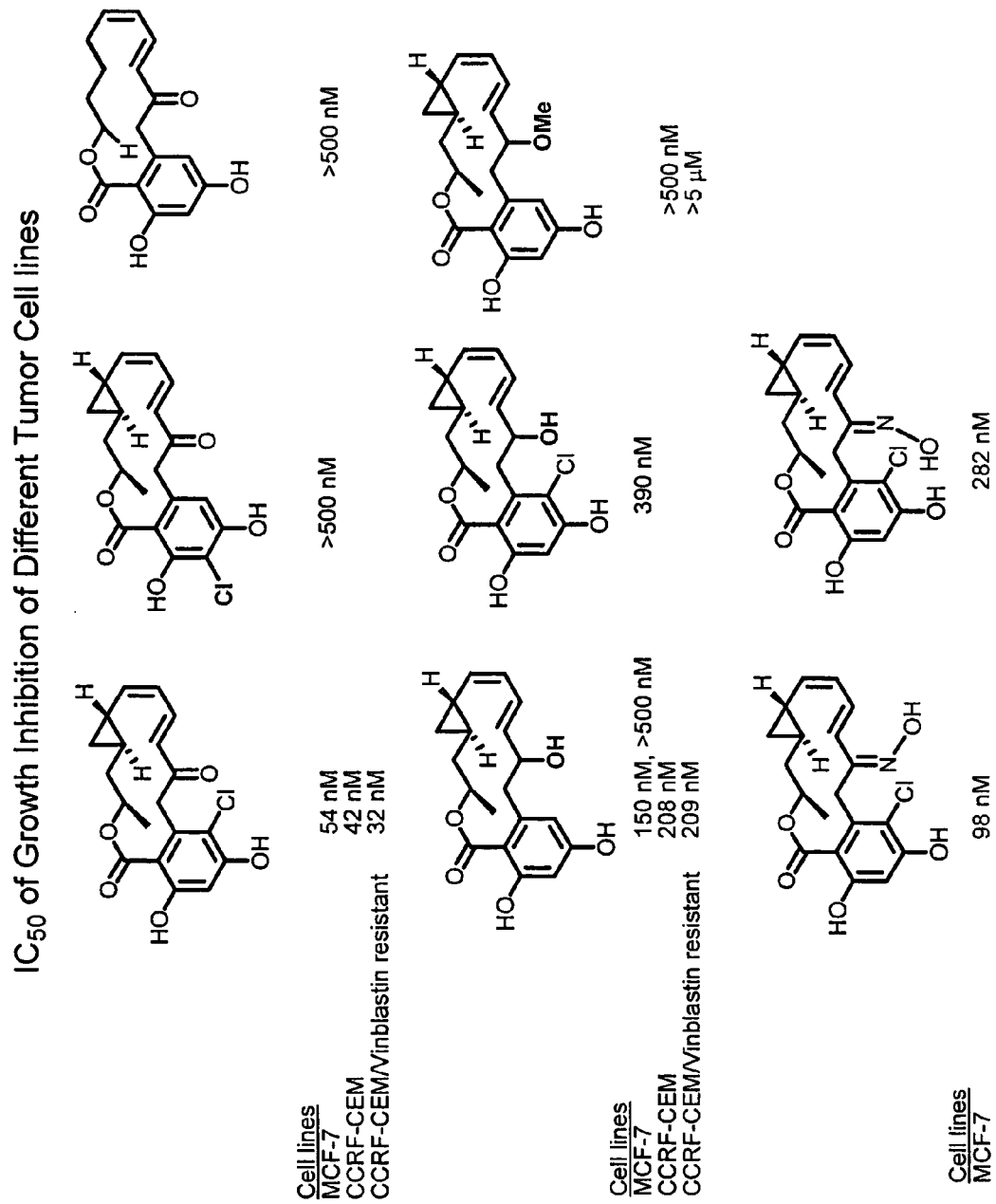
FIG. 25 lists the $IC_{50}$s of various radidicicol analogues on growth inhibition in different tumor cell lines.
Figure 26:
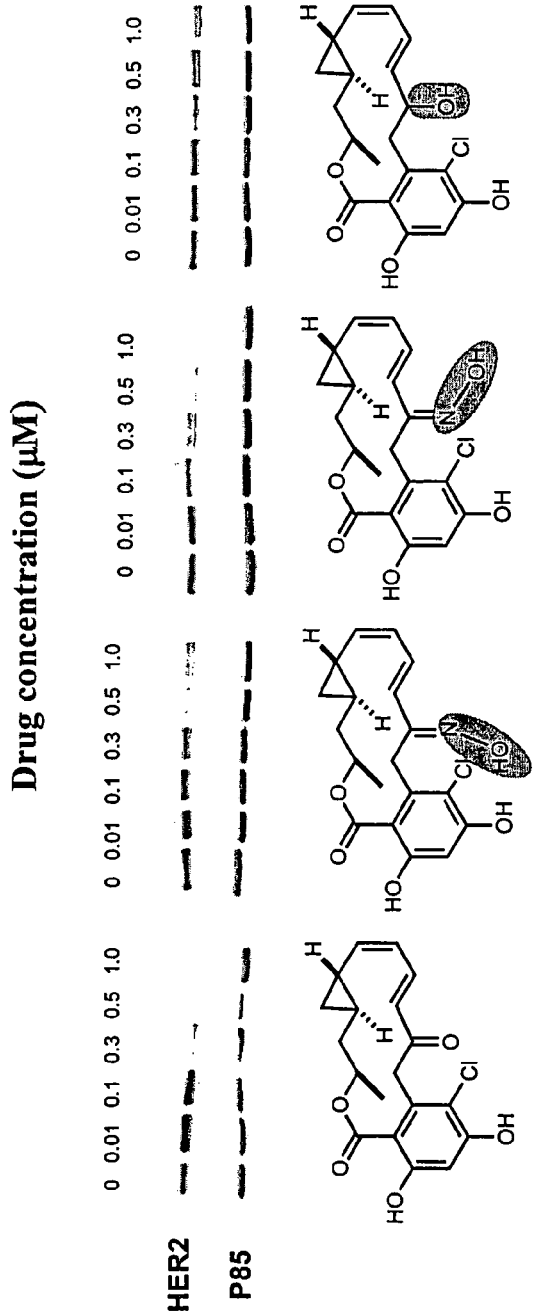
FIG. 26 shows the effect of four different cycloproparadicicol analogues on the degradation of HER2
Figure 27:
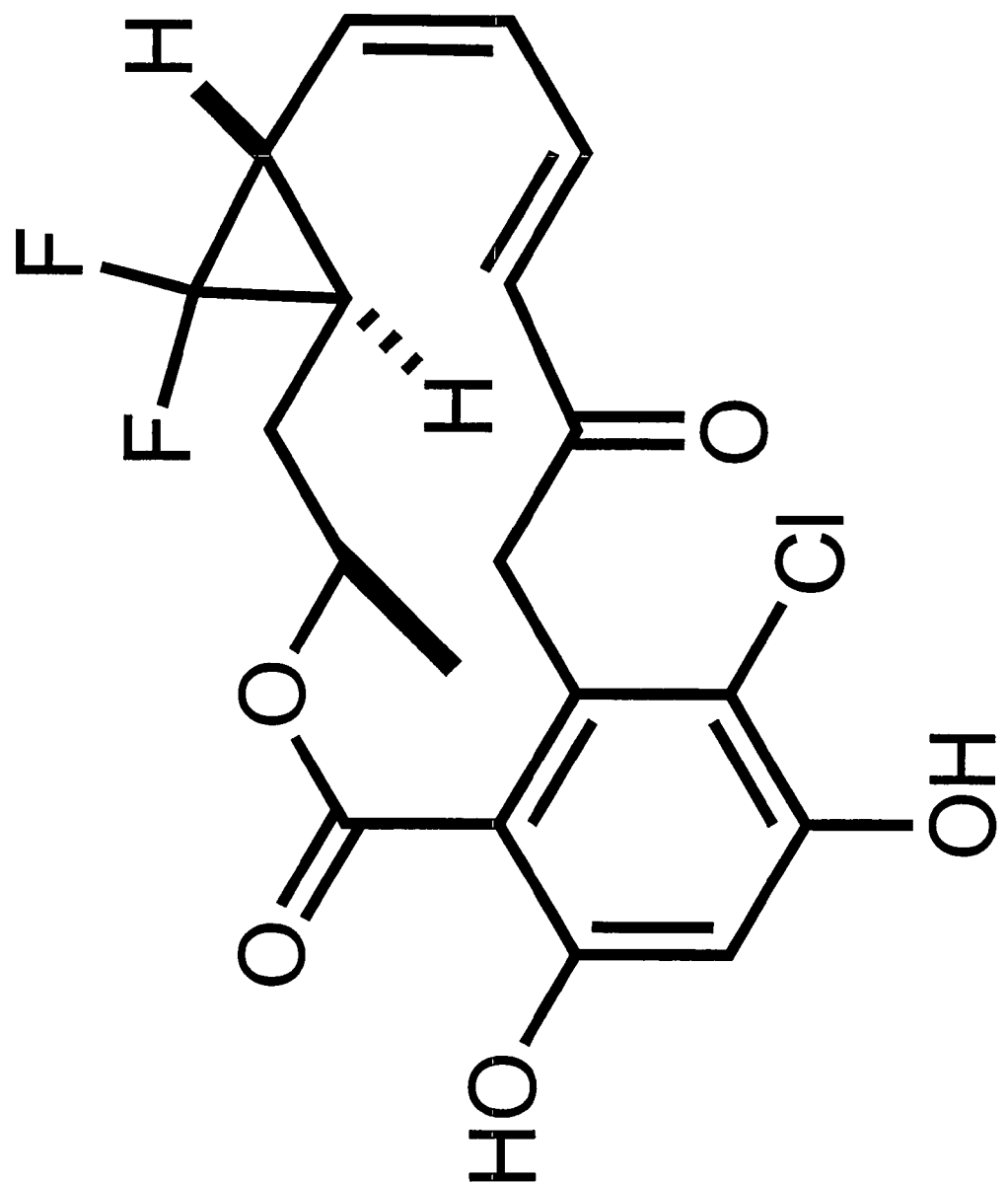
FIG. 27 depicts the structure of difluoro-cycloproparadicicol.

As discussed herein, the compounds of the present invention have been shown to reduce HER2 in MCF-7 and BT474 cells, and are cytotoxic against a panel of cancer cell lines (see exemplification herein and FIGS. 19, 20 and 21), in particular against Rb negative cancer cell lines (FIGS. 20 and 21). The inventive compounds are thus useful for the inhibition of the growth of or for killing cancer cells and are useful in the treatment of cancer (or more generally useful in the treatment of proliferative disorders). In addition, compounds as described herein have been found to act as potent inhibitors of cancer cell lines comprising Rb negative cells, and thus are useful in the treatment of cancers comprising Rb negative cells. Currently, there is no effective treatment for many of these cancers comprising Rb negative cells. The method of the invention comprises administering to a subject in need thereof a therapeutically effective amount of a compound of the invention.

In certain embodiments of the present invention a "therapeutically effective amount" of the inventive compound or pharmaceutical composition is that amount effective for detectable killing or inhibiting the growth of cancer cells, and in certain embodiments of special interest an amount for detectable killing or inhibiting the growth of cancer cells comprising Rb negative cancer cells.

The compounds and compositions, according to the method of the present invention, may be administered using any amount and any route of administration effective for killing or inhibiting the growth of tumor cells. Thus, the expression "effective amount" as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like. The anticancer compounds of the invention are preferably formulated in dosage unit form for ease of administration and uniformity of dosage. The expression "dosage unit form" as used herein refers to a physically discrete unit of anticancer agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. I will also be appreciated that dosages smaller than 0.001 mg/kg or greater than 50 mg/kg (for example 50–100 mg/kg) can be administered to a subject. In certain embodiments, compounds are administered orally or parenterally.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As discussed above, in one aspect, the compounds of the present invention are useful as anticancer agents, and thus may be useful in the treatment of cancer, by effecting tumor cell death or inhibiting the growth of tumor cells. In general, the inventive anticancer agents are useful in the treatment of cancers and other proliferative disorders, including, but not limited to glioblastoma, retinoblastoms, breast cancer, cervical cancer, colon and rectal cancer, leukemia, lung cancer (including, but not limited to small cell lung cancer), melanoma, multiple myeloma, non-Hodgkin's lymphoma, ovarian cancer, pancreatic cancer, prostate cancer, and gastric cancer, to name a few. In certain embodiments, the inventive anticancer agents are active against cancers comprising Rb negative cells, including, but not limited to small cell lung cancer, retinoblastoma and glioblastoma. In certain other embodiments, the inventive anticancer agents are active against breast cancer cells, leukemia cells and melanoma cells, and thus are useful for the treatment of breast cancer, leukemias (e.g., myeloid, lymphocytic, myelocytic and lymphoblastic leukemias) and malignant melanomas. In still other embodiments, the inventive anticancer agents are active against solid tumors and also kill and/or inhibit the growth of multidrug resistant cells (MDR cells).

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with the inventive anticancer agents of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. Additionally, the present invention also encompasses the use of certain cytotoxic or anticancer agents currently in clinical trials and which may ultimately be approved by the FDA (including, but not limited to, epothilones and analogues thereof and geldanamycins and analogues thereof). For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Treatment Kits

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the substituted purine dosages, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein.

EXEMPLIFICATION

Example 1

Total Synthesis of Aigialomycin D

There are many natural products, usually bacterial metabolites, featuring a macrolide fused to a monocyclic benzenoid matrix, bearing a resorcinol-like substitution pattern. Not infrequently, the resorcinol moiety carries additional functionality, resulting in higher levels of oxidation. Natural products in this family (cf. inter alia radicicol (Delmotte, P.; Delmotte-Plaquee, *J. Nature* 1953, 171, 344; incorporated herein by reference), LL-Z-1640s (McGahren, W. J. *J. Org. Chem.* 1978, 43, 2339–2343; incorporated herein by reference), monocillins (Ayer, W. A.; Lee, S. P.; Tsuneda, A.; Hiratsuka, Y. *Can. J. Microb.* 1980, 26, 766–773; incorporated herein by reference), nordinone (Ayer, W. A.; Pena-Rodriguez, L. *Phytochemistry* 1987, 26, 1353–1355; incorporated herein by reference), and zearelenone (Sugawara, F.; Kim, K. W.; Kobayashi, K.; Uzawa, J.; Yoshida, S.; Murofushi, N.; Takahashi, N.; Strobel, G. A. *Phytochemistry* 1992, 31, 1987–1990; incorporated herein by reference) possess potentially exploitable patterns of antitumor, antibiotic and antimalarial activity. Indeed, we were first attracted to this structural series by radicicol (Delmotte, P.; Delmotte-Plaquee, *J. Nature* 1953, 171, 344; Sharma, S. V.; Agatsuma, T.; Nakano, H. *Oncogene* 1998, 16, 2639; each of which is incorporated herein by reference)—a non quinoidal inhibitor of the key molecular chaperone HSP90. Using radicicol (2) as a lead compound, we were soon led to cycloproparadicicol (3) (Yamamoto, K.; Garbaccio, R. M.; Stachel, S. J.; Solit, D. B.; Chiosis, G.; Rosen, N.; Danishefsky, S. J. *Angew. Chem., Int. Ed.* 2003, 42, 1280–1284; incorporated herein by reference) as a potentially valuable analog structure, wherein the cyclopropane simulates the conformational consequences of the epoxide, without the liabilities associated with a potentially labile alkylation site. Indeed, xenograft studies suggest that cycloproparadicicol (3) may well be a superior drug relative to radicicol (2). The promise of cycloproparadicicol, albeit in an early preclinical setting, as well as the structural diversity encountered in this family of bioactive molecules, prompted us to explore new strategies for building such compounds in the laboratory. Indeed, a new strategy was described to reach cycloproparadicicol (Yang, Z.-Q., Danishefsky, S. J. *J. Am. Chem. Soc.* 2003, 125, 9602–9603; incorporated herein by reference).

Recently, five new 14-membered resorcyclic macrolides, termed aigailomycins A–E, were isolated from the marine mangrove fungus *Aigialus parvus* BCC5311 (Isaka, M.; Suyarnsestakorn, C.; Tanticharoen, M.; Kongsaeree, P.; Thebtaranonth, Y. *J. Org. Chem.* 2002, 67, 1561–1566; incorporated herein by reference). Among those compounds, aigialomycin D (1) (shown below) exhibited potent antimalarial activity (IC$_{50}$: 6.6 µg/mL against *P. falciparum*) and antitumor activity (IC$_{50}$: 3.0 µg/mL against KB cells) (Isaka, M.; Suyarnsestakorn, C.; Tanticharoen, M.; Kongsaeree, P.; Thebtaranonth, Y. *J. Org. Chem.* 2002, 67, 1561–1566; incorporated herein by reference).

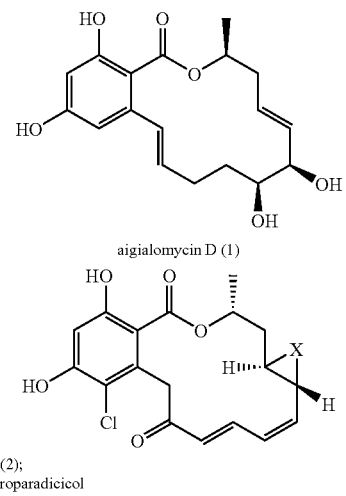

aigialomycin D (1)

X = O, radicicol (2);
X = CH$_2$, cycloproparadicicol

Resorcinylic Macrolides: Aigialomycin D, Radicicol, and Cycloproparadicicol.

Not surprisingly, our first thought was to use the synthetic paradigm developed for cyclproparadicicol (Yang, Z.-Q., Danishefsky, S. J. *J. Am. Chem. Soc.* 2003, 125, 9602–9603; incorporated herein by reference). However, unlike 3, 1 does not, in the end, contain benzylic oxygen functionality. Rather, it contains a 1', 2' styrene-like double bond, ortho to the acyloxyl group of the lactone. It was our plan to install this double bond by β-elimination of a C2' leaving group toward the benzo domain (vide infra). To bring about a pre-elimination setup, the initial bond formation would be between future carbons 1' and 2'. The more serious incremental complexity in the aigialomycin series arises from the two hdyroxy-bearing stereogenic centers at C5' and C6' in allylic and homoallylic relationships respectively to the C7'–C8' double bond. The thought was to construct this double bond by ring forming olefin metatheses via extrusion of carbons 7" and 8". Scheme 1-1 (below) sets forth the thinking that led to a remarkably straightforward total synthesis of agialomycin D.

It was recognized that, if properly managed, the functionality present in the readily available D-2-deoxyribose (9) could lead to a functional equivalent of the key proposed formal building block 6. Compound 6 would not be used as such (vide infra).

In the event, the secondary hydroxyl groups at C3 and C4 of 9, were engaged in an isopropylidene linkage (see 10 (Barbat, J.; Gelas, J.; Horton, D. Carbohydrate Res. 1983, 116, 312–316; incorporated herein by reference), Scheme 1-2). The masked aldehyde character of C1 of the pentose could be exploited in the context of a Wittig protocol. The primary alcohol in the resultant product, 11, was protected as its pivaloyl derivative (see 12). In this compound, the primary methylene group bearing the pivaolyloxy group would emerge as C7' of the ring closing metathesis (RCM) precursor (vide infra). Hydroboration of 12 followed by oxidation, as shown, led us to 13 which, following oxidation of its primary alcohol function, delivered 14.

Scheme 1-1. Synthetic Strategy

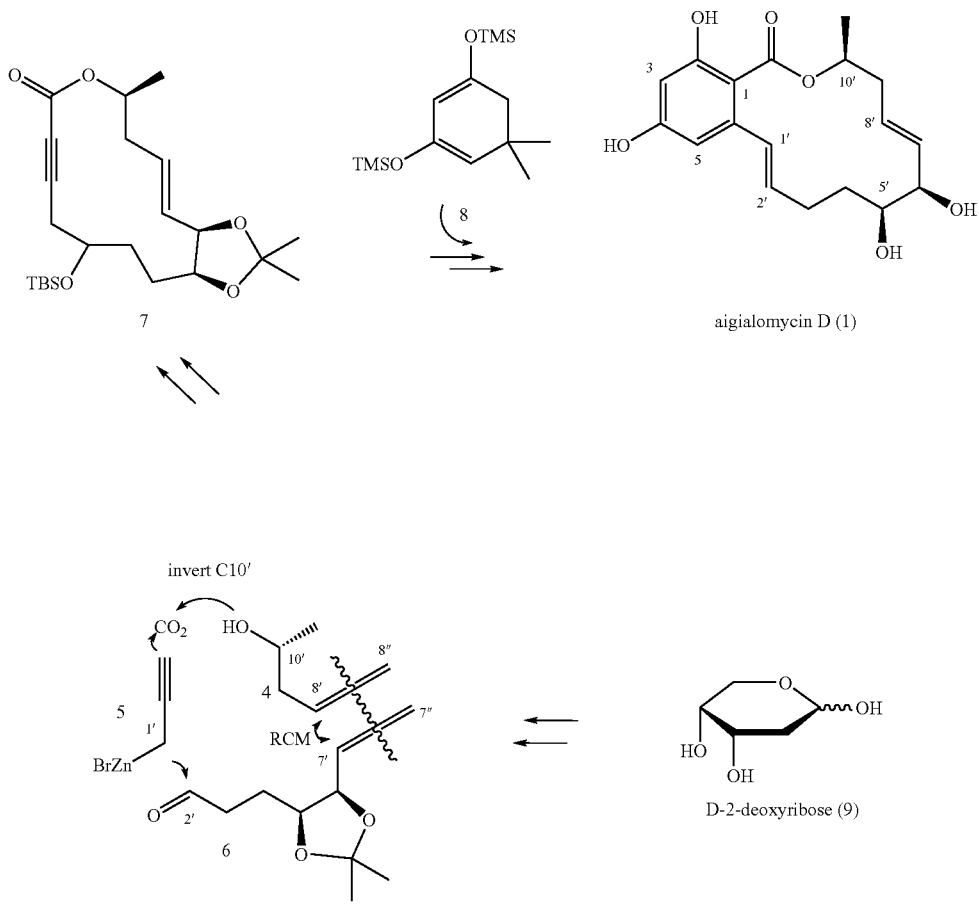

Chain extension of the aldehyde by propargylation afforded 15 as a mixture of stereoisomers. In this compound, as well as in subsequent seco intermediates, these stereoisomers manifested nearly identical chromatographic characteristics. Thus, the mixtures were treated as single entities in the progression until compound 23. The secondary hydroxyl groups in epimers 15 were protected as t-butyldimethyl silyl ethers (see 16), thus enabling installation of a vinyl group, destined to serve as the C7'–C7" moiety in the eventual RCM (see steps leading to 18).

Carboxylation of the ethynyl group in 18 occurred smoothly to afford carboxylic acid 19. The latter reacted with R alcohol 4, giving rise, through a Mitsunobu protocol, to the S-ester 20, still bearing epimeric OTBS ethers at the future carbon 2'.

Our previous experience (Yang, Z.-Q., Danishefsky, S. J. J. Am. Chem. Soc. 2003, 125, 9602–9603; incorporated herein by reference) had prepared us well for accomplishing the much needed ring closing metathesis reaction. First, it would be necessary to immobilize the ethynyl linkage in 20 as its dicobalt hexacarbonyl complex (Scheme 1-3) (Yang, Z.-Q., Danishefsky, S. J. J. Am. Chem. Soc. 2003, 125, 9602–9603; Nicholas, K. M.; Pettit, R. Tetrahedron Lett. 1971, 37, 3475–3478; Young, D. G. J.; Burlison, J. A.; Peters, U. J. Org. Chem. 2003, 68, 3494–3497; each of which is incorporated herein by reference). This step accomplishes two objectives. First, the acetylene function is insulated from diversion to an ene-yne metathesis format. Furthermore, it is likely that the formation of the complex modifies the angles of the ethynyl sector (Sternberg, H. W.; Greenfield, H.; Friedel, R. A.; Wotiz, J.; Markby, R.; Wender, I. J. Am. Chem. Soc. 1954, 76, 1457–1458; incorporated herein by reference), such as to bring carbons 7' and 8' into closer proximity. In the event, the hexacarbonyl complex 21 was obtained in 94% yield. Ring closing metathesis was easily accomplished, using the recently published catalysis methodology from the Grubbs group (Scholl, M.; Ding, S.; Lee, C. W.; Grubbs, R. H. Org. Lett. 1999, 1, 953–956; incorporated herein by reference). The 14 membered macrolide (23) was thus in hand. At this stage the two stereoisomeric products were easily separated by Scheme 1-2. Synthesis of diene 20.

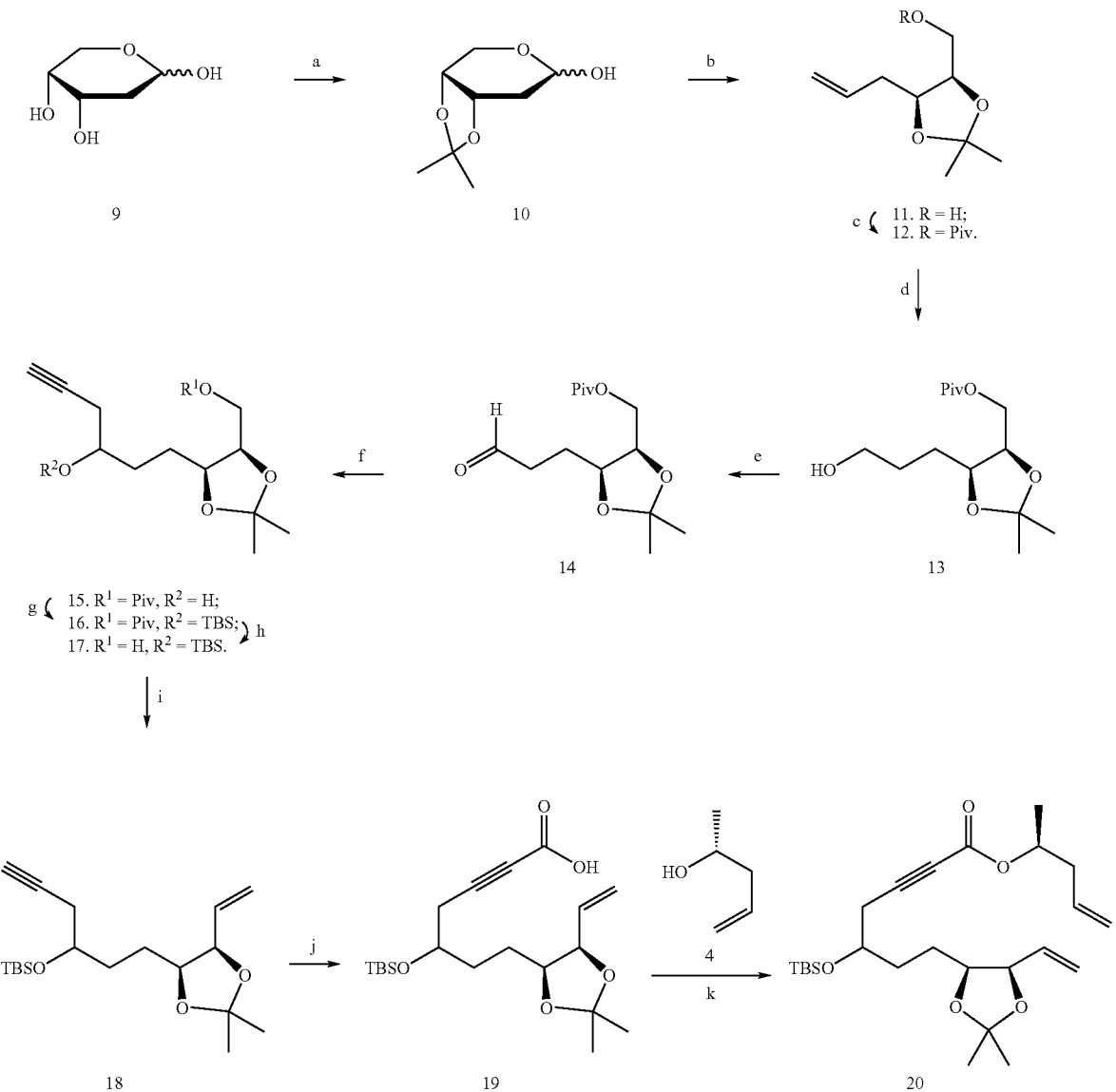

a) 2-methoxypropene, p-TSA, DMF, 3 h, 62%; b) KHMDS, Ph$_3$P$^+$CH$_3$I$^-$, THF, −78° C. to r.t., 10 h, 68%; c) PivCl, Et$_3$N, DMAP, CH$_2$Cl$_2$, 10 h, 90%; d) 9-BBN, THF, 0° C. to r.t., 4 h, then NaOH, H$_2$O$_2$, H$_2$O, 2.5 h, 88%; e) SO$_3$-Pyr., DMSO, CH$_2$Cl$_2$, Et$_3$N, 0° C., 1 h; f) propargyl bromide, zinc, THF, 0° C., 2 h; g) TBSOTf, 2,6-lutidine, CH$_2$Cl$_2$, 10 h, 89% from 13; h) NaOMe/MeOH, 10 h, 88%; i) SO$_3$-Pyr., DMSO, CH$_2$Cl$_2$, Et$_3$N, 0° C., 2 h, then KHMDS, Ph$_3$P$^+$CH$_3$I$^-$, THF, −78° C. to r.t., 10 h, 86% for two steps; j) BuLi, dry ice, −78° C. to r.t., 2 h; k) 4, DIAD, PPh$_3$, tol., 10 h, 85% for two steps.

chromatography to provide the individual compound(s) at a 1.2:1 ratio (stereochemistry not rigorously assigned). We note that in each diastereomer, only the E configured double bond was obtained (J≅15.2 Hz).

Decomplexation of the two separated compounds 23a and 23b, using standard conditions, thereby afforded "ynolide" epimers 7 (Scheme 4). Each stereoisomer was subjected to Diels Alder reaction with the disiloxydiene 8, following previously developed conditions (Yang, Z.-Q., Danishefsky, S. J. *J. Am. Chem. Soc.* 2003, 125, 9602–9603; incorporated herein by reference). In the event, cycloaddition followed by extrusion of isobutylene occurred smoothly affording macrolides 24a and 24b. It proved useful to protect the two resorcyclic hydroxyl groups in the form of their MOM derivatives (see 25a and 25b) before proceeding with installation of the styrene like double bond. At this stage, deprotection of the silyl group was accomplished through the agency of HF-pyridine. Indeed, dehydration of the resulting alcohol functions in 26a and 26b, each using Martin's sulfurane conditions (Martin, J. C.; Arhart, R. J. *J. Am. Chem. Soc.* 1971, 93, 4327–4329; incorporated herein by reference), resulted in installation of the C1′–C2′ double Scheme 1-3. Synthesis of macrolactone 23 through RCM.
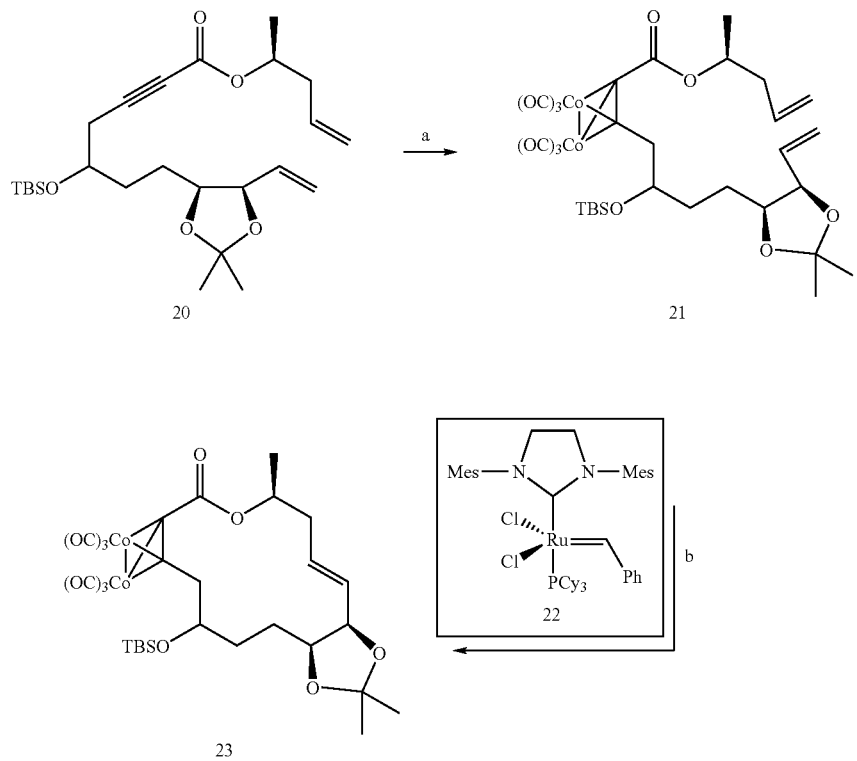
a) Co$_2$(CO)$_8$, tol., 30 min, 94%; b) 2$^{nd}$ generation Grubbs catalyst (25 mol %), CH$_2$Cl$_2$, 10 h, 23A, 38%; 23B, 42%.
Scheme 1-4. Completion of the total synthesis of aigialomycin D
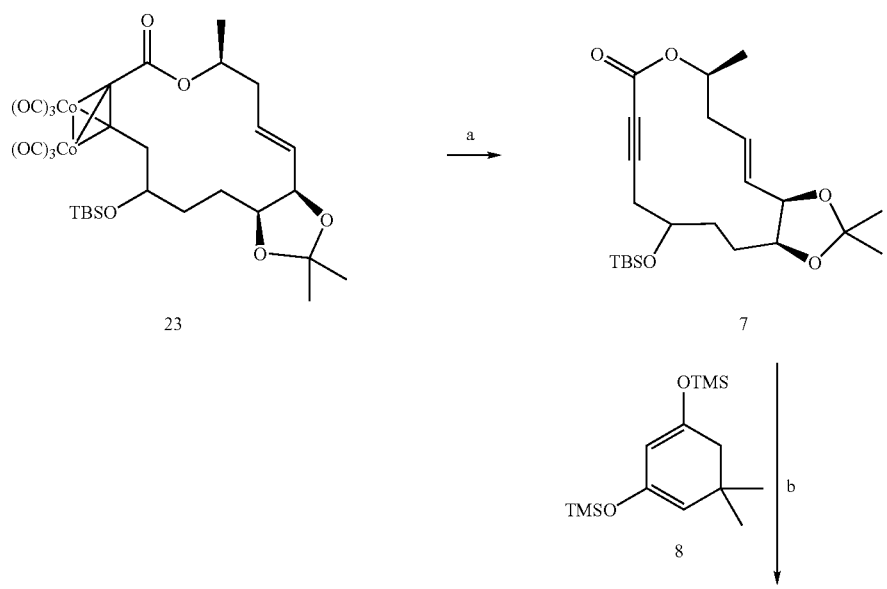

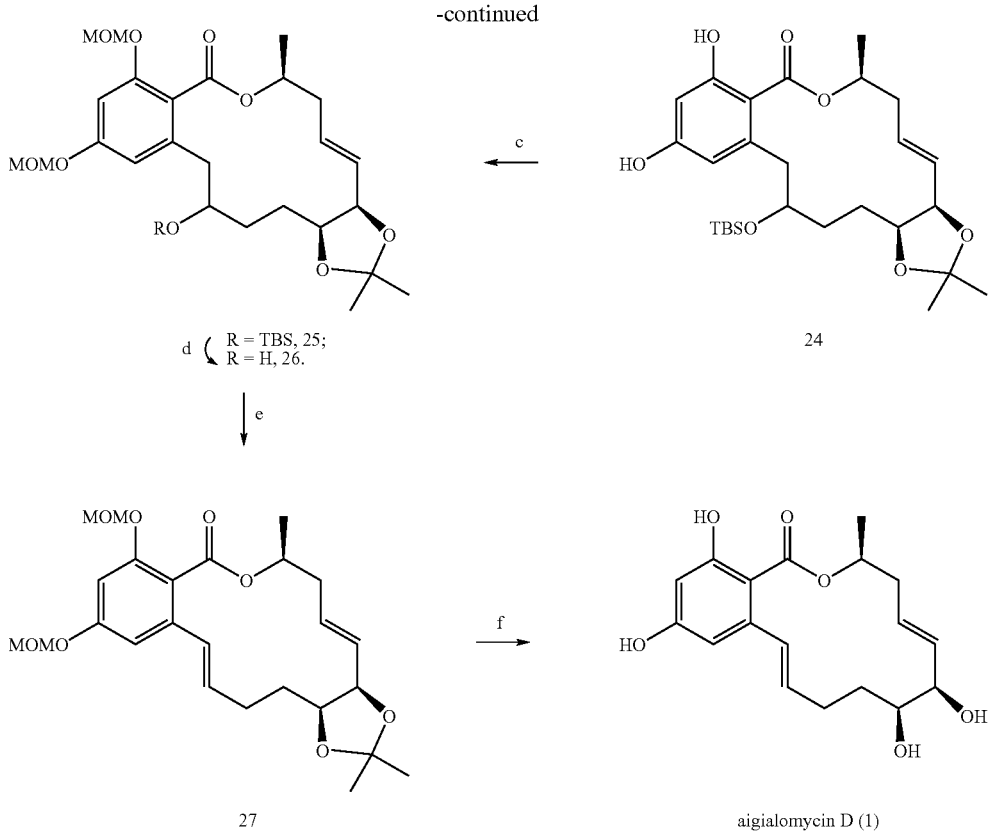

a). CAN, acetone, −10° C., 15 min, 7A, 94%; 7B 95%; b). 8 neat, 140° C., 36 h, 24A, 74%; 24B, 84%; c) MOMCl, DIPEA, CH$_2$Cl$_2$, 10 h, 25A, 78%; 25B, 83%; d) HF-pyr., pyr., THF, 10 h, 26A, 78%; 26B, 87%; e) [PhC(CF$_3$)$_2$O]$_2$ SPh$_2$, CH$_2$Cl$_2$, 0° C. to r.t., 2 h, from 26A to 27, 90%; from 26B to 27, 84%; f) 0.5 N HCl, H$_2$O/MeOH, 2 d, 69%.

bond with the formation of the identical product, 27. Global acidic deprotection of the two MOM functions and the acetonide (0.5 N HCl) served to complete the first total synthesis of aigialomycin D (1). The assignment of structural and relative configuration could well have been rigorously accomplished based on our measurements (proton NMR, carbon NMR, mass spec and IR) accumulated on the fully synthetic material. In the case at hand, further support comes from the very close correspondence of our data with those previously reported for the target structure aigialomycin D (Isaka, M.; Suyarnsestakorn, C.; Tanticharoen, M.; Kongsaeree, P.; Thebtaranonth, Y. J. Org. Chem. 2002, 67, 1561–1566; incorporated herein by reference).

The synthesis described above, serves to further demonstrate the adaptability and generalizability of the basic protocol ("seco ylolide"→"ylolide"→resorcinylic macrolide, see Scheme 1–5). The total synthesis of 1 was accomplished in 18 steps in an overall yield of approximately 8%. We note in passing that compound 1 does bind to HSP90 (though significantly less so than radicicol (2)). It will be interesting to attempt to utilize this newly acquired and highly concise route to matrices resembling radicicol for the purposes of discovering new and superior agents based on the theme of HSP90 inhibition.

Scheme 1-5. "Ynolide" synthetic protocol.

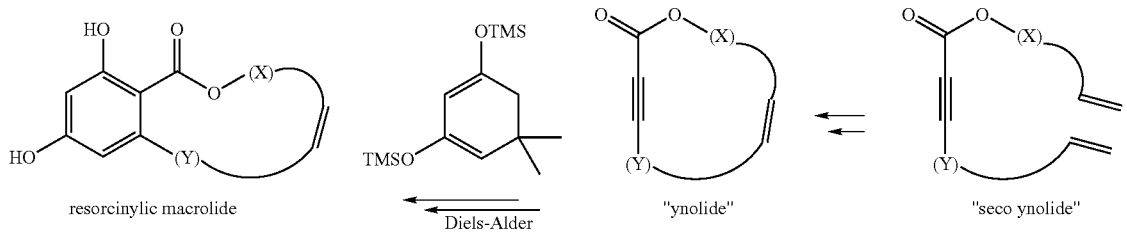

Experimentals:

General Methods: Reagents obtained from commercial suppliers were used without further purification unless otherwise noted. THF, toluene, and methylene chloride was obtained from a dry solvent system (passed through a prepacked column of alumina) and used without further drying. All air and water sensitive reactions were performed in flame-dried glassware under a positive pressure of prepurified argon gas. NMR ($^1$H and $^{13}$C) spectra were recorded on Bruker AMX-400 MHz or Bruker Advance DRX-500 MHz as noted individually, referenced to CDCl$_3$ (7.27 ppm for $^1$H and 77.0 ppm for $^{13}$C) or CD$_3$COCD$_3$ (2.09 ppm for $^1$H and 30.6 and 205.9 ppm for $^{13}$C). Infrared spectra (IR) were obtained on a Perkin-Elmer FT-IR model 1600 spectrometer. Melting point was tested on a electrothermal series IA9100 digital melting point apparatus. Optical rotations were obtained on a JASCO model DIP-370 digital polarimeter. Analytical thin-layer chromatography was performed on E. Merck silica gel 60 F254 plates. Compounds which were not UV active were visualized by dipping the plates in para-anisaldehyde solution and heating. Preparative thin layer chromatography was performed using the indicated solvent on Whatman® (LK6F Silica gel 60 Å 250 μM or Pk6F Silica Gel 60 Å 1000 μM) TLC plate.

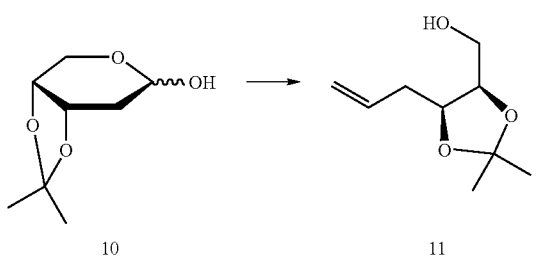

10   11

(2R, 3S)-Hex-5-ene-1,2,3-triol 2,3-acetonide (11):

To a stirring suspension of Ph$_3$P$^+$CH$_3$I$^-$ (11.2 g, 27.7 mmol) in 30 mL THF was added KHMDS (0.5 M in toluene, 46.0 mL, 23.0 mmol) at −78° C. The solution was warmed up to 0° C. and stirred for 30 min before cooled down to −78° C. Acetonide 10 (Barbat, J.; Gelas, J.; Horton, D. *Carbohydrate Res.* 1983, 116, 312–316; incorporated herein by reference) (1.6 g, 9.2 mmol) in 5 mL THF was added via cannula and the solution was warmed up to r.t. overnight (10 h) before quenched with saturated aqueous NH$_4$Cl solution, extracted with EtOAC (100 mL×3). The organic layers were combined and dried with anhydrous MgSO$_4$, filtered, and concentrated under reduced pressure vacuum. The residue was purified on a silica gel column using petroleum ether/EtOAc (4/1) as the eluant to afford 11 as a colorless oil (1.02 g, 68%). [α]$_D$$^{25}$ 54.8 (c 0.26, CHCl$_3$). $^1$H NMR (400 MHz, CDCl$_3$) δ 1.34 (s, 3H), 1.46 (s, 3H), 2.02 (b, 1H), 2.25–2.32 (m, 1H), 2.37–2.44 (m, 1H), 3.65 (m, 1H), 4.16–4.21 (m, 1H), 4.24–4.28 (m, 1H), 5.10–5.18 (m, 2H), 5.79–5.89 (m, 1H). $^{13}$C NMR (100 MHz, CDCl$_3$) δ 25.4, 28.1, 33.6, 61.6, 76.2, 77.8, 108.3, 117.3, 134.2. LRMS (ESI) calcd for C$_9$H$_{16}$O$_3$Na$^+$ [M+Na]$^+$: 195.1, found 194.9. LRMS (ESI) calcd for C$_9$H$_{16}$O$_3$Cl$^-$ [M+Cl]$^-$: 207.1, found 207.1.

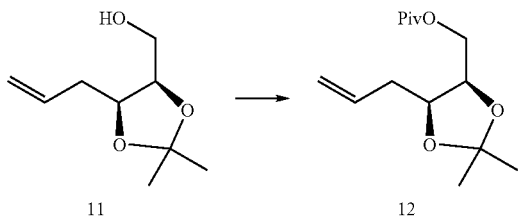

11   12

Pivalate (12):

To a solution of 11 (752 mg, 4.37 mmol), DMAP (106 mg, 0.874 mmol) and triethylamine (2.5 ml, 17.5 mmol) in CH$_2$Cl$_2$ (8 ml) was added PivCl (1.1 ml, 8.74 mmol) at 0° C. The reaction mixture was warmed up to r.t. overnight (10 h) before quenched with saturated aqueous NaHCO$_3$ solution, extracted with EtOAC (100 mL×3). The organic layers were combined and dried with anhydrous MgSO$_4$, filtered, and concentrated under reduced pressure vacuum. The residue was purified on a silica gel column using hexanes/EtOAc (4/1) as the eluant to afford 12 as a colorless oil (984 mg, 90%). [α]$_D$$^{25}$ 15.6 (c 0.32, CHCl$_3$). $^1$H NMR (400 MHz, CDCl$_3$) δ 1.22 (s, 9H), 1.33 (s, 3H), 1.47 (s, 3H), 2.28–2.41 (m, 2H), 4.10–4.13 (m, 2H), 4.22–4.29 (m, 2H), 5.10–5.17 (m, 2H), 5.81–5.91 (m, 1H). $^{13}$C NMR (100 MHz, CDCl$_3$) δ 25.9, 27.5, 28.4, 39.1, 63.2, 75.5, 77.8, 108.8, 117.7, 134.6, 178.5. LRMS (ESI) calcd for C14H$_{24}$O$_4$Na$^+$ [M+Na]$^+$279.2, found 278.9.

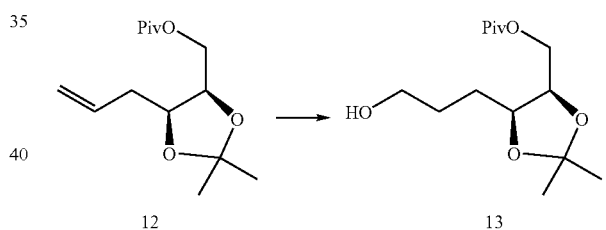

12   13

Alcohol 13:

To a solution of 12 (166 mg, 0.648 mmol) in THF (1.5 mL) was added 9-BBN (0.5 M in THF, 2.8 mL, 1.425 mmol) at 0° C. The reaction mixture was warmed up to r.t. over 4 h and H$_2$O (0.1 mL), NaOH (3 M, 0.7 mL) and H$_2$O$_2$ (30%, 0.2 mL) were added. The reaction mixture was diluted with H$_2$O 2.5 h later and acidified with citric acid (5%) till pH=7. The mixture was extracted with EtOAc, washed with saturated aqueous Na$_2$S$_2$O$_3$, H$_2$O and brine. The organic layers were combined and dried with anhydrous MgSO$_4$, filtered, and concentrated under reduced pressure vacuum. The residue was purified on a silica gel column using petroleum ether /EtOAc (1/1) as the eluant to afford 13 as a colorless oil (156 mg, 88%). [α]$_D$$^{25}$ 82.4 (c 0.07, CHCl$_3$). $^1$H NMR (400 MHz, CDCl$_3$) δ 1.21 (s, 9H), 1.36 (s, 3H), 1.46 (s, 3H), 1.59–1.80 (m, 4 H), 2.30 (b, 1H), 3.54 (m, 2H), 4.08 (dd, J=6.1, 11.5 Hz, 1H), 4.12 (dd, J=5.6, 11.5 Hz, 1H), 4.19 (m, 1H), 4.25 (m, 1H). $^{13}$C NMR (100 MHz, CDCl$_3$) δ 25.5, 25.9, 27.1, 28.0, 29.9, 38.7, 62.3, 62.9, 75.3, 77.0, 108.3, 178.2. HRMS (ESI) calcd for C$_{14}$H$_{26}$O$_5$Na$^+$ [M+Na]$^+$ 297.1678, found 297.1660, Δ=−6.0 ppm.

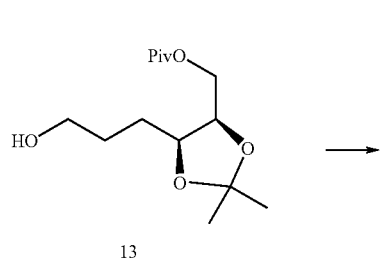

13

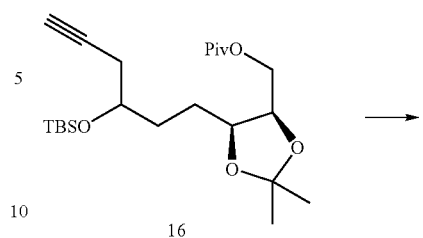

16

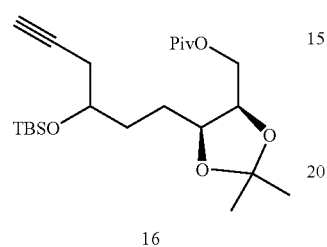

16

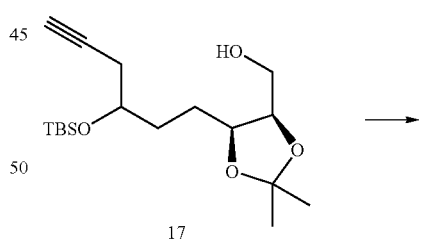

17

Alkyne 16:

To a solution of 13 (682 mg, 2.485 mmol) in CH$_2$Cl$_2$ (5 mL), DMSO (5 mL) and Et$_3$N (3 mL) as added SO$_3$-pyridine complex (1.6 g, 10.2 mmol) at 0° C. The reaction mixture was stirred for 1 h before diluted with EtOAc and washed with HCl (0.5 N), H$_2$O, saturated aqueous NaHCO$_3$ solution and brine. The organic layers were dried with anhydrous MgSO$_4$, filtered, and concentrated under reduced pressure vacuum. The crude aldehyde 14 was used directly for next step without any further purification.

To a suspension of Zn (Nano-size power, pre-activated, 390 mg, 5.949 µmmol) in THF (10 mL) was added propargyl bromide (80% in toluene, 0.53 mL, 4.759 mmol) at 0° C. The reaction mixture was stirred for 1 h at 0° C. and a solution of aldehyde 14 thus obtained in THF (5 mL) was added and reaction mixture was warmed up to r.t. over 2 h before quenched with saturated aqueous NH$_4$Cl solution and extracted with EtOAc. The organic layers were dried with anhydrous MgSO$_4$, filtered, and concentrated under vacuum. To a solution of crude alcohol 15 thus obtained and 2,6-lutidine (0.6 mL, 4.76 mmol) in CH$_2$Cl$_2$ (8 mL) was added TBSOTf (0.82 mL, 3.57 mmol) and the reaction mixture was stirred for 10 h before quenched with saturated aqueous NH$_4$Cl solution, extracted with EtOAc (100 mL×3). The organic layers were combined and dried with anhydrous MgSO$_4$, filtered, and concentrated under reduced pressure vacuum. The residue was purified on a silica gel column using petroleum ether/EtOAc (20/1) as the eluant to afford 16 as a colorless oil (896 mg, 89% from 13). $^1$H NMR (400 MHz, CDCl$_3$) δ −0.02–0.05 (m, 6H), 0.80 (s, 9H), 1.13 (s, 9H), 1.26 (s, 3H), 1.36 (s, 3H), 1.42–1.74 (m, 4H), 1.81 (m, 1H), 2.22–2.29 (m, 2H), 3.78 (m, 1H), 4.01–4.08 (m, 3H), 4.12–4.17 (m, 1H). $^{13}$C NMR (100 MHz, CDCl$_3$) δ 18.0, 18.1, 24.3, 24.7, 25.6, 25.8, 27.0, 27.1, 27.2, 28.06, 28.07, 33.2, 33.3, 38.7, 62.8, 62.9, 70.1, 70.2, 70.4, 70.5, 75.2, 76.1, 77.1, 81.2, 108.20, 108.24, 178.1. HRMS (FAB) calcd for C$_{23}$H$_{42}$O$_5$SiH$^+$ [M+H]$^+$: 427.2880, found 427.2880, Δ=−0.1 ppm.

Alcohol 17:

To a solution of 16 (124 mg, 0.291 mmol) in MeOH (6 mL) was added NaOMe/MeOH (25%, 0.2 mL) and the reaction mixture was stirred for 10 h before quenched with saturated aqueous NH$_4$Cl solution, extracted with EtOAc (100 mL×3). The organic layers were combined and dried with anhydrous MgSO$_4$, filtered, and concentrated under reduced pressure vacuum. The residue was purified on a silica gel column using petroleum ether/EtOAc (8/1) as the eluant to afford 17 as a colorless oil (87 mg, 88%). $^1$H NMR (400 MHz, CDCl$_3$) δ −0.02–0.00 (m, 6H), 0.80 (s, 9H), 1.32 (s, 3H), 1.38 (s, 3H), 1.32–1.91 (m, 4H), 1.90 (m, 1H), 1.96 (b, 1H), 2.23–2.31 (m, 2H), 3.53 (m, 2H), 3.75 (m, 1H), 4.08 (m, 1H). $^{13}$C NMR (100 MHz, CDCl$_3$) δ −4.7, −4.6, −4.5, 18.0, 24.5, 24.7, 25.5, 25.6, 25.8, 27.2, 27.4, 28.2, 33.2, 33.4, 61.7, 70.1, 70.2, 70.46, 70.52, 76.9, 77.0, 77.9, 81.16, 81.24, 108.08, 108.14. HRMS (FAB) calcd for C$_{18}$H$_{34}$O$_4$SiH$^+$ [M+H]$^+$: 343.2305, found 343.2305, Δ=−0.1 ppm.

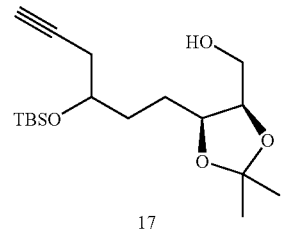

17

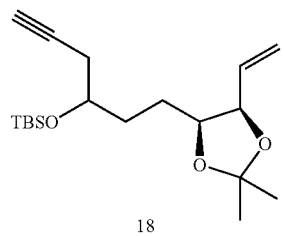

18

Enyne 18:

To a solution of 17 (87 mg, 0.254 mmol) in DMSO (1.0 mL), CH$_2$Cl$_2$ (1.0 mL) and Et$_3$N (1.0 mL) was added SO₃-Pyrdine complex (200 mg, 2.032 mmol) at 0° C. The reaction mixture was stirred for 2 h before diluted with EtOAc and washed with HCl (0.5 N), H₂O, saturated aqueous NaHCO₃ solution and brine. The organic layers were dried with anhydrous MgSO₄, filtered, and concentrated under reduced pressure vacuum. The crude aldehyde was used directly for next step without any further purification.

To a stirring suspension of Ph₃P+CH₃r (204 mg, 0.505 mmol) in 3 mL THF was added KHMDS (0.5 M in toluene, 0.9 mL, 0.454 mmol) at −78° C. The solution was warmed up to 0° C. and stirred for 30 min before cooled down to −78° C. Aldehyde obtained as mention above in 2 mL THF was added via cannula and the solution was warmed up to r.t. overnight (10 h) before quenched with saturated aqueous NH₄Cl solution, extracted with EtOAc (100 mL×3). The organic layers were combined and dried with anhydrous MgSO₄, filtered, and concentrated under reduced pressure vacuum. The residue was purified on a silica gel column using petroleum ether/EtOAc (40/1) as the eluant to afford 18 as a colorless oil (73 mg, 86%). $^1$H NMR (400 MHz, CDCl₃) δ −0.05 (s, 3H), 0.02 (s, 3H), 0.83 (s, 9H), 1.27 (s, 3H), 1.43 (s, 3H), 1.43–1.78 (m, 4H), 1.92 (b, 1H), 2.23–2.31 (m, 2H), 3.76 (m, 1H), 4.05–4.10 (m, 1H), 4.43–4.45 (m, 1H), 5.02–5.05 (m, 2H), 5.71–5.80 (m, 1H). $^{13}$C NMR (100 MHz, CDCl₃) δ −4.30, −4.11, 18.4, 26.0, 26.1, 26.2, 26.5, 26.8, 27.7, 27.8, 28.62, 28.64, 33.2, 33.6, 70.4, 70.5, 71.07, 71.13, 78.6, 78.8, 80.2, 81.78, 81.82, 108.5, 118.6, 118.7, 134.7, 134.9. HRMS (FAB) calcd for C₁₉H₃₄O₃SiNa⁺ [M+Na]⁺: 361.2175, found 361.2175, Δ=0.0 ppm.

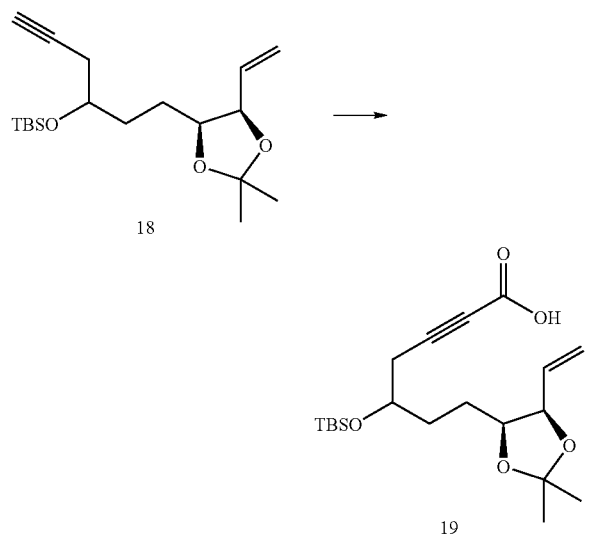

Acid 19:

To a solution of 18 (586 mg, 1.731 mmol) in Et₂O (16 mL) was added BuLi (1.6 M in hexane, 1.817 mmol) at −78° C. and stirred for 5 min before quenched with dry ice and warmed up to r.t. The reaction mixture was washed with NaOH (0.1 M) and the aqueous layers were combined and acidified by HCl (0.1 M) until the pH=2. The aqueous layer was extracted with EtOAc and the organic layers were combined and dried with anhydrous MgSO₄, filtered, and concentrated under reduced pressure vacuum and dried on high vacuum. $^1$H NMR (400 MHz, CDCl₃) δ 0.03 (s, 3H), 0.00 (s, 3H), 0.79 (s, 9H), 1.17 (s, 3H), 1.40 (s, 3H), 0.95–1.68 (m, 4H), 2.38–2.39 (m, 2H), 3.80 (b, 1H), 4.06 (m, 1H), 4.43 (m, 1H), 5.14–5.36 (m, 2H), 5.67–5.76 (m, 1H), 10.5 (bs, 1H). This crude was used directly for next step without any further purification.

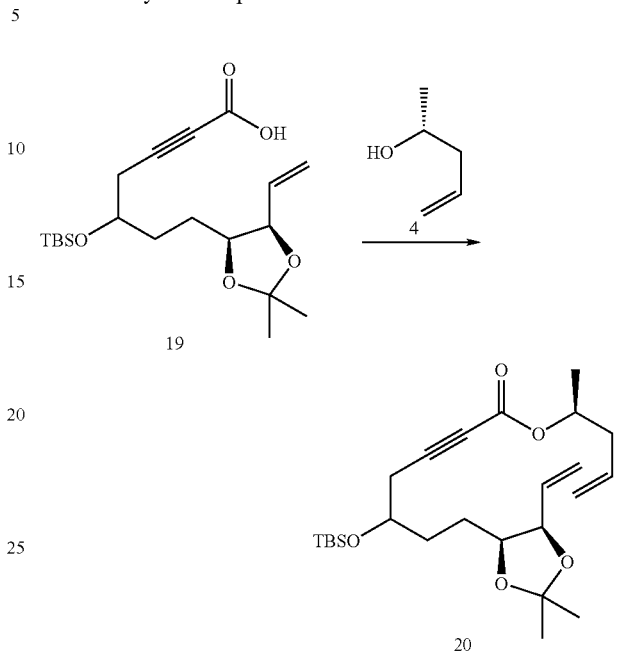

Ester 20:

To a solution of acid 19 (249 mg, 0.651 mmol) in toluene (15 mL) was added alcohol 4 (0.081 mL, 0.781 mmol), PPh₃ (205 mg, 0.781 mmol), DIAD (0.154 mL, 0.781 mmol). The reaction mixture was stirred for 10 h and the solvent was removed under reduced pressure vacuum. The residue was purified on a silica gel column using petroleum ether/EtOAc (40/1) as the eluant to afford 20 as a colorless oil (255 mg, 85% for two steps). $^1$H NMR (400 MHz, CDCl₃) δ −0.06–0.00 (m, 6H), 0.80 (s, 9H), 1.17 (d, J=6.2 Hz, 3H), 1.28 (s, 3H), 1.38 (s, 3H), 1.44–1.54 (m, 4H), 2.20–2.24 (m, 1H), 2.237–2.31 (m, 1H), 2.35–2.37 (m, 2H), 3.78–3.81 (m, 1H), 4.03–4.05 (m, 1H), 4.40–4.43 (m, 1H), 4.94–4.96 (m, 1H), 5.00–5.04 (m, 2H), 5.14 (m, 1H), 5.22 (dd, J=6.7, 7.1 Hz, 1H), 5.67–5.72 (m, 2H). $^{13}$C NMR (100 MHz, CDCl₃) δ −4.64, −4.58, −4.55, 0.0, 18.0, 19.3, 25.6, 25.7, 25.8, 26.1, 26.3, 27.6, 27.7, 28.2, 28.3, 33.3, 33.6, 40.0, 70.10, 70.12, 72.0, 74.9, 78.1, 78.3, 79.80, 79.82, 86.1, 108.2, 108.3, 118.1, 118.3, 118.4, 133.2, 134.2, 134.4, 153.2. HRMS (FAB) calcd for C₂₅H₄₂O₅SiH⁺ [M+H]⁺: 451.2880, found 451.2881, Δ=−0.3 ppm.

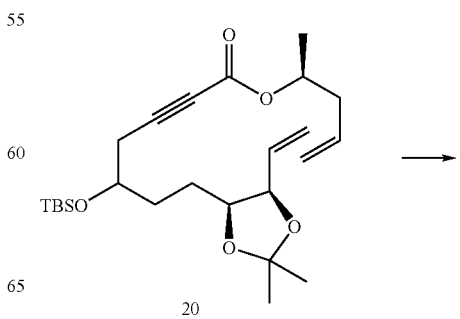

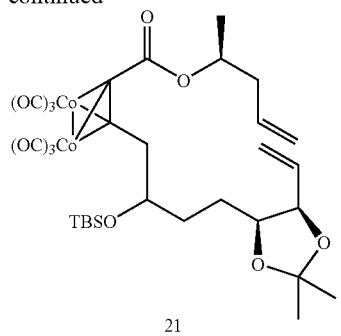

21

Cobalt-Complex 21:

To a solution of 20 (20 mg, 0.044 mmol) in toluene (2.5 mL) was added Co$_2$(CO)$_8$ (21.2 mg, 0.062 mmol). The reaction mixture was stirred for 30 min before filtered through neutral alumina and concentrated under reduced pressure vacuum. The residue was purified on preparative TLC (Whatman® Pk6F Silica Gel 60 Å 1000 μM) using Hexanes/EtOAc (20/1) as the eluant to afford 21 as a purple oil (30 mg, 94%). $^1$H NMR (400 MHz, CDCl$_3$) δ 0.07–0.09 (m, 6H), 0.90 (s, 9H), 1.30 (d, J=8.1 Hz, 3H), 1.33 (s, 1.6H), 1.34 (s, 1.4H), 1.45 (s, 1.6H), 1.47 (s, 1.4H), 1.25–1.46 (m, 1H), 1.58–1.89 (m, 2.5H), 1.89–1.95 (m, 0.5H), 2.37–2.40 (m, 2H), 3.00–3.12 (m, 2H), 3.82–3.86 (m, 1H), 4.08–4.14 (m, 1H), 4.47–4.51 (m, 1H), 5.07–5.14 (m, 3H), 5.21 (d, J=10.4 Hz, 1H), 5.29 (d, J=17.1 Hz, 1H), 5.73–5.84 (m, 2H). $^{13}$C NMR (100 MHz, CDCl$_3$) δ 18.1, 19.4, 25.6, 25.8, 26.5, 27.0, 28.16, 28.2, 32.7, 33.0, 40.3, 41.9, 42.1, 71.9, 72.8, 73.0, 78.2, 169.0, 197. HRMS (FAB) calcd for C$_{31}$H$_{42}$Co$_2$O$_{11}$SiH$^+$ [M+H]$^+$: 737.1239, found 737.1240, Δ=−0.2 ppm.

Macrolactone 23:

To a solution of 21 (339 mg, 0.460 mmol) in CH$_2$Cl$_2$ (80 mL) was added 2$^{nd}$ generation Grubbs catalyst (97 mg, 0.115 mol) in CH$_2$Cl$_2$ (15 mL) via cannula at r.t. The reaction mixture was stirred overnight and then the solvent was removed under reduced pressure vacuum and residue purified on preparative TLC (Whatman® Pk6F Silica Gel 60 Å 1000 μM) using Hexanes/EtOAc (10/1) as the eluant to afford 23A as a purple oil (123 mg, 38%). [α]$_D^{25}$ −44.7 (c 0.25, CHCl$_3$). $^1$H NMR (400 MHz, CDCl$_3$) δ0.08 (s, 3H), 0.09 (s, 3H), 0.91 (s, 9H), 1.31 (d, J=6.3 Hz, 3H), 1.35 (s, 3H), 1.45 (s, 3H), 1.39–1.59 (m, 2H), 1.65–1.72 (m, 1H), 1.93–1.97 (m, 1H), 2.22–2.31 (m, 1H), 2.42 (dt, J=12.9, 1.83 Hz, 1H), 3.08 (dd, J=16.0, 1.5 Hz, 1H), 3.23 (dd, J=16.0, 9.4 Hz, 1H), 3.92–3.95 (m, 1H), 4.01–4.06 (m, 1H), 4.40 (dd, J=9.4, 5.7 Hz, 1H), 5.53 (ddd, J=15.2, 10.9, 1.52 Hz, 1H), 5.72 (ddd, J=15.2, 10.7, 3.8 Hz, 1H). $^{13}$C NMR (100 MHz, CDCl$_3$) δ −4.5, −4.4, 18.5, 21.2, 23.1, 26.1, 26.2, 28.8, 30.5, 41.0, 42.7, 71.6, 71.8, 79.3, 80.0, 81.3, 92.9, 108.1, 129.1, 132.6, 169.9, 198.8. HRMS (FAB) calcd for C$_{29}$H$_{38}$CO$_2$$_9$H$_{38}$Co$_2$O$_{11}$SiH$^+$ [M+H]$^+$: 709.0926, found: 709.0924, Δ=0.2 ppm.

23B (136 mg, 42%). [α]$_D^{25}$ −5.9 (c 0.27, CHCl$_3$). $^1$H NMR (400 MHz, CDCl$_3$) δ 0.12 (s, 3H), 0.15 (s, 3H), 0.93 (s, 9H), 1.32 (d, J=6.3 Hz, 3H), 1.35 (s, 3H), 1.42 (s, 3H), 1.11–1.54 (m, 2H, 1.67 (m, 1H), 1.88–1.93 (m, 1H), 2.24–2.33 (m, 1H), 2.41–2.45 (m, 1H), 3.05 (dd, J=14.9, 9.5 Hz, 1H), 3.18 (dd, J=14.9, 2.4 Hz, 1H), 3.54–3.59 (m, 1H), 4.03–4.09 (m, 1H), 4.42 (dd, J=9.5 Hz, 6.0 Hz, 1H), 5.28 (m, 1H), 5.53 (ddd, J=15.2, 7.9, 4.0 Hz, 1H), 5.77 (ddd, J=15.2, 10.5, 3.5 Hz, 1H). $^{13}$C NMR (100 MHz, CDCl$_3$)δ −4.3, −4.0, 18.4, 21.1, 25.8, 26.1, 26.2, 26.3, 26.9, 28.6, 32.4, 40.7, 44.6, 71.8, 73.8, 78.6, 79.8, 81.1, 93.3, 107.9, 128.6, 133.6, 169.6, 198.6. HRMS (FAB) calcd for C$_{29}$H$_{38}$Co$_2$O$_{11}$SiH$^+$ [M+H]$^+$: 709.0926, found: 709.0924, Δ=0.2 ppm.

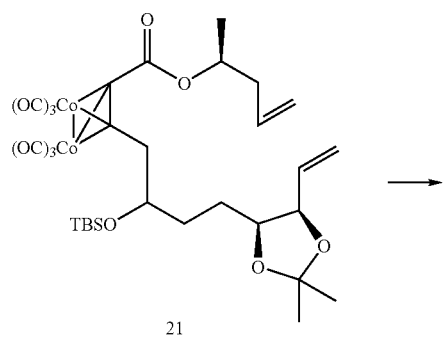

21

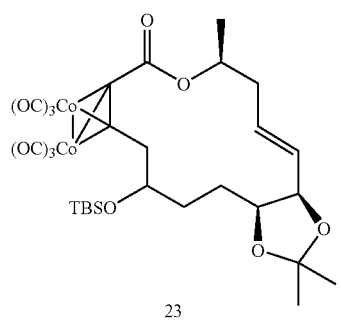

23

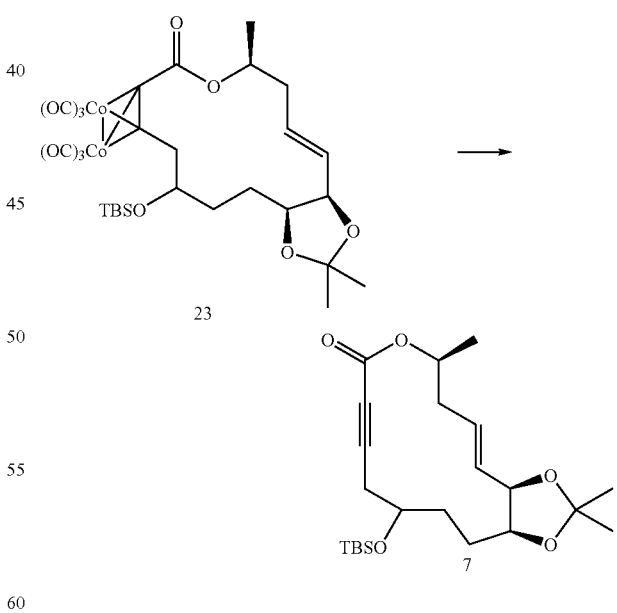

23

7

Macrolide 7:

To a solution of 23A (123 mg, 0.174 mmol) in acetone (10 mL) was added CAN (475 mg, 0.868 mmol) at −10° C. After 20 min, the reaction mixture was filtered through neutral alumina and the solvent was removed under reduced pressure vacuum. The residue was purified on a silica gel column using petroleum ether/EtOAc (20/1) as the eluant to afford 7A as a colorless oil (69 mg, 94%). $[\alpha]_D^{25}$ −124.6 (c 0.17, CHCl$_3$). $^1$H NMR (400 MHz, CDCl$_3$) δ −0.06, (s, 3H), 0.00 (s, 3H), 0.81 (s, 9H), 1.24 (d, J=6.2 Hz, 1H), 1.33, (s, 3H), 1.40 (s, 3H), 1.59–1.81 (m, 4H), 2.18–2.22 (m, 1H), 2.28–2.31 (m, 1H), 2.34–2.45 (m, 2H), 3.90–3.93 (m, 1H), 3.98–4.01 (m, 1H), 4.33–4.36 (m, 1H), 4.83–4.87 (m, 1H), 5.42–5.53 (m, 2H). $^{13}$C NMR (100 MHz, CDCl$_3$) δ −4.8, 18.4, 20.6, 26.1, 26.3, 28.4, 28.8, 30.1, 36.5, 40.6, 70.0, 71.7, 78.9, 80.1, 88.5, 108.7, 129.7, 132.0, 153.8.

7B was prepared by same procedure from 23B. 7B: (81 mg, 95%). $[\alpha]_D^{25}$ −173.3 (c 0.41, CHCl$_3$). $^1$H NMR (400 MHz, CDCl$_3$) δ 0.00, (s, 3H), 0.01 (s, 3H), 0.81 (s, 9H), 1.26 (d, J=6.1 Hz, 3H), 1.34 (s, 3H), 1.41 (s, 3H), 1.53–1.59 (m, 2H), 1.77–1.81 (m, 2H), 2.19–2.24 (m, 1H), 2.24–2.26 (m, 1H), 2.31–2.47 (m, 2H), 3.80 (b, 1H), 3.91–3.93 (m, 1H), 4.34–4.40 (m, 1H), 4.75–4.78 (m, 1H), 4.82–4.86 (m, 1H), 5.43–5.60 (m, 2H). $^{13}$C NMR (100 MHz, CDCl$_3$) δ −5.0, −4.8, 17.9, 20.17, 20.24, 25.5, 25.6, 25.7, 25.9, 28.0, 28.2, 28.3, 28.4, 29.6, 36.0, 36.7, 40.0, 40.1, 69.5, 70.8, 71.2, 71.4, 78.5, 78.6, 79.4, 79.6, 78.8, 108.2, 129.2, 131.3, 153.0. HRMS (FAB) calcd for C$_{25}$H$_{42}$O$_5$SiNa$^+$ [M+Na]$^+$: 473.2699, found: 473.2700, Δ=0.2 ppm.

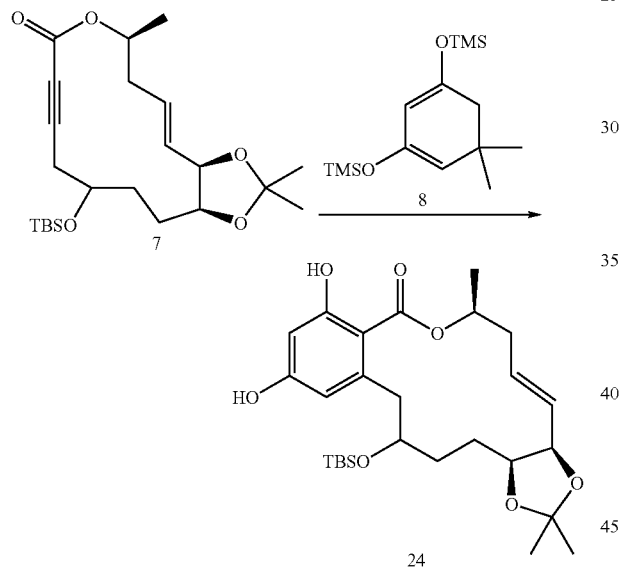

Resorcyclic Macrolide 24:

Macrolide 7A (26 mg, 0.065 mmol) was transferred to a vial and 0.2 mL diene 8 was added. The vial was sealed and heated to 140 0° C. for 36 h. The crude mixture was purified on preparative TLC (Whatman® Pk6F Silica Gel 60 Å 1000 μM) using Hexanes/EtOAc (2/1) as the eluant to afford 24A as a colorless oil (23 mg, 74%). $[\alpha]_D^{25}$ −99.1 (c 0.08, CHCl$_3$). $^1$H NMR (400 MHz, CDCl$_3$) δ −0.15, (s, 3H), 0.09 (s, 3H), 0.89 (s, 9H), 1.36 (s, 3H), 1.38 (s, J=6.1 Hz, 1H), 1.50 (s, 3H), 1.25–1.39 (m, 4H), 1.71–1.76 (m, 1H), 2.54–2.57 (m, 2H), 2.60–2.64 (m, 1H), 3.63–3.68 (m, 2H), 4.08–4.11 (m, 1H), 4.48 (m, 1H), 5.22–5.26 (m, 1H), 5.54 (bs, 1H), 5.70–5.75 (m, 2H), 6.27 (d, J=2.6 Hz, 1H), 6.28 (d, J=2.6 Hz, 1H), 11.3 (s, 1H). $^{13}$C NMR (100 MHz, CDCl$_3$) δ −4.5, −4.1, 0.4, 14.6, 18.4, 21.3, 21.5, 24.1, 25.9, 26.3, 28.6, 32.4, 40.1, 42.4, 70.0, 73.5, 73.7, 77.7, 79.7, 101.9, 106.6, 108.7, 111.6, 130.5, 131.6, 145.7, 160.4, 165.0, 172.1. HRMS (FAB) calcd for C$_{27}$H$_{42}$O$_7$SiH$^+$ [M+H]$^+$: 507.2778, found: 507.2777, Δ=0.2 ppm.

24B was prepared by same procedure from 7B. 24B: (81 mg, 84%). $[\alpha]_D^{25}$ −124.2 (c 0.42, CHCl$_3$). $^1$H NMR (400 MHz, CDCl$_3$) δ 0.00, (s, 3H), 0.14 (s, 3H), 0.99 (s, 9H), 1.50 (s, 3H), 1.58 (d, J=6.1 Hz, 1H), 1.40–1.67 (m, 2H), 1.64 (s, 3H), 1.87–1.92 (m, 2H), 2.64–2.72 (m, 2H), 3.09 (dd, J=3.8 Hz, 2.5 Hz, 1H), 3.45 (dd, J=13.8, 7.8 Hz, 1H), 4.02–4.04 (m, 1H), 4.20–4.22 (m, 1H), 4.70–4.74 (m, 1H), 5.50–5.52 (m, 1H), 5.76 (dd, J=15.5, 8.1 Hz, 1H), 5.93–5.95 (m, 2H), 6.42 (m, 1H), 6.48 (m, 1H), 11.62 (s, 1H). $^{13}$C NMR (100 MHz, CDCl$_3$) δ −4.3, −4.0, 14.5, 18.3, 18.4, 20.5, 21.5, 25.8, 26.2, 28.3, 28.4, 28.5, 33.1, 61.1, 72.7, 73.5, 79.1, 102.1, 107.1, 108.5, 112.7, 130.1, 130.5, 144.2, 160.7, 164.9, 171.7. LRMS (ESI) calcd for C$_{27}$H$_{42}$O$_7$SiNa$^+$ [M+Na]$^+$: 529.2, found: 529.1. LRMS (ESI) calcd for C$_{27}$H$_{42}$O$_7$SiCl$^-$ [M+Cl]$^-$: 541.3, found: 541.2.

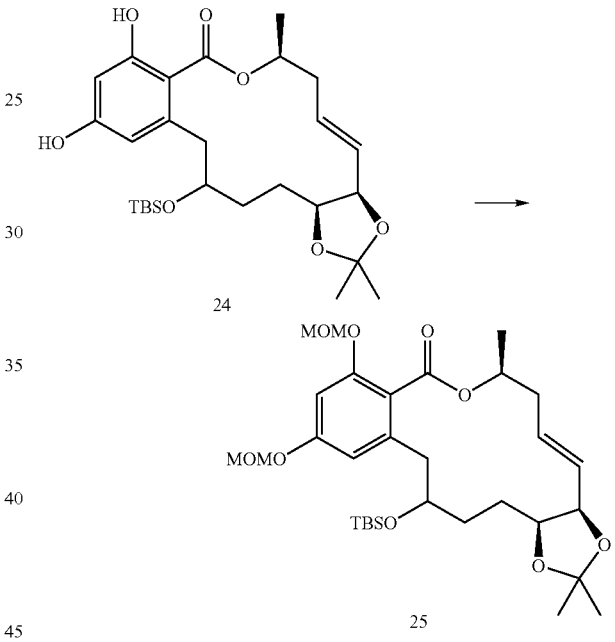

MOM Ether 25:

To a solution of 24A (23 mg, 0.045 mmol) in CH$_2$Cl$_2$ (0.5 mL) was added diethylpropylethylamine (0.08 mL, 0.450 mmol) and MOMCl (0.018 mL, 0.227 mmol). The reaction mixture was stirred for 10 h before quenched with saturated aqueous NH$_4$Cl solution, extracted with EtOAC (100 mL×3). The organic layers were combined and dried with anhydrous MgSO$_4$, filtered, and concentrated under reduced pressure vacuum. The residue was purified on preparative TLC (Whatman® Pk6F Silica Gel 60 Å 1000 μM) using Hexanes/EtOAc (2/1) as the eluant to afford 25A as a colorless oil (21 mg, 78%). $[\alpha]_D^{25}$ −2.86 (c 0.07, CHCl$_3$).). $^1$H NMR (400 MHz, CDCl$_3$) δ 0.00, (s, 3H), 0.10 (s, 3H), 0.93 (s, 9H), 1.39 (s, 3H), 1.39 (d, 3H), 1.48 (s, 3H), 1.42–1.48 (m, 1H), 1.60–1.64 (m, 2H), 1.72–1.77 (m, 1H), 2.41–2.45 (m, 2H), 2.66 (dd, J=5.6, 4.6 Hz, 1H), 2.89 (dd, J=4.5, 1.6 Hz, 1H), 3.47 (s, 3H), 3.48 (s, 3H), 3.97–3.98 (m, 1H), 4.09–4.15 (m, 1H), 4.73 (dd, J=9.0, 6.0 Hz, 1H), 5.13–5.19 (m, 4H), 5.30–5.36 (m, 1H), 5.57 (dd, J=15.4, 9.1 Hz, 1H), 5.70–5.77 (m, 1H), 6.68 (d, J=2.0 Hz, 1H), 6.86 (d, J=2.0 Hz, 1H). $^{13}$C NMR (100 MHz, CDCl$_3$) δ −4.3, −4.2, 0.5, 18.4, 21.6, 24.0, 25.9, 26.3, 28.7, 30.1, 32.3, 40.1, 40.4, 56.5, 56.6, 71.4, 71.6, 80.3, 94.7, 94.9, 101.8, 108.5, 111.4, 119.8, 130.2, 132.4, 139.4, 155.3, 158.6, 168.4.

25B was prepared by same procedure from 24B. 25B: (58 mg, 83%). $[\alpha]_D^{25}$ −16.2 (c 0.29, CHCl$_3$). $^1$H NMR (400 MHz, CDCl$_3$) δ −0.17 (s, 3H), −0.06 (s, 3H), 0.81 (s, 9H), 1.26 (s, 3H), 1.33 (d, J=6.1 Hz, 1H), 1.38 (s, 3H), 1.17–1.52 (m, 4H), 2.30–2.36 (m, 2H), 2.61 (dd, J=14.2, 6.0 Hz, 1H), 2.71 (dd, J=14.2, 6.9 Hz, 1H), 3.39 (s, 3H), 3.40 (s, 3H), 3.80–3.83 (m, 1H), 4.10–4.14 (m, 1H), 4.41 (dd, J=8.9, 6.1 Hz, 1H), 5.04–5.09 (m, 4H), 5.20–5.23 (m, 1H), 5.43 (dd, J=15.3, 9.1 Hz, 1H), 5.60–5.67 (m, 1H), 6.46 (s, 1H), 6.60 (s, 1H). $^{13}$C NMR (100 MHz, CDCl$_3$) δ − 4.2, −3.8, 18.4, 21.3, 25.8, 26.2, 26.25, 26.3, 28.6, 33.0, 39.8, 40.0, 42.0, 56.5, 56.6, 71.7, 74.5, 78.6, 79.9, 94.7, 94.9, 101.5, 108.3, 111.2, 119.8, 131.0, 131.4, 139.2, 155.8, 158.9, 168.5. HRMS (FAB) calcd for C$_{31}$H$_{50}$O$_9$SiH$^+$ [M+H]$^+$: 595.3302, found: 595.3304, Δ=−0.3 ppm.

5.59 (dd, J=15.4, 9.2 Hz, 1 H), 5.70–5.75 (m, 1H), 6.66 (d, J=2.0 Hz, 1H), 6.70 (d, J=2.0 Hz, 1H). $^{13}$C NMR (100 MHz, CDCl$_3$) δ 21.5, 25.1, 25.7, 28.6, 30.1, 32.3, 40.0, 41.6, 56.6, 56.7, 70.5, 72.0, 80.1, 94.7, 94.9, 101.9, 108.2, 111.0, 119.7, 130.6, 132.7, 138.3, 155.8, 159.1, 168.4. HRMS (FAB) calcd for C$_{25}$H$_{36}$O$_9$H$^+$ [M+H]$^+$: 482.2438, found: 482.2437, Δ=0.1 ppm.

26B was prepared by same procedure from 25B. 26B: (20 mg, 87%). $[\alpha]_D^{25}$ −32.0 (c 0.10, CHCl$_3$). $^1$H NMR (500 MHz, CDCl$_3$) δ 1.18 (m, 2H), 1.35 (s, 3H), 1.37 (d, J=6.2 Hz, 1H), 1.42 (s, 3H), 1.55–1.69 (m, 2H), 1.98–2.06 (m, 1H), 2.42–2.48 (m, 3H), 2.78 (dd, J=13.8, 2.4 Hz, 1H), 3.41–3.50 (m, 6H), 3.62–3.67 (m, 1H), 4.19–4.25 (m, 1H), 4.49 (dd, J=9.4, 6.0 Hz, 1H), 5.11–5.18 (m, 4H), 5.36–5.42 (m, 1H), 5.56 (dd, J=15.4, 9.5 Hz, 1H), 5.65–5.72 (m, 1H), 6.57 (d, J=2.0 Hz, 1H), 6.66 (d, J=2.0 Hz, 1H). $^{13}$C NMR (100 MHz, CDCl$_3$) δ 21.6, 25.8, 26.8, 28.6, 32.0, 39.8, 42.6, 56.5, 56.7, 72.3, 74.8, 80.3, 94.7, 94.9, 101.8, 108.6, 110.7, 108.6, 110.7, 119.5, 129.9, 132.8, 138.7, 155.9, 159.0, 168.7. HRMS (FAB) calcd for C$_{25}$H$_{36}$O$_9$H$^+$[M+H]$^+$: 482.2438, found: 482.2437, Δ=0.1 ppm.

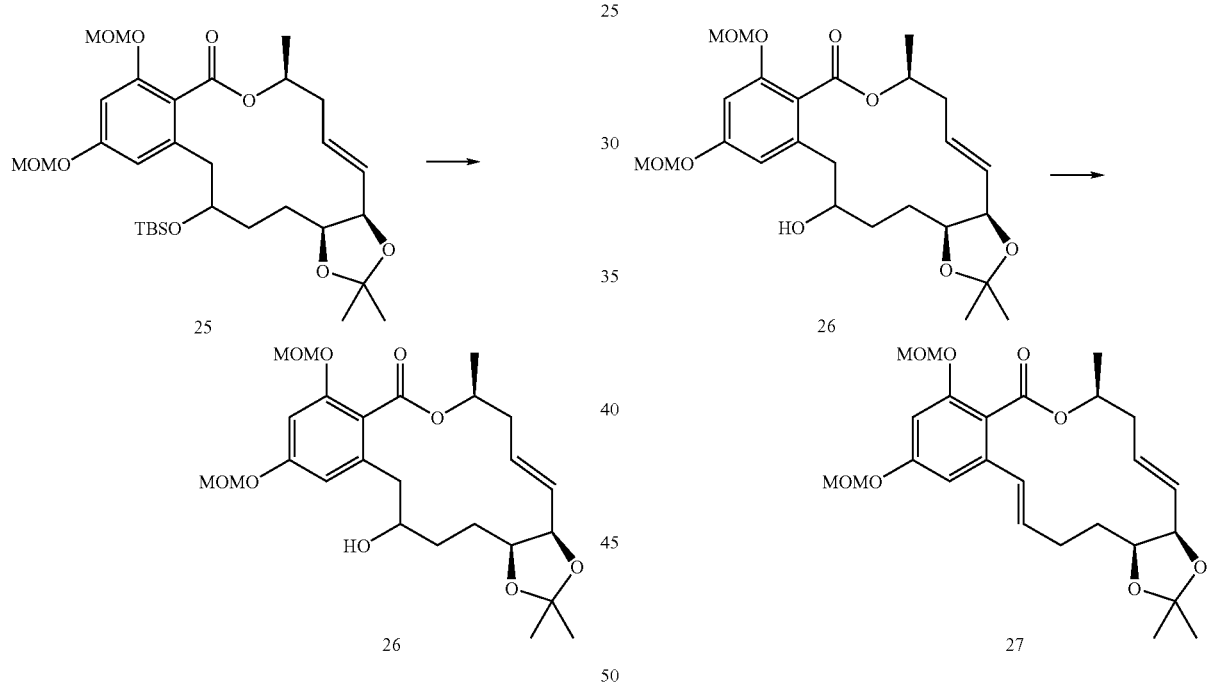

Alcohol 26:

To a solution of 25A (21 mg, 0.035 mmol) in THF (1.4 mL) was added pyridine (0.6 mL) and HF-pyridine (30%, 0.3 mL). The reaction mixture was stirred for 10 h before quenched with MeOTf (2 mL) and stirred for 1 h. The solvent was removed under reduced pressure vacuum. The residue was purified on preparative TLC (Whatman® Pk6F Silica Gel 60 Å 1000 μM) using Hexanes/EtOAc (1/1) as the eluant to afford 26A as a colorless oil (12 mg, 78%). $[\alpha]_D^{25}$−105.2 (c 0.06, CHCl$_3$). $^1$H NMR (400 MHz, CDCl$_3$) δ −0.05 (s, 3H), 0.05 (s, 3H), 1.35 (s, 3H), 1.38 (d, J=6.2 Hz, 3H), 1.46 (s, 3H), 1.61–1.81 (m, 4H), 2.40–2.46 (m, 2H), 2.70 (dd, J=14.1, 6.1 Hz, 1H), 2.81 (dd, J=14.1, 4.7 Hz, 1H), 3.46 (s, 6H), 3.89 (b, 1H), 4.10–4.14 (m, 1H), 4.56 (dd, J=9.1, 6.1 Hz, 1H), 5.13–5.17 (m, 4H), 5.32–5.37 (m, 1H), Diene 27:

A solution of Martin's sulfurane dehydration agent (140 mg, 0.208) was added into a vial containing 26B (20 mg, 0.042) at 0° C. The reaction mixture was warmed up to r.t. over 2 h and the crude was purified on preparative TLC (Whatman® Pk6F Silica Gel 60 Å 1000 μM) using Hexanes/EtOAc (1/1) as the eluant to afford 27 as a colorless oil (16 mg, 84%). $[\alpha]_D^{25}$ −123.8 (c 0.08, CHCl$_3$). $^1$H NMR (500 MHz, CDCl$_3$) δ 1.35 (s, 3H), 1.36 (d, J=6.0 Hz, 3H), 1.46 (s, 3 H), 1.49–1.55 (m, 1H), 1.80–1.85 (m, 1H), 2.07–2.11 (m, 1H), 2.29–2.32 (m, 1H), 2.45–2.55 (m, 2H), 3.41–3.50 (m, 6H), 4.16–4.21 (m, 1H), 4.56 (dd, J=9.5, 5.4 Hz, 1H, 1H), 5.10–5.20 (m, 4H), 5.32–5.36 (m, 1H), 5.59 (dd, J=15.5, 9.6 Hz, 1H), 5.70–5.77 (m, 1H), 5.15 (m, 1H), 6.24 (d, J=15.4 Hz, 1H), 6.80 (d, J=1.8 HZ, 1H), 6.68 (d, J=1.8

HZ, 1H). $^{13}$C NMR (125 MHz, CDCl$_3$) δ 21.1, 25.8, 28.6, 28.7, 29.0, 39.5, 71.6, 80.1, 84.3, 94.6, 102.6, 104.8, 108.3, 117.9, 124.8, 128.4, 129.3, 131.9, 132.3, 136.8, 155.1, 158.9, 167.3. HRMS (FAB) calcd for $C_{25}H_{34}O_8H^+$ [M+H]$^+$: 463.2332, found: 463.2333, Δ=−0.2 ppm.

27 could also be obtained from 26A using same procedure (90%).

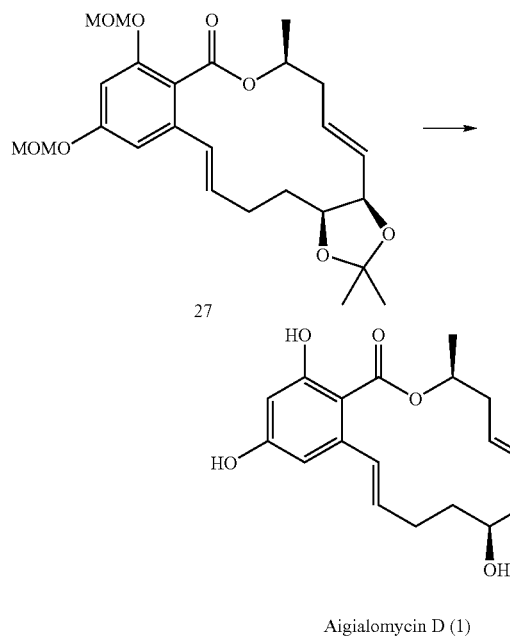

Aigialomycin D (1):

To a solution of 27 (16 mg, 0.035) in MeOH (1.5 mL) was added HCl (1 N, 1.5 mL) and stirred for 2 d. The reaction was quenched with saturated aqueous NaHCO$_3$ solution and extracted with EtOAc. The organic layers were combined and dried over anhydrous MgSO$_4$, filtered and concentrated under reduced vacuum. The crude was purified on preparative TLC (Whatman® Pk6F Silica Gel 60 Å 1000 μM) using MeOH/CH$_2$Cl$_2$ (5%) as the eluant to afford 1 as a white solid (8 mg, 69%). Mp: 84.2–86.9° C. [α]$_D^{25}$ −18.0 (c 0.03, MeOH). IR (neat) 3346, 1643, 1607, 1311, 1261, 1166, 1017, 968. $^1$H NMR (500 MHz, acetone-d$_6$) δ 1.39 (d, J=6.4 Hz, 3H), 1.58–1.61 (m, 1H), 2.14 (m, 1H), 2.32–2.36 (m, 2H), 2.43–2.46 (m, 1H), 2.57 (ddd, J=14.5, 7.3, 3.1 Hz, 1H), 3.56 (br, 1H), 3.64 (m, 1H), 3.76 (br, 1H), 4.35 (brd, J=4.1 Hz, 1H), 5.41–5.47 (m, 1H), 5.69 (dd, J=15.6, 5.1 Hz, 1H), 5.87 (dddd, J=15.6, 7.4, 7.4, 1.4 Hz, 1H), 6.10 (ddd, J=15.9, 5.5, 5.7 Hz, 1H), 6.28 (d, J=2.3 Hz, 1H), 6.53 (d, J=2.3 Hz, 1H), 7.16 (d, J=15.9 Hz, 1H), 9.10 (bs, 1H), 11.7 (s, 1H). $^{13}$C NMR (125 MHz, acetone-d$_6$) δ 19.2, 28.1, 28.8, 38.1, 73.1, 73.4, 76.7, 102.6, 104.6, 107.9, 125.6, 130.8, 133.8, 135.9, 144.5, 163.2, 166.0, 172.3. LRMS (ESI) calcd for $C_{18}H_{22}O_6Na^+$ [Na+H]$^+$: 357.1, found: 357.3. LRMS (ESI) calcd for $C_{18}H_{21}O_6^-$ [M−H]$^-$: 333.1, found: 333.1. LRMS (ESI) calcd for $C_{18}H_{22}O_6Cl^-$ [M+Cl]$^-$: 369.1, found: 369.0. HRMS (TOF) calcd for $C_{18}H_{22}O_6Na^+$ [M+Na]$^+$: 357.1314, found: 357.1325, Δ=3.1 ppm. All the physical data are consistent with the reported value (Isaka, M.; Suyarnsesta-korn, C.; Tanticharoen, M.; Kongsaeree, P.; Thebtaranonth, Y. *J. Org. Chem.* 2002, 67, 1561–1566; incorporated herein by reference).

| | $^1$H NMR Data of Aigialomycin D | |
|---|---|---|
| position | Isolated Aigialomycin D by Isaka | Synthetic Aigailomycin D |
| 3 | 6.27 (d, 2.4) | 6.28 (d, 2.3) |
| 5 | 6.52 (d, 2.4) | 6.53 (d, 2.3) |
| 1' | 7.14 (d, 15.9) | 7.16 (d, 15.9) |
| 2' | 6.09 (ddd, 15.9, 5.6, 5.4) | 6.10 (ddd, 15.9, 5.7, 5.5) |
| 3' | 2.31–2.34 (m) | 2.32–2.36 (m) |
|  | 2.31–2.34 (m) | 2.32–2.36 (m) |
| 4' | 2.14 (m) | 2.14 (m) |
|  | 1.58 (m) | 1.58–1.61 (m) |
| 5' | 3.62 (m) | 3.64 (m) |
| 6' | 4.35 (brd, 4.3) | 4.35 (brd, 4.1) |
| 7' | 5.68 (dd, 15.7, 5.0) | 5.69 (dd, 15.6, 5.1) |
| 8' | 5.87 (dddd, 15.7, 7.3, 7.3, 1.2) | 5.87 (dddd, 15.6, 7.4, 7.4, 1.4) |
| 9' | 2.55 (ddd, 14.6, 7.5, 3.2) | 2.55 (ddd, 14.5, 7.3, 3.1) |
|  | 2.42 (m) | 2.43–2.46 (m) |
| 10' | 5.42 (m) | 5.41–5.47 (m) |
| 10'-CH$_3$ | 1.38 (d, 6.4) | 1.39 (d, 6.4) |
| 2-OH | 11.65 (s) | 11.7 (s) |
| 4-OH | 9.5 (br) | 9.1 (br) |
| 5'-OH | not detected | 3.56 (br) |
| 6'-OH | not detected | 3.76 (br) |

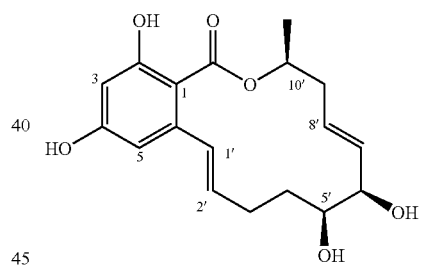

aigialomycin D

Example 2

Concise Route to Benzofused Macrolactones Via Ynolides: Cycloproparadicicol

Structures of Hsp90 Inhibitors

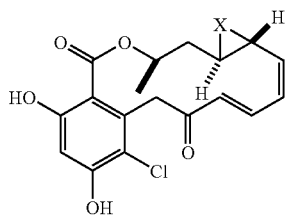

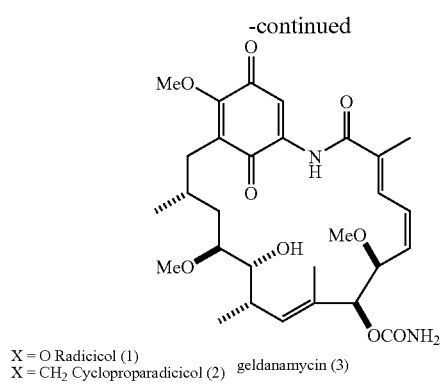

X = O Radicicol (1)
X = CH₂ Cycloparadicicol (2)    geldanamycin (3)

In this Example, we report a new approach to the broad family of resorcinylic fused macrolides. The underlying concept is captured graphically in Scheme 2-1, which is directed to our focusing target, cycloproapradicicol (2). However, as is suggested by the very facile synthesis of model compound 13 (vide infra), and has been further established in ongoing work, the method is quite general. The central element of our plan is the building of an "ynolide" intermediate and its advancement to the benzomacrolide by a Diels-Alder cycloaddition. The ynolide is constructed through olefin metathesis, enabled only by presentation of the acetylene linakge as its dicobalt hexacarbonyl cluster (see 9→10 and 14→15) (Young, D. G.; Burlison, J. A.; Peters, U. *J. Org. Chem.* 2003, 68, 3494; incorporated herein by reference).

Scheme 2-1. New Synthetic Strategy

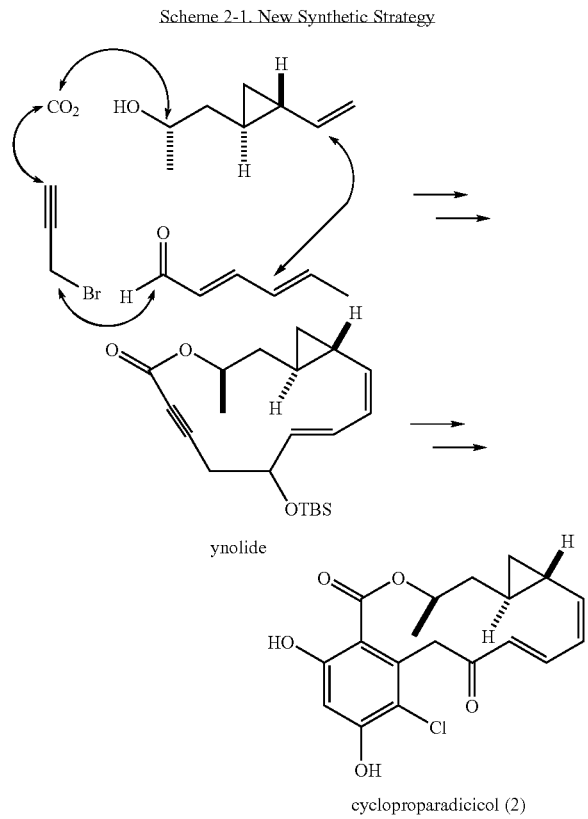

Our synthesis commenced with commercial 2,4-hexadienal (sorbaldehyde, 5, Scheme 2-2). Reformatsky-like condensation of propargyl bromide (4) with 5, followed by TBS ether protection and subsequent reaction of the lithium alkynide ion with $CO_2$, provided acid 6. Following reaction of racemic 6 and the known optically pure and defined alcohol 7 (Yamamoto, K.; Gabaccio, R. M.; Stachel, S. J.; Solit, D. B.; Chiosis, G., Rosen, N.; Danishefsky, S. J. *Angew. Chem. Int. Ed.* 2003, 42, 1280; incorporated herein by reference) under Mitsonobu conditions, ester 8 was obtained.

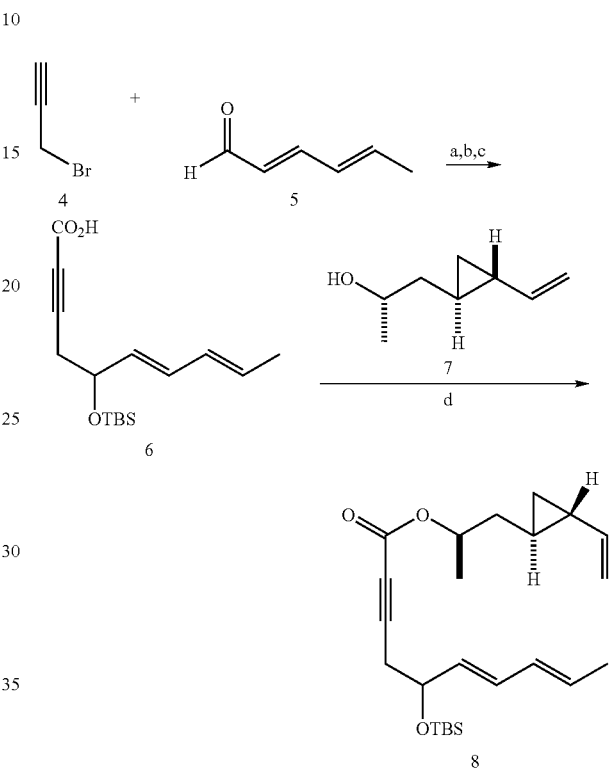

Reagents and conditions: (a) (i) Zn, THF, 66%; (b) TBSCl, imidazole, DMAP, $CH_2Cl_2$, 100%; (c) BuLi, −78° C.; then $CO_2$; (d) DIAD, Ph₃P, THF, −20° C., 47% (two steps).

Projected ring-closing metathesis (RCM) reactions were conducted with a cyclic alkyne. Unfortunately, triene 8 failed to cyclize under a variety of RCM conditions. We took this negative finding to reflect impediments to cyclization arising from the linear character of the acetylene, possibly aggravated by rigidities associated with the trans-disubstituted cyclopropane. A more flexible model compound was prepared from acid 6 and 5-hexen-1-ol, and subjected to RCM reactions (Scheme 2-3). Again, only starting material was recovered. Aside from the constraint to cyclization imposed by linear alkyne, the cyclization could further be complicated by non productive coordination of the acetylene to the RCM catalytic machinery. It is well known that reaction of dicobalt carbonyl with acetylenes can lead to stable complexes (Greenfield, H.; Sternberg, H, W,; Friedel, R. A.; Wotiz, J. H.; Markby, R.; Wender, I. *J. Am. Chem. Soc.* 1956, 78, 120; Nicholas, K. M.; Pettit, R. *Tetrahedron Lett.* 1971, 3475; each of which is incorporated herein by reference), wherein the geometry of cobalt-complexed alkynes is distorted to approximately 140° (Dickson, R. S.; Fraser, P. J. *Adv. Organomet. Chem.* 1974, 12, 323; incorporated herein by reference).

In the event, cyclization of 9 proceeded smoothly under the conditions shown. Following oxidative removal of the cobalt using ammonium cerium (IV) nitrate (CAN), the desired cyclic alkynoic ester 11 was generated in high yield (Scheme 2–3).

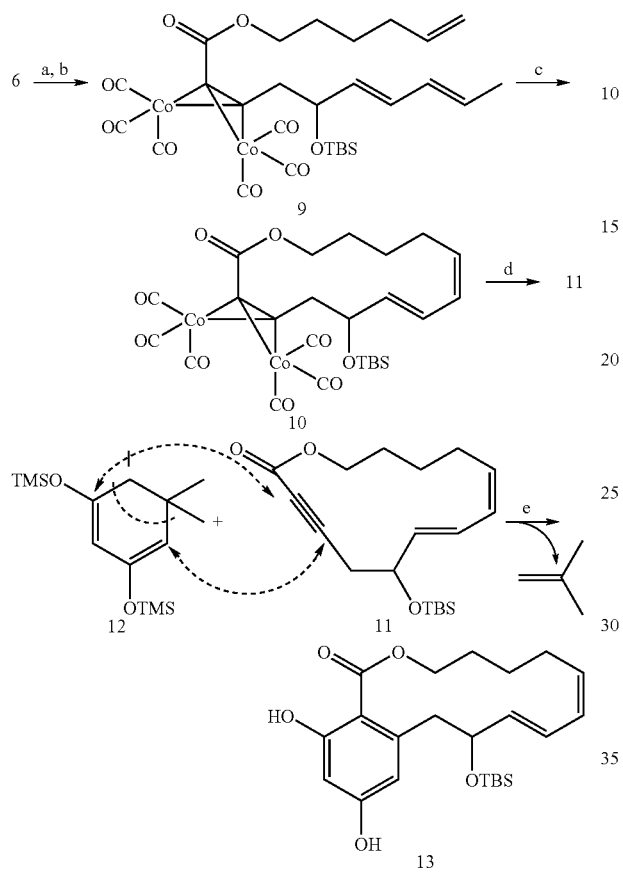

Scheme 2-3. Synthesis of the Model Resorcinylic Marcrolactone

Reagents and conditions: (a) 5-hexen-1-ol, EDC/DMAP, $CH_2Cl_2$, 59%; (b) $Co_2(CO)_8$, PhMe, 86%; (c) $2^{nd}$ generation Grubbs catalyst (25 mol %), $CH_2Cl_2$ (0.2 mM), 45° C., 71%; (d) CAN, acetone, −10° C., 92%; (e) 140° C., neat; then $SiO_2$, 60%.

Construction of the resorcinylic skeleton called for a Diels-Alder reaction of 11 with a 1,3-bis-oxygenated diene. We found that the known dimedone-derived diene, 5,5-dimethyl-1,3-bis-trimethylsilyloxy-cyclohexa-1,3-diene (Ibuka, T.; Mori, Y.; Aoyama, T.; Inubushi, Y. Chem. Pharm. Bull. 1978, 26, 456; Langer, P.; Schneider, T.; Stoll, M. Chem. Eur. J. 2000, 6, 320; each of which is incorporated herein by reference) (12, Scheme 2-3), served our purpose best. Indeed, Diels-Alder reaction of cyclic alkyne 11 with 12 proceeded smoothly at 140° C., providing the desired aromatic product 13 in 60% yield, after concomitant retro-Diels-Alder loss of isobutene from the initial adduct, and hydrolysis of the trimethylsilyl ether groups during chromatography.

We applied this strategy to the targeted system (8). Gratifyingly, under the same RCM conditions, cyclopropane-containing cobalt complex 14 cyclized to give 15 in 57% yield, as a 2:1 mixture of two diatereomers (Scheme 2-4) (Here, we described only the conversion of the major isomer of 15 to 2. The other isomer worked equally well). In this case, removal of cobalt on 15, however, proved to be challenging, presumably due to the presence of the sensitive vinyl cyclopropane functionality. After screening a variety of conditions, we found that $I_2$-THF worked well (Tanaka, S.; Tsukiyama, T.; Isobe, M. Tetrahedron Lett. 1993, 34, 5757; incorporated herein by reference). The key cyclic alkyne dienophile 16 was thus obtained in 69% yield.

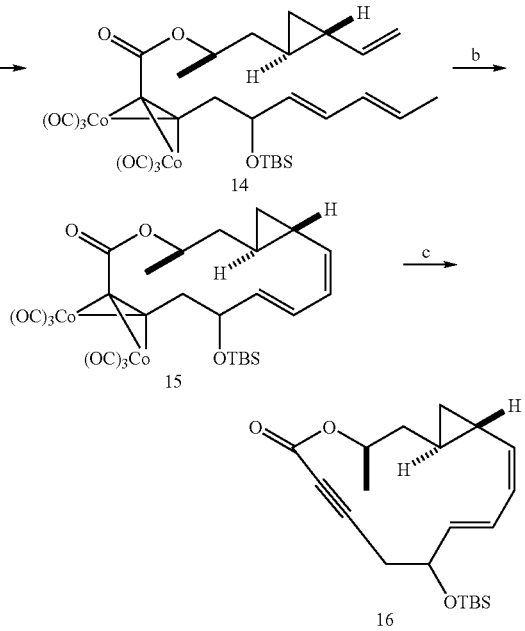

Reagents and conditions: (a) $Co_2(CO)_8$, PhMe, 100%; (b) $2^{nd}$ genera-tion Grubbs catalyst (25 mol %), $CH_2Cl_2$ (0.2 mM), 45° C., 57%; (c) $I_2$, THF, 0° C., 69%.

Diels-Alder reaction of 16 with diene 12 furnished the desired product 17 in 75% yield (Scheme 2-5). Transformation of 17 to the desired ketone by direct oxidation turned out to be a non-trival matter. In the end, it was accomplished following protection of the two phenolic functions, as shown, by straightford transformations to afford dechlorinated analogue 19 (Scheme 2–5). Finally, regioselective chlorination of 19 using $SO_2Cl_2$ in $CH_2Cl_2$ (Yamamoto, K.; Gabaccio, R. M.; Stachel, S. J.; Solit, D. B.; Chiosis, G., Rosen, N.; Danishefsky, S. J. Angew. Chem. Int. Ed. 2003, 42, 1280; Garbaccio, R. M.; Stachel, S. J.; Baseschlin, D. K.; Danishefsky, S. J. J. Chem. Soc. 2001, 123, 1090; each of which is incorporated herein by reference), converted 19 into cycloproparadicicol (2).

Scheme 2-5. Completion of the Synthesis

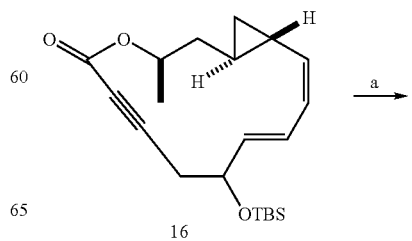

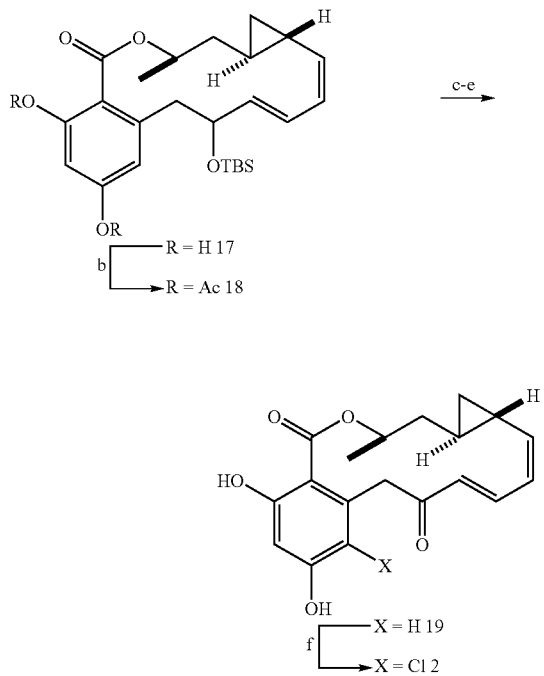

Reagents and conditions: (a) 12, 140° C., neat, 75%; (b) Ac₂O, DMAP, DMF, 87%; (c) HF/Pyr. THF; (d) Dess-Martin periodinane, CH₂Cl₂, 68% (two steps); (e) 5% NaHCO₃/MeOH, 92%; (f) SO₂Cl₂, CH₂Cl₂, 0° C., 61%.

In summary, a new efficient synthetic route has been developed for a pre-clinical candidate, cycloproparadicicol (2) and, by extension, to a broad range of benzofused macrolactones.

Experimentals:

General Methods: Reagents obtained from commercial suppliers were used without further purification unless otherwise noted. THF, toluene, and methylene chloride was obtained from a dry solvent system (passed through a prepacked column of alumina) and used without further drying. All air and water sensitive reactions were performed in oven or flame-dried glassware. NMR ($^1$H and $^{13}$C) spectra were recorded on Bruker AMX-400 MHz or Bruker Advance DRX-500 MHz as noted individually, referenced to CDCl₃ (7.27 ppm for $^1$H and 77.23 ppm for $^{13}$C). Optical rotations were obtained on a JASCO model DIP-370 digital polarimeter. Low resolution mass spectra (ESI) were determined with a PESciex AP 130 spectrometer. High resolution mass spectra (FAB) were determined at Chemistry Department of Columbia University. Flash chromatography was performed with silica gel (230–400 mesh) from EM Science as the stationary phase. Analytical thin-layer chromatography was performed on E. Merck silica gel 60 F254 plates. Compounds which were not UV active were visualized by dipping the plates in phosphomolybdic acid solution and heating. Preparative thin layer chromatography was performed using the indicated solvent on Whatman® (LK6F Silica gel 60 Å 250 μM or Pk6F Silica Gel 60 Å 1000 μM) TLC plate.

Acid 6. To a suspension of activated zinc (15 g, 230 mmol) in dry THF (50 mL) at 0° C. was added propargyl bromide 4 (19.2 mL 80 wt % in toluene, 172 mmol). The resulting mixture was stirred at 0° C. for 1 hr, and sorbaldehyde 5 (12.7 mL, 115 mmol) was added. After 1 hr at 0° C., additional zinc (4.5 g, 69 mmol) was added, and stirring was continued for 2.5 hrs at room temperature (the reaction was exothermic and ice bath was needed occasionally to keep the temperature down). The reaction was quenched by slow addition of sat. aqueous NH₄Cl (500 mL), followed by diluting with Et₂O (1 L). The layers were separated, and the organic layer was washed with H₂O (300 mL), brine (300 mL), dried (Na₂SO₄), filtered and concentrated in vacuum. The residue was dissolved in CH₂Cl₂ (750 mL) with imidazole (9.8 g, 144 mmol), t-butyldimethylsilyl chloride (19 g, 126 mmol) and 4-(dimethylamino) pyridine (1.4 g, 11.5 mmol), and stirred at room temperature for 3 hrs. Additional imidazole (4.9 g, 72 mmol) and t-butyldimethylsilyl chloride (9.5 g, 63 mmol) were added, and stirring was continued for 9 hrs. The reaction was quenched by addition of sat. aqueous NH₄Cl (200 mL). The layers were separated, and the organic layer was washed with H₂O (200 mL), brine (200 mL), dried (Na₂SO₄), filtered and concentrated in vacuum. The residue was purified by flash chromatography (silica, 0 to 10% Et₂O in hexane) to give the terminal alkyne precursor of 6 (15 g, 52%). $^1$H NMR (CDCl₃, 400 MHz) δ 6.18 (dd, J=15.1, 10.5 Hz, 1H), 6.03 (ddd, J=15.0, 10.6, 1.3 Hz, 1H), 5.72 (dd, J=14.9, 6.9 Hz, 1H), 5.61 (dd, J=15.1, 6.4 Hz, 1H), 4.30 (q, J=6.3 Hz, 1H), 2.43 (ddd, J 16.5, 6.2, 2.7 Hz, 1H), 2.34 (ddd, J=16.5, 6.8, 1.7 Hz, 1H), 2.60 (t, J=2.6 Hz, 1H), 1.77 (d, J=6.8 Hz, 3H), 0.91 (s, 9H), 0.09, 0.06 (2s, 6H); $^{13}$C NMR (CDCl₃, 100 Hz) δ 132.5, 131.1, 130.7, 130.0, 81.7, 72.1, 70.1, 28.9, 26.1, 18.4, −2.7; IR (film) ν$_{max}$ 3313, 2956, 2930, 2856, 2121, 1255, 1115, 1079, 987, 837; ESIMS m/z 273 ([M+Na⁺], C₁₅H₂₆NaOSi requires 273).

To a solution of the terminal alkyne precursor of 6 (15.0 g, 59.9 mmol) in Et₂O (270 mL) at −78° C., was added a solution of BuLi (1.6 M in hexane, 41.5 mL, 66.4 mmol). After 45 min, excess crushed dry ice was added and the reaction was allowed to warm to room temperature. The solution was acidified by addition of 0.5 M aqueous citric acid (300 mL). The layers were separated, and the aqueous layer was extracted with additional Et₂O (300 mL×2). The combined organic layers were dried (MgSO₄), filtered and concentrated in vacuum. The residue was purified by flash chromatography (silica, 50% to 100% EtOAc in hexane) to give the product as a light yellow solid (17.5 g, 99%). $^1$H NMR (CDCl₃, 400 MHz) δ 6.19 (dd, J=15.1, 10.4 Hz, 1H), 6.03 (ddd, J=14.9, 10.6, 1.3 Hz, 1H), 5.75 (dd, J=15.0, 6.8 Hz, 1H), 5.55 (dd, J=15.1, 6.4 Hz, 1H), 4.36 (q, J=6.3 Hz, 1H), 2.61–2.48 (m, 2H), 1.77 (d, J=6.8 Hz, 3H), 0.91 (s, 9H), 0.10, 0.06 (2s, 6H); $^{13}$C NMR (CDCl₃, 100 Hz) δ 157.6, 131.6, 131.3, 130.7, 89.7, 74.0, 71.4, 29.3, 26.0, 18.4, 18.3, −4.3, −4.7; IR (film) ν$_{max}$ 2956, 2930, 2857, 2242, 1689, 1281, 1257, 1080; ESIMS m/z 317 ([M+Na$^+$], C$_{16}$H$_{26}$NaO$_3$Si requires 317).

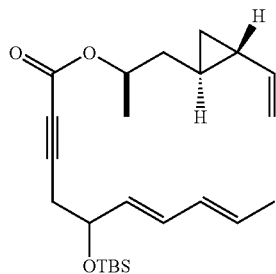

Alkynoic ester 8. To a solution of DIAD (14.7 mL, 72.9 mmol) in dry THF (350 mL) was added Ph$_3$P (15.8 g, 60.2 mmol), and the mixture was stirred at room temperature for one hour. At −20° C., a solution of acid 6 (13.1 g, 44.4 mmol) in 100 mL THF was added. After 15 min, a solution of alcohol 7 (4.0 g, 31.7 mmol) in 150 mL THF was added, and stirring was continued for 2 hours at −20° C. The reaction was quenched by addition of 250 mL of pH 7.2 phosphate buffer, followed by warming to room temperature and diluting with EtOAc (1.5 L). The layers were separated, and the aqueous layer was extracted with EtOAc (2×250 mL). The combined organic layers were washed with brine (250 mL), dried (Na$_2$SO$_4$), filtered and concentrated in vacuum. The residue was purified by flash chromatography (silica, 50:1→20:1 hexanes/EtOAc) to give ester 8 as a mixture of two inseparable diastereoisomers (5.9 g, 47%). $^1$H NMR (CDCl$_3$, 400 MHz) δ 6.17 (dd, J=15.1, 10.5 Hz, 1H), 6.03 (ddd, J=12.3, 10.6, 1.4 Hz, 1H), 5.70 (dd, J=14.8, 6.8 Hz, 1H), 5.55 (dd, J=15.2, 6.4 Hz, 1H), 5.37 (ddd, J=17.1, 10.2, 8.7 Hz, 1H), 5.06 (q, J=6.4 Hz, 1H), 5.03 (dd, J=17.0, 1.5 Hz, 1H), 4.84 (dd, J=10.2, 1.6 Hz, 1H), 4.34 (q, J=6.4 Hz, 1H), 2.56–2.42 (m, 2H), 1.76 (d, J=6.8 Hz, 3H), 1.57–1.53 (m, 2H), 1.29 (d, J=6.4 Hz, 3H), 1.20–1.10 (m, 1H), 0.90 (s, 9H), 0.79–0.68 (m, 1H), 0.65–0.57 (m, 2H), 0.10, 0.05 (2s, 6H); $^{13}$C NMR(CDCl$_3$, 100 Hz) 6154.5, 141.4, 131.8, 131.1, 130.8, 130.4, 112.1, 86.2, 74.9, 73.0, 71.5, 39.7, 29.2, 26.0, 22.4, 19.8, 18.4, 18.3, 17.2, 13.7, −4.3, −4.7; IR (film) ν$_{max}$ 2955, 2930, 2856, 2238, 1710, 1253, 1068; ESIMS m/z 437 ([M+Cl$^-$], C$_{24}$H$_{38}$ClO$_3$Si requires 437); HRMS (FAB$^+$) m/z 403.2687 ([M+H]$^+$, C$_{24}$H$_{39}$O$_3$Si requires 403.2668).

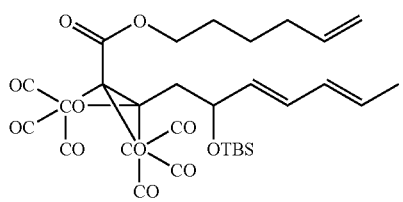

Cobalt complex 9. To a solution of acid 6 (192 mg, 0.653 mmol) and 5-hexen-1-ol (0.118 mL, 0.979 mmol) in dry CH$_2$Cl$_2$ (3 mL) was added EDCI (150 mg, 0.784 mmol) and 4-(dimethylamino)pyridine (8.0 mg, 0.065 mmol). After 3 hrs at room temperature, the reaction mixture was loaded on PTLC plates and purified (12:1 hexane/EtOAc) to give the model ester (146 mg, 59%). $^1$H NMR (CDCl$_3$, 400 MHz) δ 6.18 (dd, J=15.1, 10.5 Hz, 1H), 6.04 (ddd, J=15.0, 10.5, 1.5 Hz, 1H), 5.79 (ddt, J=17.1, 10.3, 7.2 Hz, 1H), 5.71 (dq, J=15.0, 6.8 Hz, 1H), 5.56 (dd, J=15.1, 6.4 Hz, 1H), 5.03 (dq, J=17.1, 1.6 Hz, 1H), 4.97 (dd, J=10.2, 1.6 Hz, 1H), 4.35 (q, J=6.3 Hz, 1H), 4.16 (t, J=6.6 Hz, 2H), 2.57–2.44 (m, 2H), 2.09 (q, J=7.2 Hz, 1H), 1.77 (d, J=6.9 Hz, 3H), 1.74–1.63 (m, 2H), 1.52–1.44 (m, 2H), 0.90 (s, 9H), 0.10, 0.06 (2s, 6H); $^{13}$C NMR (CDCl$_3$, 100 Hz) 8154.0, 138.4, 131.8, 131.1, 130.8, 130.5, 115.1, 86.6, 74.6, 71.5, 65.9, 33.4, 29.3, 28.1, 26.0, 25.3, 18.4, 18.3, −4.3, −4.7; IR (film) ν$_{max}$ 2955, 2930, 2856, 2238, 1713, 1249, 1072; ESIMS m/z 399 ([M+Na$^+$], C$_{22}$H$_{36}$NaO$_3$Si requires 399). HRMS (FAB$^+$) m/z 375.2363 ([M−H]$^+$, C$_{22}$H$_{35}$O$_3$Si requires 375.2355).

To a solution of the above alkynoic ester (77.8 mg, 0.207 mmol) in toluene (9 mL) was added Co$_2$(CO)$_8$ (99.0 mg, 0.289 mmol). The mixture was stirred at room temperature for 45 min, and then concentrated in vacuum. The dark residue was purified by PTLC (15:1 hexane/EtOAc) to give cobalt complex 9 (117.5 mg, 86%) as a red oil. $^1$H NMR (CDCl$_3$, 400 MHz) δ 6.17 (dd, J=15.3, 10.6 Hz, 1H), 6.03 (ddd, J=15.3, 11.3 Hz, 1H), 5.68 (dd, J=14.9, 6.9 Hz, 1H), 5.61 (dd, J=15.2, 6.8 Hz, 1H), 5.38 (ddd, J=17.1, 10.1, 8.7 Hz, 1H), 5.10 (q, J=6.4 Hz, 1H), 5.04 (dd, J=17.1, 1.3 Hz, 1H), 4.85 (dd, J=10.3, 1.4 Hz, 1H), 4.41, (m, 1H), 3.20–3.15 (m, 2H), 1.76 (d, J=6.7 Hz, 3H), 1.59 (t, J=6.6 Hz, 2H), 1.32 (d, J=6.2 Hz, 3H), 1.22–1.17 (m, 1H), 0.90 (s, 9H), 0.82–0.72 (m, 1H), 0.66–0.59 (m, 2H), 0.09, 0.08 (2s, 6H); $^3$C NMR (CDCl$_3$, 100 Hz) δ 198.7, 169.2, 141.4, 134.3, 132.5, 132.4, 132.2, 131.0, 130.2, 128.8, 127.2, 127.1, 112.0, 93.0, 81.0, 73.7, 73.6, 73.1, 40.0, 26.1, 22.4, 19.9, 18.6, 18.4, 17.4, 13.9, 13.5, −4.2, −4.3, −4.6; IR (film) ν$_{max}$ 2956, 2930, 2858, 2097, 2058, 2029, 1703, 1221, 1065; ESIMS m/z 685 ([M+Na$^+$], C$_{28}$H$_{36}$Co$_2$NaO$_9$Si requires 685).

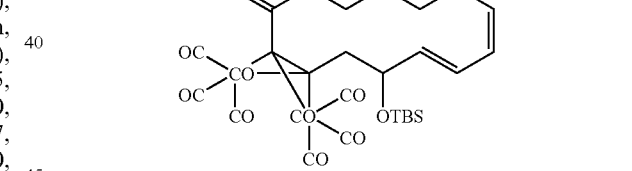

RCM product 10. To a solution of cobalt complex 9 (16 mg, 0.024 mmol) in dry CH$_2$Cl$_2$ (120 mL) was added tricyclohexyl phosphine[1,3-bis(2,4,6-trimethylphenyl)-4,5-dihydroimidazol-2-ylidene]-[bezyli-dene]ruthenium(IV) dichloride (second generation Grubbs catalyst) (6.1 mg, 0.0072 mmol). The resulting solution was heated to 45° C. for 1 hr and 10 min, then cooled to room temperature and filtered through a plug of silica gel. The solvent was removed under reduced pressure. The residue was purified by PTLC (15:1 hexane/EtOAc) to give cyclic product 10 (10.5 mg, 71%). $^1$H NMR (CDCl$_3$, 400 MHz) δ 6.44 (dd, J=15.3, 10.8 Hz, 1H), 5.97 (t, J=10.8 Hz, 1H), 5.58 (dd, J=15.4, 7.5 Hz, 1H), 5.54 (dt, J=10.1, 4.5 Hz, 1H), 4.57–4.47 (m, 2H), 4.25–4.20 (m, 1H), 3.45–3.36 (m, 2H), 2.45–2.37 (m, 1H), 2.13–1.05 (m, 1H), 1.99–1.79 (m, 1H), 1.80–1.62 (m, 2H), 1.51–1.41 (m, 1H), 0.92 (s, 9H), 0.11, 0.08 (2s, 6H); $^{13}$C NMR (CDCl$_3$, 100 Hz) δ 199.9, 170.4, 135.2, 132.7, 129.0, 127.1, 92.8, 77.4, 73.1, 65.0, 45.2, 26.4, 26.1, 25.4, 18.5, 1.2, −4.2, −4.6; IR (film) ν$_{max}$ 2955, 2930, 2857, 2098, 2059, 2027, 1702, 1213, 1057; ESIMS m/z 643 ([M+Na$^+$], C$_{25}$H$_{30}$Co$_2$NaO$_9$Si requires 643).

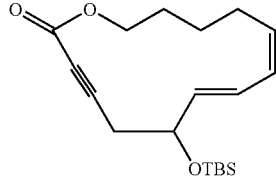

11

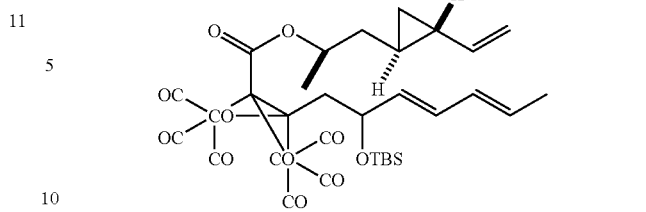

14

Model cyclic alkyne 11. To a solution of compound 10 (35.6 mg, 0.0574 mmol) in acetone at −10° C. was added ammonium cerium (IV) nitrate (189 mg, 0.344 mmol) portionwise. After 10 min at −10° C., the reaction was quenched by addition of diisopropylethylamine (0.18 mL, 1.03 mmol). The resulting mixture was filtered through a plug of neutral alumina, and the solvent was removed under reduced pressure. Purification by PTLC (15:1 hexane/EtOAc) afforded cyclic alkyne 11 (17.6 mg, 92%). $^1$H NMR (CDCl$_3$, 400 MHz) δ 6.64 (dd, J=15.5, 11.1 Hz, 1H), 6.07 (t, J=11.0 Hz, 1H), 5.53 (dd, J=15.5, 7.1 Hz, 1H), 5.40 (dt, J=10.4, 4.8 Hz, 1H), ), 4.41–4.25 (m, 2H), 4.06–4.01 (m, 1H), 2.69–2.62 (m, 1H), 2.56 (dd, J=17.1, 4.4 Hz, 1H), 2.46 (dd, J=17.1, 9.5 Hz, 1H), 2.26–2.21 (m, 1H), 1.75–1.61 (m, 4H), 0.89 (s, 9H), 0.08, 0.07 (2s, 6H); $^{13}$C NMR (CDCl$_3$, 100 Hz) δ 153.9, 133.2, 132.9, 128.5, 128.2, 87.7, 77.0, 72.9, 68.0, 29.0, 28.2, 26.7, 26.0, 25.6, 18.3, −4.3, −4.7; IR (film) ν$_{max}$ 2954, 2929, 2857, 2238, 1716, 1245, 1110, 1075, 837; ESIMS m/z 357 ([M+Na$^+$], C$_{19}$H$_{30}$NaO$_3$Si requires 357). HRMS(FAB$^+$) m/z 333.1888 ([M−H]$^+$, C$_{19}$H$_{29}$O$_3$Si requires 333.1886).

Cobalt complex 14. To a solution of alkyne 8 (526 mg, 1.31 mmol) in toluene (60 mL) was added Co$_2$(CO)$_8$ (625 mg, 1.83 mmol). The mixture was stirred at room temperature for 30 min, and the solvent was removed under reduced pressure. The dark residue was purified by flash chromatography (silica, 0 to 5% EtOAc in hexane) to give cobalt complex 14 (902 mg, 100%) as an inseparable mixture of two diastereomers. $^1$H NMR (CDCl$_3$, 400 MHz) δ 6.17 (dd, J=15.3, 10.6 Hz, 1H), 6.03 (ddd, J=15.3, 11.3 Hz, 1H), 5.68 (dd, J=14.9, 6.9 Hz, 1H), 5.61 (dd, J=15.2, 6.8 Hz, 1H), 5.38 (ddd, J=17.1, 10.1, 8.7 Hz, 1H), 5.10 (q, J=6.4 Hz, 1H), 5.04 (dd, J=17.1, 1.3 Hz, 1H), 4.85 (dd, J=10.3, 1.4 Hz, 1H), 4.41, (m, 1H), 3.20–3.15 (m, 2H), 1.76 (d, J=6.7 Hz, 3H), 1.59 (t, J=6.6 Hz, 2H), 1.32 (d, J=6.2 Hz, 3H), 1.22–1.17 (m, 1H), 0.90 (s, 9H), 0.82–0.72 (m, 1H), 0.66–0.59 (m, 2H), 0.09, 0.08 (2s, 6H); $^{13}$C NMR (CDCl$_3$, 100 Hz) δ 198.7, 169.2, 141.4, 134.3, 132.5, 132.4, 132.2, 131.0, 130.2, 128.8, 127.2, 127.1, 112.0, 93.0, 81.0, 73.7, 73.6, 73.1, 40.0, 26.1, 22.4, 19.9, 18.6, 18.4, 17.4, 13.9, 13.5, −4.2, −4.3, −4.6; IR (film) ν$_{max}$ 2956, 2930, 2858, 2097, 2058, 2029, 1703, 1221, 1065; ESIMS m/z 711 ([M+Na$^+$], C$_{30}$H$_{38}$Co$_2$NaO$_9$Si requires 711).

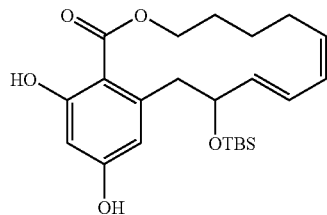

13

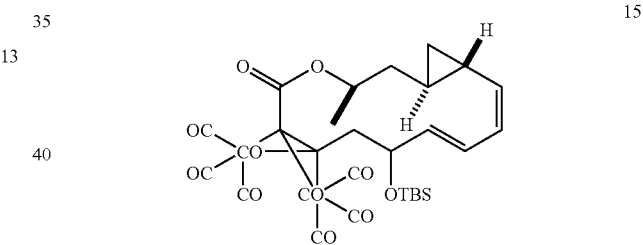

15

Diels-Alder product 13. Cyclic alkyne 11 (27 mg, 0.081 mmol) and excess diene 12 (0.30 mL, 0.90 mmol) were mixed and heated in a sealed vial to 140° C. for 48.5 hours. The mixture was cooled to room temperature, loaded onto a PTLC plate, and purified (4:1 hexane/EtOAc) to afford aromatic product 13 (20 mg, 60%). $^1$H NMR (CDCl$_3$, 400 MHz) δ 11.64, (s, 1H), 6.38 (dd, J=15.4, 10.9 Hz, 1H), 6.35 (d, J=2.6 Hz, 1H), 6.30 (d, J=2.6 Hz, 1H), 6.23 (t, J=10.6 Hz, 1H), 5.95 (s, 1H), 5.78 (dd, J=15.3, 8.4 Hz, 1H), 5.60 (q, J=9.9 Hz, 1H), 4.69 (q, J=9.1 Hz, 1H), 4.12 (t, J=8.5 Hz, 2H), 3.63 (d, J=13.0 Hz, 1H), 2.62 (dd, J=13.1, 8.9 Hz, 1H), 2.50–2.40 (m, 1H), 2.12–2.05 (m, 1H), 1.87–1.76 (m, 2H), 1.56–1.44 (m, 2H), 0.78 (s, 9H), −0.20, −0.25 (2s, 6H); $^{13}$C NMR (CDCl$_3$, 100 Hz) δ 172.2, 165.7, 160.3, 144.8, 135.4, 131.0, 129.9, 126.0, 113.0, 105.3, 102.2, 78.7, 64.3, 46.6, 25.9, 24.2, 23.7, 23.0, 18.4, −4.7, −5.0; IR (film) ν$_{max}$ 3380, 2954, 2929, 2856, 1648, 1620, 1254, 1169, 1106, 1061, 837; ESIMS m/z 441 ([M+Na$^+$], C$_{23}$H$_{34}$NaO$_5$Si requires 441). HRMS (FAB$^+$) m/z 418.2173 ([M]$^+$, C$_{23}$H$_{34}$O$_5$Si requires 418.2176).

RCM product 15. To a solution of alkyne-cobalt complex 14 (67 mg, 0.097 mmol) in dry CH$_2$Cl$_2$ (485 mL) was added tricyclohexyl phosphine[1,3-bis(2,4,6-trimethylphenyl)-4,5-dihydroimidazol-2-ylidene][bezylidene]ruthenim(IV) dichloride (second generation Grubbs catalyst) (21 mg, 0.025 mmol). The resulting mixture was heated to 45° C. for 1.5 hours, and filtered through a short column of silica gel. The filtrate was concentrated in vacuum. The residue was purified by PTLC (15:1 hexanes/EtOAc) to give cyclic product 15 as a 2:1 mixture of two separable diastereomers. Major isomer (23.1 mg, 37%): $^1$H NMR (CDCl$_3$, 400 MHz) δ 6.49 (dd, J=15.4, 10.9 Hz, 1H), 5.84 (t, J=10.6 Hz, 1H), 5.50 (dd, J=15.4, 8.5 Hz, 1H), 5.06 (dd, J=10.5, 6.9 Hz, 1H), 5.02–4.94 (m, 1H), 4.81–4.75 (m, 1H). 3.48–3.36 (m, 2H), 2.22–2.25 (m, 1H), 1.58–1.50 (m, 1H), 1.50–1.46 (m, 1H), 1.32 (d, J=6.2 Hz, 3H), 0.91 (s, 9H), 0.90–0.80 (m, 1H), 0.89 (s, 9H), 0.67–0.63 (m, 1H), 0.59–0.55 (m, 1H), 0.12, 0.09 (2s, 6H); $^{13}$C NMR (CDCl$_3$, 100 Hz) δ 199.0, 170.4, 135.7, 134.9, 129.2, 127.8, 92.0, 77.5, 72.5, 72.1, 45.5, 38.0, 26.1, 10.3, 18.4, 16.4, 16.0, −4.2, −4.6; IR (film) ν$_{max}$ 2955, 2928, 2854, 2097, 2060, 2029, 1692, 1232, 1056; ESIMS m/z 669 ([M+Na$^+$], C$_{27}$H$_{32}$Co$_2$NaO$_9$Si requires 669); [α]$_D^{25}$ −127 (c 0.11, CHCl$_3$). Minor isomer (12.6 mg, 20%): $^1$H NMR (CDCl$_3$, 500 MHz) δ 6.60 (dd, J=15.7, 9.9 Hz, 1H), 5.86 (t, J=10.3 Hz, 1H), 5.81 (dd, J=15.7, 4.4 Hz, 1H), 5.12–5.05 (m, 1H), 4.99 (t, J=9.9 Hz, 1H), 4.46–4.44 (m, 1H), 3.58 (dd, J=15.3, 9.4 Hz, 1H), 3.32 (dd, J=15.3, 4.2 Hz, 1H), 2.16 (dt, J=15.3, 4.2 Hz, 1H), 1.65–1.59 (m, 2H), 1.36 (d, J=6.5 Hz, 3H), 0.94 (s, 9H), 0.64–0.59 (m, 2H), 0.14 (s, 6H); $^{13}$C NMR (CDCl$_3$, 125 Hz) δ 198.6, 169.7, 135.9, 132.6, 126.8, 126.5, 92.0, 80.7, 73.4, 73.0, 41.8, 37.7, 26.1, 19.3, 18.5, 18.4, 15.1, 13.7, −4.5, −4.6; IR (film) ν$_{max}$ 2929, 2856, 2097, 2059, 2028, 1702, 1220, 1059; ESIMS m/z 669 ([M+Na$^+$], C$_{27}$H$_{32}$CO$_2$NaO$_9$Si requires 669). [α]$^{25}_D$ +48 (c 0.19, CHCl$_3$).

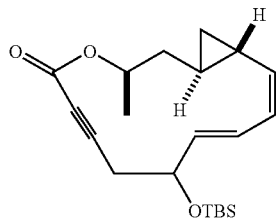

16

Cyclic alkyne 16. The major isomer of 15 (23.1 mg, 0.0358 mmol) was dissolved in dry THF (1 mL). At 0° C., a solution of 12 (135 mg, 0.536 mmol) in THF (5 mL) was added. After 35 minutes at 0° C., the reaction was quenched by the addition of a 2 mL 1:1 mixture of sat. aqueous Na$_2$S$_2$O$_3$ and NaHCO$_3$, followed by warming to room temperature and diluting with EtOAc (20 mL). The layers were separated, and the organic layer was washed with sat. aqueous NH$_4$Cl, dried (Na$_2$SO$_4$), filtered and concentrated. The residue was purified by PTLC (15:1, hexanes/EtOAc) to cyclic alkyne 16 as colorless oil (8.9 mg, 69%). $^1$H NMR (CDCl$_3$, 400 MHz) δ 6.70 (dd, J=15.6, 11.1 Hz, 1H), 5.98 (t, J=10.8 Hz, 1H), 5.51 (dd, J=15.6, 7.7 Hz, 1H), 5.20–5.14 (m, 1H), 4.92 (t, J=10.7 Hz, 1H), 4.38–4.33 (m, 1H), 2.59 (dd, J=16.8, 4.3 Hz, 1H), 2.41 (dd, J=16.7, 10.9 Hz, 1H), 2.07 (dt, J=14.8, 1.8 Hz, 1H), 1.74–1.67 (m, 1H), 1.33 (d, J=6.5 Hz, 3H), 1.19–1.12 (m, 1H), 0.93–0.87 (m, 1H), 0.89 (s, 9H), 0.69–0.65 (m, 1H), 0.63–0.58 (m, 1H), 0.07 (s, 6H); $^{13}$C NMR (CDCl$_3$, 100 Hz) δ 153.4, 136.5, 132.5, 128.3, 125.4, 85.7, 77.4, 73.8, 72.0, 38.6, 29.2, 26.0, 20.4, 18.4, 18.2, 14.6, 12.8; IR (film) ν$_{max}$ 2954, 2928, 2856, 2238, 1706, 1252, 1105, 1072, 1004; ESIMS m/z 383 ([M+Na$^+$], C$_{21}$H$_{32}$NaO$_3$Si requires 383); HRMS (FAB$^+$) m/z 360.2130 ([M]+, C$_{21}$H$_{32}$O$_3$Si requires 360.2121). [α]$^{25}_D$ +56 (c 0.95, CHCl$_3$).

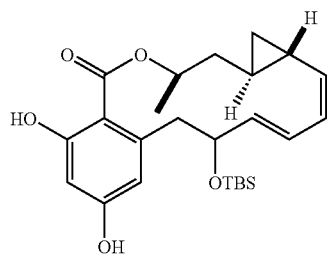

17

Diels-Alder product 17. Compound 16 (156 mg, 0.43 mmol) was dissolved in diene 12 (0.75 mL, 2.3 mmol) and heated to 140° C. in a sealed vial for 66 hours. The reaction mixture was cooled to room temperature and purified by PTLC (4:1, hexanes/EtOAc) to give 17 (143 mg, 75%). $^1$H NMR (CDCl$_3$, 400 MHz) δ 11.58 (s, 1H), 6.56 (dd, J=15.9, 9.3 Hz, 1H), 6.38 (d, J=2.4 Hz, 1H), 6.33 (d, J=2.4 Hz, 1H), 5.94 (t, J=9.5 Hz, 1H), 5.68 (dd, J=15.9, 6.8 Hz, 1H), 5.46–5.43 (m, 1H), 5.34 (dd, J=10.1, 4.3 Hz, 1H), 4.51 (q, J=6.7 Hz, 1H), 3.79 (dd, J=13.6, 6.2 Hz, 1H), 2.81 (dd, J=13.1, 8.9 Hz, 1H), 1.99–1.81 (m, 2H), 1.44 (d, J=6.5 Hz, 3H), 1.21–1.13 (m, 1H), 0.93–0.87 (m, 1H), 0.88 (s, 9H), 0.58–0.51 (m, 2H), −0.02 (s, 6H); $^{13}$C NMR (CDCl$_3$, 100 Hz) δ 164.8, 160.5, 143.8, 134.8, 133.7, 129.6, 128.0, 112.3, 106.1, 102.1, 75.7, 72.9, 42.6, 38.0, 26.1, 18.7, 18.4, 16.4, 16.1, 14.8, 1.4, −4.4, −4.6; IR (film) ν$_{max}$ 3376, 2954, 2928, 2856, 1644, 1619, 1257, 1062, 835; ESIMS m/z 467 ([M+Na$^+$], C$_{25}$H$_{36}$NaO$_5$Si requires 467). HRMS FAB$^+$) m/z 444.2336 ([M]$^+$, C$_{25}$H$_{36}$O$_5$Si requires 444.2332). [α]$^{25}_D$ +3.1 (c 1.3, CHCl$_3$).

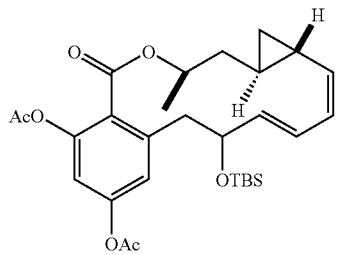

18

To a solution of 17 (243 mg, 0.546 mmol) in anhydrous DMF (13.5 mL) was added acetic anhydride (2.9 mL) and 4-(dimethylamino)pyridine (12.0 mg, 0.0546 mmol) sequentially. After 30 min at room temperature, the reaction was quenched by addition of 50 mL of pH 7.2 phosphate buffer. The resulting mixture was diluted with EtOAc (75 mL), separated and the aqueous layer was extracted with additional EtOAc (2×50 mL). The combined organic layers were washed with 5% aqueous NaCl (2×45 mL). The combined washings were extracted with EtOAc (2×30 mL). The combined organic layers were washed with sat. aqueous NaCl (30 mL), dried (Na$_2$SO$_4$), filtered and concentrated. Purification of the residue by PTLC (4:1 hexane/EtOAc) gave diacetate 18 (250 mg, 87%). $^1$H NMR (CDCl$_3$, 400 MHz) δ 6.96 (d, J=2.1 Hz, 1H), 6.88 (d, J=2.1 Hz, 1H), 6.59 (dd, J=16.0, 10.5 Hz, 1H), 5.89 (t, J=10.5 Hz, 1H), 5.66 (dd, J=16.1, 4.9 Hz, 1H), 5.26–5.23 (m, 2H), 4.51 (q, J=5.8 Hz, 1H), 3.12–3.02 (m, 2H), 2.28, 2.23 (2s, 6H), 1.47 (d, J=6.2 Hz, 3H), 1.46–1.39 (m, 1H), 1.14 (ddd, J=14.9, 10.1, 2.0 Hz, 1H), 0.96–0.87 (m, 1H), 0.87 (s, 9H), 0.52–0.48 (m, 2H), −0.01, −0.02 (2s, 6H); $^{13}$C NMR (CDCl$_3$, 100 Hz) δ 168.6, 168.4, 166.4, 151.4, 148.7, 139.1, 135.9, 133.6, 129.2, 127.2, 125.6, 120.4, 114.7, 73.8, 73.2, 43.2, 40.0, 26.0, 21.3, 21.0, 19.3, 18.3, 16.9, 16.2, 17.7, −4.6, −4.7; IR (film) ν$_{max}$ 2954, 2928, 2856, 1775, 1720, 1612, 1191, 1134, 1069; ESIMS m/z 551 ([M+Na$^+$], C$_{29}$H$_{40}$NaO$_7$Si requires 551); HRMS (FAB$^+$) m/z 528.2569 ([M]$^+$, C$_{29}$H$_{40}$O$_7$Si requires 528.2543). [α]$^{25}_D$ −38 (c 1.1, CHCl$_3$).

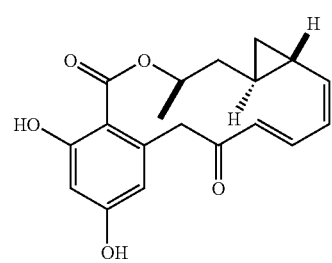

19

Cyclopropamonocillin 19. To a solution of diacetate 18 (250 mg, 0.473 mmol) in THF (10.2 mL) at 0° C. was added pyridine (3.4 mL) and HF-Pyridine complex (1.7 mL) sequentially. The resulting mixture was stirred at room temperature for 10.5 hrs. TMSOMe (30 mL) was added, and stirring was continued for 45 min to quench the remaining HF. The solvents were removed under reduced pressure. The alcohol isolated was dried under high vacuum, and dissolved in $CH_2Cl_2$ (15 mL) and cooled to 0° C. Dess-Martin periodinane (301 mg, 0.710 mmol) was added, and the resulting mixture was stirred at room temperature for 15 min. The solution was then directly loaded on PTLC plates and purified (1:1 hexane/EtOAc) to give the desired ketone (133 mg, 68%). $^1$H NMR ($CDCl_3$, 500 MHz) δ 8.01 (dd, J=16.1, 11.3 Hz, 1H), 6.97 (d, J=1.4 Hz, 1H), 6.92 (d, J=2.0 Hz, 1H), 6.20 (t, J=10.4 Hz, 1H), 5.96 (d, J=16.0 Hz, 1H), 5.60 (dd, J=10.0, 7.2 Hz, 1H), 5.47–5.41 (m, 1H), 4.20 (d, J=13.8 Hz, 1H), 3.77 (d, J=13.8 Hz, 1H), 2.31 (dt, J=15.3, 4.4 Hz, 1H), 2.25, 2.24 (2s, 6H), 1.73–1.71 (m, 1H), 1.50 (d, J=6.5 Hz, 3H), 1.26–1.21 (m, 1H), 1.00–0.97 (m, 1H), 0.75–0.69 (m, 2H); $^{13}$C NMR ($CDCl_3$, 125 Hz) δ 198.4, 168.5, 165.0, 152.1, 149.2, 145.6, 143.7, 135.7, 129.6, 128.8, 124.6, 119.1, 115.6, 72.8, 43.0, 38.3, 21.2, 18.2, 16.7, 16.5, 15.6; IR (film) $v_{max}$ 2928, 1774, 1728, 1657, 1621, 1586, 1290, 1190, 1132, 1029; ESIMS m/z 435 ([M+Na$^+$], $C_{23}H_{24}NaO_7$ requires 435); HRMS (FAB$^+$) m/z 413.1616 ([M+H]$^+$, $C_{23}H_{25}O_7$ requires 413.1600). $[\alpha]^{25}_D$ −269 (c 1.43, $CHCl_3$).

The above ketone (169 mg, 0.409 mmol) was dissolved in 26 mL 1:1 MeOH and 5% aqueous $NaHCO_3$, and stirred at room temperature for 14 hrs to remove the phenolic acetates. The resulting solution was diluted with sat. aqueous $NH_4Cl$ (80 mL) and EtOAc (100 mL) and separated. The aqueous layer was extracted with additional EtOAc (3×75 mL). The combined organic layers were dried ($Na_2SO_4$), filtered and concentrated in vacuum. Purification by PTLC (1:1 hexane/EtOAc) provided 19 (124 mg, 92%). $^1$H NMR ($CDCl_3$, 500 MHz) δ 11.33 (s, 1H), 8.36 (dd, J=16.1, 11.7 Hz, 1H), 6.48 (d, J=1.6 Hz, 1H), 6.40 (d, J=2.5 Hz, 1H), 6.20 (t, J=11.3 Hz, 1H), 6.01 (d, J=15.9 Hz, 1H), 5.72 (dd, J=9.8, 6.2 Hz, 1H), 5.49–5.45 (m, 1H), 5.32 (d, J=13.6 Hz, 1H), 3.51 (d, J=13.7 Hz, 1H), 2.31 (dt, J=15.8, 3.3 Hz, 1H), 1.61–1.55 (m, 1H), 1.55 (d, J=6.7 Hz, 3H), 1.32–1.28 (m, 1H), 1.03–0.97 (m, 1H), 0.74–0.72 (m, 1H), 0.64–0.63 (m, 1H); $^{13}$C NMR ($CDCl_3$, 125 Hz) δ 201.8, 170.1, 165.6, 161.6, 145.3, 139.2, 129.5, 128.5, 109.4, 104.5, 102.7, 73.5, 43.2, 27.6, 17.9, 17.2, 15.9, 13.9; IR (film) $v_{max}$ 3260, 1650, 1618, 1586, 1447, 1259, 1160, 1099, 996, 854; ESIMS m/z 351 ([M+Na$^+$], $C_{19}H_{20}NaO_5$ requires 351); HRMS (FAB$^+$) m/z 329.1382 ([M+H]$^+$, $C_{19}H_{21}O_5$ requires 329.1389). (+)-(R, R, S)-19: $[\alpha]^{25}_D$ −189 (c 0.77, $CH_2Cl_2$).

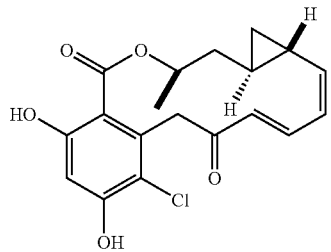

2

Cycloproparadicicol 2. Compound 19 (26.5 mg, 0.081 mmol) was dissolved in dry $CH_2Cl_2$ (5 mL) and cooled to 0° C. A solution of $SO_2Cl_2$ in $CH_2Cl_2$ (4.5 mL, diluted from 0.123 mL 1 M solution in $CH_2Cl_2$, 0.123 mmol) was added dropwise. After 45 minutes, the reaction was quenched by the addition of 5 mL of 5% $NH_4Cl$, and diluted with $CH_2Cl_2$. The layers were separated, and the organic phase was washed with brine, dried ($MgSO_4$), filtered and concentrated in vacuum. Purification of the residue by PTLC (3:1, hexanes/EtOAc) gave 2 as a white solid (17.8 mg, 61%). $^1$H NMR ($CDCl_3$, 500 MHz) δ 10.89 (s, 1H), 8.00 (dd, J=15.9, 11.3 Hz, 1H), 6.63 (s, 1H), 6.42 (s, 1H), 6.13 (t, J=11.2 Hz, 1H), 6.04 (d, J=16.3 Hz, 1H), 5.62 (dd, J=9.9, 5.8 Hz, 1H), 5.46–5.42 (m, 1H), 4.90 (broad d, J=15.9 Hz, 1H), 3.77 (bs, 1H), 2.22 (dt, J=15.8, 3.2 Hz, 1H), 1.60–1.52 (m, 1H), 1.48 (d, J=6.7 Hz, 3H), 1.15–1.11 (m, 1H), 0.90–0.85 (m, 1H), 0.69–0.65 (m, 1H), 0.57–0.54 (m, 1H); $^3$C NMR ($CDCl_3$, 125 Hz) δ 199.2, 169.4, 162.7, 155.6, 143.5, 142.5, 136.9, 129.9, 128.9, 115.6, 107.8, 103.5, 74.4, 46.4, 37.4, 17.9, 17.3, 15.6, 13.6; IR (film) $v_{max}$ 3341, 1716, 1651, 1609, 1578 cm$^{-1}$; ESIMS m/z 385 ([M+Na$^+$], $C_{19}H_{19}NaO_5Cl$ requires 385); HRMS (ESI) m/z 385.0820 ([M+Na$^+$], $C_{19}H_{19}NaO_5Cl$ requires 385.0819). (+)-(R, R, S)-2: $[\alpha]^{25}_D$ +69 (c 0.87, $CH_2Cl_2$).

Example 3—In Vitro and In Vivo Testing

Cell Culture Experimental:

The human cancer cell lines MCF7, BT474 and N417 were obtained from the American Type Culture Collection (Manassas, Va., USA) and maintained in a 1:1 mixture of DME:F12 supplemented with 2 mM glutamine, 50 U/mL penicillin, 50 U/mL streptomycin and 5% heat inactivated fetal bovie serum (Gemini Bioproducts) and incubated at 37° C. in 5% $CO_2$.

Protein Assays:

Cells were grown to 60–70% confluence and exposed to drugs or DMSO vehicle for the indicated time periods. Lysates were prepared using 5 mM Tris pH 7.4, 2% SDS and 10% glycerol lysis buffer. Protein concentration was determined using the BCA kit (Pierce Chemical Co.) according to the manufacturer's instructions. Clarified protein lysates (20–50 μg) were electrophoretically resolved on denaturing SDS-PAGE, transferred to ntirocellulose and probed with the following primary antibodies: anti-Her2 (C-18).

Antiproliferative Index:

Growth assays were performed by seeding 10000 cells (MCF7, BT474 or N417) per well in 6-well dishes and incubating for 24 h before drug treatment. Drugs or vehicle were administered as outlined for each experiment, and cells were incubated for the time periods depcited and then the number quantified by a Coulter counter.

Flow Cytometry:

Cell cycle distribution was assayed according to Nusse et al. with a Becton Dickinson fluorescence-activated cell sorter and analyzed by a Cell Cycle Multi-cycle system (*Phoenix* Flow System, San Diego, Calif., USA).

In Vivo Activity:

Although a variety of methods known in the art can be utilized, one exemplary method by which the in vivo activity of the inventive compounds is determined is by subcutaneously transplanting a desired tumor mass in mice. Drug treatment is then initiated when tumor mass reaches approximately 100 mm$^3$ after transplantation of the tumor mass. A suitable composition, comprising any one inventive compounds described above, including classes thereof, subclasses thereof, or species thereof, optionally further comprising a pharmaceutically acceptable carrier and optionally further comprising an additional therapeutic agenthas, is then administered to the mice, preferably in saline and also administered once a day at doses in the range of 0.001 mg/kg, to about 50 mg/kg, although it will be appreciated that other doses can also be administered, as described herein (e.g., 0.01 mg/kg to about 25 mg/kg of body weight, or 0.1 mg/kg to about 10 mg/kg of body weight), or, in some embodiments, at dosages in the range of about 50 mg/kg to about 100 mg/kg, or dosages below 0.001 mg/kg. Body weight and tumor size are then measured daily and changes in percent ratio to initial values are plotted. In cases where the transplanted tumor ulcerates, the weight loss exceeds 25–30% of control weight loss, the tumor weight reaches 10% of the body weight of the cancer-bearing mouse, or the cancer-bearing mouse is dying, the animal is sacrificed in accordance with NIH guidelines for animal welfare.

$R_7$ is hydrogen, $-OR_K$, $-SR_K$, $-C(O)OR_K$, $-S(O)_2R_K$, $-O(C=O)R_K$, $-N(R_K)(C=O)(R_K)$, $-C(O)R_K$, $-CON(R_K)_2$, $-OCO_2R_K$, or an aliphatic, heteroaliphatic, aryl, heteroaryl, alkylaryl, or alkylheteroaryl moiety, wherein each occurrence of $R_K$ is independently hydrogen, or an aliphatic, heteroaliphatic, aryl, heteroaryl, alkylaryl, or alkylheteroaryl moiety,

What is claimed is:

1. A compound having the structure:

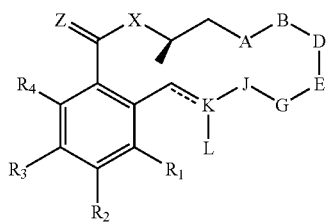

wherein the dotted line - - - represents an optional bond, such that either a single or a double bond is present;

$R_1$ is hydrogen, halogen, an aliphatic, heteroaliphatic, aryl, heteroaryl, alkylaryl, or alkylheteroaryl moiety, or $N(R_A)_2$, wherein each occurrence of $R_A$ is independently hydrogen, or an aliphatic, heteroaliphatic, aryl, heteroaryl, alkylaryl, or alkylheteroaryl moiety;

$R_2$ is hydrogen, halogen, cyano, $-OR_B$, $-N(R_B)_2$, $-SR_B$, $-O(C=O)R_B$, $-N(R_B)(C=O)(R_B)$, $-C(O)R_B$, $-C(O)OR_B$, $-CON(R_B)_2$, $-OCO_2R_B$, or an aliphatic, heteroaliphatic, aryl, heteroaryl, alkylaryl, or alkylheteroaryl moiety, wherein each occurrence of $R_B$ is independently hydrogen, or an aliphatic, heteroaliphatic, aryl, heteroaryl, alkylaryl, or alkylheteroaryl moiety;

$R_3$ is hydrogen, halogen, an aliphatic, heteroaliphatic, aryl, heteroaryl, alkylaryl, or alkylheteroaryl moiety, or $-N(R_C)_2$, wherein each occurrence of $R_C$ is independently hydrogen, or an aliphatic, heteroaliphatic, aryl, heteroaryl, alkylaryl, or alkylheteroaryl moiety;

$R_4$ is hydrogen, halogen, cyano, $-OR_D$, $-N(R_D)_2$, $-SR_D$, $-O(C=O)R_D$, $-N(R_D)(C=O)(R_D)$, $-C(O)R_D$, $-C(O)OR_D$, $-CON(R_D)_2$, $-OCO_2R_D$, or an aliphatic, heteroaliphatic, aryl, heteroaryl, alkylaryl, or alkylheteroaryl moiety, wherein each occurrence of $R_D$ is independently hydrogen, or an aliphatic, heteroaliphatic, aryl, heteroaryl, alkylaryl, or alkylheteroaryl moiety;

Z is O;

X is O;

A and B together represent

$-CHR_5-CHR_6-$, $-CR_5=CR_6-$, wherein $R_5$ and $R_6$ are each independently hydrogen, halogen, cyano, $-OR_J$, $-N(R_J)_2$, $-SR_J$, $-O(C=O)R_J$, $-O(S=O)R_J$, $-N(R_J)(C=O)(R_J)$, $-C(=O)R_J$, $-C(=O)OR_J$, $-CON(R_J)_2$, $-OCO_2R_J$, $-OSO_2R_J$, or an aliphatic, heteroaliphatic, aryl, heteroaryl, alkylaryl, or alkylheteroaryl moiety, wherein each occurrence of $R_J$ is independently hydrogen, or an aliphatic, heteroaliphatic, aryl, heteroaryl, alkylaryl, or alkylheteroaryl moiety, and wherein $R_7$ is hydrogen, $-OR_K$, $-SR_K$, $-C(O)OR_K$, $-S(O)_2R_K$, $-O(C=O)R_K$, $-N(R_K)(C=O)(R_K)$, $-C(O)R_K$, $-C(O)OR_K$, $-CON(R_K)_2$, $-OCO_2R_K$, or an aliphatic, heteroaliphatic, aryl, heteroaryl, alkylaryl, or alkylheteroaryl moiety, wherein each occurrence of $R_K$ is independently hydrogen, or an aliphatic, heteroaliphatic, aryl, heteroaryl, alkylaryl, or alkylheteroaryl moiety, or when A and B together represent $-CHR_5-CHR_6-$, $R_5$ and $R_6$ taken together represent a substituted or unsubstituted 3–7 membered aliphatic, heteroaliphatic, aryl or heteroaryl ring, D and E together represent $-CHR_8-CHR_9-$, $-CR_8=CR_9-$, wherein $R_8$ and $R_9$ are each independently hydrogen or lower alkyl;

G and J together represent $-CHR_{10}-CHR_{11}-$, $-CR_{10}=CR_{11}-$, wherein $R_{10}$ and $R_{11}$ are each independently hydrogen or lower alkyl;

K and L together represent C=O, C=S, CH—CH$_3$, CH—CH(R$_L$)$_2$, C=C(R$_L$)$_2$, —CH$_2$—, —C(—S(CH$_2$)$_3$S—)—, CH—OR$_L$, CH—SR$_L$, CH—N(R$_L$)$_2$, CH—N(R$_L$)(C=O)(R$_L$), C=N—O—R$_L$, CH—N=O, C=C(R$_L$)—N(R$_L$)$_2$, C=N—R$_L$, C=N—N(R$_L$)$_2$, or, if the dotted line - - - represents a bond, whereby a double bond is present, then K and L together represent C—N(R$_L$)$_2$, wherein each occurrence of $R_L$ is independently hydrogen, an aliphatic, heteroaliphatic, aryl, heteroaryl, alkylaryl, or alkylheteroaryl moiety, or two occurrences of $R_L$ taken together represent a 3 to 7-membered cyclic aliphatic, heteroaliphatic, aromatic or heteroaromatic moiety;

whereby each of the foregoing aliphatic and heteroaliphatic moieties may independently be substituted or unsubstituted, cyclic or acyclic, or branched or unbranched, and each aryl, heteroaryl, alkylaryl, and alkylheteroaryl moiety may be substituted or unsubstituted;

wherein one or any two of $R_1$, $R_A$, $R_2$, $R_B$, $R_3$, $R_C$, $R_4$, $R_D$, $R_5$, $R_6$, $R_J$, or $R_L$ are optionally a linker covalently bonded to a compound selected from the group consisting of radicicol, monocillin, geldanamycin, and steroids; and pharmaceutically acceptable derivatives thereof, with the proviso that:

(1) if A and B together are

and $R_5$ and $R_6$ are each hydrogen; if D and E together are $-CH=CH-$; if G and J together are $-CH=CH-$; if K and L together are C=O; if $R_1$ is hydrogen or Cl; and if $R_3$ is hydrogen, then $R_2$ is not $-OR_B$ or $-O(C=O)R_B$, wherein $R_B$ is hydrogen, or an aliphatic, heteroaliphatic, aryl, heteroaryl, alkylaryl, or alkylheteroaryl moiety; and $R_4$ is not $-OR_D$ or $-O(C=O)R_D$, wherein $R_D$ is hydrogen, or an aliphatic, heteroaliphatic, aryl, heteroaryl, alkylaryl, or alkylheteroaryl moiety;

(2) if A and B together are

and $R_5$ and $R_6$ are each hydrogen; if D and E together are —$CH_2$—$CH_2$—; if G and J together are —$CH_2$—$CH_2$— or —CH=CH—; if K and L together are C=O; if $R_1$ is hydrogen or Cl; and if $R_3$ is hydrogen, then $R_2$ is not —$OR_B$ or —O(C=O)$R_B$, wherein $R_B$ is hydrogen or an alkyl, alkoxy, alkenyl, alkenyloxy, alkynyl, aryl, aryloxy, heterocycle, cycloalkyl, cycloalkenyl, or cycloalkenyl fused to an aryl group; and $R_4$ is not —$OR_D$ or —O(C=O)$R_D$, wherein $R_D$ is hydrogen or an alkyl, alkoxy, alkenyl, alkenyloxy, alkynyl, aryl, aryloxy, heterocycle, cycloalkyl, cycloalkenyl, or cycloalkenyl fused to an aryl group;

(3) if $R_1$ is Cl; if $R_2$ is $OR_B$ and $R_B$ is hydrogen, methyl, alkanoyl, alkenoyl, tert-butyl dimethylsilyl or tert-butyldiphenylsilyl; if $R_3$ is hydrogen; if $R_4$ is $OR_D$ and $R_D$ is hydrogen, methyl, alkanoyl, alkenoyl, tert-butyldimethylsilyl, or tert-butyldiphenylsilyl; if D and E together are —CH=CH—; if G and J together are —CH=CH—; if A and B together are

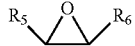

or if A and B together are —$CHR_5$—$CHR_6$— and $R_6$ is hydrogen or halogen or —OH or —$OCH_3$ and $R_5$ is $OR_J$, wherein $R_J$ is hydrogen, benzoyl, alkanoyl, or alkenoyl, or $R_5$ is —O(S=O)$R_J$, wherein $R_J$ is a second compound of formula (I) linked via an oxygen atom present at $R_5$ in the second compound of formula (I), and wherein $R_6$ of the second compound of formula (I) is halogen; Z of the second compound of formula (I) is O; X of the second compound of formula (I) is O, $R_1$ of the second compound of formula (I) is Cl; $R_2$ of the second compound of formula (I) is $OR_B$ and $R_B$ is hydrogen, alkanoyl, alkenoyl, tert-butyl dimethylsilyl or tert-butyldiphenylsilyl; $R_3$ of the second compound of formula (I) is hydrogen; $R_4$ of the second compound of formula (I) is $OR_D$ and $R_D$ is hydrogen, alkanoyl, alkenoyl, tert-butyldimethylsilyl, or tert-butyldiphenylsilyl;

then K and L together are not C=O or C=N—O—$R_L$, when $R_L$ is hydrogen, or substituted or unsubstituted lower alkyl, a substituted or unsubstituted alkenyl moiety, a substituted or unsubstituted heteroaliphatic moiety, a substituted or unsubstituted heteroarylalkyl moiety, a substituted or unsubstituted arylalkyl moiety, a substituted acyl moiety or a substituted or unsubstituted aryl moiety;

except that K and L together can be C=N—O—$R_L$, when $R_L$ is a linker covalently bonded to a compound selected from the group consisting of radicicol, monocillin, geldanamycin, and steroids;

(4) if D and E together are —$CH_2$—$CH_2$—; if G and J together are —$CH_2$—$CH_2$—; if K and L together are $CH_2$,
then A and B together are not —$CH_2$—$CH_2$—;

(5) if D and E together are —$CH_2$—$CH_2$—; if G and J together are —$CH_2$—$CH_2$—; if K and L together are $CH_2$; if $R_1$ is hydrogen; if $R_2$ is —$OR_B$, or —O(C=O)$R_B$, wherein $R_B$ is hydrogen, or an aliphatic, heteroaliphatic, aryl, or heteroaryl moiety; if $R_3$ is hydrogen; and if $R_4$ is hydrogen, —$OR_D$, or —O(C=O)$R_D$, wherein each occurrence of $R_D$ is independently hydrogen, or an aliphatic, aryl, or heteroaryl moiety;

then A and B together are not —$CH_2$—$CHR_6$—, wherein $R_6$ is substituted aliphatic, heteroaliphatic, —CHO, or —$CO_2H$; and (6) the compound is other than:

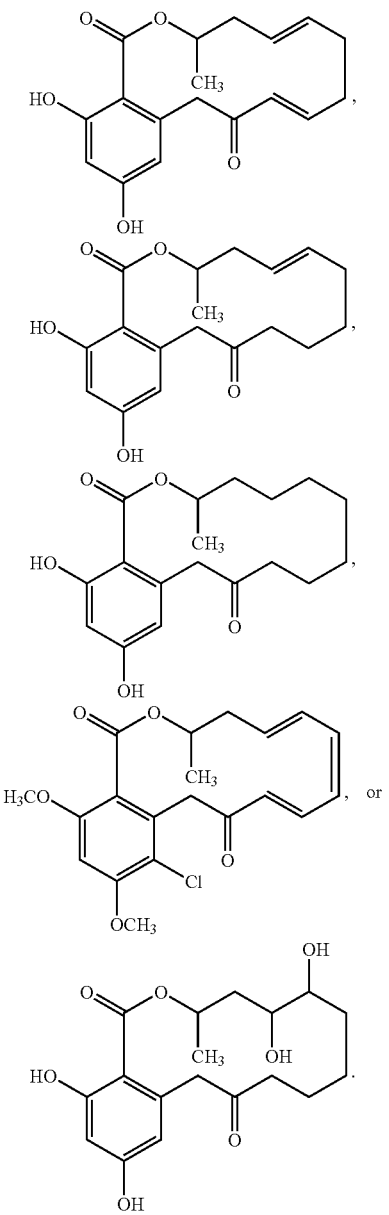

2. A compound having the structure:

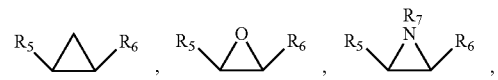

wherein the dotted line - - - represents an optional bond, such that either a single or a double bond is present;

R₁ is hydrogen, halogen, an aliphatic, heteroaliphatic, aryl, heteroaryl, alkylaryl, or alkylheteroaryl moiety, or N(R_A)₂, wherein each occurrence of R_A is independently hydrogen, or an aliphatic, heteroaliphatic, aryl, heteroaryl, alkylaryl, or alkylheteroaryl moiety;

R₂ is hydrogen, halogen, cyano, —OR_B, —N(R_B)₂, —SR_B, —O(C=O)R_B, —N(R_B)(C=O)(R_B), —C(O)R_B, —C(O)OR_B, —CON(R_B)₂, —OCO₂R_B, or an aliphatic, heteroaliphatic, aryl, heteroaryl, alkylaryl, or alkylheteroaryl moiety, wherein each occurrence of R_B is independently hydrogen, or an aliphatic, heteroaliphatic, aryl, heteroaryl, alkylaryl, or alkylheteroaryl moiety;

R₃ is hydrogen, halogen, an aliphatic, heteroaliphatic, aryl, heteroaryl, alkylaryl, or alkylheteroaryl moiety, or —N(R_C)₂, wherein each occurrence of R_C is independently hydrogen, or an aliphatic, heteroaliphatic, aryl, heteroaryl, alkylaryl, or alkylheteroaryl moiety;

R₄ is hydrogen, halogen, cyano, —OR_D, —N(R_D)₂, —SR_D, —O(C=O)R_D, —N(R_D)(C=O)(R_D), —C(O)R_D, —C(O)OR_D, —CON(R_D)₂, —OCO₂R_D, or an aliphatic, heteroaliphatic, aryl, heteroaryl, alkylaryl, or alkylheteroaryl moiety, wherein each occurrence of R_D is independently hydrogen, or an aliphatic, heteroaliphatic, aryl, heteroaryl, alkylaryl, or alkylheteroaryl moiety;

Z is O;
X is O;
A and B together represent

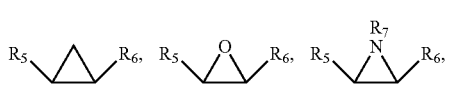

—CHR₅—CHR₆—, —CR₅=CR₆—, wherein R₅ and R₆ are each independently hydrogen, halogen, cyano, —OR_J, —N(R_J)₂, —SR_J, —O(C=O)R_J, —O(S=O)R_J, —N(R_J)(C=O)(R_J), —C(=O)R_J, —C(=O)OR_J, —CON(R_J)₂, —OCO₂R_J, —OSO₂R_J, or an aliphatic, heteroaliphatic, aryl, heteroaryl, alkylaryl, or alkylheteroaryl moiety, wherein each occurrence of R_J is independently hydrogen, or an aliphatic, heteroaliphatic, aryl, heteroaryl, alkylaryl, or alkylheteroaryl moiety, and wherein R₇ is hydrogen, —OR_K, —SR_K, —C(O)OR_K, —S(O)₂R_K, —O(C=O)R_K, —N(R_K)(C=O)(R_K), —C(O)R_K, —C(O)OR_K, —CON(R_K)₂, —OCO₂R_K, or an aliphatic, heteroaliphatic, aryl, heteroaryl, alkylaryl, or alkylheteroaryl moiety, wherein each occurrence of R_K is independently hydrogen, or an aliphatic, heteroaliphatic, aryl, heteroaryl, alkylaryl, or alkylheteroaryl moiety, or when A and B together represent —CHR₅—CHR₆—, R₅ and R₆ taken together represent a substituted or unsubstituted 3–7 membered aliphatic, heteroaliphatic, aryl or heteroaryl ring, D and E together represent —CHR₈—CHR₉—, —CR₈=CR₉—, wherein R₈ and R₉ are each independently hydrogen or lower alkyl;

G and J together represent —CHR₁₀—CHR₁₁—, —CR₁₀=CR₁₁—, wherein R₁₀ and R₁₁ are each independently hydrogen or lower alkyl;

K and L together represent C=O, C=S, CH—CH₃, CH—CH(R_L)₂, C=C(R_L)₂, —CH₂—, —C(—S(CH₂)₃S—)—, CH—OR_L, CH—SR_L, CH—N(R_L)₂, CH—N(R_L)(C=O)(R_L), C=N—O—R_L, CH—N=O, C=C(R_L)—N(R_L)₂, C=N—R_L, C=N—N(R_L)₂, or, if the dotted line - - - represents a bond, whereby a double bond is present, then K and L together represent C—N(R_L)₂, wherein each occurrence of R_L is independently hydrogen, an aliphatic, heteroaliphatic, aryl, heteroaryl, alkylaryl, or alkylheteroaryl moiety, or two occurrences of R_L taken together represent a 3 to 7-membered cyclic aliphatic, heteroaliphatic, aromatic or heteroaromatic moiety;

whereby each of the foregoing aliphatic and heteroaliphatic moieties may independently be substituted or unsubstituted, cyclic or acyclic, or branched or unbranched, and each aryl, heteroaryl, alkylaryl, and alkylheteroaryl moiety may be substituted or unsubstituted;

wherein one or any two of R₁, R_A, R₂, R_B, R₃, R_C, R₄, R_D, R₅, R₆, R_J, or R_L are a linker covalently bonded to a compound selected from the group consisting of radicicol, monocillin, geldanamycin, and steroids wherein the linker is an aliphatic or heteroaliphatic moiety, whereby said aliphatic or heteroaliphatic moiety is substituted or unsubstituted, branched or unbranched, or cyclic or acyclic; and pharmaceutically acceptable derivatives thereof,
with the proviso that:
(1) if A and B together are

and R₅ and R₆ are each hydrogen; if D and E together are —CH=CH—; if G and J together are —CH=CH—; if K and L together are C=O; if R₁ is hydrogen or Cl; and if R₃ is hydrogen,
then R₂ is not —OR_B or —O(C=O)R_B, wherein R_B is hydrogen, or an aliphatic, heteroaliphatic, aryl, heteroaryl, alkylaryl, or alkylheteroaryl moiety; and R₄ is not —OR_D or —O(C=O)R_D, wherein R_D is hydrogen, or an aliphatic, heteroaliphatic, aryl, heteroaryl, alkylaryl, or alkylheteroaryl moiety;

(2) if A and B together are

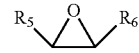

and R₅ and R₆ are each hydrogen; if D and E together are —CH₂—CH₂—; if G and J together are —CH₂—CH₂—; if K and L together are C=O; if R₁ is Cl; and if R₃ is hydrogen,
then R₂ is not —OR_B or —O(C=O)R_B, wherein R_B is hydrogen or an alkyl, alkoxy, alkenyl, alkenyloxy, alkynyl, aryl, aryloxy, heterocycle, cycloalkyl, cycloalkenyl, or cycloalkenyl fused to an aryl group; and R₄ is not —OR_D or —O(C=O)R_D, wherein R_D is hydrogen or an alkyl, alkoxy, alkenyl, alkenyloxy, alkynyl, aryl, aryloxy, heterocycle, cycloalkyl, cycloalkenyl, or cycloalkenyl fused to an aryl group;

(3) if R₁ is Cl; if R₂ is OR_B and R_B is hydrogen, alkanoyl, alkenoyl, tert-butyl dimethylsilyl or tert-butyldiphenylsilyl; if R₃ is hydrogen; if R₄ is OR_D and R_D is hydrogen, alkanoyl, alkenoyl, tert-butyldimethylsilyl, or tert-butyldiphenylsilyl; if D and E together are —CH=CH—; if G and J together are —CH=CH—; if A and B together are

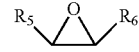

or if A and B together are —CHR₅—CHR₆— and R₆ is halogen and R₅ is OR_J, wherein R_J is hydrogen, alkanoyl, or alkenoyl, or R₅ is —O(S=O)R_J, wherein R_J is a second compound of formula (I) linked via an oxygen atom present at R₅ in the second compound of formula (I), and wherein R₆ of the second compound of formula (I) is halogen; Z of the second compound of formula (I) is O; X of the second compound of formula (I) is O, R₁ of the second compound of formula (I) is Cl; R₂ of the second compound of formula (I) is OR_B and R_B is hydrogen, alkanoyl, alkenoyl, tert-butyl dimethylsilyl or tert-butyldiphenylsilyl; $R_3$ of the second compound of formula (I) is hydrogen; $R_4$ of the second compound of formula (I) is $OR_D$ and $R_D$ is hydrogen, alkanoyl, alkenoyl, tert-butyldimethylsilyl, or tert-butyldiphenylsilyl;

then K and L together are not C=O or C=N—O—$R_L$, when $R_L$ is hydrogen, or substituted or unsubstituted lower alkyl, a substituted or unsubstituted alkenyl moiety, a substituted acyl moiety or a substituted or unsubstituted aryl moiety;

except that K and L together can be C=N—O—$R_L$, when $R_L$ is a linker covalently bonded to a compound selected from the group consisting of radicicol, monocillin, geldanamycin, and steroids.

3. The compound of claim 2, wherein one or any two of $R_1$, $R_A$, $R_2$, $R_B$, $R_3$, $R_C$, $R_4$, $R_D$, $R_5$, $R_6$, $R_J$, or $R_L$ are a linker covalently bonded to a compound selected from the group consisting of radicicol, monocillin, geldanamycin, and steroids, wherein the linker is a moiety having one of the structures —$(CH_2)_n$—CH=CH—$(CH_2)_m$—, —$(CH_2)_p$—C≡C—$(CH_2)_q$—, or —$CH_2(CH_2)_s CH_2$—, wherein each occurrence of n, m, p, q and s is independently an integer from 0–10, and wherein one or more of the hydrogen atoms are optionally replaced with an alkyl, heteroalkyl, aryl, heteroaryl, alkylaryl or alkylheteroaryl moiety or a secondary or tertiary amine, hydroxyl, or thiol.

4. The compound of claim 1, wherein G and J together represent —$CH_2$—$CH_2$— and the compound has the structure:

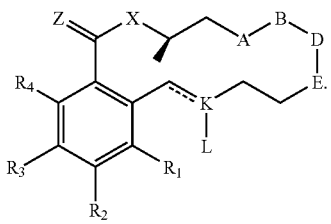

5. A compound having the structure:

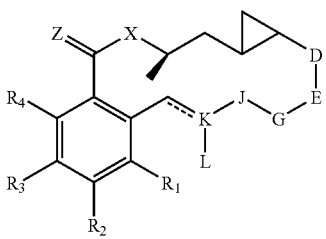

wherein the dotted line - - - represents an optional bond, such that either a single or a double bond is present;

$R_1$ is hydrogen, halogen, an aliphatic, heteroaliphatic, aryl, heteroaryl, alkylaryl, or alkylheteroaryl moiety, or $N(R_A)_2$, wherein each occurrence of $R_A$ is independently hydrogen, or an aliphatic, heteroaliphatic, aryl, heteroaryl, alkylaryl, or alkylheteroaryl moiety;

$R_2$ is hydrogen, halogen, cyano, —$OR_B$, —$N(R_B)_2$, —$SR_B$, —O(C=O)$R_B$, —N($R_B$)(C=O)($R_B$), —C(O)$R_B$, —C(O)O$R_B$, —CON($R_B$)$_2$, —OCO$_2R_B$, or an aliphatic, heteroaliphatic, aryl, heteroaryl, alkylaryl, or alkylheteroaryl moiety, wherein each occurrence of $R_B$ is independently hydrogen, or an aliphatic, heteroaliphatic, aryl, heteroaryl, alkylaryl, or alkylheteroaryl moiety;

$R_3$ is hydrogen, halogen, an aliphatic, heteroaliphatic, aryl, heteroaryl, alkylaryl, or alkylheteroaryl moiety, or —$N(R_C)_2$, wherein each occurrence of $R_C$ is independently hydrogen, or an aliphatic, heteroaliphatic, aryl, heteroaryl, alkylaryl, or alkylheteroaryl moiety;

$R_4$ is hydrogen, halogen, cyano, —$OR_D$, —$N(R_D)_2$, —$SR_D$, —O(C=O)$R_D$, —N($R_D$)(C=O)($R_D$), —C(O)$R_D$, —C(O)O$R_D$, —CON($R_D$)$_2$, —OCO$_2R_D$, or an aliphatic, heteroaliphatic, aryl, heteroaryl, alkylaryl, or alkylheteroaryl moiety, wherein each occurrence of $R_D$ is independently hydrogen, or an aliphatic, heteroaliphatic, aryl, heteroaryl, alkylaryl, or alkylheteroaryl moiety;

Z is O;

X is O;

D and E together represent —$CHR_8$—$CHR_9$—, —$CR_8$=$CR_9$—, wherein $R_8$ and $R_9$ are each independently hydrogen or lower alkyl;

G and J together represent —$CHR_{10}$—$CHR_{11}$—, —$CR_{10}$=$CR_{11}$—, wherein $R_{10}$ and $R_{11}$ are each independently hydrogen or lower alkyl;

K and L together represent C=O, C=S, CH—$CH_3$, CH—CH($R_L$)$_2$, C=C($R_L$)$_2$, —$CH_2$—, —C(—S($CH_2$)$_3$S—)—, CH—O$R_L$, CH—S$R_L$, CH—N($R_L$)$_2$, CH—N($R_L$)(C=O)($R_L$), C=N—O—$R_L$, CH—N=O, C=C($R_L$)—N($R_L$)$_2$, C=N—$R_L$, C=N—N($R_L$)$_2$, or, if the dotted line - - - represents a bond, whereby a double bond is present, then K and L together represent C—N($R_L$,)$_2$, wherein each occurrence of $R_L$ is independently hydrogen, an aliphatic, heteroaliphatic, aryl, heteroaryl, alkylaryl, or alkylheteroaryl moiety, or two occurrences of $R_L$ taken together represent a 3 to 7-membered cyclic aliphatic, heteroaliphatic, aromatic or heteroaromatic moiety;

whereby each of the foregoing aliphatic and heteroaliphatic moieties may independently be substituted or unsubstituted, cyclic or acyclic, or branched or unbranched, and each aryl, heteroaryl, alkylaryl, and alkylheteroaryl moiety may be substituted or unsubstituted;

wherein one or any two of $R_1$, $R_A$, $R_2$, $R_B$, $R_3$, $R_C$, $R_4$, $R_D$, or $R_L$ are optionally a linker covalently bonded to a compound selected from the group consisting of radicicol, monocillin, geldanamycin, and steroids; and pharmaceutically acceptable derivatives thereof.

6. The compound of claim 1, wherein A and B together represent —$CHR_5$—$CHR_6$— and the compound has the structure:

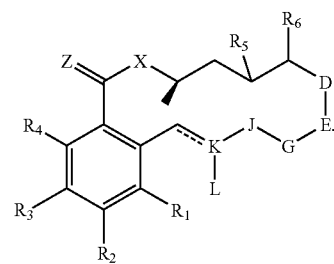

7. The compound of claim 1, wherein A and B together represent —CH=CH— and the compound has the structure:

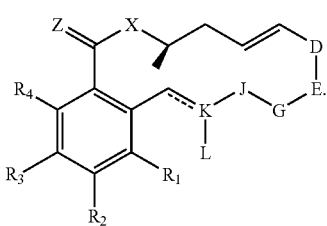

8. A compound having the structure:

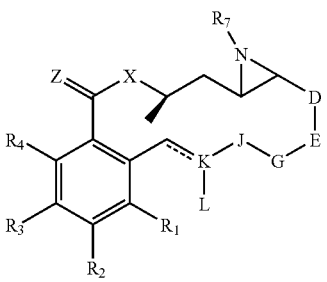

wherein the dotted line - - - represents an optional bond, such that either a single or a double bond is present;

$R_1$ is hydrogen, halogen, an aliphatic, heteroaliphatic, aryl, heteroaryl, alkylaryl, or alkylheteroaryl moiety, or $N(R_A)_2$, wherein each occurrence of $R_A$ is independently hydrogen, or an aliphatic, heteroaliphatic, aryl, heteroaryl, alkylaryl, or alkylheteroaryl moiety;

$R_2$ is hydrogen, halogen, cyano, —$OR_B$, —$N(R_B)_2$, —$SR_B$, —$O(C=O)R_B$, —$N(R_B)(C=O)(R_B)$, —$C(O)R_B$, —$C(O)OR_B$, —$CON(R_B)_2$, —$OCO_2R_B$, or an aliphatic, heteroaliphatic, aryl, heteroaryl, alkylaryl, or alkylheteroaryl moiety, wherein each occurrence of $R_B$ is independently hydrogen, or an aliphatic, heteroaliphatic, aryl, heteroaryl, alkylaryl, or alkylheteroaryl moiety;

$R_3$ is hydrogen, halogen, an aliphatic, heteroaliphatic, aryl, heteroaryl, alkylaryl, or alkylheteroaryl moiety, or —$N(R_C)_2$, wherein each occurrence of $R_C$ is independently hydrogen, or an aliphatic, heteroaliphatic, aryl, heteroaryl, alkylaryl, or alkylheteroaryl moiety;

$R_4$ is hydrogen, halogen, cyano, —$OR_D$, —$N(R_D)_2$, —$SR_D$, —$O(C=O)R_D$, —$N(R_D)(C=O)(R_D)$, —$C(O)R_D$, —$C(O)OR_D$, —$CON(R_D)_2$, —$OCO_2R_D$, or an aliphatic, heteroaliphatic, aryl, heteroaryl, alkylaryl, or alkylheteroaryl moiety, wherein each occurrence of $R_D$ is independently hydrogen, or an aliphatic, heteroaliphatic, aryl, heteroaryl, alkylaryl, or alkylheteroaryl moiety;

Z is O;

X is O $R_7$ is hydrogen, —$OR_K$, —$SR_K$, —$C(O)OR_K$, —$S(O)_2R_K$, —$O(C=O)R_K$, —$N(R_K)(C=O)(R_K)$, —$C(O)R_K$, —$CON(R_K)_2$, —$OCO_2R_K$, or an aliphatic, heteroaliphatic, aryl, heteroaryl, alkylaryl, or alkylheteroaryl moiety, wherein each occurrence of $R_K$ is independently hydrogen, or an aliphatic, heteroaliphatic, aryl, heteroaryl, alkylaryl, or alkylheteroaryl moiety;

D and E together represent —$CHR_8$—$CHR_9$—, —$CR_8$=$CR_9$—, wherein $R_8$ and $R_9$ are each independently hydrogen or lower alkyl;

G and J together represent —$CHR_{10}$—$CHR_{11}$—, —$CR_{10}$=$CR_{11}$—, wherein $R_{10}$ and $R_{11}$ are each independently hydrogen or lower alkyl;

K and L together represent C=O, C=S, CH—$CH_3$, CH—$CH(R_L)_2$, C=$C(R_L)_2$, —$CH_2$—, —C(—S($CH_2)_3$S—)—, CH—$OR_L$, CH—$SR_L$, CH—$N(R_L)_2$, CH—N($R_L$)(C=O)($R_L$), C=N—O—$R_L$, CH—N=O, C=C($R_L$)—N($R_L$)_2, C=N—$R_L$, C=N—N($R_L$)_2, or, if the dotted line - - - represents a bond, whereby a double bond is present, then K and L together represent C—N($R_L$)_2, wherein each occurrence of $R_L$ is independently hydrogen, an aliphatic, heteroaliphatic, aryl, heteroaryl, alkylaryl, or alkylheteroaryl moiety, or two occurrences of $R_L$ taken together represent a 3 to 7-membered cyclic aliphatic, heteroaliphatic, aromatic or heteroaromatic moiety;

whereby each of the foregoing aliphatic and heteroaliphatic moieties may independently be substituted or unsubstituted, cyclic or acyclic, or branched or unbranched, and each aryl, heteroaryl, alkylaryl, and alkylheteroaryl moiety may be substituted or unsubstituted;

wherein one or any two of $R_1$, $R_A$, $R_2$, $R_B$, $R_3$, $R_C$, $R_4$, $R_D$, or $R_L$ are optionally a linker covalently bonded to a compound selected from the group consisting of radicicol, monocillin, geldanamycin, and steroids; and pharmaceutically acceptable derivatives thereof.

9. The compound of claim 1, wherein the optional bond represented by the dotted line - - - is absent so that a single bond is present, K and L together represent —$CH_2$— and the compound has the structure:

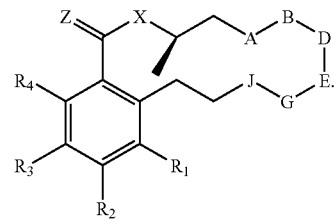

10. The compound of claim 1, wherein the optional bond represented by the dotted line - - - is absent so that a single bond is present, K—L together represent C=O and the compound has the structure:

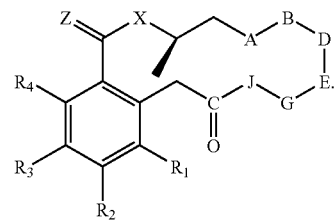

11. The compound of claim 1, wherein the optional bond represented by the dotted line - - - is absent so that a single bond is present, K and L together represent C=N—O—$R_L$ and the compound has the structure:

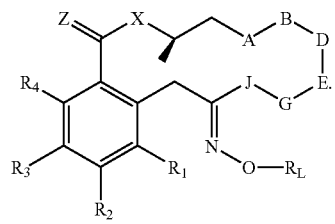

12. The compound of claim 5, wherein the optional bond represented by the dotted line - - - is absent so that a single bond is present, A and B together represent a cyclopropyl group, K and L together represent C=N—O—$R_L$ and the compound has the structure:

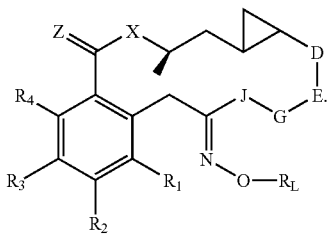

13. A compound having the structure:

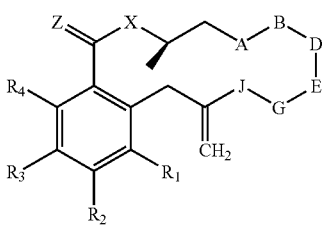

wherein $R_1$ is hydrogen, halogen, an aliphatic, heteroaliphatic, aryl, heteroaryl, alkylaryl, or alkylheteroaryl moiety, or $N(R_A)_2$, wherein each occurrence of $R_A$ is independently hydrogen, or an aliphatic, heteroaliphatic, aryl, heteroaryl, alkylaryl, or alkylheteroaryl moiety;

$R_2$ is hydrogen, halogen, cyano, —$OR_B$, —$N(R_B)_2$, —$SR_B$, —$O(C=O)R_B$, —$N(R_B)(C=O)(R_B)$, —$C(O)R_B$, —$C(O)OR_B$, —$CON(R_B)_2$, —$OCO_2R_B$, or an aliphatic, heteroaliphatic, aryl, heteroaryl, alkylaryl, or alkylheteroaryl moiety, wherein each occurrence of $R_B$ is independently hydrogen, or an aliphatic, heteroaliphatic, aryl, heteroaryl, alkylaryl, or alkylheteroaryl moiety;

$R_3$ is hydrogen, halogen, an aliphatic, heteroaliphatic, aryl, heteroaryl, alkylaryl, or alkylheteroaryl moiety, or —$N(R_C)_2$, wherein each occurrence of $R_C$ is independently hydrogen, or an aliphatic, heteroaliphatic, aryl, heteroaryl, alkylaryl, or alkylheteroaryl moiety;

$R_4$ is hydrogen, halogen, cyano, —$OR_D$, —$N(R_D)_2$, —$SR_D$, —$O(C=O)R_D$, —$N(R_D)(C=O)(R_D)$, —$C(O)R_D$, —$C(O)OR_D$, —$CON(R_D)_2$, —$OCO_2R_D$, or an aliphatic, heteroaliphatic, aryl, heteroaryl, alkylaryl, or alkylheteroaryl moiety, wherein each occurrence of $R_D$ is independently hydrogen, or an aliphatic, heteroaliphatic, aryl, heteroaryl, alkylaryl, or alkylheteroaryl moiety;

Z is O;

X is O;

A and B together represent

—$CHR_5$—$CHR_6$—, —$CR_5$=$CR_6$—, wherein $R_5$ and $R_6$ are each independently hydrogen, halogen, cyano, —$O R_J$, —$N(R_J)_2$, —$SR_J$, —$O(C=O)R_J$, —$O(S=O)R_J$, —$N(R_J)(C=O)(R_J)$, —$C(=O)R_J$, —$C(=O)OR_J$, —$CON(R_J)_2$, —$OCO_2R_J$, —$OSO_2R_J$, or an aliphatic, heteroaliphatic, aryl, heteroaryl, alkylaryl, or alkylheteroaryl moiety, wherein each occurrence of $R_J$ is independently hydrogen, or an aliphatic, heteroaliphatic, aryl, heteroaryl, alkylaryl, or alkylheteroaryl moiety, and wherein $R_7$ is hydrogen, —$OR_K$, —$SR_K$, —$C(O)OR_K$, —$S(O)_2R_K$, —$O(C=O)R_K$, —$N(R_K)(C=O)(R_K)$, —$C(O)R_K$, —$C(O)OR_K$, —$CON(R_K)_2$, —$OCO_2R_K$, or an aliphatic, heteroaliphatic, aryl, heteroaryl, alkylaryl, or alkylheteroaryl moiety, wherein each occurrence of $R_K$ is independently hydrogen, or an aliphatic, heteroaliphatic, aryl, heteroaryl, alkylaryl, or alkylheteroaryl moiety, or when A and B together represent —$CHR_5$—$CHR_6$—, $R_5$ and $R_6$ taken together represent a substituted or unsubstituted 3–7 membered aliphatic, heteroaliphatic, aryl or heteroaryl ring;

D and E together represent —$CHR_8$—$CHR_9$—, —$CR_8$=$CR_9$—, wherein $R_8$ and $R_9$ are each independently hydrogen or lower alkyl;

G and J together represent —$CHR_{10}$—$CHR_{11}$—, —$CR_{10}$=$CR_{11}$—, wherein $R_{10}$ and $R_{11}$ are each independently hydrogen or lower alkyl;

whereby each of the foregoing aliphatic and heteroaliphatic moieties may independently be substituted or unsubstituted, cyclic or acyclic, or branched or unbranched, and each aryl, heteroaryl, alkylaryl, and alkylheteroaryl moiety may be substituted or unsubstituted;

wherein one or any two of $R_1$, $R_A$, $R_2$, $R_B$, $R_3$, $R_C$, $R_4$, $R_D$, $R_5$, $R_6$, or $R_J$, are optionally a linker covalently bonded to a compound selected from the group consisting of radicicol, monocillin, geldanamycin, and steroids; and pharmaceutically acceptable derivatives thereof.

14. A compound having the structure:

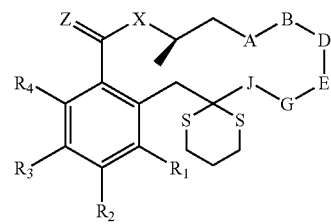

wherein $R_1$ is hydrogen, halogen, an aliphatic, heteroaliphatic, aryl, heteroaryl, alkylaryl, or alkylheteroaryl moiety, or $N(R_A)_2$, wherein each occurrence of $R_A$ is independently hydrogen, or an aliphatic, heteroaliphatic, aryl, heteroaryl, alkylaryl, or alkylheteroaryl moiety;

$R_2$ is hydrogen, halogen, cyano, —$OR_B$, —$N(R_B)_2$, —$SR_B$, —$O(C=O)R_B$, —$N(R_B)(C=O)(R_B)$, —$C(O)R_B$, —$C(O)OR_B$, —$CON(R_B)_2$, —$OCO_2R_B$, or an aliphatic, heteroaliphatic, aryl, heteroaryl, alkylaryl, or alkylheteroaryl moiety, wherein each occurrence of $R_B$ is independently hydrogen, or an aliphatic, heteroaliphatic, aryl, heteroaryl, alkylaryl, or alkylheteroaryl moiety;

$R_3$ is hydrogen, halogen, an aliphatic, heteroaliphatic, aryl, heteroaryl, alkylaryl, or alkylheteroaryl moiety, or —$N(R_C)_2$, wherein each occurrence of $R_C$ is independently hydrogen, or an aliphatic, heteroaliphatic, aryl, heteroaryl, alkylaryl, or alkylheteroaryl moiety;

$R_4$ is hydrogen, halogen, cyano, —$OR_D$, —$N(R_D)_2$, —$SR_D$, —$O(C=O)R_D$, —$N(R_D)(C=O)(R_D)$, —$C(O)R_D$, —$C(O)OR_D$, —$CON(R_D)_2$, —$OCO_2R_D$, or an aliphatic, heteroaliphatic, aryl, heteroaryl, alkylaryl, or alkylheteroaryl moiety, wherein each occurrence of $R_D$ is independently hydrogen, or an aliphatic, heteroaliphatic, aryl, heteroaryl, alkylaryl, or alkylheteroaryl moiety;

Z is O;

X is O;

A and B together represent

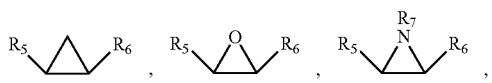

—CHR$_5$—CHR$_6$—, —CR$_5$=CR$_6$—, wherein R$_5$ and R$_6$ are each independently hydrogen, halogen, cyano, —OR$_J$, —N(R$_J$)$_2$, —SR$_J$, —O(C=O)R$_J$, —O(S=O)R$_J$, —N(R$_J$)(C=O)(R$_J$), —C(=O)R$_J$, —C(=O)OR$_J$, —CON(R$_J$)$_2$, —OCO$_2$R$_J$, —OSO$_2$R$_J$, or an aliphatic, heteroaliphatic, aryl, heteroaryl, alkylaryl, or alkylheteroaryl moiety, wherein each occurrence of R$_J$ is independently hydrogen, or an aliphatic, heteroaliphatic, aryl, heteroaryl, alkylaryl, or alkylheteroaryl moiety, and wherein R$_7$ is hydrogen, —OR$_K$, —SR$_K$, —C(O)OR$_K$, —S(O)$_2$R$_K$, —O(C=O)R$_K$, —N(R$_K$)(C=O)(R$_K$), —C(O)R$_K$, —C(O)OR$_K$, —CON(R$_K$)$_2$, —OCO$_2$R$_K$, or an aliphatic, heteroaliphatic, aryl, heteroaryl, alkylaryl, or alkylheteroaryl moiety, wherein each occurrence of R$_K$ is independently hydrogen, or an aliphatic, heteroaliphatic, aryl, heteroaryl, alkylaryl, or alkylheteroaryl moiety, or when A and B together represent —CHR$_5$—CHR$_6$—, R$_5$ and R$_6$ taken together represent a substituted or unsubstituted 3–7 membered aliphatic, heteroaliphatic, aryl or heteroaryl ring, D and E together represent —CHR$_8$—CHR$_9$—, —CR$_8$=CR$_9$—, wherein R$_8$ and R$_9$ are each independently hydrogen or lower alkyl;

G and J together represent —CHR$_{10}$—CHR$_{11}$, —CR$_{10}$=CR$_{11}$—, wherein R$_{10}$ and R$_{11}$ are each independently hydrogen or lower alkyl;

whereby each of the foregoing aliphatic and heteroaliphatic moieties may independently be substituted or unsubstituted, cyclic or acyclic, or branched or unbranched, and each aryl, heteroaryl, alkylaryl, and alkylheteroaryl moiety may be substituted or unsubstituted;

wherein one or any two of R$_1$, R$_A$, R$_2$, R$_B$, R$_3$, R$_C$, R$_4$, R$_D$, R$_5$, R$_6$, or R$_J$, are optionally a linker covalently bonded to a compound selected from the group consisting of radicicol, monocillin, geldanamycin, and steroids; and pharmaceutically acceptable derivatives thereof.

15. The compound of claim 1, wherein A and B together represent an epoxide and the compound has the structure:

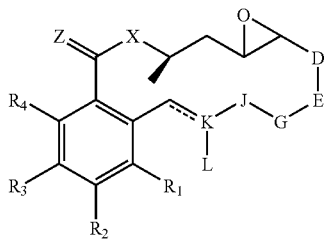

wherein at least one of the D—E, G—J, K—L, R$_2$ and R$_4$ are defined as:

R$_2$ is hydrogen, halogen, cyano, —N(R$_B$)$_2$, —SR$_B$, —N(R$_B$)(C=O)(R$_B$); —C(O)R$_B$, —C(O)OR$_B$, —CON(R$_B$)$_2$, or an aliphatic, heteroaliphatic, aryl, heteroaryl, alkylaryl, or alkylheteroaryl moiety, wherein each occurrence of R$_B$ is independently hydrogen, or an aliphatic, heteroaliphatic, aryl, heteroaryl, alkylaryl, or alkylheteroaryl moiety;

R$_3$ is not hydrogen;

R$_4$ is hydrogen, halogen, cyano, —N(R$_D$)$_2$, —SR$_D$, —N(R$_D$)(C=O)(R$_D$), —C(O)R$_D$, —C(O)OR$_D$, —CON(R$_D$)$_2$, or an aliphatic, heteroaliphatic, aryl, heteroaryl, alkylaryl, or alkylheteroaryl moiety, wherein each occurrence of R$_D$ is independently hydrogen, or an aliphatic, heteroaliphatic, aryl, heteroaryl, alkylaryl, or alkylheteroaryl moiety;

D and E together represent —CHR$_8$—CHR$_9$— wherein R$_8$ and R$_9$ are each independently hydrogen or lower alkyl;

G and J together represent —CHR$_{10}$—CHR$_{11}$—, wherein R$_{10}$ and R$_{11}$ are each independently hydrogen or lower alkyl;

K and L together represent C=S, CH—CH$_3$, CH—CH(R$_L$)$_2$, C=C(R$_L$)$_2$, —CH$_2$—, —C(—S(CH$_2$)$_3$S—)—, CH—OR$_L$, CH—SR$_L$, CH—N(R$_L$)$_2$, CH—N(R$_L$)(C=O)(R$_L$), CH—N=O, C=C(R$_L$)—N(R$_L$)$_2$, C=N—R$_L$, C=N—N(R$_L$)$_2$, or, if the optional bond represented by the dotted line - - - is present so that a double bond is present, then K and L together represent C—N(R$_L$)$_2$, wherein each occurrence of R$_L$ is independently hydrogen, an aliphatic, heteroaliphatic, aryl, heteroaryl, alkylaryl, or alkylheteroaryl moiety, or two occurrences of R$_L$ taken together represent a 3 to 7-membered cyclic aliphatic, heteroaliphatic, aromatic or heteroaromatic moiety; or any two of R$_1$, R$_A$, R$_2$, R$_B$, R$_3$, R$_C$, R$_4$, R$_D$, R$_J$, or R$_L$ are a linker covalently bonded to a compound selected from the group consisting of radicicol, monocillin, geldanamycin, and steroids.

16. The compound of claim 1, wherein A and B together are —CHR$_5$—CHR$_6$— or —CR$_5$=CR$_6$— and R$_5$ and R$_6$ are each independently hydrogen, halogen, cyano, —OR$_J$, —N(R$_J$)$_2$, —SR$_J$, —O(C=O)R$_J$, O(S=O)R$_J$, —N(R$_J$)(C=O)(R$_J$), —OCO$_2$R$_J$ or —OSO$_2$R$_J$ and each occurrence of R$_J$ is independently hydrogen, or an aliphatic, heteroaliphatic, aryl, heteroaryl, alkylaryl, or alkylheteroaryl moiety.

17. The compound of claim 16, wherein R$_5$ and R$_6$ are each independently hydrogen.

18. The compound of claim 1, wherein R$_1$ and R$_3$ are each independently halogen, hydrogen, or lower alkyl; R$_2$ is hydrogen or —OR$_B$, wherein each occurrence of R$_B$ is independently hydrogen, or an aliphatic, heteroaliphatic, aryl, heteroaryl, alkylaryl, or alkylheteroaryl moiety, and R$_4$ is hydrogen or —OR$_D$, wherein each occurrence of R$_D$ is independently hydrogen, or an aliphatic, heteroaliphatic, aryl, heteroaryl, alkylaryl, or alkylheteroaryl moiety.

19. A compound having the structure:

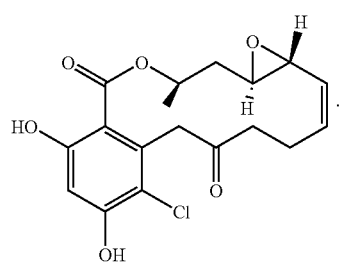

20. A compound having the structure:

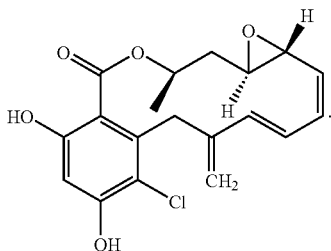

21. A compound having the structure:

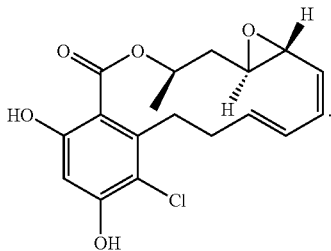

22. A compound having the structure:

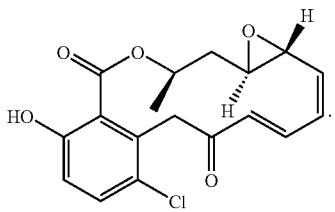

23. A compound having the structure:

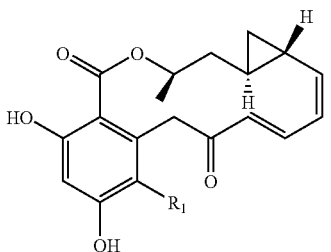

wherein $R_1$ is hydrogen or Cl.

24. A compound having the structure:

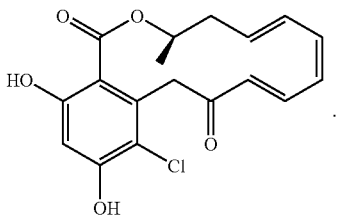

25. A pharmaceutical composition for treating a cancer selected from the group consisting of breast cancers, lung cancers, glioblastoma (brain), and retinoblastoma (eye) comprising a compound of claim 1, 2, 5, 8, 13, or 14 and a pharmaceutically acceptable carrier.

26. A method for treating a cancer selected from the group consisting of breast cancers, lung cancers, glioblastoma (brain), and retinoblastoma (eye) comprising: administering a therapeutically effective amount of a compound of claim 1, 2, 5, 8, 13, or 14 to a subject in need thereof.

27. The method of claim 26, wherein the therapeutically effective amount is in the range of 0.001 mg/kg to 50 mg/kg of body weight.

28. The method of claim 26, wherein the therapeutically effective amount is in the range of 0.01 mg/kg to about 25 mg/kg of body weight.

29. A method for inhibiting the growth of or killing cancer cells, said method comprising:
contacting cancer cells with an amount of a compound of claim 1, 2, 5, 8, 13, or 14 effective to inhibit the growth of or kill the cancer cells, wherein the cancer cells are selected from the group consisting of breast cancer cells, lung cancer cells, glioblastoma (brain) cells, and retinoblastoma (eye) cells.

30. A compound having the structure:

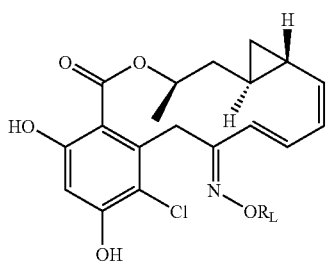

wherein $R_L$ is independently hydrogen, an aliphatic, heteroaliphatic, aryl, heteroaryl, alkylaryl, or alkylheteroaryl moiety.

31. A compound having the structure:

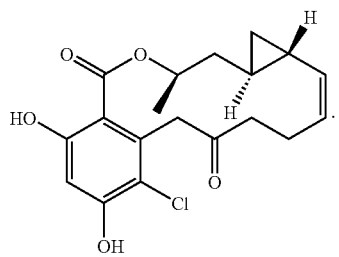

32. A pharmaceutical composition for treating a cancer selected from the group consisting of breast cancers, lung cancers, glioblastoma (brain), and retinoblastoma (eve) comprising a compound having the structure:

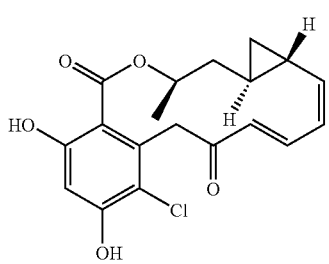

and a pharmaceutically acceptable carrier.

33. A pharmaceutical composition for treating a cancer selected from the group consisting of breast cancers, lung cancers, glioblastoma (brain), and retinoblastoma (eye) comprising a compound having the structure:

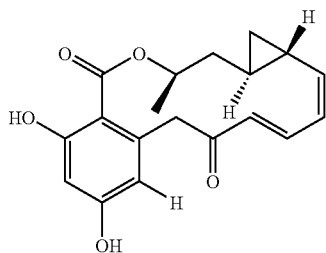

and a pharmaceutically acceptable carrier.

34. A method for treating a cancer selected from the group consisting of breast cancers, lung cancers, glioblastoma (brain), and retinoblastoma (eye) comprising:

administering a therapeutically effective amount of a compound having the structure:

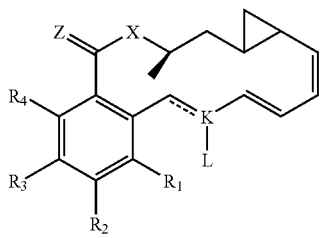

wherein the dotted line - - - represents an optional bond, such that either a single or a double bond is present;

$R_1$ is hydrogen, halogen, an aliphatic, heteroaliphatic, aryl, heteroaryl, alkylaryl, or alkylheteroaryl moiety, or $N(R_A)_2$, wherein each occurrence of $R_A$ is independently hydrogen, or an aliphatic, heteroaliphatic, aryl, heteroaryl, alkylaryl, or alkylheteroaryl moiety;

$R_2$ is hydrogen, halogen, cyano, $-OR_B$, $-N(R_B)_2$, $-SR_B$, $-O(C=O)R_B$, $-N(R_B)(C=O)(R_B)$, $-C(O)R_B$, $-C(O)OR_B$, $-CON(R_B)_2$, $-OCO_2R_B$, or an aliphatic, heteroaliphatic, aryl, heteroaryl, alkylaryl, or alkylheteroaryl moiety, wherein each occurrence of $R_B$ is independently hydrogen, or an aliphatic, heteroaliphatic, aryl, heteroaryl, alkylaryl, or alkylheteroaryl moiety;

$R_3$ is hydrogen, halogen, an aliphatic, heteroaliphatic, aryl, heteroaryl, alkylaryl, or alkylheteroaryl moiety, or $-N(R_C)_2$, wherein each occurrence of $R_C$ is independently hydrogen, or an aliphatic, heteroaliphatic, aryl, heteroaryl, alkylaryl, or alkylheteroaryl moiety;

$R_4$ is hydrogen, halogen, cyano, $-OR_D$, $-N(R_D)_2$, $-SR_D$, $-O(C=O)R_D$, $-N(R_D)(C=O)(R_D)$, $-C(O)R_D$, $-C(O)OR_D$, $-CON(R_D)_2$, $-OCO_2R_D$, or an aliphatic, heteroaliphatic, aryl, heteroaryl, alkylaryl, or alkylheteroaryl moiety, wherein each occurrence of $R_D$ is independently hydrogen, or an aliphatic, heteroaliphatic, aryl, heteroaryl, alkylaryl, or alkylheteroaryl moiety;

Z is O;

X is O;

K and L together represent C=O, C=S, CH—CH$_3$, CH—CH($R_L$)$_2$, C=C($R_L$)$_2$, —CH$_2$—, —C(—S(CH$_2$)$_3$S—)—, CH—OR$_L$, CH—SR$_L$, CH—N($R_L$)$_2$, CH—N($R_L$)(C=O)($R_L$), C=N—O—$R_L$, CH—N=O, C=C($R_L$)—N($R_L$)$_2$, C=N—$R_L$, C=N—N($R_L$)$_2$, or, if the dotted line - - - represents a bond, whereby a double bond is present, then K and L together represent C—N ($R_L$)$_2$, wherein each occurrence of $R_L$ is independently hydrogen, an aliphatic, heteroaliphatic, aryl, heteroaryl, alkylaryl, or alkylheteroaryl moiety, or two occurrences of $R_L$ taken together represent a 3 to 7-membered cyclic aliphatic, heteroaliphatic, aromatic or heteroaromatic moiety;

whereby each of the foregoing aliphatic and heteroaliphatic moieties may independently be substituted or unsubstituted, cyclic or acyclic, or branched or unbranched, and each aryl, heteroaryl, alkylaryl, and alkylheteroaryl moiety may be substituted or unsubstituted;

wherein one or any two of $R_1$, $R_A$, $R_2$, $R_B$, $R_3$, $R_C$, $R_4$, $R_D$, or $R_L$ are optionally a linker covalently bonded to a compound selected from the group consisting of radicicol, monocillin, geldanamycin, and steroids; and pharmaceutically acceptable derivatives thereof, to a subject in need thereof.

35. A method for inhibiting the growth of or killing cancer cells, said method comprising:

contacting cancer cells with an amount of a compound having the structure:

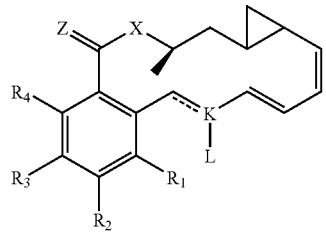

wherein the dotted line - - - represents an optional bond, such that either a single or a double bond is present;

$R_1$ is hydrogen, halogen, an aliphatic, heteroaliphatic, aryl, heteroaryl, alkylaryl, or alkylheteroaryl moiety, or $N(R_A)_2$, wherein each occurrence of $R_A$ is independently hydrogen, or an aliphatic, heteroaliphatic, aryl, heteroaryl, alkylaryl, or alkylheteroaryl moiety;

$R_2$ is hydrogen, halogen, cyano, $-OR_B$, $-N(R_B)_2$, $-SR_B$, $-O(C=O)R_B$, $-N(R_B)(C=O)(R_B)$, $-C(O)R_B$, $-C(O)OR_B$, $-CON(R_B)_2$, $-OCO_2R_B$, or an aliphatic, heteroaliphatic, aryl, heteroaryl, alkylaryl, or alkylheteroaryl moiety, wherein each occurrence of $R_B$ is independently hydrogen, or an aliphatic, heteroaliphatic, aryl, heteroaryl, alkylaryl, or alkylheteroaryl moiety;

$R_3$ is hydrogen, halogen, an aliphatic, heteroaliphatic, aryl, heteroaryl, alkylaryl, or alkylheteroaryl moiety, or $-N(R_C)_2$, wherein each occurrence of $R_C$ is independently hydrogen, or an aliphatic, heteroaliphatic, aryl, heteroaryl, alkylaryl, or alkylheteroaryl moiety;

$R_4$ is hydrogen, halogen, cyano, $-OR_D$, $-N(R_D)_2$, $-SR_D$, $-O(C=O)R_D$, $-N(R_D)(C=O)(R_D)$, $-C(O)R_D$, $-C(O)OR_D$, $-CON(R_D)_2$, $-OCO_2R_D$, or an aliphatic, heteroaliphatic, aryl, heteroaryl, alkylaryl, or alkylheteroaryl moiety, wherein each occurrence of $R_D$ is independently hydrogen, or an aliphatic, heteroaliphatic, aryl, heteroaryl, alkylaryl, or alkylheteroaryl moiety;

Z is O;

X is O;

K and L together represent C=O, C=S, CH—CH$_3$, CH—CH($R_L$)$_2$, C=C($R_L$)$_2$, —CH$_2$—, —C(—S(CH$_2$)$_3$S—)—, CH—OR$_L$, CH—SR$_L$, CH—N($R_L$)$_2$, CH—N($R_L$)(C=O)($R_L$), C=N—O—$R_L$, CH—N=O, C=C($R_L$)—N($R_L$)$_2$, C=N—$R_L$, C=N—N($R_L$)$_2$, or, if the dotted line - - - represents a bond, whereby a double bond is present, then K and L together represent C—N (R$_L$)$_2$, wherein each occurrence of R$_L$ is independently hydrogen, an aliphatic, heteroaliphatic, aryl, heteroaryl, alkylaryl, or alkylheteroaryl moiety, or two occurrences of R$_L$ taken together represent a 3 to 7-membered cyclic aliphatic, heteroaliphatic, aromatic or heteroaromatic moiety;

whereby each of the foregoing aliphatic and heteroaliphatic moieties may independently be substituted or unsubstituted, cyclic or acyclic, or branched or unbranched, and each aryl, heteroaryl, alkylaryl, and alkylheteroaryl moiety may be substituted or unsubstituted;

wherein one or any two of R$_1$, R$_A$, R$_2$, R$_B$, R$_3$, R$_C$, R$_4$, R$_D$, or R$_L$ are optionally a linker covalently bonded to a compound selected from the group consisting of radicicol, monocillin, geldanamycin, and steroids; and pharmaceutically acceptable derivatives thereof;

effective to inhibit the growth of or kill the cancer cells, wherein the cancer cells are selected from the group consisting of breast cancer cells, lung cancer cells, glioblastoma (brain) cells, and retinoblastoma (eye) cells.

36. The method of claim 34 or 35, wherein the compound has the structure:

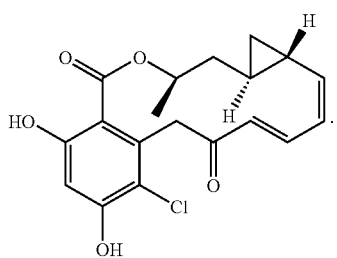

37. The method of claim 34 or 35, wherein the compound has the structure:

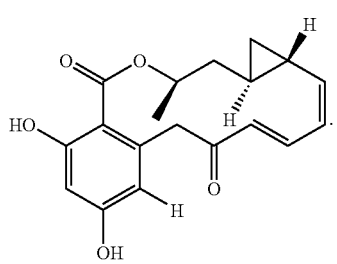

38. A compound having the structure:

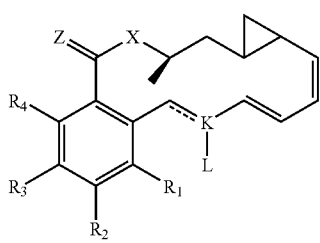

wherein the dotted line - - - represents an optional bond, such that either a single or a double bond is present;

R$_1$ is hydrogen, halogen, an aliphatic, heteroaliphatic, aryl, heteroaryl, alkylaryl, or alkylheteroaryl moiety, or N(R$_A$)$_2$, wherein each occurrence of R$_A$ is independently hydrogen, or an aliphatic, heteroaliphatic, aryl, heteroaryl, alkylaryl, or alkylheteroaryl moiety;

R$_2$ is hydrogen, halogen, cyano, —OR$_B$, —N(R$_B$)$_2$, —SR$_B$, —O(C=O)R$_B$, —N(R$_B$)(C=O)(R$_B$), —C(O)R$_B$, —C(O)OR$_B$, —CON(R$_B$)$_2$, —OCO$_2$R$_B$, or an aliphatic, heteroaliphatic, aryl, heteroaryl, alkylaryl, or alkylheteroaryl moiety, wherein each occurrence of R$_B$ is independently hydrogen, or an aliphatic, heteroaliphatic, aryl, heteroaryl, alkylaryl, or alkylheteroaryl moiety;

R$_3$ is hydrogen, halogen, an aliphatic, heteroaliphatic, aryl, heteroaryl, alkylaryl, or alkylheteroaryl moiety, or —N(R$_C$)$_2$, wherein each occurrence of R$_C$ is independently hydrogen, or an aliphatic, heteroaliphatic, aryl, heteroaryl, alkylaryl, or alkylheteroaryl moiety;

R$_4$ is hydrogen, halogen, cyano, —OR$_D$, —N(R$_D$)$_2$, —SR$_D$, —O(C=O)R$_D$, —N(R$_D$)(C=O)(R$_D$), —C(O)R$_D$, —C(O)OR$_D$, —CON(R$_D$)$_2$, —OCO$_2$R$_D$ or an aliphatic, heteroaliphatic, aryl, heteroaryl, alkylaryl, or alkylheteroaryl moiety, wherein each occurrence of R$_D$ is independently hydrogen, or an aliphatic, heteroaliphatic, aryl, heteroaryl, alkylaryl, or alkylheteroaryl moiety;

Z is O;

X is O;

K and L together represent C=O, C=S, CH—CH$_3$, CH—CH(R$_L$)$_2$, C=C(R$_L$)$_2$, —CH$_2$—, —C(—S(CH$_2$)$_3$S—)—, CH—OR$_L$, CH—SR$_L$, CH—N(R$_L$)$_2$, CH—N(R$_L$)(C=O)(R$_L$), C=N—O—R$_L$, CH—N=O, C=C(R$_L$)—N(R$_L$)$_2$, C=N—R$_L$, C=N—N(R$_L$)$_2$, or, if the dotted line - - - represents a bond, whereby a double bond is present, then K and L together represent C—N (R$_L$)$_2$, wherein each occurrence of R$_L$ is independently hydrogen, an aliphatic, heteroaliphatic, aryl, heteroaryl, alkylaryl, or alkylheteroaryl moiety, or two occurrences of R$_L$ taken together represent a 3 to 7-membered cyclic aliphatic, heteroaliphatic, aromatic or heteroaromatic moiety;

whereby each of the foregoing aliphatic and heteroaliphatic moieties may independently be substituted or unsubstituted, cyclic or acyclic, or branched or unbranched, and each aryl, heteroaryl, alkylaryl, and alkylheteroaryl moiety may be substituted or unsubstituted;

wherein one or any two of R$_1$, R$_A$, R$_2$, R$_B$, R$_3$, R$_C$, R$_4$, R$_D$, or R$_L$ are optionally a linker covalently bonded to a compound selected from the group consisting of radicicol, monocillin, geldanamycin, and steroids; and pharmaceutically acceptable derivatives thereof.

39. The compound of claim 38, wherein R$_1$ and R$_3$ are each independently halogen, hydrogen, or lower alkyl;

R$_2$ is hydrogen or —OR$_B$, wherein R$_B$ is independently hydrogen, or an aliphatic, heteroaliphatic, aryl, heteroaryl, alkylaryl, or alkylheteroaryl moiety; and R$_4$ is hydrogen or —OR$_D$, wherein R$_D$ is independently hydrogen, or an aliphatic, heteroaliphatic, aryl, heteroaryl, alkylaryl, or alkylheteroaryl moiety.

40. The compound of claim 38, wherein K and L taken together are C=N—O—R$_L$.

41. The compound of claim 39, wherein K and L taken together are C=N—O—R$_L$.

42. A pharmaceutical composition for treating a cancer selected from the group consisting of breast cancers, lung cancers, glioblastoma (brain), and retinoblastoma (eye) comprising a compound having the structure:

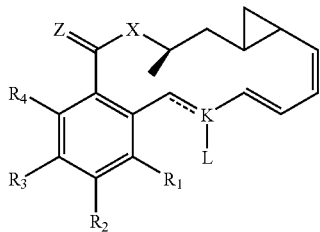

wherein the dotted line - - - represents an optional bond, such that either a single or a double bond is present;

$R_1$ is hydrogen, halogen, an aliphatic, heteroaliphatic, aryl, heteroaryl, alkylaryl, or alkylheteroaryl moiety, or $N(R_A)_2$, wherein each occurrence of $R_A$ is independently hydrogen, or an aliphatic, heteroaliphatic, aryl, heteroaryl, alkylaryl, or alkylheteroaryl moiety;

$R_2$ is hydrogen, halogen, cyano, —$OR_B$, —$N(R_B)_2$, —$SR_B$, —$O(C=O)R_B$, —$N(R_B)(C=O)(R_B)$, —$C(O)R_B$, —$C(O)OR_B$, —$CON(R_B)_2$, —$OCO_2R_B$, or an aliphatic, heteroaliphatic, aryl, heteroaryl, alkylaryl, or alkylheteroaryl moiety, wherein each occurrence of $R_B$ is independently hydrogen, or an aliphatic, heteroaliphatic, aryl, heteroaryl, alkylaryl, or alkylheteroaryl moiety;

$R_3$ is hydrogen, halogen, an aliphatic, heteroaliphatic, aryl, heteroaryl, alkylaryl, or alkylheteroaryl moiety, or —$N(R_C)_2$, wherein each occurrence of $R_C$ is independently hydrogen, or an aliphatic, heteroaliphatic, aryl, heteroaryl, alkylaryl, or alkylheteroaryl moiety;

$R_4$ is hydrogen, halogen, cyano, —$OR_D$, —$N(R_D)_2$, —$SR_D$, —$O(C=O)R_D$, —$N(R_D)(C=O)(R_D)$, —$C(O)R_D$, —$C(O)OR_D$, —$CON(R_D)_2$, —$OCO_2R_D$, or an aliphatic, heteroaliphatic, aryl, heteroaryl, alkylaryl, or alkylheteroaryl moiety, wherein each occurrence of $R_D$ is independently hydrogen, or an aliphatic, heteroaliphatic, aryl, heteroaryl, alkylaryl, or alkylheteroaryl moiety;

Z is O;

X is O;

K and L together represent C=O, C=S, CH—CH$_3$, CH—CH($R_L$)$_2$, C=C($R_L$)$_2$, —CH$_2$—, —C(—S(CH$_2$)$_3$S—)—, CH—OR$_L$, CH—SR$_L$, CH—N(R$_L$)$_2$, CH—N(R$_L$)(C=O)(R$_L$), C=N—O—R$_L$, CH—N=O, C=C(R$_L$)—N(R$_L$)$_2$, C=N—R$_L$, C=N—N(R$_L$)$_2$, or, if the dotted line - - - represents a bond, whereby a double bond is present, then K and L together represent C—N(R$_L$)$_2$, wherein each occurrence of R$_L$ is independently hydrogen, an aliphatic, heteroaliphatic, aryl, heteroaryl, alkylaryl, or alkylheteroaryl moiety, or two occurrences of R$_L$ taken together represent a 3 to 7-membered cyclic aliphatic, heteroaliphatic, aromatic or heteroaromatic moiety;

whereby each of the foregoing aliphatic and heteroaliphatic moieties may independently be substituted or unsubstituted, cyclic or acyclic, or branched or unbranched, and each aryl, heteroaryl, alkylaryl, and alkylheteroaryl moiety may be substituted or unsubstituted;

wherein one or any two of $R_1$, $R_A$, $R_2$, $R_B$, $R_3$, $R_C$, $R_4$, $R_D$, or $R_L$ are optionally a linker covalently bonded to a compound selected from the group consisting of radicicol, monocillin, geldanamycin, and steroids; and pharmaceutically acceptable derivatives thereof, and a pharmaceutically acceptable carrier.

* * * * *

UNITED STATES PATENT AND TRADEMARK OFFICE
CERTIFICATE OF CORRECTION

| | |
|---|---|
| PATENT NO. | : 7,115,651 B2 |
| APPLICATION NO. | : 09/938754 |
| DATED | : October 3, 2006 |
| INVENTOR(S) | : Danishefsky et al. |

Page 1 of 1

It is certified that error appears in the above-identified patent and that said Letters Patent is hereby corrected as shown below:

In column 1, beginning at line 18 and ending at line 24, under the subtitle "Government Support," please delete:

"The present invention was made with support from a grant from the National Institutes of Health (Number CA-28824; Samuel J. Danishefsky). Additionally, the present invention was made with support from a grant from the United States Army Breast Cancer Research Program (Xudong Geng). Therefore, the government may have certain rights in the invention."

and insert:

--This invention was made with U.S. government support under grants CA-28824, CA-85894-01, CA-81704, and CA-68425 awarded by the National Institutes of Health, and a grant awarded by the United States Army Breast Cancer Research Program. The U.S. government has certain rights in the invention.--

Signed and Sealed this

Twenty-ninth Day of July, 2008

JON W. DUDAS
*Director of the United States Patent and Trademark Office*